(12) United States Patent
Apicella et al.

(10) Patent No.: US 7,261,901 B2
(45) Date of Patent: Aug. 28, 2007

(54) VACCINE AND COMPOSITIONS FOR THE PREVENTION AND TREATMENT OF NEISSERIAL INFECTIONS

(75) Inventors: Michael A. Apicella, Solon, IA (US); Jennifer L. Edwards, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 166 days.

(21) Appl. No.: 10/665,990

(22) Filed: Sep. 19, 2003

(65) Prior Publication Data

US 2004/0253222 A1    Dec. 16, 2004

Related U.S. Application Data

(63) Continuation-in-part of application No. 10/621,184, filed on Jul. 15, 2003, now abandoned, which is a continuation-in-part of application No. 10/066,551, filed on Jan. 31, 2002.

(60) Provisional application No. 60/344,452, filed on Oct. 23, 2001, provisional application No. 60/310,356, filed on Aug. 6, 2001, provisional application No. 60/266,070, filed on Jan. 31, 2001.

(51) Int. Cl.
*A61K 39/095* (2006.01)
*A61K 39/02* (2006.01)
*C12P 21/04* (2006.01)
*C07H 21/04* (2006.01)
*C07K 1/00* (2006.01)

(52) U.S. Cl. ............... 424/249.1; 424/184.1; 435/69.1; 435/69.7; 536/23.7; 530/300; 530/350

(58) Field of Classification Search ............ 424/249.1, 424/184.1; 435/69.1, 69.7; 536/23.7; 530/300, 530/350
See application file for complete search history.

(56) References Cited

U.S. PATENT DOCUMENTS

| | | | |
|---|---|---|---|
| 4,533,630 | A | 8/1985 | Wilkins et al. |
| 4,554,101 | A | 11/1985 | Hopp |
| 4,559,157 | A | 12/1985 | Smith et al. |
| 4,608,392 | A | 8/1986 | Jacquet et al. |
| 4,820,508 | A | 4/1989 | Wortzman |
| 4,873,192 | A | 10/1989 | Kunkel |
| 4,938,949 | A | 7/1990 | Borch et al. |
| 4,992,478 | A | 2/1991 | Geria |
| 2003/0100071 | A1 | 5/2003 | Apicella et al. |

FOREIGN PATENT DOCUMENTS

| | | |
|---|---|---|
| EP | 0 184 187 | 6/1986 |
| WO | WO98/02547 | 1/1998 |
| WO | WO99/24578 | 5/1999 |
| WO | WO99/57280 | 11/1999 |
| WO | WO 00/71725 | 11/2000 |
| WO | WO 02/60936 | 8/2002 |

OTHER PUBLICATIONS

Paz et al 1995, Microbiology 141, 913-920.*
Accession No. B81859.*
Accession No. AAY 75751 and Accession No. AAY 75753.*
GenBank Accession No. B81859.
Alpuche-Aranda et al., "*Salmonella* Stimulate Macrophage Macropinocytosis and Persist within Spacious Phagosomes, " *J. Exp. Med.*, 1994, 179:601-608.
Altieri, "Occupancy of CDllb/CD18 (Mac-1) Divalent Ion Binding Site(s) Induces Leukocyte Adhesion," *J. Immunol.*, 1991, 147:1891-1898.
Altschul et al., "Basic Local Alignment Search Tool," *J. Mol. Biol.*, 1990, 215:403-410.
Altschul et al., "Gapped BLAST and PSI-BLAST: a new generation of protein database search programs," *Nucl. Acids Res.*, 1997, 25:3389-3402.
Apicella, "Antigenically Distinct Populations of *Neisseria gonorrhoeae*: Isolation and Characterization of the Responsible Determinants," *J. Infect. Dis.*, 1974, 130:619-625.
Batzer et al., "Enhanced evolutionary PCR using oligonucleotides with inosine at the 3'-terminus," *Nucl. Acids. Res.*, 1991, 19:5081.
Becherer et al., "Cell Surface Proteins Reacting with Activated Complement Components," *Complement Inflamm.*, 1989, 6:142-165.
Bessen and Gotschlich, "Interactions of Gonococci with HeLa Cells: Attachement, Detachment, Replication, Penetration, and the Role of Protein II," *Infect. Immun.*, 1986, 54:154-160.
Bjerknes et al., "Neisserial Porins Inhibit Human Neutrophil Actin Polymerization, Degranulation, Opsonin Receptor Expression, and Phagocytosis but Prime the Neutrophils To Increase Their Oxidative Burst," *Infect. Immun.*, 1995, 63:160-167.
Cann et al., "Detection of antibodies to common antigens of pathogenic and commensal *Neisseria* species," *J. Med. Microbiol.*, 1989, 30:23-30.
Caron et al., "Identification of Two Distinct Mechanisms of Phagocytosis Controlled by Different Rho GTPases," *Science*, 1998, 282:1717-1721.
Carrea et al., "Purification and properties of two phospholipases D from *Streptomyces* sp.," *Biochim. Biophys. Acta.*, 1995, 1255:273-279.
Chen et al., "Heparin Protects Opa+*Neisseria gonorrhoeae* from the Bactericidal Action of Normal Human Serum," *Infect. Immun.*, 1995, 63:1790-1795.

(Continued)

*Primary Examiner*—Susan Ungar
*Assistant Examiner*—Padma Baskar
(74) *Attorney, Agent, or Firm*—Viksnins Harris & Padys PLLP

(57) ABSTRACT

The present invention is directed to novel polypeptides, polynucleotides and vaccines for use against *Neisseria gonorrhoeae* colonization or infection and/or *Neisseria meningitidis* colonization or infection. The vaccines contain an immunogenic amount of a neisserial protein.

9 Claims, 23 Drawing Sheets
(15 of 23 Drawing Sheet(s) Filed in Color)

OTHER PUBLICATIONS

Christodoulides et al., "Interaction of primary human endometrial cells with *Neisseria gonorrhoeae* expressing green fluorescent protein," *Mol. Microbiol.*, 2000, 35:32-43.

Clarke and Spudich, "Nonmuscle Contractile Proteins: The Role of Actin and Myosin in Cell Motility and Shape Determination," *Ann. Rev. Biochem.*, 1977, 46:797-822.

Clauser et al., "Role of Accurate Mass Measurement (±10 ppm) in Protein Indentification Strategies Employing MS or MS/MS and Database Searching," *Anal. Chem.*, 1999, 71:2871-2882.

Clerc and Sansonetti, "Entry of *Shigella flexneri* into HeLa Cells: Evidence for Directed Phagocytosis Involving Actin Polymerization and Myosin Accumulation," *Infect. Immun.*, 1987, 55:2681-2688.

Cohen et al., "Human experimentation with *Neisseria gonorrhoeae*: Rationale, Methods, and Implications for the Biology of Infection and Vaccine Development," *J. Infect. Dis.*, 1994, 169:532-537.

Colley et al., "Phospholipase D2, a distinct phospholipase D isoform with novel regulatory properties that provokes cytoskeletal reorganization," *Curr. Biol.*, 1997, 7:191-201.

Cooper, "Complement evasion strategies of microorganisms," *Immun. Today*, 1991, 12(9):327-331.

Corpet, "Multiple sequence alignment with hierarchical clustering," *Nucl Acids Res.*, 1988, 16:10881-10890.

Dayhoff et al., "A Model of Evolutionary Change in Proteins," *Atlas of Protein Sequence and Structure*, Natl. Biomed. Res. Found., 1978, pp. 345-352.

de la Paz et al., "Effect of sialylation of lipopolysaccharide of *Neisseria gonorrhoeae* on recognition and complement-mediated killing by monoclonal antibodies directed against different outer-membrane antigens," *Microbiology*, 1995, 141:913-920.

Dehio et al., "The role of neisserial Opa proteins in interactions with host cells," *Trends Microbiol.*, 1998, 6:489-495.

Densen et al., "Dissemination of Gonococcal Infection is Associated with Delayed Stimulation of Complement-Dependent Neutrophil Chemotaxis In Vitro," *Infection and Immunity*, 1982, 38:563-572.

DiPaolo et al., "Cellular and Molecular Alterations in Human Epithelia Cells Transformed by Recombinant Human Papillomavirus DNA," *Crit. Rev. Oncogen.*, 1993, 4:337-360.

Dramsi and Cossart, "Intracellular Pathogens and the Actin Cytoskeleton," *Annu. Rev. Cell Dev. Biol.*, 1998, 14:137-166.

Draper et al., "Scanning electron microscopy of attachment of *Neisseria gonorrhoeae* colony phenotypes to surfaces of human genital epithelia," *Am. J. Obstet. Gynecol.*, 1980, 138:818-826.

Dudas and Apicella, "Selection and Immunochemical Analysis of Lipooligosaccharide Mutants of *Neisseria gonorrhoeae*," *Infect. Immun.*, 1988, 56:499-504.

Edwards and Apicella, "The role of lipooligosaccharide in *Neisseria gonorrhoae* pathogenesis of cervical epithelia: lipid A serves as a C3 acceptor molecule," *Cell. Microbiol.*, 2002, 4:585-598.

Edwards et al., "A co-operative interaction between *Neisseria gonorrhoeae* and complement receptor 3 mediates infection of primary cervical epithelial cells," *Cell. Microbiol.*, 2002, 4:571-584.

Edwards et al., "Complement Receptor Type 3 (CR 3) on Primary Cervical Epithelial Cells Serves as a Receptor for *Neisseria Gonorrhoeae*," Abstracts of the 101st General Meeting of the American Society for Microbiology, 2001, Orlando, FL, p. 303.

Edwards et al,. "The Role of Complement Receptor 3 (CR3) in *Neisseria Gonorrhoeae* Infection of Human Cervical Epithelia," *Cell. Microbiol.*, 2001, 3:611-622.

Elmer and Edgington, "Microfilament Reorganization Is Associated with Functional Activation of $\alpha_M\beta_2$ on Monocytic Cells," *J. Biol. Chem.*, 1994, 269:3159-3166.

Erdei et al., "The role of C3 in the immune response," *Immun. Today*, 1991, 12:332-337.

Evans, "Ultrastructural Study of Cervical Gonorrhea," *J. Infect. Dis.*, 1977, 136(2):248-255.

Exton, "New Developments in Phospholipase D," *J. Biol. Chem.*, 1997, 272:15579-15582.

Fällman et al., "Complement Receptor-mediated Phagocytosis Is Associated with Accumulation of Phosphatidylcholine-derived Diglyceride in Human Neutrophila," *J. Biol. Chem.*, 1992, 267:2656-2663.

Fijen et al., "The role of Fcγ receptor polymorphisms and C3 in the immune defense against *Neisseria meningitidis* in complement-deficient individuals," *Clin. Exp. Immunol.*, 2000, 120:338-345.

Finlay and Falkow, "Common Themes in Microbial Pathogenicity Revisited," *Microbiol. Mol. Biol. Rev.*, 1997, 61:136-169.

Finlay and Ruschkowski, "Cytoskeletal rearrangements accompanying *Salmonella* entry into epithelial cells," *J. Cell Sci.*, 1991, 99:283-296.

Fluhmann, "The Squamocolumnar Transitional Zone of the Cervix Uteri," *Obstet. Gynecol.*, 1959, 14:133-148.

Francis et al., "Ruffles induced by *Salmonella* and other stimuli direct macropinocytosis of bacteria," *Nature*, 1993, 364:639-642.

Frank et al., "The role of complement in inflammation and phagocytosis," *Immun. Today*, 1991, 12(9):322-326.

Fukami et al., "α-Actinin and Vinculin Are $PIP_2$-binding Proteins Involved in Signaling by Tyrosine Kinase," *J. Biol. Chem.*, 1994, 269:1518-1522.

Gazdar et al., "Characterization of Paired Tumor and Non-Tumor Cell Lines Established from Patients with Breast Cancer," *Int. J. Cancer*, 1998, 78:766-774.

Garcia-del Portillo and Finlay, "*Salmonella* Invasion of Nonphagocytic Cells Induces Formation of Macropinosomes in the Host Cell," *Infect. Immun.*, 1994, 62:4641-4645.

Goeddel et al., "Synthesis of human fibroblast interferon by *E. coli*," *Nucl. Acids. Res.*, 1980, 8:4057-4074.

Grassmé et al., "Gonococcal Opacity Protein Promotes Bacterial Entry-Associated Rearrangements of the Epithelia Cell Actin Cytoskeleton," *Infect. Immun.*, 1996, 64(5):1621-1630.

Griffin, Jr. et al., "Studies on the Mechanism of Phagocytosis: The Interaction of Macrophages with Anti-Immunoglobulin IgG-Coated Bone Marrow-Derived Lymphocytes," *J. Exp. Med.*, 1976, 144:788-809.

Griffin, Jr. et al., "Studies on the Mechanism of Phagocytosis: Requirements for Circumferential Attachment of Particle-Bound Ligands to Specific Receptors on the Macrophage Plasma Membrane," *J. Exp. Med.*, 1975, 142:1263-1282.

Ha and Exton, "Activation of Actin Polymerization by Phosphatidic Acid Derived from Phosphatidylcholine in IIC9 Fibroblasts," *J. Cell Biol.*, 1993, 123:1789-1796.

Harkness, "The Pathology of *Gonorrhoea*," *Br. J. Vener. Dis.*, 1948, 24:137-147.

Harvey et al., "Ultrastructural Analysis of Primary Human Urethral Epithelial Cell Cultures Infected with *Neisseria gonorrhoeae*," *Infect. Immun.*, 1997, 65(6):2420-2427.

Harvey et al., "Receptor-mediated endocytosis of *Neisseria gonorrhoeae* into primary human urethral epithelial cells: the role of the asialoglycoprotein receptor," *Mol. Microbiol.*, 2001, 42:659-672.

Harvey et al., "Immortalization of Human Urethral Epithelial Cells: a Model for the Study of the Pathogenesis of and the Inflammatory Cytokine Response to *Neisseria gonorrhoeae* Infection," *Infect. Immun.*, 2002, 70:5808-5815.

Hauck et al.,"CD66-mediated-phagocytosis of $Opa_{52}$ *Neisseria gonorrhoeae* requires a Src-like tyrosine kinase- and Rac1-dependent signaling pathway," *EMBO J.*, 1998, 17:443-454.

Hayashi et al., "Binding of the 68-Kilodalton Protein of *Mycobacterium avium* to $\alpha v\beta_3$ on Human Monocyte-Derived Macrophages Enhances Complement Receptor Type 3 Expression" *Infect. Immun.*, 1997, 65(4):1211-1216.

Higgins and Sharp, "CLUSTAL: a package for performing multiple sequence alignment on a microcomputer," *Gene*, 1988, 73:237-244.

Higgins and Sharp, "Fast and sensitive multiple sequence alignments on a microcomputer," *CABIOS*, 1989, 5:151-153.

Hildreth and August, "The Human Lymphocyte Function-Associated (HLFA) Antigen and a Related Macrophage Differentiation Antigen (HMac-1): Functional Effects of Subunit-Specific Monoclonal Antibodies," *J. Immunol.*, 1985, 134:3272-3280.

Hinnebusch et al., "Role of *Yersinia* Murine Toxin in Survival of *Yersinia pestis*, in the Midgut of the Flea Vector," *Science*, 2002, 296:733-735.

Hodgson et al., "Rational Attenuation of *Corynebacterium pseudotuberculosis*: Potential Cheesy Gland Vaccine and Live Delivery Vehicle," *Infect. Immun.*, 1992, 60:2900-2905.

Hondalus et al., "The Intracellular Bacterium *Rhodococcus equi* Requires Mac-1 To Bind to Mammalian Cells," *Infect. Immun.*, 1993, 61:2919-2929.

Huang et al., "Parallelization of a local similarity algorithm," *CABIOS*, 1992, 8:155-165.

Hussain et al., "Investigation of the complement receptor 3 (CD11b/CD18) in human rectal epithelium," *Clin. Exp. Immun.*, 1995, 102:384-388.

Hynes, "Integrins: A Family of Cell Surface Receptors," *Cell*, 1987, 48:549-554.

Iglesias et al., "Interleukin-6 and Interleukin-6 Soluble Receptor Regulate Proliferation of Normal, Human Papillomavirus-Immortalized, and Carcinoma-Derived Cervical Cells In Vitro" *Am. J. Pathol.*, 1995, 146:944-952.

Ingalls et al., "The CD11/CD18 Integrins: Characterization of Three Novel LPS Signaling Receptors," *Prog. Clin. Biol. Res.*, 1998, 397:107-117.

Jarvis et al., "Invasion of Human Mucosal Epithelial Cells by *Neisseria gonorrhoeae* Upregulates Expression on Intercellular Adhesion Molecule 1 (ICAM-1)," *Infect. Immun.*, 1999, 67(3):1149-1156.

Jerse and Rest, "Adhesion and invasion by the pathogenic *Neisseria*" *Trends in Microbiology*, 1997, 5(6):217-221.

Jones et al., "Phospholipase D and membrane traffic: Potential roles in regulated exocytosis, membrane delivery and vesicle budding," *Biochim. Biophys. Acta*, 1999, 1439:229-234.

Jones and Walker, "Integrins: a role as cell signalling molecules," *J. Clin. Pathol: Mol. Pathol.*, 1999, 52:208-213.

Jones et al., "Two Signaling Mechanisms for Activation of $\alpha_M\beta_2$ Avidity in Polymorphonuclear Neutrophils," *J. Biol. Chem.*, 1998, 273(17):10556-10566.

Jurianz et al., "Complement resistance of tumor cells: basal and induced mechanisms," *Mol. Immunol.*, 1999, 36:929-939.

Källstroöm et al., "Membrane cofactor protein (MCP or CD46) is a cellular pilus receptor for pathogenic *Neisseria*," *Mol. Microbiol.*, 1997, 25:639-647.

Källstroöm et al., "Cholera toxin and extracellular $Ca^{2+}$ induce adherence of non-piliated *Neisseria*: evidence for an important role of G-proteins and Rho in the bacteria-cell interaction," *Cell microbiol.*, 2000, 2:341-351.

Karlin and Altschul, "Methods for assessing the statistical signifcance of molecular sequence features by using general scoring schemes," *Proc. Natl. Acad. Sci. USA*, 87:2264-2268.

Karlin and Altschul, "Applications and statistics for multiple high-scoring segments in molecular sequences," *Proc. Natl. Acad. Sci. USA*, 1993, 90:5873-5877.

Kaur and McDougall, "Characterization of Primary Human Keratinocytes Transformed by Human Papillomavirus Type 18," *J. Virol.*, 1988, 62:1917-1924.

Ketterer et al., "Infection of Primary Human Bronchial Epithelial Cells by *Haemophilus influenzae*: Macropinocytosis as a Mechanism of Airway Epithelial Cell Entry," *Infect. Immun.*, 1999, 4161-4170.

Kishimoto et al., "The Leukocyte Integrins," *Advances in Immunology*, 1989, 46:149-182.

Köhler et al., "Continuous cultures of fused cells secreting antibody of predefined specificity," *Nature*, 1975, 256:495.

Kondo et al., "Phospholipase D Mimics Platelet-derived Growth Factor as a Competence Factor in Vascular Smooth Muscle Cells," *J. Biol. Chem.*, 1992, 267:23609-23616.

Kondo et al., "Two-dimensional electrophoretic studies on down-regulated intracellular transferrin in human fibroblasts immortalized by treatment with either 4-nitroquinoline 1-oxide or $^{60}$Co gamma rays," *Electrophoresis*, 1996, 17:1638-1642.

Kragsbjerg et al., "The effects of live *Neisseria minigitidis* and tumour necrosis factor-α on neutrophil oxidative burst and β2-integrin expression," *APMIS*, 2000, 108:276-282.

Kunkel, "Rapid and efficient site-specific mutagenesis without phenotypic selection," *Proc. Natl. Acad. Sci. USA*, 1985, 82:488-492.

Kunkel et al., "Rapid and Efficient Site-Specific Mutagenesis without Phenotypic Selection," *Meth. Enzymol.*, 1987, 154:367-382.

Kusner et al., "Regulation of Phospholipase D Activity by Actin: Actin Exerts Bidirectional Modulation of Mammalian Phospholipase D Activity in a Polymerization-Dependent, Isoform-Specific Manner," *J. Biol. Chem.*, 2002, 277:50683-50692.

Kusner et al., "Evolutionary conservation of physical and functional interactions between phospholipase D and actin," *Arch. Biochem. Biophys*, 2003, 412:231-241.

Lawn et al., "The sequence of human serum albumin cDNA and its expression in *E. coli*," *Nucl. Acids. Res.*, 1981, 9:6103-6114.

Lehninger, "The amino acid building blocks of proteins" *Biochemistry*, 2nd ed., 1975, 73-75.

Lin et al., "Increased Expression of Luteinizing Hormone/Human Chorionic Gonadotropin Receptor Gene in Human Endometrial Carcinomas," *J. Clin. Endocrinol. Metab.*, 1994, 79:1483-1491.

Lukowski et al., "Inhibition of Phospholipase D Activity by Fodrin: An Active Role for the Cytoskeleton," *J. Biol. Chem.*, 1996, 271:24164-24171.

Lynch et al., "Studies of Porins: Spontaneously Transferred from Whole Cells and Reconstituted from Purified Proteins of *Neisseria gonorrhoeae* and *Neisseria meningitides*," *Biophys. J.*, 1984, 45:104-107.

Maisner et al., "Membrane Cofactor Protein (CD46) Is a Basolateral Protein That Is Not Endocytosed," *J. Biol. Chem.*, 1997, 272:20793-20799.

Maitra et al., "Enrichment of epithelial cells for molecular studies," *Nature Med.*, 1999, 5:459-463.

Mandell et al. (eds.), Principles and Practice of Infectious Diseases, 3rd ed., 1990, Churchill Livingstone Inc. (TOC only).

McGee et al., "Mechanisms of Mucosal Invasion by Pathogenic *Neisseria*," *Rev. Infect. Dis.*, 1983, 5:S708-S714.

McGhee et al., "New Perspectives in Mucosal Immunity with Emphasis on Vaccine Development," *Sem. Hematol.*, 1993, 30:3-15.

McNamara et al., "Toxic phospholipases D of *Corynebacterium pseudotuberculosis*, *C. ulcerans* and *Arcanobacterium haemolyticum*: cloning and sequence homology," *Gene*, 1995, 156:113-118.

McNeely, Jr., et al., "Treatment of Chlamydial Infections of the Cervix During Pregnancy," *Sex. Trans. Dis.* 1989, 16:60-62.

McQuillen et al., "Complement Processing and Immunoglobulin Binding to *Neisseria gonorrhoeae* Determined In Vietro Simulates In Vivo Effects," *J. Infect. Dis.*, 1999, 179:124-135.

Meinkoth and Wahl, "Hybridization of Nucleic Acids Immobilized on Solid Supports," *Anal. Biochem.*, 1984, 138:267-284.

Mesri et al., "Dual Regulation of Ligand Binding by CD11b I Domain: Inhibition of Intercellular Adhesion and Monocyte Procoagulant Activity by a Factor X-Derived Peptide," *J. Biol. Chem.*, 1998, 723(2):744-748.

Meyer, "Pathogenic *Neisseriae*: Complexity of Pathogen—Host Cell Interplay," *Clinical Infectious Diseases*, 1999, 28:433-441.

Moll et al., "The Catalog of Human Cytokeratins: Patterns of Expression in Normal Epithelia, Tumors and Cultured Cells," *Cell*, 1982, 31:11-24.

Morse and Bartenstein, "Purine metabolism in *Neisseria gonorrhoeae*: the requirement for hypoxanthine," *Can. J. Microbiol.*, 1980, 26:13-20.

Mosser and Edelson, "The third component of complement (C3) is responsible for the intracellular survival of *Leishmania major*" *Nature*, 1987, 327:329-331.

Moulder, "Comparative Biology of Intracellular Parasitism," *Microbiol. Rev.*, 1985, 49:298-337.

Mukherjee et al., "Endocytosis," *Physiol. Rev.*, 1997, 77:759-803.

Myers and Miller, "Optimal alignments in linear space," *CABIOS*, 1988, 4:11-17.

Nassif and So,, "Interaction of Pathogenic *Neisseriae* with Nonphagocytic Cells," *Clin. Microbiol. Rev.*, 1995, 8:376-388.

Nassif et al., "Interactions of pathogenic *Neisseria* with host cells. It is possible to assemble the puzzle?" *Mol. Microbiol.*, 1999, 32(6):1124-1132.

Naumann et al., "Host cell interactions and signalling with *Neisseria gonorrhoeae*" *Curr. Opin. Microbiol.*, 1999, 2:62-70.

Needleman and Wunsch, "A General Applicable to the Search for Similarities in the Amino Acid Sequence of Two Proteins," *J. Mol. Biol.*, 1970, 48:443-453.

Obermeier et al., "PAK promotes morphological changes by acting upstream of Rac," *EMBO J.*, 1998, 17:4328-4339.

Oelschlaeger et al., "Unusual microtubule-dependent endocytosis mechanisms triggered by *Campylobacter jejuni* and *Citrobacter freundii*," *Proc. Natl. Acad. Sci. USA*, 1993, 90:6884-6888.

O'Gorman et al., "Decreased Insulin-like Growth Factor-II/Mannose 6-Phosphate Receptor Expression Enhances Tumorigenicity in JEG-3 Cells," *Cancer Res.*, 1999, 59:5692-5694.

Ohtsuka et al., "An Alternative Approach to Deoxyoligonucleotides as Hybridization Probes by Insertion of Deoxyinosine at Ambiguous Codon Positions," *J. Biol. Chem.*, 1985, 260:2605-2608.

Parkhill et al., "Complete DNA sequence of a serogroup A strain of *Neisseria meningitidis* Z2491," *Nature*, 2000, 404:502-506.

Pearson and Lipman, "Improved tools for biological sequence comparison," *Proc. Natl. Acad. Sci. USA*, 1988, 85:2444-2448.

Pearson et al., "Using the FASTA Program to Search Protein and DNA Sequence Databases," *Meth. Mol. Biol.*1994, 24:307-331.

Ponting and Kerr, "A novel family of phospholipase D homologues that includes phospholipid synthases and putative endonucleases: Identification of duplicated repeats and potential active site residues," *Prot. Science*, 1996, 5:914-922.

Price and Boettcher, "The Presence of Complement in Human Cervical Mucus and its Possible Relevance to Infertility in Women with Complement-Dependent Sperm-Immobilizing Antibodies," *Fertil. Steril.*, 1979, 32:61-66.

Rabinovitch, "Professional and non-professional phagocytes: an introduction," *Trends Cell Biol.*, 1995, 5:85-88.

Ram et al., "A Novel Sialic Acid Biding Site on Factor H Mediates Serum Resistance of Sialylated *Neisseria gonorrhoeae*," *J. Exp. Med.*, 1998, 187(5):743-752.

Ram et al., "The contrasting mechanisms of serum resistance of *Neisseria gonorrhoeae* and group B *Neisseria meningitidis*," *Mol. Immun.*, 1999, 36:915-928.

Ramos et al., "The Elevated Natural Killer Sensitivity of Targets Carrying Surface-Attached C3 Fragments Require the availability of the iC3b Receptor (CR3) on the Effectors," *J. Immunol.*, 1988, 140:1239-1243.

Ramos et al., "Complement-dependent cellularcytotoxicity: Lymphoblastoid lines that activate complement component 3 (C3) and express C3 receptors have increased sensitivity to lymphocyte-mediated lysis in the presence of fresh human serum," *Proc. Natl. Acad. Sci. USA*, 1985, 82:5470-5474.

Relman et al., "recognition of a Bacterial Adhesin by an Integrin: Macrophage CR3 ($\alpha_M\beta_2$, CD11b/CD18) Binds Filamentous Hemagglutinin of *Bordetella pertussis*" *Cell*, 1990, 61:1375-1382.

Richardson and Sadoff, "Induced Engulfment of *Neisseria gonorrhoeae* by Tissue Culture Cells," *Infect. Immun.*, 1988, 56:2512-2514.

Robinson, "The role of clathrin, adaptors and dynamin in endocytosis," *Curr. Opin. Cell Biol.*, 1994, 6:538-544.

Rosqvist et al., "Functional conservation of the secretion and translocation machinery for virulence proteins of yersiniae, salmonellae and shigellae," *EMBO J.*, 1995, 14:4187-4195.

Ross and Densen, "Opsonophagocytosis of *Neisseria gonorrhoeae*: Interaction of Local and Disseminated Isolates with Complement and Neutrophils," *J. Infect. Dis.*, 1985, 151:33-41.

Rossolini et al., "Use of deoxyinosine-containing primers vs degenerate primers for polymerase chain reaction based on ambiguous sequence information," *Mol. Cell Probes*, 1994, 8:91-98.

Schmidt and Hall, "Signaling to the Actin Cytoskeleton," *Annu. Rev. Cell Dev. Biol.*, 1998, 14:305-338.

Schoolnik et al., "*Gonococcal pili*: Primary Structure and Receptor Binding Domain," *J. Exp. Med.*, 1984, 159:1351-1370.

Segal et al., "Role of Chromosomal Rearrangement in *N. gonorrhoeae* Pilus Phase Variation," *Cell*, 1985, 40:293-300.

Sells et al., "Human p21-activated kinase (Pak 1) regulates actin organization in mammalian cells," *Curr. Biol.*, 1997, 7:202-210.

Seya et al., "Quantitative Analysis of Membrane Cofactor Protein (MCP) of Complement," *J. Immunol.*, 1990, 145:238-245.

Silverstein et al., "Endocytosis," *Ann. Rev. Biochem.*, 1977, 46:669-722.

Simmons et al., "Vaccine Potential Attenuated Mutants of *Corynebacterium pseudotuberculosis* in Sheep," *Infect. Immun.*, 1998, 66:474-479.

Sizemore and Rorke, "Human Papillomavirus 16 Immortalization of Normal Human Ectocervical Epithelial Cells Alters Retinoic Acid Regulation of Cell Growth and Epidermal Growth Factor Receptor Expression," *Cancer Res.*, 1993, 53:4511-4517.

Skoudy et al., "A functional role for ezrin during *Shigella flexneri* entry into epithelial cells," *J. Cell Sci.*, 1999, 112:2059-2068.

Smedts et al., "Changing Patterns of Keratin Expression During Progression of Cervical Intraepithelial Neoplasia," *Am. J. Pathol.*, 1990, 136:657-668.

Smedts et al., "Keratin Expression in Cervical Cancer," *Am. J. Pathol.*, 1992, 141:497-511.

Smith and Waterman, "Comparison of Biosequences," *Adv. Appl. Math.*, 1981, 2:482-489.

Steed et al., "Intracellular Signaling by Phospholipase D as a Therapeutic Target," *Current Pharmaceutical Biotechnology*, 2001, 2:241-256.

Stephens, "Gonococcal and Meningococcal Pathogenesis as Defined by Human Cell, Cell Culture, and Organ Culture Assays," *Clin. Microbiol. Rev.*, 1989, 2:S104-S111.

Stewart et al., "T Cell Adhesion to Intercellular Adhesion Molecule-1 (ICAM-1) Is Controlled by Cell Spreading and the Activation of Integrin LFA-$1^1$," *J. Immunol.*, 1996, 156:1810-1817.

Stocks et al., "CD66-dependent neutrophil activation: a possible mechanism for vascular selectin-mediated regulation of neutrophil adhesion" *J. Leuk. Biol.*, 1995, 58:40-48.

Stocks et al., "CD66: role in the regulation of neutrophil effector function," *Eur. J. Immunol.*, 1996, 26:2924-2932.

Stryer, "Conformation and Synamics," *Biochemistry*, $2^{nd}$ ed., 1981, 14-15.

Sülz et al., "The expression of $\alpha_v$ and $\beta_3$ integrin subunits in the normal human Fallopian tube epithelium suggests the occurrence of a tubal implantation window," *Hum. Reprod.*, 1998, 13:2916-2920.

Sun et al., "In Vivo Cytokeratin-Expression Pattern of Stratified Squamous Epithelium from Human Papillomavirus-Type-16-Immortalized Ectocervical and Foreskin Keratinocytes," *Int. J. Cancer*, 1993, 54:656-662.

Swanson and Baer, "Pagocytosis by zippers and triggers," *Trends Cell Biol.*, 1995, 5:89-93.

Swanson and Watts, "Macropinocytosis," *Trends Cell Biol.*, 1995, 5:424-428.

Tettelin et al., "Complete Genome Sequence of *Neisseria meningitidis* Serogroup B Strain MC58," *Science*, 2000, 287:1809-1815.

Tran Van Nhieu and Sansonetti, "Mechanism of *Shigella* entry into epithelial cells," *Curr. Opin. Microbiol.*, 1999, 2:51-55.

Turner and Foster, "The Potential Exploitation of Plant Viral Translational Enhancers in Biotechnology for Increased Gene Expression;" *Mol. Biotech.*1995, 3:225-236.

van Dijk et al., "Exogenous phospholipase D generates lysophosphatidic acid and activates Ras, Rho and $Ca^{2+}$signaling pathways," *Curr. Biol.*, 1998, 8:386-392.

van Kooyk et al., "The Actin Cytoskeleton Regulates LFA-1 Ligand Binding through Avidity Rather than Affinity Changes," *J. Biol. Chem.*, 1999, 274(38):26869-26877.

Vanderpuye et al., "The Complement System in Human Reproduction," *Am. J. Reprod. Immunol.*, 1992, 27:145-155.

Violette et al., "Differences in the Binding of Blocking Anti-CD11b Monoclonal Antibodies to the A-Domain of CD11b," *J. Immunol.*, 1995, 155:3092-3101.

Vogel and Frosch, "Mechanisms of neisserial serum resistance," *Mol. Microbiol.*, 1999, 32:1133-1139.

Wåhlin et al., "C3 Receptors on Human Lymphocyte Subsets and Recruitment of ADCC Effector Cells by C3 Fragments," *J. Immunol.*, 1983, 130:2831-2836.

Waite, "The PLD superfamily: insights into catalysis," *Biochim. Biophys. Acta*, 1999, 1439:187-197.

Watarai et al., "Interaction of Ipa Proteins of *Shigella flexneri* with $\alpha_5\beta_1$ Integrin Promotes Entry of the Bacteria into Mammalian Cells," *J. Exp. Med.*, 1996, 183:991-999.

Wen et al., "Interaction of the Gonococcal Porin P.IB with G- and F-Actin," *Biochem.*, 2000, 39:8638-8647.

Wetzler et al., "Gonococcal Lipooligosaccharide Sialylation Prevents Complement-Dependent Killing by Immune Sera," *Infect. Immun.*, 1992, 60:39-43.

Wright et al., "Identification of the C3bi receptor of human monocytes and macrophages by using monoclonal antibodies," *Proc. Natl. Acad. Sci. USA*, 1983, 80:5699-5703.

Würzner, "Evasion of pathogens by avoiding recognition or eradication by complement, in part via molecular mimicry," *Mol. Immun.*, 1999, 36:249-260.

Zhang and Chait, "ProFound: An Expert System for Protein Identification Using Mass Spectrometric Peptide Mapping Information," *Anal. Chem.*, 2000, 72:2482-2489.

Zipfel et al., "Factor H and disease: a complement regulator affects vital body functions," *Mol. Immunol.*, 1999, 36:241-248.

GenBank Accession No. AL162756 dated Oct. 1, 2000.

GenBank Accession No. ABP79466 dated Oct. 10, 2002.

GenBank Accession No. AAZ54515 dated Mar. 21, 2000.

GenBank Accession No. ABZ40436 dated Oct. 10, 2002.

GenBank Accession No. AAY75753 dated Mar. 21, 2000.

Edwards et al., "The role of complement receptor 3 (CR3) in *Neisseria gonorrhoeae* infection of human cervical epithelia," *Cellular Microbiology*, 2001, 3(9):611-622.

Edwards et al., "Gonococcal phospholipase D modulates the expression and function of complement receptor 3 in primary cervical epithelial cells," *Infection and Immunity*, 2003, 71(11):6381-6391.

International Search Report for International Application Serial No. PCT/US02/02881, (2003).

International Search Report for International Application Serial No. PCT/US2004/022708, (2004).

Barritt et al., "Antigenic and structural differences among six proteins II expressed by a single strain of *Neisseria gonorrhoeae*," *Infect Immun.*, 55(9), 2026-2031 (1987).

Cohen et al., "Human experimentation with *Neisseria gonorrhoeae*: Progress and goals", *J Infect Dis.*, 179, Suppl 2, S375-S379 (1999).

Densen, "Interaction of complement with *Neisseria meningitidis* and *Neisseria gonorrhoeae*," *Clin Microbiol Rev.*, 2, Suppl:S11-17 (1989).

Edwards et al., "*Neisseria gonorrhoeae* elicits membrane ruffling and cytoskeletal rearrangements upon infection of primary human endocervical and ectocervical cells", *infect Immun.*, 68(9), 5354-5363 (2000).

Edwards et al., "*Neisseria gonorrhoeae* PLD directly interacts with Akt kinase upon infection of primary, human, cervical epithelial cells", *Cell Microbiol.*, 8(8), 1253-1271 (2006).

Thankavel et al., "Localization of a domain in the FimH adhesin of *Escherichia coli* type 1 fimbriae capable of receptor recognition and use of a domain-specific antibody to confer protection against experimental urinary tract infection", *J Clin Invest*, 100(5), 1123-1136 (1997).

Zhang et al., "Enhanced immunogenicity of a genetic chimeric protein consisting of two virulence antigens of *Streptococcus mutans* and protection against infection", *Infect Immun.*, 70(12), 6779-6787 (2002).

* cited by examiner

**The Effect of *Clostridium* C3 Toxin on Gonococcal Invasion of Primary Cervical Cells**

| | Ectocervical | Endocervical |
|---|---|---|
| No Toxin | 2.5868 | 1.6153 |
| C3 toxin | 0.0945 | 0.3123 |

Cell Type

Figure 3

α-Phosphotyrosine

α-Phosphothreonine

SEQUENCE LISTING

<160> NUMBER OF SEQ ID NOS: 32

<210> SEQ ID NO 1
<211> LENGTH: 2015
<212> TYPE: PRT
<213> ORGANISM: Neisseria gonorrhoeae

<400> SEQUENCE: 1

```
Met Asn Lys Gly Leu His Arg Ile Ile Phe Ser Lys Lys His Ser Thr
1               5                   10                  15

Met Val Ala Val Ala Glu Thr Ala Asn Ser Gln Gly Lys Gly Lys Gln
                20                  25                  30

Ala Gly Ser Ser Val Ser Val Ser Leu Lys Thr Ser Gly Asp Leu Cys
            35                  40                  45

Gly Lys Leu Lys Thr Thr Leu Lys Thr Leu Val Cys Ser Leu Val Ser
        50                  55                  60

Leu Ser Met Val Leu Pro Ala His Ala Gln Ile Thr Thr Asp Lys Ser
65                  70                  75                  80

Ala Pro Lys Asn Gln Gln Val Val Ile Leu Lys Thr Asn Thr Gly Ala
                85                  90                  95

Pro Leu Val Asn Ile Gln Thr Pro Asn Gly Arg Gly Leu Ser His Asn
            100                 105                 110

Arg Tyr Thr Gln Phe Asp Val Asp Asn Lys Gly Ala Val Leu Asn Asn
        115                 120                 125

Asp Arg Asn Asn Asn Pro Phe Leu Val Lys Gly Ser Ala Gln Leu Ile
    130                 135                 140

Leu Asn Glu Val Arg Gly Thr Ala Ser Lys Leu Asn Gly Ile Val Thr
145                 150                 155                 160

Val Gly Gly Gln Lys Ala Asp Val Ile Ile Ala Asn Pro Asn Gly Ile
                165                 170                 175

Thr Val Asn Gly Gly Phe Lys Asn Val Gly Arg Gly Ile Leu Thr
            180                 185                 190

Ile Gly Ala Pro Gln Ile Gly Lys Asp Gly Ala Leu Thr Gly Phe Asp
        195                 200                 205

Val Arg Gln Gly Thr Leu Thr Val Gly Ala Ala Gly Trp Asn Asp Lys
    210                 215                 220

Gly Gly Ala Asp Tyr Thr Gly Val Leu Ala Arg Ala Val Ala Leu Gln
225                 230                 235                 240

Gly Lys Leu Gln Gly Lys Asn Leu Ala Val Ser Thr Gly Pro Gln Lys
                245                 250                 255

Val Asp Tyr Ala Ser Gly Glu Ile Ser Ala Gly Thr Ala Ala Gly Thr
            260                 265                 270

Lys Pro Thr Ile Ala Leu Asp Thr Ala Ala Leu Gly Gly Met Tyr Ala
        275                 280                 285

Asp Ser Ile Thr Leu Ile Ala Asn Glu Lys Gly Val Gly Val Lys Asn
```

-continued

```
                290                 295                 300
Ala Gly Thr Leu Glu Ala Ala Lys Gln Leu Ile Val Thr Ser Ser Gly
305                 310                 315                 320

Arg Ile Glu Asn Ser Gly Arg Ile Ala Thr Thr Ala Asp Gly Thr Glu
                325                 330                 335

Ala Ser Pro Thr Tyr Leu Ser Ile Glu Thr Thr Glu Lys Gly Ala Ala
                340                 345                 350

Gly Thr Phe Ile Ser Asn Gly Arg Ile Glu Ser Lys Gly Leu Leu
                355                 360                 365

Val Ile Glu Thr Gly Glu Asp Ile Ser Leu Arg Asn Gly Ala Val Val
370                 375                 380

Gln Asn Gly Ser Arg Pro Ala Thr Thr Val Leu Asn Ala Gly His
385                 390                 395                 400

Asn Leu Val Ile Glu Ser Lys Thr Asn Val Asn Asn Ala Lys Gly Ser
                405                 410                 415

Ala Asn Leu Ser Ala Gly Gly Arg Thr Thr Ile Asn Asp Ala Thr Ile
                420                 425                 430

Gln Ala Gly Ser Ser Val Tyr Ser Ser Thr Lys Gly Asp Thr Glu Leu
                435                 440                 445

Gly Glu Asn Thr Arg Ile Ile Ala Glu Asn Val Thr Val Leu Ser Asn
450                 455                 460

Gly Ser Ile Gly Ser Ala Ala Val Ile Glu Ala Lys Asp Thr Ala His
465                 470                 475                 480

Ile Glu Ser Gly Lys Pro Leu Ser Leu Glu Thr Ser Thr Val Ala Ser
                485                 490                 495

Asn Ile Arg Leu Asn Asn Gly Asn Ile Lys Gly Gly Lys Gln Leu Ala
                500                 505                 510

Leu Leu Ala Asp Asp Asn Ile Thr Ala Lys Thr Thr Asn Leu Asn Thr
                515                 520                 525

Pro Gly Asn Leu Tyr Val His Thr Gly Lys Asp Leu Asn Leu Asn Val
                530                 535                 540

Asp Lys Asp Leu Ser Ala Ala Ser Ile His Leu Lys Ser Asp Asn Ala
545                 550                 555                 560

Ala His Ile Thr Gly Thr Ser Lys Thr Leu Thr Ala Ser Lys Asp Met
                565                 570                 575

Gly Val Glu Ala Gly Leu Leu Asn Val Thr Asn Thr Asn Leu Arg Thr
                580                 585                 590

Asn Ser Gly Asn Leu His Ile Gln Ala Ala Lys Gly Asn Ile Gln Leu
                595                 600                 605

Arg Asn Thr Lys Leu Asn Ala Ala Lys Ala Leu Glu Thr Thr Ala Leu
                610                 615                 620

Gln Gly Asn Ile Val Ser Asp Gly Leu His Ala Val Ser Ala Asp Gly
625                 630                 635                 640

His Val Ser Leu Leu Ala Asn Gly Asn Ala Asp Phe Thr Gly His Asn
                645                 650                 655

Thr Leu Thr Ala Lys Ala Asp Val Asn Ala Gly Ser Val Gly Lys Gly
                660                 665                 670

Arg Leu Lys Ala Asp Asn Thr Asn Ile Thr Ser Ser Gly Asp Ile
                675                 680                 685

Thr Leu Val Ala Gly Asn Gly Ile Gln Leu Gly Asp Gly Lys Gln Arg
                690                 695                 700

Asn Ser Ile Asn Gly Lys His Ile Ser Ile Lys Asn Asn Gly Gly Asn
705                 710                 715                 720
```

```
Ala Asp Leu Lys Asn Leu Asn Val His Ala Lys Ser Gly Ala Leu Asn
            725                 730                 735

Ile His Ser Asp Arg Ala Leu Ser Ile Glu Asn Thr Lys Leu Glu Ser
            740                 745                 750

Thr His Asn Thr His Leu Asn Ala Gln His Glu Arg Val Thr Leu Asn
            755                 760                 765

Gln Val Asp Ala Tyr Ala His Arg His Leu Ser Ile Thr Gly Ser Gln
            770                 775                 780

Ile Trp Gln Asn Asp Lys Leu Pro Ser Ala Asn Lys Leu Val Ala Asn
785                 790                 795                 800

Gly Val Leu Ala Leu Asn Ala Arg Tyr Ser Gln Ile Ala Asp Asn Thr
            805                 810                 815

Thr Leu Arg Ala Gly Ala Ile Asn Leu Thr Ala Gly Thr Ala Leu Val
            820                 825                 830

Lys Arg Gly Asn Ile Asn Trp Ser Thr Val Ser Thr Lys Thr Leu Glu
            835                 840                 845

Asp Asn Ala Glu Leu Lys Pro Leu Ala Gly Arg Leu Asn Ile Glu Ala
850                 855                 860

Gly Ser Gly Thr Leu Thr Ile Glu Pro Ala Asn Arg Ile Ser Ala His
865                 870                 875                 880

Thr Asp Leu Ser Ile Lys Thr Gly Gly Lys Leu Leu Ser Ala Lys
            885                 890                 895

Gly Gly Asn Ala Gly Ala Pro Ser Ala Gln Val Ser Ser Leu Glu Ala
            900                 905                 910

Lys Gly Asn Ile Arg Leu Val Thr Gly Glu Thr Asp Leu Arg Gly Ser
            915                 920                 925

Lys Ile Thr Ala Gly Lys Asn Leu Val Val Ala Thr Thr Lys Gly Lys
            930                 935                 940

Leu Asn Ile Glu Ala Val Asn Asn Ser Phe Ser Asn Tyr Phe Pro Thr
945                 950                 955                 960

Gln Lys Ala Ala Glu Leu Asn Gln Lys Ser Lys Glu Leu Glu Gln Gln
            965                 970                 975

Ile Ala Gln Leu Lys Lys Ser Ser Pro Lys Ser Lys Leu Ile Pro Thr
            980                 985                 990

Leu Gln Glu Glu Arg Asp Arg Leu Ala Phe Tyr Ile Gln Ala Ile Asn
            995                 1000                1005

Lys Glu Val Lys Gly Lys Lys Pro Lys Gly Lys Glu Tyr Leu Gln Ala
            1010                1015                1020

Lys Leu Ser Ala Gln Asn Ile Asp Leu Ile Ser Ala Gln Gly Ile Glu
1025                1030                1035                1040

Ile Ser Gly Ser Asp Ile Thr Ala Ser Lys Lys Leu Asn Leu His Ala
            1045                1050                1055

Ala Gly Val Leu Pro Lys Ala Ala Asp Ser Glu Ala Ala Ile Leu
            1060                1065                1070

Ile Asp Gly Ile Thr Asp Gln Tyr Glu Ile Gly Lys Pro Thr Tyr Lys
            1075                1080                1085

Ser His Tyr Asp Lys Ala Ala Leu Asn Lys Pro Ser Arg Leu Thr Gly
            1090                1095                1100

Arg Thr Gly Val Ser Ile His Ala Ala Ala Leu Asp Asp Ala Arg
1105                1110                1115                1120

Ile Ile Ile Gly Ala Ser Glu Ile Lys Ala Pro Ser Gly Ser Ile Asp
            1125                1130                1135
```

```
Ile Lys Ala His Ser Asp Ile Val Leu Glu Ala Gly Gln Asn Asp Ala
            1140                1145                1150

Tyr Thr Phe Leu Lys Thr Lys Gly Lys Ser Gly Lys Ile Ile Arg Lys
            1155                1160                1165

Thr Lys Phe Thr Ser Thr Arg Asp His Leu Ile Met Pro Ala Pro Val
            1170                1175                1180

Glu Leu Thr Ala Asn Gly Ile Thr Leu Gln Ala Gly Gly Asn Ile Glu
1185                1190                1195                1200

Ala Asn Thr Thr Arg Phe Asn Ala Pro Ala Gly Lys Val Thr Leu Val
            1205                1210                1215

Ala Gly Glu Glu Leu Gln Leu Leu Ala Glu Gly Ile His Lys His
            1220                1225                1230

Glu Leu Asp Val Gln Lys Ser Arg Arg Phe Ile Gly Ile Lys Val Gly
            1235                1240                1245

Lys Ser Asn Tyr Ser Lys Asn Glu Leu Asn Glu Thr Lys Leu Pro Val
            1250                1255                1260

Arg Val Val Ala Gln Thr Ala Ala Thr Arg Ser Gly Trp Asp Thr Val
1265                1270                1275                1280

Leu Glu Gly Thr Glu Phe Lys Thr Thr Leu Ala Gly Ala Asp Ile Gln
            1285                1290                1295

Ala Gly Val Gly Glu Lys Ala Arg Val Asp Ala Lys Ile Ile Leu Lys
            1300                1305                1310

Gly Ile Val Asn Arg Ile Gln Ser Glu Glu Lys Leu Glu Thr Asn Ser
            1315                1320                1325

Thr Val Trp Gln Lys Gln Ala Gly Arg Gly Ser Thr Ile Glu Thr Leu
            1330                1335                1340

Lys Leu Pro Ser Phe Glu Ser Pro Thr Pro Lys Leu Ser Ala Pro
1345                1350                1355                1360

Gly Gly Tyr Ile Val Asp Ile Pro Lys Gly Asn Leu Lys Thr Glu Ile
            1365                1370                1375

Glu Lys Leu Ser Lys Gln Pro Glu Tyr Ala Tyr Leu Lys Gln Leu Gln
            1380                1385                1390

Val Ala Lys Asn Ile Asn Trp Asn Gln Val Gln Leu Ala Tyr Asp Arg
            1395                1400                1405

Trp Asp Tyr Lys Gln Glu Gly Leu Thr Glu Ala Gly Ala Ala Ile Ile
            1410                1415                1420

Ala Leu Ala Val Thr Val Val Thr Ser Gly Ala Gly Thr Gly Ala Val
1425                1430                1435                1440

Leu Gly Leu Asn Gly Ala Ala Ala Ala Thr Asp Ala Ala Phe Ala
            1445                1450                1455

Ser Leu Ala Ser Gln Ala Ser Val Ser Phe Ile Asn Asn Lys Gly Asp
            1460                1465                1470

Val Gly Lys Thr Leu Lys Glu Leu Gly Arg Ser Ser Thr Val Lys Asn
            1475                1480                1485

Leu Val Val Ala Ala Thr Ala Gly Val Ala Asp Lys Ile Gly Ala
            1490                1495                1500

Ser Ala Leu Asn Asn Val Ser Asp Lys Gln Trp Ile Asn Asn Leu Thr
1505                1510                1515                1520

Val Asn Leu Ala Asn Ala Gly Ser Ala Ala Leu Ile Asn Thr Ala Ile
            1525                1530                1535

Asn Gly Gly Ser Leu Lys Asp Asn Leu Gly Asp Ala Ala Leu Gly Ala
            1540                1545                1550

Ile Val Ser Thr Val His Gly Glu Val Ala Ser Lys Ile Lys Phe Asn
```

-continued

```
                1555                1560                1565
Leu Ser Glu Asp Tyr Ile Thr His Lys Ile Ala His Ala Ile Ala Gly
    1570                1575                1580
Cys Ala Ala Ala Ala Asn Lys Gly Lys Cys Gln Asp Gly Ala Ile
1585                1590                1595                1600
Gly Ala Ala Val Gly Glu Ile Val Gly Glu Ala Leu Thr Asn Gly Lys
            1605                1610                1615
Asn Pro Ala Thr Leu Thr Ala Lys Glu Arg Glu Gln Ile Leu Ala Tyr
        1620                1625                1630
Ser Lys Leu Val Ala Gly Thr Val Ser Gly Val Val Gly Gly Asp Val
    1635                1640                1645
Asn Thr Ala Ala Asn Ala Ala Lys Val Ala Ile Glu Asn Asn Leu Leu
    1650                1655                1660
Ser Gln Glu Glu Tyr Ala Leu Arg Glu Lys Leu Ile Lys Lys Ala Lys
1665                1670                1675                1680
Gly Lys Gly Leu Leu Ser Leu Asp Trp Gly Ser Leu Thr Glu Gln Glu
            1685                1690                1695
Ala Arg Gln Phe Ile Tyr Leu Ile Glu Lys Asp Arg Tyr Ser Asn Gln
        1700                1705                1710
Leu Leu Asp Arg Tyr Gln Lys Asn Pro Ser Ser Leu Asn Asn Gln Glu
        1715                1720                1725
Lys Asn Ile Leu Ala Tyr Phe Ile Asn Gln Thr Ser Gly Gly Asn Thr
    1730                1735                1740
Ala Trp Ala Ala Ser Ile Leu Lys Thr Pro Gln Ser Met Gly Asn Leu
1745                1750                1755                1760
Thr Ile Pro Ser Lys Asp Ile Asn Asn Thr Leu Ser Lys Ala Tyr Gln
            1765                1770                1775
Thr Leu Ser Arg Tyr Asp Ser Phe Asp Tyr Lys Ser Ala Val Ala Ala
        1780                1785                1790
Gln Pro Ala Leu Tyr Leu Leu Asn Gly Pro Leu Gly Phe Ser Val Lys
        1795                1800                1805
Ala Ala Thr Val Ala Ala Gly Gly Tyr Asn Ile Gly Gln Gly Ala Lys
    1810                1815                1820
Ala Ile Ser Asn Gly Glu Tyr Leu His Gly Thr Val Gln Val Val Asn
1825                1830                1835                1840
Gly Thr Leu Met Val Ala Gly Ser Val Ser Ala Gln Ala Ala Ile Ser
            1845                1850                1855
Ala Lys Pro Ala Pro Val Thr Arg Tyr Leu Ser Asn Asp Ser Ala Pro
        1860                1865                1870
Ala Leu Arg Gln Ala Leu Thr Ala Glu Ser Gln Arg Ile Arg Met Lys
        1875                1880                1885
Leu Pro Glu Glu Tyr Arg Gln Ile Gly Asn Leu Ala Ile Ala Lys Ile
    1890                1895                1900
Asp Val Lys Gly Leu Pro Gln Arg Met Glu Ala Phe Ser Ser Phe Gln
1905                1910                1915                1920
Lys Gly Glu His Gly Phe Ile Ser Leu Pro Glu Thr Lys Ile Phe Lys
            1925                1930                1935
Pro Ile Ser Val Asp Lys Tyr His Asn Ile Ala Ser Pro Arg Gly
        1940                1945                1950
Thr Leu Arg Asn Ile Asp Gly Glu Tyr Lys Leu Leu Glu Thr Ile Ala
        1955                1960                1965
Gln Gln Leu Gly Asn Asn Arg Asn Val Ser Gly Arg Ile Asp Leu Phe
    1970                1975                1980
```

```
Thr Glu Leu Lys Ala Cys Gln Ser Cys Ser Asn Val Ile Leu Glu Phe
1985                1990                1995                2000

Arg Asn Arg Tyr Pro Asn Ile Gln Leu Asn Ile Phe Thr Gly Lys
                2005                2010                2015

<210> SEQ ID NO 2
<211> LENGTH: 764
<212> TYPE: PRT
<213> ORGANISM: Neisseria gonorrhoeae

<400> SEQUENCE: 2

Met Arg Arg Glu Ala Lys Met Ala Gln Thr Thr Leu Lys Pro Ile Val
 1               5                  10                  15

Leu Ser Ile Leu Leu Ile Asn Thr Pro Leu Ser Gln Ala His Gly
                20                  25                  30

Thr Glu Gln Ser Val Gly Leu Glu Thr Val Ser Val Gly Lys Ser
                    35                  40                  45

Arg Pro Arg Ala Thr Ser Gly Leu Leu His Thr Ser Thr Ala Ser Asp
         50                  55                  60

Lys Ile Ile Ser Gly Asp Thr Leu Arg Gln Lys Ala Val Asn Leu Gly
 65                  70                  75                  80

Asp Ala Leu Asp Gly Val Pro Gly Ile His Ala Ser Gln Tyr Gly Gly
                    85                  90                  95

Gly Ala Ser Ala Pro Val Ile Arg Gly Gln Thr Gly Arg Arg Ile Lys
                100                 105                 110

Val Leu Asn His His Gly Glu Thr Gly Asp Met Ala Asp Phe Ser Pro
                115                 120                 125

Asp His Ala Ile Met Val Asp Ser Ala Leu Ser Gln Gln Val Glu Ile
        130                 135                 140

Leu Arg Gly Pro Val Thr Leu Leu Tyr Ser Ser Gly Asn Val Ala Gly
145                 150                 155                 160

Leu Val Asp Val Ala Asp Gly Lys Ile Pro Glu Lys Met Pro Glu Asn
                165                 170                 175

Gly Val Ser Gly Glu Leu Gly Leu Arg Leu Ser Ser Gly Asn Leu Glu
                180                 185                 190

Lys Leu Thr Ser Gly Gly Ile Asn Ile Gly Leu Gly Lys Asn Phe Val
                195                 200                 205

Leu His Thr Glu Gly Leu Tyr Arg Lys Ser Gly Asp Tyr Ala Val Pro
        210                 215                 220

Arg Tyr Arg Asn Leu Lys Arg Leu Pro Asp Ser His Ala Asp Ser Gln
225                 230                 235                 240

Thr Gly Ser Ile Gly Leu Ser Trp Val Gly Glu Lys Gly Phe Ile Gly
                245                 250                 255

Ala Ala Tyr Ser Asp Arg Arg Asp Gln Tyr Gly Leu Pro Ala His Ser
                260                 265                 270

His Glu Tyr Asp Asp Cys His Ala Asp Ile Ile Trp Gln Lys Ser Leu
        275                 280                 285

Ile Asn Lys Arg Tyr Leu Gln Leu Tyr Pro His Leu Leu Thr Glu Glu
        290                 295                 300

Asp Ile Asp Tyr Asp Asn Pro Gly Leu Ser Cys Gly Phe His Asp Asp
305                 310                 315                 320

Asp Asp Ala His Ala His Ala His Asn Gly Lys Pro Trp Ile Asp Leu
                325                 330                 335

Arg Asn Lys Arg Tyr Glu Leu Arg Ala Glu Trp Lys Gln Pro Phe Pro
```

```
                     340                 345                 350
Gly Phe Glu Ala Leu Arg Val His Leu Asn Arg Asn Asp Tyr Arg His
            355                 360                 365
Asp Glu Lys Ala Gly Asp Ala Val Glu Asn Phe Phe Asn Asn Gln Thr
        370                 375                 380
Gln Asn Ala Arg Ile Glu Leu Arg His Gln Pro Ile Gly Arg Leu Lys
385                 390                 395                 400
Gly Ser Trp Gly Val Gln Tyr Leu Gly Gln Lys Ser Ser Ala Leu Ser
                405                 410                 415
Ala Thr Ser Glu Ala Val Lys Gln Pro Met Leu Leu Asp Asn Lys Val
            420                 425                 430
Gln His Tyr Ser Phe Phe Gly Val Glu Gln Ala Asn Trp Asp Asn Phe
        435                 440                 445
Thr Leu Glu Gly Gly Val Arg Val Glu Lys Gln Lys Ala Ser Ile Arg
    450                 455                 460
Tyr Asp Lys Ala Leu Ile Asp Arg Glu Asn Tyr Tyr Asn His Pro Leu
465                 470                 475                 480
Pro Asp Leu Gly Ala His Arg Gln Thr Ala Arg Ser Phe Ala Leu Ser
                485                 490                 495
Gly Asn Trp Tyr Phe Thr Pro Gln His Lys Leu Ser Leu Thr Ala Ser
                500                 505                 510
His Gln Glu Arg Leu Pro Ser Thr Gln Glu Leu Tyr Ala His Gly Lys
            515                 520                 525
His Val Ala Thr Asn Thr Phe Glu Val Gly Asn Lys His Leu Asn Lys
        530                 535                 540
Glu Arg Ser Asn Asn Ile Glu Leu Ala Leu Gly Tyr Glu Gly Asp Arg
545                 550                 555                 560
Trp Gln Tyr Asn Leu Ala Leu Tyr Arg Asn Arg Phe Gly Asn Tyr Ile
                565                 570                 575
Tyr Ala Gln Thr Leu Asn Asp Gly Arg Gly Pro Lys Ser Ile Glu Asp
                580                 585                 590
Asp Ser Glu Met Lys Leu Val Arg Tyr Asn Gln Ser Gly Ala Asp Phe
            595                 600                 605
Tyr Gly Ala Glu Gly Glu Ile Tyr Phe Lys Pro Thr Pro Arg Tyr Arg
        610                 615                 620
Ile Gly Val Ser Gly Asp Tyr Val Arg Gly Arg Leu Lys Asn Leu Pro
625                 630                 635                 640
Ser Leu Pro Gly Arg Glu Asp Ala Tyr Gly Asn Arg Pro Leu Ile Ala
                645                 650                 655
Gln Ala Asp Gln Asn Ala Pro Arg Val Pro Ala Ala Arg Leu Gly Val
            660                 665                 670
His Leu Lys Ala Ser Leu Thr Asp Arg Ile Asp Ala Asn Leu Asp Tyr
        675                 680                 685
Tyr Arg Val Phe Ala Gln Asn Lys Leu Ala Arg Tyr Glu Thr Arg Thr
    690                 695                 700
Pro Gly His His Met Leu Asn Leu Gly Ala Asn Tyr Arg Arg Asn Thr
705                 710                 715                 720
Arg Tyr Gly Glu Trp Asn Trp Tyr Val Lys Ala Asp Asn Leu Leu Asn
                725                 730                 735
Gln Ser Val Tyr Ala His Ser Ser Phe Leu Ser Asp Thr Pro Gln Met
            740                 745                 750
Gly Arg Ser Phe Thr Gly Gly Val Asn Val Lys Phe
        755                 760
```

<210> SEQ ID NO 3
<211> LENGTH: 720
<212> TYPE: PRT
<213> ORGANISM: Neisseria gonorrhoeae

<400> SEQUENCE: 3

```
Met Asn Thr Pro Leu Phe Arg Leu Ser Leu Leu Ser Leu Thr Leu Ala
 1               5                  10                  15

Ala Gly Phe Ala His Ala Ala Glu Asn Asn Ala Lys Val Val Leu Asp
            20                  25                  30

Thr Val Thr Val Lys Gly Asp Arg Gln Gly Ser Lys Ile Arg Thr Asn
         35                  40                  45

Ile Val Thr Leu Gln Gln Lys Asp Glu Ser Thr Ala Thr Asp Met Arg
     50                  55                  60

Glu Leu Leu Lys Glu Glu Pro Ser Ile Asp Phe Gly Gly Asn Gly
 65                  70                  75                  80

Thr Ser Gln Phe Leu Thr Leu Arg Gly Met Gly Gln Asn Ser Val Asp
                 85                  90                  95

Ile Lys Val Asp Asn Ala Tyr Ser Asp Ser Gln Ile Leu Tyr His Gln
            100                 105                 110

Gly Arg Phe Ile Val Asp Pro Ala Leu Val Lys Val Ser Val Gln
         115                 120                 125

Lys Gly Ala Gly Ser Ala Ser Ala Gly Ile Gly Ala Thr Asn Gly Ala
130                 135                 140

Ile Ile Ala Lys Thr Val Asp Ala Gln Asp Leu Leu Lys Gly Leu Asp
145                 150                 155                 160

Lys Asn Trp Gly Val Arg Leu Asn Ser Gly Phe Ala Ser Asn Glu Gly
                165                 170                 175

Val Ser Tyr Gly Ala Ser Val Phe Gly Lys Glu Gly Asn Phe Asp Gly
            180                 185                 190

Leu Phe Ser Tyr Asn Arg Asn Asp Glu Lys Asp Tyr Glu Ala Gly Lys
         195                 200                 205

Gly Phe Arg Asn Val Asn Gly Gly Lys Thr Val Pro Tyr Ser Ala Leu
     210                 215                 220

Asp Lys Arg Ser Tyr Leu Ala Lys Ile Gly Thr Thr Phe Gly Asp Asp
225                 230                 235                 240

Asp His Arg Ile Val Leu Ser His Met Lys Asp Gln His Arg Gly Ile
                245                 250                 255

Arg Thr Val Arg Glu Glu Phe Thr Val Gly Asp Lys Ser Ser Arg Ile
            260                 265                 270

Asn Ile Asp Arg Gln Ala Pro Ala Tyr Arg Glu Thr Thr Gln Ser Asn
         275                 280                 285

Thr Asn Leu Ala Tyr Thr Gly Lys Asn Leu Gly Phe Val Glu Lys Leu
     290                 295                 300

Asp Ala Asn Ala Tyr Val Leu Glu Lys Glu Arg Tyr Ser Ala Asp Asp
305                 310                 315                 320

Ser Gly Thr Gly Tyr Ala Gly Asn Val Lys Gly Pro Asn His Thr Arg
                325                 330                 335

Ile Thr Thr Arg Gly Ala Asn Phe Asn Phe Asp Ser Arg Leu Ala Glu
            340                 345                 350

Gln Thr Leu Leu Lys Tyr Gly Ile Asn Tyr Arg His Gln Glu Ile Lys
         355                 360                 365

Pro Gln Ala Phe Leu Asn Ser Lys Phe Ser Ile Pro Thr Thr Glu Glu
```

```
                    370                 375                 380
Lys Asn Gly Gln Lys Val Asp Lys Pro Met Glu Gln Met Lys Asp
385                 390                 395                 400

Arg Ala Asp Glu Asp Thr Val His Ala Tyr Lys Leu Ser Asn Pro Thr
                405                 410                 415

Lys Thr Asp Thr Gly Val Tyr Val Glu Ala Ile His Asp Ile Gly Asp
                420                 425                 430

Phe Thr Leu Thr Gly Gly Leu Arg Tyr Asp Arg Phe Lys Val Lys Thr
                435                 440                 445

His Asp Gly Lys Thr Val Ser Ser Ser Asn Leu Asn Pro Ser Phe Gly
            450                 455                 460

Val Ile Trp Gln Pro His Glu His Trp Ser Phe Ser Ala Ser His Asn
465                 470                 475                 480

Tyr Ala Ser Arg Ser Pro Arg Leu Tyr Asp Ala Leu Gln Thr His Gly
                485                 490                 495

Lys Arg Gly Ile Ile Ser Ile Ala Asp Gly Thr Lys Ala Glu Arg Ala
                500                 505                 510

Arg Asn Thr Glu Ile Gly Phe Asn Tyr Asn Asp Gly Thr Phe Ala Ala
            515                 520                 525

Asn Gly Ser Tyr Phe Trp Gln Thr Ile Lys Asp Ala Leu Ala Asn Pro
            530                 535                 540

Gln Asn Arg His Asp Ser Val Ala Val Arg Glu Ala Val Asn Ala Gly
545                 550                 555                 560

Tyr Ile Lys Asn His Gly Tyr Glu Leu Gly Ala Ser Tyr Arg Thr Gly
                565                 570                 575

Gly Leu Thr Ala Lys Val Gly Val Ser His Ser Lys Pro Arg Phe Tyr
            580                 585                 590

Asp Thr His Lys Asp Lys Leu Leu Ser Ala Asn Pro Glu Phe Gly Ala
            595                 600                 605

Gln Val Gly Arg Thr Trp Thr Ala Ser Leu Ala Tyr Arg Phe Gln Asn
            610                 615                 620

Pro Asn Leu Glu Ile Gly Trp Arg Gly Arg Tyr Val Gln Lys Ala Thr
625                 630                 635                 640

Gly Ser Ile Leu Ala Ala Gly Gln Lys Asp Arg Lys Gly Asn Leu Glu
                645                 650                 655

Asn Val Val Arg Lys Gly Phe Gly Val Asn Asp Val Phe Ala Asn Trp
                660                 665                 670

Lys Pro Leu Gly Lys Asp Thr Leu Asn Val Asn Leu Ser Val Asn Asn
            675                 680                 685

Val Phe Asn Lys Phe Tyr Tyr Pro His Ser Gln Arg Trp Thr Asn Thr
            690                 695                 700

Leu Pro Gly Val Gly Arg Asp Val Arg Leu Gly Val Asn Tyr Lys Phe
705                 710                 715                 720

<210> SEQ ID NO 4
<211> LENGTH: 525
<212> TYPE: PRT
<213> ORGANISM: Neisseria gonorrhoeae

<400> SEQUENCE: 4

Met Arg Ala Asn Pro Lys Thr Gln Ala Met Pro Ser Glu Thr Ile Ser
  1               5                  10                  15

Leu Met Lys Thr Arg Ser Leu Ile Ser Leu Leu Cys Leu Leu Leu Cys
                20                  25                  30
```

-continued

```
Ser Cys Ser Ser Trp Leu Pro Pro Leu Glu Glu Arg Thr Glu Ser Arg
         35                  40                  45

His Phe Asn Thr Ser Lys Pro Val Arg Leu Asp Asn Ile Leu Gln Ile
     50                  55                  60

Arg His Thr Pro His Thr Asn Gly Leu Ser Asp Ile Tyr Leu Leu Asn
 65                  70                  75                  80

Asp Pro His Glu Ala Phe Ala Ala Arg Ala Ala Leu Ile Glu Ser Ala
                 85                  90                  95

Glu His Ser Leu Asp Leu Gln Tyr Tyr Ile Trp Arg Asn Asp Ile Ser
             100                 105                 110

Gly Arg Leu Leu Phe Asn Leu Tyr Leu Ala Ala Glu Arg Gly Val
         115                 120                 125

Arg Val Arg Leu Leu Asp Asp Asn Asn Thr Arg Gly Leu Asp Asp
 130                 135                 140

Leu Leu Leu Ala Leu Asp Ser His Pro Asn Ile Glu Val Arg Leu Phe
145                 150                 155                 160

Asn Pro Phe Val Leu Arg Lys Trp Arg Ala Leu Gly Tyr Leu Thr Asp
                 165                 170                 175

Phe Pro Arg Leu Asn Arg Arg Met His Asn Lys Ser Phe Thr Ala Asp
             180                 185                 190

Asn Arg Ala Thr Ile Leu Gly Gly Arg Asn Ile Gly Asp Glu Tyr Phe
         195                 200                 205

Lys Val Gly Glu Asp Thr Val Phe Ala Asp Leu Asp Ile Leu Ala Thr
     210                 215                 220

Gly Ser Val Val Gly Glu Val Ser His Asp Phe Asp Arg Tyr Trp Ala
225                 230                 235                 240

Ser His Ser Ala His Asn Ala Thr Arg Ile Ile Arg Ser Gly Asn Ile
                 245                 250                 255

Gly Lys Gly Leu Gln Ala Leu Gly Tyr Asn Asp Glu Thr Ser Arg His
             260                 265                 270

Ala Leu Leu Arg Tyr Arg Glu Thr Val Glu Gln Ser Pro Leu Tyr Gln
         275                 280                 285

Lys Ile Gln Thr Gly Arg Ile Asp Trp Gln Ser Val Gln Thr Arg Leu
     290                 295                 300

Ile Ser Asp Asp Pro Ala Lys Gly Leu Asp Arg Asp Arg Arg Lys Pro
305                 310                 315                 320

Pro Ile Ala Gly Arg Leu Gln Asp Ala Leu Lys Gln Pro Glu Lys Ser
                 325                 330                 335

Val Tyr Leu Val Ser Pro Tyr Phe Val Pro Thr Lys Ser Gly Thr Asp
             340                 345                 350

Ala Leu Ala Lys Leu Val Gln Asp Gly Ile Asp Val Thr Val Leu Thr
         355                 360                 365

Asn Ser Leu Gln Ala Thr Asp Val Ala Ala Val His Ser Gly Tyr Val
     370                 375                 380

Lys Tyr Arg Lys Pro Leu Leu Lys Ala Gly Ile Lys Leu Tyr Glu Leu
385                 390                 395                 400

Gln Pro Asn His Ala Val Pro Ala Thr Lys Asp Lys Gly Leu Thr Gly
                 405                 410                 415

Ser Ser Val Thr Ser Leu His Ala Lys Thr Phe Ile Val Asp Gly Lys
             420                 425                 430

Arg Ile Phe Ile Gly Ser Phe Asn Leu Asp Pro Arg Ser Ala Arg Leu
         435                 440                 445

Asn Thr Glu Met Gly Val Val Ile Glu Ser Pro Lys Ile Ala Glu Gln
```

```
            450                 455                 460
Met Glu Arg Thr Leu Ala Asp Thr Ser Pro Glu Tyr Ala Tyr Arg Val
465                     470                 475                 480

Thr Leu Asp Arg His Asn Arg Leu Gln Trp His Asp Pro Ala Thr Arg
                    485                 490                 495

Lys Thr Tyr Pro Asn Glu Pro Glu Ala Lys Leu Trp Lys Arg Ile Ala
                500                 505                 510

Ala Lys Ile Leu Ser Leu Leu Pro Ile Glu Ser Leu Leu
            515                 520                 525

<210> SEQ ID NO 5
<211> LENGTH: 330
<212> TYPE: PRT
<213> ORGANISM: Neisseria gonorrhoeae

<400> SEQUENCE: 5

Met Gly Lys Gly Ile Leu Ser Leu Gln Gln Glu Met Ser Leu Glu Tyr
1               5                   10                  15

Ser Glu Lys Ser Tyr Gln Glu Val Leu Lys Ile Arg Gln Glu Ser Tyr
                20                  25                  30

Trp Lys Arg Met Lys Ser Phe Ser Leu Phe Glu Val Ile Met His Trp
            35                  40                  45

Thr Ala Ser Leu Asn Lys His Thr Cys Arg Ser Tyr Arg Gly Ser Phe
    50                  55                  60

Leu Ser Leu Glu Lys Ile Gly Leu Leu Ser Leu Asp Met Asn Leu Gln
65                  70                  75                  80

Glu Phe Ser Leu Leu Asn His Asn Leu Ile Leu Asp Ala Ile Lys Lys
                85                  90                  95

Val Ser Ser Ala Lys Thr Ser Trp Thr Glu Gly Thr Lys Gln Val Arg
            100                 105                 110

Ala Ala Ser Tyr Ile Ser Leu Thr Arg Phe Leu Asn Arg Met Thr Gln
        115                 120                 125

Gly Ile Val Ala Ile Ala Gln Pro Ser Lys Gln Glu Asn Ser Arg Thr
    130                 135                 140

Phe Phe Lys Thr Arg Glu Ile Val Lys Thr Asp Ala Met Asn Ser Leu
145                 150                 155                 160

Gln Thr Ala Ser Phe Leu Lys Glu Leu Lys Lys Ile Asn Ala Arg Asp
                165                 170                 175

Trp Leu Ile Ala Gln Thr Met Leu Gln Gly Gly Lys Arg Ser Ser Glu
            180                 185                 190

Val Leu Ser Leu Glu Ile Ser Gln Ile Cys Phe Gln Gln Ala Thr Ile
        195                 200                 205

Ser Phe Ser Gln Leu Lys Asn Arg Gln Thr Glu Lys Arg Ile Ile Ile
    210                 215                 220

Thr Tyr Pro Gln Lys Phe Met His Phe Leu Gln Glu Tyr Ile Gly Gln
225                 230                 235                 240

Arg Arg Gly Phe Val Phe Val Thr Arg Ser Gly Lys Met Val Gly Leu
                245                 250                 255

Arg Gln Ile Ala Arg Thr Phe Ser Gln Ala Gly Leu Gln Ala Ala Ile
            260                 265                 270

Pro Phe Lys Ile Thr Pro His Val Leu Arg Ala Thr Ala Val Thr Glu
        275                 280                 285

Tyr Lys Arg Leu Gly Cys Ser Asp Ser Asp Ile Met Lys Val Thr Gly
    290                 295                 300
```

```
His Ala Thr Ala Lys Met Ile Phe Ala Tyr Asp Lys Ser Ser Arg Glu
305                 310                 315                 320

Asp Asn Ala Ser Lys Lys Met Ala Leu Ile
                325                 330

<210> SEQ ID NO 6
<211> LENGTH: 6048
<212> TYPE: DNA
<213> ORGANISM: Neisseria gonorrhoeae

<400> SEQUENCE: 6
```

| | | | | | |
|---|---|---|---|---|---|
| atgaataaag | gtttacatcg | cattatcttt | agtaaaaagc | acagcaccat | ggttgcagta | 60 |
| gccgaaactg | ccaacagcca | gggcaaaggt | aaacaggcag | gcagttcggt | ttctgtttca | 120 |
| ctgaaaactt | caggcgacct | ttgcggcaaa | ctcaaaacca | cccttaaaac | cttggtctgc | 180 |
| tctttggttt | ccctgagtat | ggtattgcct | gcccatgccc | aaattaccac | cgacaaatca | 240 |
| gcacctaaaa | accagcaggt | cgttatcctt | aaaaccaaca | ctggtgcccc | cttggtgaat | 300 |
| atccaaactc | cgaatggacg | cggattgagc | acaaccgct | atacgcagtt | tgatgttgac | 360 |
| aacaaagggg | cagtgttaaa | caacgaccgt | aacaataatc | cgtttctggt | caaaggcagt | 420 |
| gcgcaattga | ttttgaacga | ggtacgcggt | acggctagca | aactcaacgg | catcgttacc | 480 |
| gtaggcggtc | aaaaggccga | cgtgattatt | gccaacccca | acggcattac | cgttaatggc | 540 |
| ggcggcttta | aaaatgtcgg | tcgggcatc | ttaactatcg | gtgcgcccca | aatcggcaaa | 600 |
| gacggtgcac | tgacaggatt | tgatgtgcgt | caaggcacat | tgaccgtagg | agcagcaggt | 660 |
| tggaatgata | aaggcggagc | cgactacacc | ggggtacttg | ctcgtgcagt | tgctttgcag | 720 |
| gggaaattac | agggtaaaaa | cctggcggtt | tctaccggtc | ctcagaaagt | agattacgcc | 780 |
| agcggcgaaa | tcagtgcagg | tacggcagcg | ggtacgaaac | cgactattgc | ccttgatact | 840 |
| gccgcactgg | gcgtatgta | cgccgacagc | atcacactga | ttgccaatga | aaaaggcgta | 900 |
| ggcgtcaaaa | atgccggcac | actcgaagcg | gccaagcaat | tgattgtgac | ttcgtcaggc | 960 |
| cgcattgaaa | cagcggccg | catcgccacc | actgccgacg | gcaccgaagc | ttcaccgact | 1020 |
| tatctctcca | tcgaaaccac | cgaaaaagga | gcggcaggca | catttatctc | caatggtggt | 1080 |
| cggatcgaga | gcaaaggctt | attggttatt | gagacgggag | aagatatcag | cttgcgtaac | 1140 |
| ggagccgtgg | tgcagaataa | cggcagtcgc | ccagctacca | cggtattaaa | tgctggtcat | 1200 |
| aatttggtga | ttgagagtaa | aactaatgtg | aacaatgcca | aaggctcggc | taatctgtcg | 1260 |
| gccggcggtc | gtactacgat | caatgatgct | actattcaag | cgggcagttc | cgtgtacagc | 1320 |
| tccaccaaag | gcgatactga | attgggtgaa | aatacccgta | ttattgctga | aaacgtaacc | 1380 |
| gtattatcta | acggtagtat | tggcagtgct | gctgtaattg | aggctaaaga | cactgcacac | 1440 |
| attgaatcgg | gcaaaccgct | ttcttagaa | acctcgaccg | ttgcctccaa | catccgtttg | 1500 |
| aacaacggta | acattaaagg | cggaaagcag | cttgctttac | tggcagacga | taacattact | 1560 |
| gccaaaacta | ccaatctgaa | tactcccggc | aatctgtatg | ttcatacagg | taaagatctg | 1620 |
| aatttgaatg | ttgataaaga | tttgtctgcc | gccagcatcc | atttgaaatc | ggataacgct | 1680 |
| gcccatatta | ccggcaccag | taaaaccctc | actgcctcaa | agacatggg | tgtggaggca | 1740 |
| ggcttgctga | atgttaccaa | taccaatctg | cgtaccaact | cggtaatct | gcacattcag | 1800 |
| gcagccaaag | gcaatattca | gcttcgcaat | accaagctga | acgcagccaa | ggctctcgaa | 1860 |
| accaccgcat | tgcagggcaa | tatcgtttca | gacggccttc | atgctgtttc | tgcagacggt | 1920 |
| catgtatcct | tattggccaa | cggtaatgcc | gactttaccg | gtcacaatac | cctgacagcc | 1980 |

```
aaggccgatg tcaatgcagg atcggttggt aaaggccgtc tgaaagcaga caataccaat    2040
atcacttcat cttcaggaga tattacgttg gttgccggca acggtattca gcttggtgac    2100
ggaaaacaac gcaattcaat caacggaaaa cacatcagca tcaaaaacaa cggtggtaat    2160
gccgacttaa aaaaccttaa cgtccatgcc aaaagcgggg cattgaacat tcattccgac    2220
cgggcattga gcatagaaaa taccaagctg gagtctaccc ataatacgca tcttaatgca    2280
caacacgagc gggtaacgct caaccaagta gatgcctacg cacaccgtca tctaagcatt    2340
accggcagcc agatttggca aaacgacaaa ctgccttctg ccaacaagct ggtggctaac    2400
ggtgtattgg cactcaatgc gcgctattcc caaattgccg acaacaccac gctgagagcg    2460
ggtgcaatca accttactgc cggtaccgcc ctagtcaagc gcggcaacat caattggagt    2520
accgtttcga ccaagacttt ggaagataat gccgaattaa aaccattggc cggacggctg    2580
aatattgaag caggtagcgg cacattaacc atcgaacctg ccaaccgcat cagtgcgcat    2640
accgacctga gcatcaaaac aggcggaaaa ttgctgttgt ctgcaaaagg aggaaatgca    2700
ggtgcgccta gtgctcaagt ttcctcattg gaagcaaaag gcaatatccg tctggttaca    2760
ggagaaacag atttaagagg ttctaaaatt acagccggta aaaacttggt tgtcgccacc    2820
accaaaggca agttgaatat cgaagccgta acaactcat tcagcaatta ttttcctaca     2880
caaaaagcgg ctgaactcaa ccaaaaatcc aaagaattgg aacagcagat tgcgcagttg    2940
aaaaaagct cgcctaaaag caagctgatt ccaaccctgc aagaagaacg cgaccgtctc      3000
gctttctata ttcaagccat caacaaggaa gttaaaggta aaaacccaa aggcaaagaa       3060
tacctgcaag ccaagctttc tgcacaaaat attgacttga tttccgcaca aggcatcgaa    3120
atcagcggtt ccgatattac cgcttccaaa aaactgaacc ttcacgccgc aggcgtattg    3180
ccaaaggcag cagattcaga ggcggctgct attctgattg acggcataac cgaccaatat    3240
gaaattggca agcccaccta caagagtcac tacgacaaag ctgctctgaa caagccttca    3300
cgtttgaccg gacgtacggg ggtaagtatt catgcagctg cggcactcga tgatgcacgt    3360
attattatcg gtgcatccga aatcaaagct ccctcaggca gcatagacat caaagcccat    3420
agtgatattg tactggaggc tggacaaaac gatgcctata ccttcttaaa aaccaaaggt    3480
aaaagcggca aaatcatcag aaaaaccaag tttaccagca cccgcgacca cctgattatg    3540
ccagcccccg tcgagctgac cgccaacggt atcacgcttc aggcaggcgg caacatcgaa    3600
gctaatacca cccgcttcaa tgcccctgca ggtaaagtta ccctggttgc gggtgaagag    3660
ctgcaactgc tggcagaaga aggcatccac aagcacgagt tggatgtcca aaaaagccgc    3720
cgctttatcg gcatcaaggt aggtaagagc aattacagta aaaacgaact gaacgaaacc    3780
aaattgcctg tccgcgtcgt cgcccaaact gcagccaccc gttcaggctg ggataccgtg    3840
ctcgaaggta ccgaattcaa aaccacgctg gccggtgccg acattcaggc aggtgtaggc    3900
gaaaaagccc gtgtcgatgc gaaaattatc ctcaaaggca ttgtgaaccg tatccagtcg    3960
gaagaaaaat tagaaaccaa ctcaaccgta tggcagaaac aggccggacg cggcagcact    4020
atcgaaacgc taaaactgcc cagcttcgaa agccctactc cgcccaaatt gtccgcaccc    4080
ggcggctata tcgtcgacat tccgaaaggc aatctgaaaa ccgaaatcga aaagctgtcc    4140
aaacagcccg agtatgccta tctgaaacag ctccaagtag cgaaaaacat caactggaat    4200
caggtgcagc ttgcttacga cagatgggac tacaaacagg agggcttaac cgaagcaggt    4260
gcggcgatta tcgcactggc cgttaccgtg gtcacctcag gcgcaggaac cggagccgta    4320
```

-continued

```
ttgggattaa acggtgcggc cgccgccgca accgatgcag cattcgcctc tttggccagc      4380
caggcttccg tatcgttcat caacaacaaa ggcgatgtcg gcaaaaccct gaaagagctg      4440
ggcagaagca gcacggtgaa aaatctggtg gttgccgccg ctaccgcagg cgtagccgac      4500
aaaatcggcg cttcggcact gaacaatgtc agcgataagc agtggatcaa caacctgacc      4560
gtcaacctag ccaatgcggg cagtgccgca ctgattaata ccgccatcaa cggcggcagc      4620
ctcaaagaca acttgggcga tgccgcactg ggtgcgatag tcagtaccgt acacggagaa      4680
gtagcgagca aaatcaaatt taatctcagc gaagactaca ttaccacaa gattgcccat       4740 gccatagcgg gctgtgcggc agcggcggcg aataagggta gtgtcagga tggtgcgatc       4800 ggtgcggctg tgggcgagat agtcggggag gctttgacaa acggcaaaaa tcctgccact      4860
ttgacagcta aagaacgcga acagattttg gcatacagca aactggttgc cggtacggta      4920
agcggtgtgg tcggcggcga tgtgaataca gcggcgaatg cggctaaagt cgcgattgaa      4980
aataacctat tatctcaaga gagtatgct cttagagaaa aattgatcaa aaagccaaa        5040 gggaaaggcc tattatcttt agattggggc agcctgaccg aacaagaggc aaggcagttt      5100
atctatttga ttgagaaaga tcgatattct aatcaattgc ttgaccgata tcaaaaaaat     5160
ccaagtagtt taaataatca agaaaaaaat attcttgcat attttattaa ccaaacctct     5220
ggaggtaaca cagcttgggc agcttcgata ctgaaaacgc cccagtcaat gggtaatctc     5280
actattcctt ccaaagatat taataacacc ttatcgaaag cctatcaaac attgagtcgt     5340
tatgattctt ttgattacaa atcagctgtt gccgcacaac ctgcacttta cttattaaac    5400
ggaccgcttg gcttcagtgt caaagcagct actgtggcag caggaggata taacattgga     5460
cagggagcga aagcaatctc taatggagaa tatctgcatg gtacagttca ggttgttaat     5520
ggcacattga tggttgcagg atctgtatct gcacaggctg caatatcggc caagcctgca     5580
cctgttaccc gttatctgag caatgacagt gctcctgctt taagacaagc tttaactgct    5640
gaaagccaga gaatccgcat gaaactgccg gaagagtatc gacaaatagg gaatcttgcg     5700
atagcaaaaa ttgatgttaa aggattaccg caaggatgg aagcatttag ttctttccaa     5760 aaagggaac atggatttat ttcgttacct gaaacaaaaa tttttaaacc tatatctgtt     5820
gataaatatc ataatattgc ctctcctcct agaggaacat taagaaatat agatggagaa     5880
tataaattac ttgaaactat agcacagcaa ctcggaaata atcgtaatgt atcaggtaga    5940
attgatctat ttacagaatt aaaggcctgt caatcttgca gcaatgttat tttagagttt    6000
agaaatcgct atccaaatat tcaattaaat atttttacag gaaaatag                  6048
```

<210> SEQ ID NO 7
<211> LENGTH: 2295
<212> TYPE: DNA
<213> ORGANISM: Neisseria gonorrhoeae
<400> SEQUENCE: 7

```
atgcgacgag aagccaaaat ggcacaaact acactcaaac ccattgtttt atcaattctt      60
ttaatcaaca caccctcct ctcccaagcg catggaactg agcaatcagt gggcttggaa       120
acggtcagcg tcgtcggcaa aagccgtccg cgcgccactt cggggctgct gcacacttct      180
accgcctccg acaaaatcat cagcggcgac accttgcgac aaaaagccgt caacttgggt     240
gatgctttag acggcgtacc gggcattcat gcctcgcaat acggcggcgg cgcatccgct     300
cccgttattc gcggtcaaac aggcagacgg attaaagtgt tgaaccatca cggcgaaacg     360
ggcgacatgg cggacttctc tccagaccat gcaatcatgg tggacagcgc cttgtcgcaa    420
```

-continued

```
caggtcgaaa tcctgcgcgg tccggttacg ctcttgtaca gctcgggcaa tgtggcgggg    480
ctggtcgatg ttgccgatgg caaaatcccc gaaaaaatgc ctgaaaacgg cgtatcgggc    540
gaactcggat tgcgtttgag cagcggcaat ctggaaaaac tcacgtccgg cggcatcaat    600
atcggtttgg gcaaaaactt tgtattgcac acggaagggc tgtaccgcaa atcgggggat    660
tacgccgtac cgcgttaccg caatctgaaa cgcctgcccg acagccacgc cgattcgcaa    720
acgggcagca tcgggctgtc ttgggttggc gaaaaaggct ttatcggcgc agcatacagc    780
gaccgtcgcg accaatatgg tctgcctgcc cacagccacg aatacgatga ttgccacgcc    840
gacatcatct ggcaaaagag tttgattaac aaacgctatt gcagcttta tccgcacctg     900 ttgaccgaag aagacatcga ttacgacaat ccgggcttga gctgcggctt tcacgacgac    960
gatgatgcac acgcccatgc ccacaacggc aaaccttgga tagacctgcg caacaaacgc    1020
tacgaactcc gcgccgaatg gaagcaaccg ttccccggtt tgaagccct gcgcgtacac     1080 ctgaaccgca acgactaccg ccacgacgaa aaagcaggcg atgcagtaga aaactttttt    1140
aacaaccaaa cgcaaaacgc ccgtatcgag ttgcgccacc aacccatagg ccgtctgaaa    1200
ggcagctggg gcgtgcaata tttgggacaa aaatccagtg ctttatctgc cacatccgaa    1260
gcggtcaaac aaccgatgct gcttgacaat aaagtgcaac attacagctt tttcggtgta    1320
gaacaggcaa actgggacaa cttcacgctt gaaggcggcg tacgcgtgga aaaacaaaaa    1380
gcctccatcc gctacgacaa agcattgatt gatcggaaa actactacaa ccatcccctg     1440
cccgacctcg gcgcgcaccg ccaaaccgcc cgctcattcg cactttcggg caactggtat    1500
ttcacgccac aacacaaact cagcctgacc gcctcccatc aggaacgcct gccgtcaacg    1560
caagagctgt acgcacacgg caaacacgtc gccaccaaca cctttgaagt cggcaacaaa    1620
cacctcaaca aagagcgttc caacaatatc gaactcgcgc tgggctacga aggcgaccgc    1680
tggcaataca atctggcact ctaccgcaac cgcttcggca actacattta cgcccaaacc    1740
ttaaacgacg gacgcggccc caaatccatc gaagacgaca gcgaaatgaa gctcgtgcgc    1800
tacaaccaat ccggtgcgga cttctacggc gcggaaggcg aaatctactt caaaccgaca    1860
ccgcgctacc gcatcggcgt ttccggcgac tatgtacgag gccgtctgaa aaacctgcct    1920
tccctacccg gcagggaaga cgcctacggc aaccgcccac tcattgccca agccgaccaa    1980
aacgccccct cgcgttccgg ctgcgcgcctc ggcgtccacc tgaaagcctc gctgaccgac   2040
cgcatcgatg ccaatttgga ctactaccgc gtgttcgccc aaaacaaact cgcccgctac    2100
gaaacgcgca cgcccggaca ccatatgctc aacctcggcg caaactaccg ccgcaatacg    2160
cgctatggcg agtggaattg gtacgtcaaa gccgacaacc tgctcaacca atccgtttac    2220
gcccacagca gcttcctctc tgatacgccg caaatgggcc gcagctttac cggcggcgtg    2280
aacgtgaagt tttaa                                                     2295
```

<210> SEQ ID NO 8
<211> LENGTH: 2307
<212> TYPE: DNA
<213> ORGANISM: Neisseria gonorrhoeae

<400> SEQUENCE: 8

```
tgttaatata aataaaaata attattaatt attttttctta tcctgccaaa tcttaacggt    60
ttggatttac ttcccttcat actcaagagg acgattgaat gaatacccca ttgttccgtc    120
tcagcctgct ctcgctcaca cttgcggcag gttttgccca cgcggcagaa aataatgcca    180
```

| | |
|---|---|
| aggtcgtact ggataccgtt actgtaaaag gcgaccgcca aggcagcaaa atccgtacca | 240 |
| acatcgttac gctgcaacaa aaagacgaaa gcaccgcaac cgatatgcgc gaactcttaa | 300 |
| aagaagagcc gtccatcgat ttcggcggcg gcaacggcac gtcccaattc ctgacgctgc | 360 |
| gcggcatggg tcagaactct gtcgacatca aggtggacaa cgcctattcc gacagccaaa | 420 |
| tcctttacca ccaaggcaga tttattgtcg atcccgcttt ggttaaagtc gtttccgtac | 480 |
| aaaaaggcgc gggttccgcc tctgccgta tcggcgcgac caacgcgcg atcatcgcca | 540 |
| aaaccgtcga tgcccaagac ctgctcaaag gcttggataa aaactggggc gtgcgcctca | 600 |
| acagcggctt tgccagcaac gaaggcgtaa gctacgcgc aagcgtattc ggaaaagagg | 660 |
| gcaacttcga cggcttgttc tcttacaacc gcaacgatga aaagattac gaagccggca | 720 |
| aaggtttccg caatgtcaac ggcggcaaaa ccgtaccgta cagcgcgctg acaaacgca | 780 |
| gctacctcgc caaaatcgga acaaccttcg gcgacgacga ccaccgcatc gtgttgagcc | 840 |
| acatgaaaga ccaacaccgg ggcatccgca ctgtgcgtga agaatttacc gtcggcgaca | 900 |
| aaagttcacg gataaatatt gaccgccaag cccctgctta ccgcgaaact acccaatcca | 960 |
| acaccaactt ggcgtacacg ggtaaaaacc tgggctttgt cgaaaaactg gatgccaacg | 1020 |
| cctatgtgtt ggaaaaagaa cgctattccg ccgatgacag cggcaccggc tacgcaggca | 1080 |
| atgtaaaagg ccccaaccat acccgaatca ccactcgtgg tgcgaacttc aacttcgaca | 1140 |
| gccgccttgc cgaacaaacc ctgttgaaat acggtatcaa ctaccgccat caggaaatca | 1200 |
| aaccgcaagc attttttgaac tcgaaattct ccatcccgac gacagaagag aaaaacggtc | 1260 |
| aaaaagtcga taaccgatg gaacaacaaa tgaaagaccg tgcagatgaa gacactgttc | 1320 |
| acgcctacaa actttccaac ccgaccaaaa ccgataccgg cgtatatgtt gaagccattc | 1380 |
| acgacatcgg cgatttcacg ctgaccggcg ggctgcgtta cgaccgcttc aaggtgaaaa | 1440 |
| cccatgacgg caaaaccgtt tcaagcagca accttaaccc gagtttcggt gtgatttggc | 1500 |
| agccgcacga acactggagc ttcagcgcga gccacaacta cgccagccgc agcccgcgcc | 1560 |
| tgtatgacgc gctgcaaacc cacggtaaac gcggcatcat ctcgattgcc gacggcacaa | 1620 |
| aagccgaacg cgcgcgcaat accgaaatcg gcttcaacta caacgacggc acgtttgccg | 1680 |
| caaacggcag ctacttctgg cagaccatca agacgcgct tgccaatccg caaaaccgcc | 1740 |
| acgactctgt cgccgtccgt gaagccgtca atgccggtta catcaaaaac cacggttacg | 1800 |
| aattgggcgc gtcctaccgc accggcggcc tgactgccaa agtcggcgtc agccacagca | 1860 |
| aaccgcgctt ttacgatacg cacaaagaca agctgttgag cgcgaatcct gaatttggcg | 1920 |
| cacaagtcgg ccgcacttgg acggcctccc ttgcctaccg cttccaaaat ccgaatctgg | 1980 |
| aaatcggctg gcgcggccgt tatgttcaaa agctacgggg ttcgatattg gcggcaggtc | 2040 |
| aaaaagaccg caaaggcaac ttggaaaacg ttgtacgcaa aggtttcggt gtgaacgatg | 2100 |
| tcttcgccaa ctggaaaccg ctgggcaaag acacgctcaa tgtcaatctt tcggttaaca | 2160 |
| acgtgttcaa caagttctac tatccgcaca gccaacgctg gaccaatacc ctgccgggcg | 2220 |
| tgggacgtga tgtacgcttg ggcgtgaact acaagttcta aaacgcacat cccgaaaaaa | 2280 |
| tgccgtctga aagcctttca gacggca | 2307 |

<210> SEQ ID NO 9
<211> LENGTH: 1578
<212> TYPE: DNA
<213> ORGANISM: Neisseria gonorrhoeae

<400> SEQUENCE: 9

```
atgcgcgcca accccaaaac acaggcaatg ccgtctgaaa ccatatccct gatgaaaaca      60
cgcagcctaa tttcccttttt atgcctcctt ctctgttcat gttcttcatg gttgccccca    120
ctggaagaac ggacggaaag ccgtcatttc aatacttcca aacccgtccg cctggacaac    180
atcctgcaaa tccggcacac ccctcatacc aacgggctat ccgatatcta tctgttgaac    240
gaccccacg aagcctttgc cgcccgcgcc gcccttatcg aatctgccga acacagcctc     300
gatttgcaat actacatctg gcgcaacgac atttccggcc gactgctgtt caacctcgtg    360
taccttgccg cagaacgcgg tgtgcgcgta cgcctgctgt tggacgacaa caacacgcgc    420
ggattggacg acctcctgct cgccctcgac agccatccca atatcgaagt gcgcctgttc    480
aaccccttcg tcttacgaaa atggcgcgca ctcggctacc tgaccgactt cccccgcctc    540
aaccgccgca tgcacaacaa atcctttacc gccgacaacc gcgccaccat actcggcgga    600
cgcaatatcg gcgacgaata cttcaaagtc ggtgaggaca ccgttttcgc cgacctggac    660
atcctcgcca ccggcagcgt cgtcggcgaa gtatcgcacg acttcgaccg ctactgggca    720
agccattccg cccacaacgc cacgcgcatc atccgcagcg gcaacatcgg caagggtctt    780
caagcactcg gatacaacga cgaaacgtcc agacacgcgc tcctgcgcta ccgcgaaacc    840
gtcgaacagt cgcccctcta ccaaaaaata cagacaggac gcatcgactg gcagagcgtc    900
caaacccgcc tcatcagcga cgaccctgca aaaggactcg accgcgaccg ccgcaaaccg    960
ccgattgccg ggcggctgca agacgcgctc aaacagcccg aaaaaagcgt ctatctggtt   1020
tcaccctatt tcgtccccac aaaatccggc acagacgcac tggcaaaact ggtgcaggac   1080
ggcatagacg ttaccgtcct gaccaactcg ctacaggcga ccgacgttgc cgccgtccat   1140
tccggctatg tcaaataccg aaaaccgctg ctcaaagccg gcatcaaact ctacgagctg   1200
caacccaacc atgccgtccc tgccacaaaa gacaaaggcc tgaccggcag ctccgtaacc   1260
agcctgcatg ccaaaacctt cattgtggac ggcaaacgca tcttcatcgg ctcattcaac   1320
ctcgaccccc gttccgcacg gctcaatact gaaatgggcg ttgttatcga aagccccaaa   1380
atcgcagaac agatggagcg cacccttgcc gatacctcac ccgaatacgc ctaccgcgtt   1440
accctcgaca ggcacaaccg cctgcaatgg cacgatcccg ccacccgaaa acctacccg    1500
aacgaacccg aagccaaact ttggaaacgc atcgccgcaa aaatcctatc cctgctgccc   1560
atagaaagtt tattatag                                                1578

<210> SEQ ID NO 10
<211> LENGTH: 993
<212> TYPE: DNA
<213> ORGANISM: Neisseria gonorrhoeae

<400> SEQUENCE: 10
atgggtaaag ggatttttatc tttgcagcaa gaaatgtcgt tagaatatag tgaaaagtct     60
tatcaggaag tttttaaaaat tcgccaagaa tcctattgga aacgcatgaa aagcttctcc    120
ttattcgaag ttattatgca ttggaccgca tcactcaaca acatacttg tagatcatat     180
cgaggatctt ttttgtcttt agaaaagatt ggtctattgt ccttggatat gaatctgcaa    240
gagttttccc ttttaaatca taatctaatc ctagatgcga ttaaaaaagt ttcctctgcc    300
aagacttctt ggaccgaagg tactaaacaa gttcgagcag caagctatat ttccttaaca    360
agattcctaa acaggatgac tcaaggaata gtcgctatag cgcaaccttc taaacaagaa    420
aatagtcgaa cattttttaa aaccagggaa atagtaaaaa cggatgcgat gaacagtttg    480
```

```
caaacagcat ccttcctaaa agagctaaaa aaaatcaatg cccgggattg gttgatcgcc    540
cagacaatgc tccaaggagg taaacgctcc tctgaagtct taagcttgga gattagtcag    600
atttgtttcc aacaagctac catttctttc tcccagctta agaaccgtca gacagaaaag    660
aggattatta taacttatcc tcagaagttt atgcactttc tacaagagta catcggtcaa    720
cgaagaggtt ttgtcttcgt aactcgctcc ggaaaaatgg tggggttaag gcaaatcgcc    780
cgcacgttct ctcaagcagg actacaagct gcaatccctt ttaaaataac cccgcacgtg    840
cttcgagcaa ccgctgtgac ggagtacaaa cgcctagggt gctcagactc cgacataatg    900
aaggtcacag acacgcaac cgcaaagatg atatttgcgt acgataaatc ttctcgagaa    960
gacaacgctt caaagaagat ggctctaata tag                                 993
```

```
<210> SEQ ID NO 11
<211> LENGTH: 199
<212> TYPE: PRT
<213> ORGANISM: Mus musculus

<400> SEQUENCE: 11
```

```
Phe Pro Gln Gln Glu Ser Asp Ile Val Phe Leu Ile Asp Gly Ser Gly
 1               5                  10                  15

Ser Ile Asn Asn Ile Asp Phe Gln Lys Met Lys Glu Phe Val Ser Thr
            20                  25                  30

Val Met Glu Gln Phe Lys Lys Ser Lys Thr Leu Phe Ser Leu Met Gln
        35                  40                  45

Tyr Ser Asp Glu Phe Arg Ile His Phe Thr Phe Asn Asp Phe Lys Arg
    50                  55                  60

Asn Pro Ser Pro Arg Ser His Val Ser Pro Ile Lys Gln Leu Asn Gly
65                  70                  75                  80

Arg Thr Lys Thr Ala Ser Gly Ile Arg Lys Val Val Arg Glu Leu Phe
                85                  90                  95

His Lys Thr Asn Gly Ala Arg Glu Asn Ala Ala Lys Ile Leu Val Val
            100                 105                 110

Ile Thr Asp Gly Glu Lys Phe Gly Asp Pro Leu Asp Tyr Lys Asp Val
        115                 120                 125

Ile Pro Glu Ala Asp Arg Ala Gly Val Ile Arg Tyr Val Ile Gly Val
    130                 135                 140

Gly Asn Ala Phe Asn Lys Pro Gln Ser Arg Arg Glu Leu Asp Thr Ile
145                 150                 155                 160

Ala Ser Lys Pro Ala Gly Glu His Val Phe Gln Val Asp Asn Phe Glu
                165                 170                 175

Ala Leu Asn Thr Ile Gln Asn Gln Leu Gln Glu Lys Ile Phe Ala Ile
            180                 185                 190

Pro Ala Ala Ala Ser Phe Leu
        195
```

```
<210> SEQ ID NO 12
<211> LENGTH: 597
<212> TYPE: DNA
<213> ORGANISM: Mus musculus

<400> SEQUENCE: 12
ttccctcagc aggagagtga cattgtcttc ttgattgatg gctccggtag catcaacaac     60
attgactttc agaagatgaa ggagtttgtc tcaactgtga tggagcagtt caaaaagtct    120
aaaaccttgt tctctttgat gcagtactcg gacgagttcc ggattcactt caccttcaat    180
```

-continued

| | |
|---|---|
| gacttcaaga gaaaccctag cccaagatca catgtgagcc cataaagca gctgaatggg | 240 |
| aggacaaaaa ctgcctcagg gatccggaaa gtagtgagag aactgtttca caaaaccaat | 300 |
| ggggcccggg agaatgctgc gaagatccta gttgtcatca cagatggaga aaaattcggt | 360 |
| gatcccttgg attataagga tgtcatcccc gaggcagaca gagcagggggt cattcgctac | 420 |
| gtaattgggg tgggaaatgc cttcaacaaa ccacagtccc gcagagagct cgacaccatc | 480 |
| gcatctaagc cagctggtga acacgtgttc caagtggaca actttgaagc cctgaatacc | 540 |
| attcagaacc agcttcagga aaagatcttt gcaattcccg cggccgccag ctttcta | 597 |

<210> SEQ ID NO 13
<211> LENGTH: 1561
<212> TYPE: DNA
<213> ORGANISM: Neisseria gonorrhoeae 1291

<400> SEQUENCE: 13

| | |
|---|---|
| caaaatacag gcaatgccgt ctgaaactat atccccgatg aaaacacgca gcctcatttc | 60 |
| ccttttatgc ctccttctct gttcatgttc ttcatggttg cccccactgg aagaacggac | 120 |
| ggaaagccgt catttcaata cttccaaacc tgtcctcctg acaacatcc tgcaaatccg | 180 |
| gcacacccct cataacaacg ggctatccga catctacctg ctcgacgacc cccacgaagc | 240 |
| ccttgccgcc cgcgccgccc ttatcgaatc tgccgaacac agcctcgatt tgcaatacta | 300 |
| catttggcgc aacgacattt ccggcaggct gctgttcaac ctcatgtacc ttgccgcaga | 360 |
| acgcggcgtg cgcgtacgcc tgctgttgga cgacaacaac acgcgcgggt tggacgatct | 420 |
| cctgctcgcc ctcgacagcc atcccaatat cgaagtgcgc ctgttcaacc ccttcgtcct | 480 |
| acgcaaatgg cgcgcactcg gctacctgac cgacttcccc cgcctcaacc gccgcatgca | 540 |
| caacaaatcc tttaccgccg acaaccgcgc caccatactc ggcggacgca atatcggcga | 600 |
| cgaatacttc aaagtcggtg aggacaccgt tttcgccgac ctggacatcc tcgccaccgg | 660 |
| cagcgtcgtc ggcgaagtat cgcacgactt cgaccgctac tgggcaagcc attccgccca | 720 |
| caacgccacg cgcatcatcc gcagcggcaa catcggcaag ggtcttcaag cactcggata | 780 |
| caacgacgaa acatccagac acgcgctcct gcgctaccgc gaaaccgtcg aacagtcgcc | 840 |
| cctctaccaa aaaatacaga cgggacgcat cgactggcag agcgtccaaa cccgcctgat | 900 |
| cagcgacacc cctgcaaaag gactcgaccg cgaccgcgc aaaccgccga ttgccgggag | 960 |
| gctgcaagac gcgctcaaac agcccgaaaa aagcgtctat ctggtttcac cctatttcgt | 1020 |
| ccctacaaaa tccggcacag acgcactggc aaaactggtg caggacggca tagacgttac | 1080 |
| cgtcctgacc aactcgctac aggcgaccga cgttgccgcc gtccattccg gctacgtcaa | 1140 |
| ataccgaaaa ccgctgctca agccggcat caaactctac gagctgcaac ccaaccatgc | 1200 |
| cgtccccgcc acaaaagaca aaggcctgac cggcagctcc gtaaccagcc tgcatgccaa | 1260 |
| aaccttcatt gtgacggca acgcatctt catcggctca ttcaacctcg accccgttc | 1320 |
| cgcacggctc aataccgaaa tgggcgtcgt catcgaaagc cccaaatcg cagaacagat | 1380 |
| ggagcgcacc ctcgccgata ccacacccga atacgcctac cgcgttaccc tcgacaaaca | 1440 |
| caaccgcctg caatggcacg atcccgccac ccgaaaaacc tacccgaacg aacccgaagc | 1500 |
| caaactttgg aaacgcatcg ccgcaaaaat cctatccctg ctgcccatcg aaggtttatt | 1560 |
| a | 1561 |

<210> SEQ ID NO 14
<211> LENGTH: 525

```
<212> TYPE: PRT
<213> ORGANISM: Neisseria gonorrhoeae 1291

<400> SEQUENCE: 14

Met His Thr Asp Pro Lys Ile Gln Ala Met Pro Ser Glu Thr Ile Ser
 1               5                  10                  15

Pro Met Lys Thr Arg Ser Leu Ile Ser Leu Leu Cys Leu Leu Leu Cys
            20                  25                  30

Ser Cys Ser Ser Trp Leu Pro Leu Glu Glu Arg Thr Glu Ser Arg
        35                  40                  45

His Phe Asn Thr Ser Lys Pro Val Leu Leu Asp Asn Ile Leu Gln Ile
     50                  55                  60

Arg His Thr Pro His Asn Asn Gly Leu Ser Asp Ile Tyr Leu Leu Asp
 65                  70                  75                  80

Asp Pro His Glu Ala Leu Ala Arg Ala Ala Leu Ile Glu Ser Ala
                85                  90                  95

Glu His Ser Leu Asp Leu Gln Tyr Tyr Ile Trp Arg Asn Asp Ile Ser
                100                 105                 110

Gly Arg Leu Leu Phe Asn Leu Met Tyr Leu Ala Ala Glu Arg Gly Val
            115                 120                 125

Arg Val Arg Leu Leu Leu Asp Asp Asn Asn Thr Arg Gly Leu Asp Asp
130                 135                 140

Leu Leu Leu Ala Leu Asp Ser His Pro Asn Ile Glu Val Arg Leu Phe
145                 150                 155                 160

Asn Pro Phe Val Leu Arg Lys Trp Arg Ala Leu Gly Tyr Leu Thr Asp
                165                 170                 175

Phe Pro Arg Leu Asn Arg Arg Met His Asn Lys Ser Phe Thr Ala Asp
            180                 185                 190

Asn Arg Ala Thr Ile Leu Gly Gly Arg Asn Ile Gly Asp Glu Tyr Phe
        195                 200                 205

Lys Val Gly Glu Asp Thr Val Phe Ala Asp Leu Asp Ile Leu Ala Thr
    210                 215                 220

Gly Ser Val Val Gly Glu Val Ser His Asp Phe Asp Arg Tyr Trp Ala
225                 230                 235                 240

Ser His Ser Ala His Asn Ala Thr Arg Ile Ile Arg Ser Gly Asn Ile
                245                 250                 255

Gly Lys Gly Leu Gln Ala Leu Gly Tyr Asn Asp Glu Thr Ser Arg His
            260                 265                 270

Ala Leu Leu Arg Tyr Arg Glu Thr Val Glu Gln Ser Pro Leu Tyr Gln
        275                 280                 285

Lys Ile Gln Thr Gly Arg Ile Asp Trp Gln Ser Val Gln Thr Arg Leu
    290                 295                 300

Ile Ser Asp Thr Pro Ala Lys Gly Leu Asp Arg Asp Arg Lys Pro
305                 310                 315                 320

Pro Ile Ala Gly Arg Leu Gln Asp Ala Leu Lys Gln Pro Glu Lys Ser
                325                 330                 335

Val Tyr Leu Val Ser Pro Tyr Phe Val Pro Thr Lys Ser Gly Thr Asp
            340                 345                 350

Ala Leu Ala Lys Leu Val Gln Asp Gly Ile Asp Val Thr Val Leu Thr
        355                 360                 365

Asn Ser Leu Gln Ala Thr Asp Val Ala Ala Val His Ser Gly Tyr Val
    370                 375                 380

Lys Tyr Arg Lys Pro Leu Leu Lys Ala Gly Ile Lys Leu Tyr Glu Leu
385                 390                 395                 400
```

```
Gln Pro Asn His Ala Val Pro Ala Thr Lys Asp Lys Gly Leu Thr Gly
                405                 410                 415
Ser Ser Val Thr Ser Leu His Ala Lys Thr Phe Ile Val Asp Gly Lys
            420                 425                 430
Arg Ile Phe Ile Gly Ser Phe Asn Leu Asp Pro Arg Ser Ala Arg Leu
        435                 440                 445
Asn Thr Glu Met Gly Val Val Ile Glu Ser Pro Lys Ile Ala Glu Gln
    450                 455                 460
Met Glu Arg Thr Leu Ala Asp Thr Thr Pro Glu Tyr Ala Tyr Arg Val
465                 470                 475                 480
Thr Leu Asp Lys His Asn Arg Leu Gln Trp His Asp Pro Ala Thr Arg
                485                 490                 495
Lys Thr Tyr Pro Asn Glu Pro Glu Ala Lys Leu Trp Lys Arg Ile Ala
                500                 505                 510
Ala Lys Ile Leu Ser Leu Leu Pro Ile Glu Gly Leu Leu
        515                 520                 525

<210> SEQ ID NO 15
<211> LENGTH: 1563
<212> TYPE: DNA
<213> ORGANISM: Neisseria gonorrhoeae 1090

<400> SEQUENCE: 15
caaaatacag gcaatgccgt ctgaaactat atccccgatg aaaacacgca gcctcatttc     60
ccttttatgc ctccttctct gttcatgttc ttcatggttg ccccccactgg aagaacggac    120
ggaaagccgt cattttaata cttccaaacc tgtcctcctg acaacatcc tgcaaatccg      180
gcacacccct cataacaacg ggctatccga catctacctg ctcgacgacc cccacgaagc    240
cttttgccgcc cgcgccgccc ttatcgaatc tgccgaacac agcctcgatt gcaatacta    300
catttggcgc aacgacattt ccggcaggct gctgttcaac ctcatgtacc ttgccgcaga    360
acgcggcgtg cgcgtacgcc tgctgttgga cgacaacaac acgcgcggct ggacgatct    420
cctgctcgcc ctcgacagcc atcccaatat cgaagtgcgc ccgttcaacc ccttcgtcct    480
acgcaaatgg cgcgcactcg gctacctgac cgacttcccc cgcctcaacc gccgcatgca    540
caacaaatcc tttaccgccg acaaccgcgc caccatactc ggcggacgca atatcggcga    600
cgaatacttc aaagtcggtg aggacaccgt tttcgccgac ctggacatcc tcgccaccgg    660
cagcgtcgtc ggcgaagtat cgcacgactt cgaccgctac tgggcaagcc attccgccca    720
caacgccacg cgcatcatcc gcagcggcaa catcggcaag ggtcttcaag cactcggata    780
caacgacgaa acatccagac acgcgctcct gcgctaccgg gaaaccgtag aacagtcgcc    840
cctctaccaa aaatacagac gggacgcatc gactggcaga gcgtccaaac ccgcttgatc    900
agcgacagcc ctgcaaaagg actcgagacc cgcgaccgcc gcaaaccgcg gattgccggg    960
aggctgcaag acgcgctcaa acagcccgaa aaaagcgtct atctggtttc accctatttc   1020
gtccctacaa aatccggcac agacgcactg gcaaaactgg tgcaggacgg catagacgtt   1080
accgtcctga ccaactcgct acaggcgacc gacgttgccg ccgtccattc cggctacgtc   1140
aaataccgaa aaccgctgct caaagccggc atcaaactct acgagctgca acccaaccat   1200
gccgtccccg ccacaaaaga caaggcctg accggcagct ccgtaaccag cctgcatgcc   1260
aaaaccttca ttgtggacgg caaacgcatc ttcatcggct cattcaacct cgaccccgt    1320
tccgcacggc tcaataccga aatgggcgtc gtcatcgaaa gccccaaaat cgcagaacag   1380
```

```
atggagcgca ccctcgccga taccacaccc gaatacgcct accgcgttac cctcgacaaa   1440
cacaaccgcc tgcaatggca cgatcccgcc acccgaaaaa cctacccgaa cgaacccgaa   1500
gccaaacttt ggaaacgcat cgccgcaaaa atcctatccc tgctgcccat cgaaggttta   1560
tta                                                                 1563
```

<210> SEQ ID NO 16
<211> LENGTH: 525
<212> TYPE: PRT
<213> ORGANISM: Neisseria gonorrhoeae 1090

<400> SEQUENCE: 16

```
Met His Thr Asp Pro Lys Ile Gln Ala Met Pro Ser Glu Thr Ile Ser
  1               5                  10                  15

Pro Met Lys Thr Arg Ser Leu Ile Ser Leu Leu Cys Leu Leu Leu Cys
             20                  25                  30

Ser Cys Ser Ser Trp Leu Pro Pro Leu Glu Glu Arg Thr Glu Ser Arg
         35                  40                  45

His Phe Asn Thr Ser Lys Pro Val Leu Leu Asp Asn Ile Leu Gln Ile
     50                  55                  60

Arg His Thr Pro His Asn Asn Gly Leu Ser Asp Ile Tyr Leu Leu Asp
 65                  70                  75                  80

Asp Pro His Glu Ala Phe Ala Ala Arg Ala Ala Leu Ile Glu Ser Ala
                 85                  90                  95

Glu His Ser Leu Asp Leu Gln Tyr Tyr Ile Trp Arg Asn Asp Ile Ser
            100                 105                 110

Gly Arg Leu Leu Phe Asn Leu Met Tyr Leu Ala Ala Glu Arg Gly Val
        115                 120                 125

Arg Val Arg Leu Leu Leu Asp Asp Asn Asn Thr Arg Gly Leu Asp Asp
    130                 135                 140

Leu Leu Leu Ala Leu Asp Ser His Pro Asn Ile Glu Val Arg Leu Phe
145                 150                 155                 160

Asn Pro Phe Val Leu Arg Lys Trp Arg Ala Leu Gly Tyr Leu Thr Asp
                165                 170                 175

Phe Pro Arg Leu Asn Arg Arg Met His Asn Lys Ser Phe Thr Ala Asp
            180                 185                 190

Asn Arg Ala Thr Ile Leu Gly Gly Arg Asn Ile Gly Asp Glu Tyr Phe
        195                 200                 205

Lys Val Gly Glu Asp Thr Val Phe Ala Asp Leu Asp Ile Leu Ala Thr
    210                 215                 220

Gly Ser Val Val Gly Glu Val Ser His Asp Phe Asp Arg Tyr Trp Ala
225                 230                 235                 240

Ser His Ser Ala His Asn Ala Thr Arg Ile Ile Arg Ser Gly Asn Ile
                245                 250                 255

Gly Lys Gly Leu Gln Ala Leu Gly Tyr Asn Asp Glu Thr Ser Arg His
            260                 265                 270

Ala Leu Leu Arg Tyr Arg Glu Thr Val Glu Gln Ser Pro Leu Tyr Gln
        275                 280                 285

Lys Ile Gln Thr Gly Arg Ile Asp Trp Gln Ser Val Gln Thr Arg Leu
    290                 295                 300

Ile Ser Asp Ser Pro Ala Lys Gly Leu Asp Arg Asp Arg Arg Lys Pro
305                 310                 315                 320

Pro Ile Ala Gly Arg Leu Gln Asp Ala Leu Lys Gln Pro Glu Lys Ser
                325                 330                 335
```

| | | | | | | | | | | | |
|---|---|---|---|---|---|---|---|---|---|---|---|
|Val|Tyr|Leu|Val|Ser|Pro|Tyr|Phe|Val|Pro|Thr|Lys|Ser|Gly|Thr|Asp|
| | | |340| | |345| | | |350| |

Ala Leu Ala Lys Leu Val Gln Asp Gly Ile Asp Val Thr Val Leu Thr
            355                 360                 365

Asn Ser Leu Gln Ala Thr Asp Val Ala Ala Val His Ser Gly Tyr Val
        370                 375                 380

Lys Tyr Arg Lys Pro Leu Leu Lys Ala Gly Ile Lys Leu Tyr Glu Leu
385                 390                 395                 400

Gln Pro Asn His Ala Val Pro Ala Thr Lys Asp Lys Gly Leu Thr Gly
                405                 410                 415

Ser Ser Val Thr Ser Leu His Ala Lys Thr Phe Ile Val Asp Gly Lys
            420                 425                 430

Arg Ile Phe Ile Gly Ser Phe Asn Leu Asp Pro Arg Ser Ala Arg Leu
            435                 440                 445

Asn Thr Glu Met Gly Val Val Ile Glu Ser Pro Lys Ile Ala Glu Gln
        450                 455                 460

Met Glu Arg Thr Leu Ala Asp Thr Thr Pro Glu Tyr Ala Tyr Arg Val
465                 470                 475                 480

Thr Leu Asp Lys His Asn Arg Leu Gln Trp His Asp Pro Ala Thr Arg
                485                 490                 495

Lys Thr Tyr Pro Asn Glu Pro Glu Ala Lys Leu Trp Lys Arg Ile Ala
            500                 505                 510

Ala Lys Ile Leu Ser Leu Leu Pro Ile Glu Gly Leu Leu
            515                 520                 525

<210> SEQ ID NO 17
<211> LENGTH: 1564
<212> TYPE: DNA
<213> ORGANISM: Neisseria gonorrhoeae ms11

<400> SEQUENCE: 17

```
caaaatacag gcaatgccgt ctgaaactat atccccgatg aaaacacgca gcctcatttc      60
cctttatgc ctccttctct gttcatgttc ttcatggttg ccccactgg aagaacggac      120
ggaaagccgt catttcaata cttccaaacc tgtcctcctg gacaacatcc tgcaaatccg      180
gcacacccct cataacaacg ggctatccga catctacctg ctcgacgacc cccacgaagc      240
ctttgccgcc cgcgccgccc ttatcgaatc tgccgaacac agcctcgatt tgcaatacta      300
catttggcgc aacgacattt ccggcaggct gctgttcaac ctcatgtacc ttgccgcaga      360
acgcggcgtg cgcgtacgcc tgctgttgga cgacaacaac acgcgcgggt tggacgatct      420
cctgctcgcc ctcgcagcc atcccaatat cgaagtgcgc ctgttcaacc ccttcgtcct      480
acgcaaatgg cgcgcactcg gctacctgac cgacttcccc cgcctcaacc gccgcatgca      540
caacaaatcc tttaccgccg acaaccgcgc caccatactc ggcggacgca atatcggcga      600
cgaatacttc aaagtcggtg aggacaccgt tttcgccgac ctggacatcc tcgccaccgg      660
cagcgtcgtc cggcgaagta tcgcacgact tcgaccgcta ctgggcaagc cattccgccc      720
acaacgccac gcgcaattat tccgcagcgg caacatcggc aagggtcttc aagcactcgg      780
atacaacgac gaaacttcca gacccgcgct tctgcgctac cgggaaaccg tcgaacagtc      840
gcccttctac caaaaaatac agacgggacg catcgactgg cagagcgtcc aaacccgcct      900
gatcagcgac aaccctgcaa aaggactcga ccgcgaccgc cgcaaaccgc cgattgccgg      960
gaggctgcaa gacgcgctca acagcccga aaaagcgtc tatctggttt caccctattt      1020
cgtccctaca aaatccggca cagacgcact ggcaaaactg gtgcaggacg gcatagacgt      1080
```

-continued

```
taccgtcctg accaactcgc tacaggcgac cgacgttgcc gccgtccatt ccggctacgt    1140
caaataccga aaccgctgc tcaaagccgg catcaaactc tacgagctgc aacccaacca     1200
tgccgtcccc gccacaaaag acaaaggcct gaccggcagc tccgtaacca gcctgcatgc    1260
caaaaccttc attgtggacg gcaaacgcat cttcatcggc tcattcaacc tcgaccccg    1320 ttccgcacgg ctcaataccg aaatgggcgt cgtcatcgaa agccccaaaa tgcagaaca    1380 gatggagcgc accctcgccg ataccacacc cgaatacgcc taccgcgtta ccctcgacaa    1440
acacaaccgc ctgcaatggc acgatcccgc cacccgaaaa acctaccgcga acgaacccga   1500 agccaaactt tggaaacgca tcgccgcaaa aatcctatcc ctgctgccca tcgaaggttt    1560
atta                                                                1564
```

<210> SEQ ID NO 18
<211> LENGTH: 525
<212> TYPE: PRT
<213> ORGANISM: Neisseria gonorrhoeae ms11

<400> SEQUENCE: 18

```
Met His Thr Asp Pro Lys Ile Gln Ala Met Pro Ser Glu Thr Ile Ser
 1               5                  10                  15

Pro Met Lys Thr Arg Ser Leu Ile Ser Leu Leu Cys Leu Leu Leu Cys
            20                  25                  30

Ser Cys Ser Ser Trp Leu Pro Pro Leu Glu Glu Arg Thr Glu Ser Arg
        35                  40                  45

His Phe Asn Thr Ser Lys Pro Val Leu Leu Asp Asn Ile Leu Gln Ile
    50                  55                  60

Arg His Thr Pro His Asn Asn Gly Leu Ser Asp Ile Tyr Leu Leu Asp
65                  70                  75                  80

Asp Pro His Glu Ala Phe Ala Ala Arg Ala Ala Leu Ile Glu Ser Ala
                85                  90                  95

Glu His Ser Leu Asp Leu Gln Tyr Tyr Ile Trp Arg Asn Asp Ile Ser
            100                 105                 110

Gly Arg Leu Leu Phe Asn Leu Met Tyr Leu Ala Ala Glu Arg Gly Val
        115                 120                 125

Arg Val Arg Leu Leu Leu Asp Asp Asn Asn Thr Arg Gly Leu Asp Asp
    130                 135                 140

Leu Leu Leu Ala Leu Asp Ser His Pro Asn Ile Glu Val Arg Leu Phe
145                 150                 155                 160

Asn Pro Phe Val Leu Arg Lys Trp Arg Ala Leu Gly Tyr Leu Thr Asp
                165                 170                 175

Phe Pro Arg Leu Asn Arg Arg Met His Asn Lys Ser Phe Thr Ala Asp
            180                 185                 190

Asn Arg Ala Thr Ile Leu Gly Gly Arg Asn Ile Gly Asp Glu Tyr Phe
        195                 200                 205

Lys Val Gly Glu Asp Thr Val Phe Ala Asp Leu Asp Ile Leu Ala Thr
    210                 215                 220

Gly Ser Val Val Gly Val Ser His Asp Phe Asp Arg Tyr Trp Ala
225                 230                 235                 240

Ser His Ser Ala His Asn Ala Thr Arg Ile Ile Arg Ser Gly Asn Ile
                245                 250                 255

Gly Lys Gly Leu Gln Ala Leu Gly Tyr Asn Asp Glu Thr Ser Arg His
            260                 265                 270

Ala Leu Leu Arg Tyr Arg Glu Thr Val Glu Gln Ser Pro Phe Tyr Gln
```

```
                275                 280                 285
Lys Ile Gln Thr Gly Arg Ile Asp Trp Gln Ser Val Gln Thr Arg Leu
            290                 295                 300
Ile Ser Asp Ser Pro Ala Lys Gly Leu Asp Arg Asp Arg Arg Lys Pro
305                 310                 315                 320
Pro Ile Ala Gly Arg Leu Gln Asp Ala Leu Lys Gln Pro Glu Lys Ser
                325                 330                 335
Val Tyr Leu Val Ser Pro Tyr Phe Val Pro Thr Lys Ser Gly Thr Asp
            340                 345                 350
Ala Leu Ala Lys Leu Val Gln Asp Gly Ile Asp Val Thr Val Leu Thr
            355                 360                 365
Asn Ser Leu Gln Ala Thr Asp Val Ala Ala Val His Ser Gly Tyr Val
        370                 375                 380
Lys Tyr Arg Lys Pro Leu Leu Lys Ala Gly Ile Lys Leu Tyr Glu Leu
385                 390                 395                 400
Gln Pro Asn His Ala Val Pro Ala Thr Lys Asp Lys Gly Leu Thr Gly
                405                 410                 415
Ser Ser Val Thr Ser Leu His Ala Lys Thr Phe Ile Val Asp Gly Lys
            420                 425                 430
Arg Ile Phe Ile Gly Ser Phe Asn Leu Asp Pro Arg Ser Ala Arg Leu
            435                 440                 445
Asn Thr Glu Met Gly Val Val Ile Glu Ser Pro Lys Ile Ala Glu Gln
        450                 455                 460
Met Glu Arg Thr Leu Ala Asp Thr Thr Pro Glu Tyr Ala Tyr Arg Val
465                 470                 475                 480
Thr Leu Asp Lys His Asn Arg Leu Gln Trp His Asp Pro Ala Thr Arg
                485                 490                 495
Lys Thr Tyr Pro Asn Glu Pro Glu Ala Lys Leu Trp Lys Arg Ile Ala
                500                 505                 510
Ala Lys Ile Leu Ser Leu Leu Pro Ile Glu Gly Leu Leu
            515                 520                 525

<210> SEQ ID NO 19
<211> LENGTH: 1564
<212> TYPE: DNA
<213> ORGANISM: Neisseria meningitidis B
<220> FEATURE:
<221> NAME/KEY: misc_feature
<222> LOCATION: (1)...(1564)
<223> OTHER INFORMATION: n = a or t or g or c.

<400> SEQUENCE: 19
caaaatacag gcaatgccgt ctgaaaccat atccctgatg aaaacacgca gcctaatttc      60
ccttttatgc ctccttctct gttcatgttc ttcatggttg cccccactgg aagaacggac     120
ggaaagccgt catttcaata cttccaaacc cgtccgcctg acaacatcc tgcaaatccg      180 gcacacccct cataccaacg ggctatccga tatctatctg ttgaacgacc cccacgaagc     240
ctttgccgcc cgcgccgccc ttatcgaatc tgccgaacac agcctcgatt tgcaatacta     300
catctggcgc aacgacattt ccggccgact gctgttcaac ctcgtgtacc ttgccgcaga     360
acgcggtgtg cgcgtacgcc tgctgttgga cgacaacaac acgcgcggat ggacgacct      420 cctgctcgcc ctcgacagcc atcccaatat cgaagtgcgc ctgttcaacc ccttcgtctt     480
acgaaaatgg cgcgcactcg gctacctgac cgacttcccc cgcctcaacc gccgcatgca     540
caacaaatcc tttaccgccg acaaccgcgc caccatactc ggcggacgca atatcggcga     600
```

-continued

```
cgaatacttc aaagtcggtg aggacaccgt tttcgccgac ctggacatnc tcgccaccgg    660
cagcgtcgtt agcgaagtat cgcacgactt tgaccgctac tgggcaagcc attncgncca    720
caacgccacg cgcataatnc gcagcggnaa catcggnaag gggttttcaa gcactcggnt    780
acaacgacga aaacgtncag acacgngntc ntgcgctacc gggagaccgt cgaacagtcg    840
cccntctacc aaaaaatata ggcaggacgc atcgactggc agagcgtcca aacccgcctc    900
atcagcgacg acccntgcaa aaggactcga ccgcgaccgc cgcaaaccgc ngattgccgg    960
gcgnctgcaa gacgcgctca aacagccnga aaaaagcgtc tatctggttt caccctattt   1020
cgtccccaca aaatccggca cagacgcact ggcaaaactg gtgcaggacg gcatagacgt   1080
taccgttctg accaactcgc tacaggcgac cgacgttgcc gccgtccatt ctggctatgt   1140
caaataccga aaaccgttgc tcaaagccgg catcaaactc tacgagctgc aacccaacca   1200
tgccgtcccc gccacaaaag acaaaggcct gaccggcagc tccgtaacca gcctgcacgc   1260
caaaaccttc attgtggacg gcaaacgcat cttcatcggc tcattcaacc tcgaccccg    1320 ttccgcacgg ctcaataccg aaatgggtgt cgtcatcgaa agccccaaaa tcgcagaaca   1380
gatggagcgc acccttgccg ataccacacc cgaatacgcc taccgcgtta ccctcggcag   1440
gcacaaccgc ctgcaatggc acgatcccgc cacccgaaaa acctacccga cgaacccga    1500 agccaaactt tggaaacgca tcgccgcaaa aatcctatcc ctgctgccca tcgaaggttt   1560
atta                                                               1564
```

<210> SEQ ID NO 20
<211> LENGTH: 525
<212> TYPE: PRT
<213> ORGANISM: Neisseria meningitidis B

<400> SEQUENCE: 20

```
Met Arg Ala Asn Pro Lys Thr Gln Ala Met Pro Ser Glu Thr Ile Ser
  1               5                  10                  15

Leu Met Lys Thr Arg Ser Leu Ile Ser Leu Leu Cys Leu Leu Leu Cys
             20                  25                  30

Ser Cys Ser Ser Trp Leu Pro Pro Leu Glu Glu Arg Thr Glu Ser Arg
         35                  40                  45

His Phe Asn Thr Ser Lys Pro Val Arg Leu Asp Asn Ile Leu Gln Ile
     50                  55                  60

Arg His Thr Pro His Thr Asn Gly Leu Ser Asp Ile Tyr Leu Asn
 65                  70                  75                  80

Asp Pro His Glu Ala Phe Ala Arg Ala Ala Leu Ile Glu Ser Ala
                 85                  90                  95

Glu His Ser Leu Asp Leu Gln Tyr Tyr Ile Trp Arg Asn Asp Ile Ser
            100                 105                 110

Gly Arg Leu Leu Phe Asn Leu Val Tyr Leu Ala Ala Glu Arg Gly Val
        115                 120                 125

Arg Val Arg Leu Leu Leu Asp Asp Asn Asn Thr Arg Gly Leu Asp Asp
    130                 135                 140

Leu Leu Leu Ala Leu Asp Ser His Pro Asn Ile Glu Val Arg Leu Phe
145                 150                 155                 160

Asn Pro Phe Val Leu Arg Lys Trp Arg Ala Leu Gly Tyr Leu Thr Asp
                165                 170                 175

Phe Pro Arg Leu Asn Arg Arg Met His Asn Lys Ser Phe Thr Ala Asp
            180                 185                 190

Asn Arg Ala Thr Ile Leu Gly Gly Arg Asn Ile Gly Asp Glu Tyr Phe
```

```
                195                 200                 205
Lys Val Gly Glu Asp Thr Val Phe Ala Asp Leu Asp Ile Leu Ala Thr
    210                 215                 220

Gly Ser Val Val Gly Glu Val Ser His Asp Phe Asp Arg Tyr Trp Ala
225                 230                 235                 240

Ser His Ser Ala His Asn Ala Thr Arg Ile Ile Arg Ser Gly Asn Ile
                245                 250                 255

Gly Lys Gly Leu Gln Ala Leu Gly Tyr Asn Asp Glu Thr Ser Arg His
            260                 265                 270

Ala Leu Leu Arg Tyr Arg Glu Thr Val Glu Gln Ser Pro Leu Tyr Gln
        275                 280                 285

Lys Ile Gln Thr Gly Arg Ile Asp Trp Gln Ser Val Gln Thr Arg Leu
    290                 295                 300

Ile Ser Asp Asp Pro Ala Lys Gly Leu Asp Arg Asp Arg Arg Lys Pro
305                 310                 315                 320

Pro Ile Ala Gly Arg Leu Gln Asp Ala Leu Lys Gln Pro Glu Lys Ser
                325                 330                 335

Val Tyr Leu Val Ser Pro Tyr Phe Val Pro Thr Lys Ser Gly Thr Asp
            340                 345                 350

Ala Leu Ala Lys Leu Val Gln Asp Gly Ile Asp Val Thr Val Leu Thr
        355                 360                 365

Asn Ser Leu Gln Ala Thr Asp Val Ala Ala Val His Ser Gly Tyr Val
    370                 375                 380

Lys Tyr Arg Lys Pro Leu Leu Lys Ala Gly Ile Lys Leu Tyr Glu Leu
385                 390                 395                 400

Gln Pro Asn His Ala Val Pro Ala Thr Lys Asp Lys Gly Leu Thr Gly
                405                 410                 415

Ser Ser Val Thr Ser Leu His Ala Lys Thr Phe Ile Val Asp Gly Lys
            420                 425                 430

Arg Ile Phe Ile Gly Ser Phe Asn Leu Asp Pro Arg Ser Ala Arg Leu
        435                 440                 445

Asn Thr Glu Met Gly Val Val Ile Glu Ser Pro Lys Ile Ala Glu Gln
    450                 455                 460

Met Glu Arg Thr Leu Ala Asp Thr Ser Pro Glu Tyr Ala Tyr Arg Val
465                 470                 475                 480

Thr Leu Asp Arg His Asn Arg Leu Gln Trp His Asp Pro Ala Thr Arg
                485                 490                 495

Lys Thr Tyr Pro Asn Glu Pro Glu Ala Lys Leu Trp Lys Arg Ile Ala
            500                 505                 510

Ala Lys Ile Leu Ser Leu Leu Pro Ile Glu Ser Leu Leu
        515                 520                 525

<210> SEQ ID NO 21
<211> LENGTH: 15
<212> TYPE: PRT
<213> ORGANISM: Neisseria gonorrhoeae

<400> SEQUENCE: 21

Arg Arg Met His Asn Lys Ser Phe Thr Ala Asp Asn Arg Ala Cys
1               5                   10                  15

<210> SEQ ID NO 22
<211> LENGTH: 32
<212> TYPE: DNA
<213> ORGANISM: Artificial Sequence
<220> FEATURE:
```

<223> OTHER INFORMATION: A synthetic primer used in a PCR.

<400> SEQUENCE: 22
ggtggtcata tgatgcatac agaccccaaa at				32

<210> SEQ ID NO 23
<211> LENGTH: 42
<212> TYPE: DNA
<213> ORGANISM: Artificial Sequence
<220> FEATURE:
<223> OTHER INFORMATION: A synthetic primer used in a PCR.

<400> SEQUENCE: 23
ggtggttgct cttccgcata ataaaccttc ttcgatgggc ag				42

<210> SEQ ID NO 24
<211> LENGTH: 1561
<212> TYPE: DNA
<213> ORGANISM: Neisseria gonorrhoeae

<400> SEQUENCE: 24
taataaactt tctatgggca gcagggatag gattttgcg gcgatgcgtt tccaaagttt			60
ggcttcgggt tcgttcgggt aggtttttcg ggtggcggga tcgtgccatt gcaggcggtt			120
gtgcctgtcg agggtaacgc ggtaggcgta ttcgggtgag gtatcggcaa gggtgcgctc			180
catctgttct gcgattttgg ggctttcgat aacaacgccc atttcagtat tgagccgtgc			240
ggaacggggg tcgaggttga atgagccgat gaagatgcgt ttgccgtcca caatgaaggt			300
tttggcatgc aggctggtta cggagctgcc ggtcaggcct ttgtcttttg tggcagggac			360
ggcatggttg ggttgcagct cgtagagttt gatgccggct ttgagcagcg gttttcggta			420
tttgacatag ccggaatgga cggcggcaac gtcggtcgcc tgtagcgagt tggtcaggac			480
ggtaacgtct atgccgtcct gcaccagttt tgccagtgcg tctgtgccgg attttgtggg			540
gacgaaatag ggtgaaacca gatagacgct ttttcgggc tgtttgagcg cgtcttgcag			600
ccgcccggca atcggcggtt tgcggcggtc gcggtcgagt cctttttgcag ggtcgtcgct			660
gatgaggcgg gtttggacgc tctgccagtc gatgcgtcct gtctgtatt tttggtagag			720
gggcgactgt tcgacggttt cgcggtagcg caggagcgcg tgtctggacg tttcgtcgtt			780
gtatccgagt gcttgaagac ccttgccgat gttgccgctg cggatgatgc gcgtggcgtt			840
gtgggcggaa tggcttgccc agtagcggtc gaagtcgtgc gatacttcgc cgacgacgct			900
gccggtggcg aggatgtcca ggtcggcgaa aacggtgtcc tcaccgactt tgaagtattc			960
gtcgccgata ttgcgtccgc cgagtatggt ggcgcggttg tcggcggtaa aggatttgtt			1020
gtgcatgcgg cggttgaggc gggggaagtc ggtcaggtag ccgagtgcgc gccattttcg			1080
taagacgaag gggttgaaca ggcgcacttc gatattggga tggctgtcga gggcgagcag			1140
gaggtcgtcc aatccgcgcg tgttgttgtc gtccaacagc aggcgtacgc gcacaccgcg			1200
ttctgcggca aggtacacga ggttgaacag cagtcggccg gaaatgtcgt tgcgccagat			1260
gtagtattgc aaatcgaggc tgtgttcggc agattcgata agggcggcgc gggcggcaaa			1320
ggcttcgtgg gggtcgttca acagatagat atcggatagc ccgttggtat gagggggtgtg			1380
ccggatttgc aggatgttgt ccaggcggac gggtttggaa gtattgaaat gacggctttc			1440
cgtccgttct tccagtgggg gcaaccatga agaacatgaa cagagaagga ggcataaaag			1500
ggaaattagg ctgcgtgttt tcatcaggga tatggtttca gacggcattg cctgtgtttt			1560
g												1561

<210> SEQ ID NO 25
<211> LENGTH: 1563
<212> TYPE: DNA
<213> ORGANISM: Neisseria gonorrhoeae

<400> SEQUENCE: 25

| | | | | | | |
|---|---|---|---|---|---|---|
| caaaatacag | gcaatgccgt | ctgaaactat | atccccgatg | aaaacacgca | gcctcatttc | 60 |
| ccttttatgc | ctccttctct | gttcatgttc | ttcatggttg | cccccactgg | aagaacggac | 120 |
| ggaaagccgt | cattttaata | cttccaaacc | tgtcctcctg | acaacatcc | tgcaaatccg | 180 |
| gcacacccct | cataacaacg | ggctatccga | catctacctg | ctcgacgacc | cccacgaagc | 240 |
| ctttgccgcc | cgcgccgccc | ttatcgaatc | tgccgaacac | agcctcgatt | tgcaatacta | 300 |
| catttggcgc | aacgacattt | ccggcaggct | gctgttcaac | ctcatgtacc | ttgccgcaga | 360 |
| acgcggcgtg | cgcgtacgcc | tgctgttgga | cgacaacaac | acgcgcggct | tggacgatct | 420 |
| cctgctcgcc | ctcgacagcc | atcccaatat | cgaagtgcgc | ccgttcaacc | ccttcgtcct | 480 |
| acgcaaatgg | cgcgcactcg | gctacctgac | cgacttcccc | cgcctcaacc | gccgcatgca | 540 |
| caacaaatcc | tttaccgccg | acaaccgcgc | caccatactc | ggcggacgca | atatcggcga | 600 |
| cgaatacttc | aaagtcggtg | aggacaccgt | tttcgccgac | ctggacatcc | tcgccaccgg | 660 |
| cagcgtcgtc | ggcgaagtat | cgcacgactt | cgaccgctac | tgggcaagcc | attccgccca | 720 |
| caacgccacg | cgcatcatcc | gcagcggcaa | catcggcaag | ggtcttcaag | cactcggata | 780 |
| caacgacgaa | acatccagac | acgcgctcct | gcgctaccgg | gaaaccgtag | aacagtcgcc | 840 |
| cctctaccaa | aaatacagac | gggacgcatc | gactggcaga | gcgtccaaac | ccgcttgatc | 900 |
| agcgacagcc | ctgcaaaagg | actcgagacc | cgcgaccgcc | gcaaaccgcg | gattgccggg | 960 |
| aggctgcaag | acgcgctcaa | acagcccgaa | aaaagcgtct | atctggtttc | accctatttc | 1020 |
| gtccctacaa | aatccggcac | agacgcactg | gcaaaactgg | tgcaggacgg | catagacgtt | 1080 |
| accgtcctga | ccaactcgct | acaggcgacc | gacgttgccg | ccgtccattc | cggctacgtc | 1140 |
| aaataccgaa | aaccgctgct | caaagccggc | atcaaactct | acgagctgca | acccaaccat | 1200 |
| gccgtccccg | ccacaaaaga | caaaggcctg | accggcagct | ccgtaaccag | cctgcatgcc | 1260 |
| aaaaccttca | ttgtggacgg | caaacgcatc | ttcatcggct | cattcaacct | cgaccccgt | 1320 |
| tccgcacggc | tcaataccga | aatgggcgtc | gtcatcgaaa | gccccaaaat | cgcagaacag | 1380 |
| atggagcgca | ccctcgccga | taccacaccc | gaatacgcct | accgcgttac | cctcgacaaa | 1440 |
| cacaaccgcc | tgcaatggca | cgatcccgcc | acccgaaaaa | cctacccgaa | cgaacccgaa | 1500 |
| gccaaacttt | ggaaacgcat | cgccgcaaaa | atcctatccc | tgctgcccat | cgaaggttta | 1560 |
| tta | | | | | | 1563 |

<210> SEQ ID NO 26
<211> LENGTH: 1561
<212> TYPE: DNA
<213> ORGANISM: Neisseria gonorrhoeae

<400> SEQUENCE: 26

| | | | | | | |
|---|---|---|---|---|---|---|
| caaaatacag | gcaatgccgt | ctgaaactat | atccccgatg | aaaacacgca | gcctcatttc | 60 |
| ccttttatgc | ctccttctct | gttcatgttc | ttcatggttg | cccccactgg | aagaacggac | 120 |
| ggaaagccgt | cattttaata | cttccaaacc | tgtcctcctg | acaacatcc | tgcaaatccg | 180 |
| gcacacccct | cataacaacg | ggctatccga | catctacctg | ctcgacgacc | cccacgaagc | 240 |

```
ctttgccgcc cgcgccgccc ttatcgaatc tgccgaacac agcctcgatt tgcaatacta      300
catttggcgc aacgacattt ccggcaggct gctgttcaac ctcatgtacc ttgccgcaga      360
acgcggcgtg cgcgtacgcc tgctgttgga cgacaacaac acgcgcggct tggacgatct      420
cctgctcgcc ctcgacagcc atcccaatat cgaagtgcgc ctgttcaacc ccttcgtcct      480
acgcaaatgg cgcgcactcg gctacctgac cgacttcccc cgcctcaacc gccgcatgca      540
caacaaatcc tttaccgccg acaaccgcgc caccatactc ggcggacgca atatcggcga      600
cgaatacttc aaagtcggtg aggacaccgt tttcgccgac ctggacatcc tcgccaccgg      660
cagcgtcgtc ggcgaagtat cgcacgactt cgaccgctac tgggcaagcc attccgccca      720
caacgccacg cgcatcatcc gcagcggcaa catcggcaag ggtcttcaag cactcggata      780
caacgacgaa acatccagac acgcgctcct gcgctaccgc gaaaccgtcg aacagtcgcc      840
cctctaccaa aaaatacaga cgggacgcat cgactggcag agcgtccaaa cccgcctgat      900
cagcgacagc cctgcaaaag gactcgaccg gaccgccgc aaaccgccga ttgccgggag      960
gctgcaagac gcgctcaaac agcccgaaaa aagcgtctat ctggtttcac cctatttcgt     1020
ccctacaaaa tccggcacag acgcactggc aaaactggtg caggacggca tagacgttac     1080
cgtcctgacc aactcgctac aggcgaccga cgttgccgcc gtccattccg gctacgtcaa     1140
ataccgaaaa ccgctgctca agccggcat caaactctac gagctgcaac caaccatgc      1200
cgtccccgcc acaaaagaca aaggcctgac cggcagctcc gtaaccagcc tgcatgccaa     1260
aaccttcatt gtggacggca aacgcatctt catcggctca ttcaacctcg acccccgttc     1320
cgcacggctc aataccgaaa tgggcgtcgt catcgaaagc cccaaaatcg cagaacagat     1380
ggagcgcacc ctcgccgata ccacacccga atacgcctac cgcgttaccc tcgacaaaca     1440
caaccgcctg caatggcacg atcccgccac ccgaaaaacc tacccgaacg aacccgaagc     1500
caaactttgg aaacgcatcg ccgcaaaaat cctatccctg ctgcccatcg aaggtttatt     1560
a                                                                    1561
```

<210> SEQ ID NO 27
<211> LENGTH: 1561
<212> TYPE: DNA
<213> ORGANISM: Neisseria gonorrhoeae

<400> SEQUENCE: 27

```
caaaatacag gcaatgccgt ctgaaactat atccccgatg aaaacacgca gcctcatttc       60
ccttttatgc ctccttctct gttcatgttc ttcatggttg cccccactgg aagaacggac      120
ggaaagccgt catttcaata cttccaaacc tgtcctcctg acaacatccc tgcaaatccg      180
gcacacccct cataacaacg ggctatccga catctacctg ctcgacgacc cccacgaagc      240
ccttgccgcc cgcgccgccc ttatcgaatc tgccgaacac agcctcgatt tgcaatacta      300
catttggcgc aacgacattt ccggcaggct gctgttcaac ctcatgtacc ttgccgcaga      360
acgcggcgtg cgcgtacgcc tgctgttgga cgacaacaac acgcgcgggt tggacgatct      420
cctgctcgcc ctcgacagcc atcccaatat cgaagtgcgc ctgttcaacc ccttcgtcct      480
acgcaaatgg cgcgcactcg gctacctgac cgacttcccc cgcctcaacc gccgcatgca      540
caacaaatcc tttaccgccg acaaccgcgc caccatactc ggcggacgca atatcggcga      600
cgaatacttc aaagtcggtg aggacaccgt tttcgccgac ctggacatcc tcgccaccgg      660
cagcgtcgtc ggcgaagtat cgcacgactt cgaccgctac tgggcaagcc attccgccca      720
caacgccacg cgcatcatcc gcagcggcaa catcggcaag ggtcttcaag cactcggata      780
```

```
caacgacgaa acatccagac acgcgctcct gcgctaccgc gaaaccgtcg aacagtcgcc      840
cctctaccaa aaaatacaga cgggacgcat cgactggcag agcgtccaaa cccgcctgat      900
cagcgacacc cctgcaaaag gactcgaccg cgaccgccgc aaaccgccga ttgccgggag      960
gctgcaagac gcgctcaaac agcccgaaaa aagcgtctat ctggtttcac cctatttcgt     1020
ccctacaaaa tccggcacag acgcactggc aaaactggtg caggacggca tagacgttac     1080
cgtcctgacc aactcgctac aggcgaccga cgttgccgcc gtccattccg gctacgtcaa     1140
ataccgaaaa ccgctgctca agccggcat caaactctac gagctgcaac caaccatgc      1200 cgtccccgcc acaaaagaca aaggcctgac cggcagctcc gtaaccagcc tgcatgccaa     1260
aaccttcatt gtggacggca aacgcatctt catcggctca ttcaacctcg accccgttc      1320 cgcacggctc aataccgaaa tgggcgtcgt catcgaaagc cccaaaatcg cagaacagat     1380
ggagcgcacc ctcgccgata ccacacccga atacgcctac cgcgttaccc tcgacaaaca     1440
caaccgcctg caatggcacg atcccgccac ccgaaaaacc tacccgaacg aacccgaagc     1500
caaactttgg aaacgcatcg ccgcaaaaat cctatccctg ctgcccatcg aaggtttatt     1560
a                                                                     1561
```

<210> SEQ ID NO 28
<211> LENGTH: 21
<212> TYPE: DNA
<213> ORGANISM: Artificial Sequence
<220> FEATURE:
<223> OTHER INFORMATION: A synthetic primer used in a PCR.

<400> SEQUENCE: 28
tccatgcaag aatctggttt c                                                 21

<210> SEQ ID NO 29
<211> LENGTH: 22
<212> TYPE: DNA
<213> ORGANISM: Artificial Sequence
<220> FEATURE:
<223> OTHER INFORMATION: A synthetic primer used in a PCR.

<400> SEQUENCE: 29
cgacaatgag cacagactca ca                                                22

<210> SEQ ID NO 30
<211> LENGTH: 21
<212> TYPE: DNA
<213> ORGANISM: Artificial Sequence
<220> FEATURE:
<223> OTHER INFORMATION: A synthetic primer used in a PCR.

<400> SEQUENCE: 30
ccttcaggat tctgtccaca a                                                 21

<210> SEQ ID NO 31
<211> LENGTH: 22
<212> TYPE: DNA
<213> ORGANISM: Artificial Sequence
<220> FEATURE:
<223> OTHER INFORMATION: A synthetic primer used in a PCR.

<400> SEQUENCE: 31
cctctctcac aaccaattct tc                                                22

<210> SEQ ID NO 32

-continued

```
<211> LENGTH: 1575
<212> TYPE: DNA
<213> ORGANISM: Neisseria gonorrhoeae 1291

<400> SEQUENCE: 32
atgcatacag accccaaaat acaggcaatg ccgtctgaaa ctatatcccc gatgaaaaca      60
cgcagcctca tttcccttttt atgcctcctt ctctgttcat gttcttcatg gttgccccca     120
ctggaagaac ggacggaaag ccgtcatttc aatacttcca aacctgtcct cctggacaac     180
atcctgcaaa tccggcacac ccctcataac aacgggctat ccgacatcta cctgctcgac     240 gaccccacg aagcccttgc cgcccgcgcc gcccttatcg aatctgccga acacagcctc      300
gatttgcaat actacatttg gcgcaacgac atttccggca ggctgctgtt caacctcatg     360
taccttgccg cagaacgcgg cgtgcgcgta cgcctgctgt tggacgacaa caacacgcgc     420
gggttggacg atctcctgct cgccctcgac agccatccca atatcgaagt gcgcctgttc     480
aaccccttcg tcctacgcaa atggcgcgca ctcggctacc tgaccgactt cccccgcctc     540
aaccgccgca tgcacaacaa atcctttacc gccgacaacc gcgccaccat actcggcgga     600
cgcaatatcg gcgacgaata cttcaaagtc ggtgaggaca ccgttttcgc cgacctggac     660
atcctcgcca ccggcagcgt cgtcggcgaa gtatcgcacg acttcgaccg ctactgggca     720
agccattccg cccacaacgc cacgcgcatc atccgcagcg gcaacatcgg caagggtctt     780
caagcactcg gatacaacga cgaaacatcc agacacgcgc tcctgcgcta ccgcgaaacc     840
gtcgaacagt cgcccctcta ccaaaaaata cagacgggac gcatcgactg gcagagcgtc     900
caaacccgcc tgatcagcga caccctgca aaaggactcg accgcgaccg ccgcaaaccg      960
ccgattgccg ggaggctgca agacgcgctc aaacagcccg aaaaaagcgt ctatctggtt    1020
tcaccctatt tcgtccctac aaaatccggc acagacgcac tggcaaaact ggtgcaggac    1080
ggcatagacg ttaccgtcct gaccaactcg ctacaggcga ccgacgttgc cgccgtccat    1140
tccggctacg tcaaataccg aaaaccgctg ctcaaagccg gcatcaaact ctacgagctg    1200
caacccaacc atgccgtccc cgccacaaaa gacaaaggcc tgaccggcag ctccgtaacc    1260
agcctgcatg ccaaaaacctt cattgtggac ggcaaacgca tcttcatcgg ctcattcaac    1320
ctcgaccccc gttccgcacg gctcaatacc gaaatgggcg tcgtcatcga aagccccaaa    1380
atcgcagaac agatggagcg caccctcgcc gataccacac ccgaatacgc ctaccgcgtt    1440
accctcgaca aacacaaccg cctgcaatgg cacgatcccg ccacccgaaa aacctacccg    1500
aacgaacccg aagccaaact ttggaaacgc atcgccgcaa aaatcctatc cctgctgccc    1560
atcgaaggtt tatta                                                     1575
```

VACCINE AND COMPOSITIONS FOR THE PREVENTION AND TREATMENT OF NEISSERIAL INFECTIONS

CLAIM OF PRIORITY

This application is a continuation-in-part application of U.S. Ser. No. 10/621,184, filed Jul. 15, 2003 now abandonded, which is a continuation-in-part application of U.S. Ser. No. 10/066,551, filed Jan. 31, 2002, which claims benefit under 35 U.S.C. 119(e) from U.S. Provisional Application Ser. No. 60/266,070, filed Jan. 31, 2001; U.S. Provisional Application Ser. No. 60/310,356, filed Aug. 6, 2001; and U.S. Provisional Application Ser. No. 60/344,452, filed Oct. 23, 2001; all of which are incorporated herein by reference.

The invention was made with the support of NIH Grant No. 5UI9 AI43924 and AI 43924-05. The U.S. government has certain rights in the invention.

BACKGROUND OF THE INVENTION

*Neisseria gonorrhoeae* is the causative agent of the disease gonorrhea. Approximately 300,000 women a year contract gonorrhea in the U.S. Worldwide, the number of women with this infection is in the millions. It is a major cause of infertility and pelvic inflammatory disease. It is also a major co-factor in the spread of HIV1.

In men, gonococcal infection develops as an acute urethritis that is typically characterized by a purulent discharge that results as a consequence of the concurrent inflammatory response to infection. In women, gonococcal infection can develop as an ascending infection of the genital tract that can lead to an acute pelvic inflammatory disease, infertility, or ectopic pregnancy. High proportions of women, however, initially develop asymptomatic gonococcal infections, in contrast to *N. gonorrhoeae* infection in men.

The mechanisms by which the gonococcus infects and invades the female genital tract are only beginning to be understood. Research has shown that gonococci are capable of invading primary human epithelial cells derived from both the endo- and the ectocervix. These studies implied that the mechanism(s) used by the gonococcus to breech the cervical epithelium are distinct from those mechanisms used to invade the urethral epithelium of men and that several endocytic mechanisms appear to play a role in gonococcal invasion of the female genital tract.

*Neisseria meningitidis* is one of the leading causes of bacterial meningitis worldwide, affecting mainly children and young adults. The genomic sequence of *Neisseria meningitidis* B and *Neisseria meningitidis* A has been published (see, for example, Tettelin et al., *Science*, 287, 1809–1815 (2000) and Parkhill et al., *Nature*, 404, 502–506 (2000), respectively). The rapid progression of meningococcal disease makes proper diagnosis and subsequent treatment often vital to the survival of infected individuals. If not properly diagnosed and treated, meningococcal infections can lead to shock and death within a matter of hours. Thus, better prevention, diagnosis and treatment of meningococcal infections would be invaluable.

Currently there is no vaccine for the prevention of gonorrhea or for the treatment of meningococcal meningitis. Therefore, there is a need for an effective means to prevent or ameliorate neisserial infections.

SUMMARY OF THE INVENTION

The present invention provides a polypeptide, polynucleotide, vaccine, and a method of vaccination effective to immunize a mammal against a neisserial infection, e.g., an infection caused by *Neisseria gonorrhoeae* or *Neisseria meningitidis*. Such immunization can prevent, ameliorate or reduce the incidence of gonorrhea and/or meningococcal infection in a human. The vaccine contains an immunogenic amount of a neisserial phospholipase D (PLD) polypeptide in combination with a physiologically-acceptable, non-toxic vehicle. Examples of neisserial PLD include gonococcal PLDs, such as SEQ ID NO:4, SEQ ID NO:14, SEQ ID NO:16 and SEQ ID NO:18, and meningococcal PLD such as SEQ ID NO:20.

In addition, the invention provides a transgenic *Neisseria* bacterium comprising a disrupted pld gene wherein the bacterium has reduced phospholipase D activity as compared to the phospholipase D activity of a corresponding wild-type *Neisseria*. In one embodiment of the invention, the transgenic *Neisseria* bacterium is *N. gonorrhoeae*, e.g., *N. gonorrhoeae* strain 1291, *N. gonorrhoeae* strain FA1090, or *N. gonorrhoeae* strain MS11. In another embodiment of the invention, the transgenic *Neisseria* bacterium is *N. meningitidis*, e.g., a *N. meningitidis* encapsulated strain or a *N. meningitidis* acapsular mutant strain.

The pld gene of a transgenic bacterium of the invention can be disrupted by mutagenesis, for example, by insertion mutagenesis, deletion mutagenesis, substitution mutagenesis, or a combination thereof. Such a transgenic bacterium may have reduced amounts of phosphatidic acid and choline as compared to a corresponding wild-type *Neisseria*. In one embodiment of the invention, the transgenic bacterium has reduced toxicity as compared to a corresponding wild-type *Neisseria*.

As an example, the pld gene of the transgenic bacterium comprises a nucleic acid sequence such as SEQ ID NO:9, SEQ ID NO:13, SEQ ID NO:15, SEQ ID NO:17, SEQ ID NO:19, or SEQ ID NO:32.

Also provided herein is an isolated and purified polynucleotide comprising a pld gene from a *Neisseria* bacterium. In one embodiment, the polynucleotide is a *N. gonorrhoeae* sequence, e.g., SEQ ID NO:9, SEQ ID NO:13, SEQ ID NO:15, SEQ ID NO:17 or SEQ ID NO:32. In another embodiment, the polynucleotide is a *N. meningitidis* sequence, e.g., SEQ ID NO:19.

The invention provides an isolated and purified polypeptide encoded by a nucleic acid sequence that is SEQ ID NO:9, SEQ ID NO:13, SEQ ID NO:15, SEQ ID NO:17, SEQ ID NO:19 or SEQ ID NO:32.

In addition, the invention provides an isolated and purified polypeptide comprising phospholipase D from a *Neisseria* bacterium, such as polypeptides including SEQ ID NO:4, SEQ ID NO:14, SEQ ID NO:16, SEQ ID NO:18 or SEQ ID NO:20.

The invention provides a vaccine comprising an immunogenic amount of a PLD polypeptide from *Neisseria*, for example, a polypeptide encoded by SEQ ID NO:9, SEQ ID NO:13, SEQ ID NO:15, SEQ ID NO:17, SEQ ID NO:19 or SEQ ID NO:32, which amount is effective to immunize a patient against a neisserial infection, in combination with a physiologically-acceptable, non-toxic vehicle. A vaccine of the invention may also include an effective amount of an immunological adjuvant. In one embodiment, the PLD polypeptide is conjugated or linked to a second peptide. In another embodiment, the PLD polypeptide is conjugated or linked to a polysaccharide.

The invention also provides a method of protecting a patient against *Neisseria* colonization or infection, for example, a *Neisseria gonorrhoeae* and/or *Neisseria meningitidis* colonization or infection, comprising administering to the patient an effective amount of a vaccine comprising an immunogenic amount of a PLD polypeptide from *Neisseria*, which amount is effective to immunize a susceptible patient against a neisserial infection, in combination with a physiologically-acceptable, non-toxic vehicle. For example, the PLD polypeptide may be encoded by a polynucleotide comprising SEQ ID NO:9, SEQ ID NO:13, SEQ ID NO:15, SEQ ID NO:17, SEQ ID NO:19 or SEQ ID NO:32. Such a vaccine may also contain an immunological adjuvant. The PLD can also be conjugated or linked to a second peptide or a polysaccharide. The vaccine can be administered orally, mucosally or by subcutaneous or intramuscular injection.

Also provided is a method of preventing infection or colonization of *Neisseria* in a patient, e.g., *Neisseria gonorrhoeae* and/or *Neisseria meningitidis*, by administering to the patient a compound that inhibits bacterial phospholipase D, e.g., neisserial PLD. In one embodiment, the compound is an antibody specific for a neisserial PLD.

Also provided is an anti-neisserial PLD antibody.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1. Anti-CR3 antibodies inhibit gonococcal attachment and invasion of CR3-transfected CHO cells. CHO-CR3 cell monolayers were pretreated with antibodies to the CR3 alpha subunit CD11b (H5A4, Bear1) or CD18 (anti-CD18, IB4) or anti-CD18 antibody and an anti-CD18 blocking peptide as outlined in the text. Antibody-treated cell monolayers were challenged for two hours with gonococci prior to gentamicin addition, cervical cell lysis, and plating of serial dilutions to determine colony-forming units. Gentamicin treatment was omitted from attachment assays. Percent inhibition was determined as a normalized function of the ability of gonococci to adhere to or invade CHO-CR3 cells in the absence of antibody. Values given are the mean values of at least three trials. A Kruskal-Wallis analysis of variance was used to determine the statistical significance of the invasion assays. ρ-values were less than 0.05 for all of the antibodies tested alone.

FIG. 2. Anti-CR3 antibodies inhibit gonococcal invasion of primary cervical cells. Invasion of primary, human, ecto- and endocervical cell monolayers by gonococci was performed as outlined in the text. Antibodies H5A4 and Bear1 recognize the CR3 alpha subunit, CD11b. Anti-CD18 and IB4 are specific for the CR3 beta subunit, CD18. Inhibition of invasion was determined as a normalized function of the ability of gonococci to invade primary ecto- and endocervical cells in the absence of antibody. Values given are the mean values of at least three trials. A Kruskal-Wallis analysis of variance was used to determine the statistical significance of the invasion assays. ρ-values were less than 0.05 for all of the antibodies tested.

FIG. 3. The effect of *Clostridium* C3 neurotoxin on the invasion of primary cervical cells by *N. gonorrhoeae*. The ability of gonococci to invade primary ecto- and endocervical cells was determined as outlined in the text. Invasion was determined as a proportion of the original infection inoculum. Values given are the mean values of three trials. A Kruskal-Wallis analysis of variance was used to determine the statistical significance of percent invasion with C3 toxin in comparison to percent invasion without C3 toxin treatment. ρ-values were 0.05 for each assay.

FIG. 4. Laser scanning confocal microscopy (LSCM) demonstrates that the characteristic cytokeratin staining pattern of the tissue biopsies has been retained in the respective primary cervical epithelial cell cultures. Sectioned tissue biopsies and primary cervical epithelial cell monolayers were incubated with a FITC-conjugated antibody to the noted specific cytokeratin. Ethidium bromide was used to counter-stain the tissue sections. Endocervical cells labeled intensely with antibody 8.12, which is specific for type I cytokeratins 13, 15, and 16 (panel A). The labeling of endocervical cells with an antibody specific for type II cytokeratin 4 (panel C) was considerably less intense, and it was not uniformly distributed. Ectocervical cells labeled positive with an antibody specific for cytokeratins 13, 15, and 16 (panel B) and cytokeratin 4 (panel D).

FIG. 5. Scanning electron microscopy (SEM) analysis shows the predominant changes that occur in the cervical cell membrane over the course of a three hour infection as the result of cervical epithelial cell-gonococcal interactions. At early (0 to 60 minutes) phases of infection *N. gonorrhoeae* could be found on the surface of endocervical cells either associated with microvilli (A) or undergoing an endocytic process (B). As the infection process continued, microvilli appeared to acquire directionality. Filopodia/lamellipodia became evident after thirty minutes post infection (C). Bacteria appeared to be in the process of internalization (D). Loss of microvilli with a smoothing of the cervical cell membrane around the periphery of some sites of gonococcal infection also became evident at approximately thirty minutes post infection (E). Membrane ruffles (F, endocervical; G, ectocervical) appeared at sixty minutes, and they became prevalent at ninety minutes post infection. Ruffles could be induced to occur at approximately thirty minutes post infection with use of a primed infection inoculum (see Example 1) (G). A visible smoothing of the cervical cell membrane encircling membrane ruffles can be seen (H). By three hours post infection large ruffles could readily be observed.

FIG. 6. Bright-field light microscopy (BFLM) and immuno-transmission electron microscopy (TEM) studies demonstrate ruffling of the cervical surface and invasion of the primary cervical epithelial cells at ninety minutes and three hours post infection. For TEM analysis, bacteria were labeled with an antibody specific to the gonococcal surface protein, H.8; cervical cells were labeled with a polyclonal antibody to actin. 30 nm and 10 nm gold bead antibody-conjugates were used to label the bacteria- and host-specific primary antibodies, respectively. Membrane protrusions can be seen that are labeled with actin and that are encompassing gonococci at ninety minutes after the onset of infection (A). Bacteria can also be seen entering the cervical cell as individual entities in actin-lined, spacious vacuoles (B). Large membrane ruffles can be seen associating with gonococci at three hours post infection C and D). For BFLM (D) thick (1 μm) paraffin sections of endocervical cells were stained with hematoxylin and eosin. Arrows denote bacteria. Bar=2 μm.

FIG. 7. This figure shows TEM studies of cervical biopsies from women with gonococcal cervicitis. Panels A and B demonstrate cytoskeletal changes and membrane ruffling occur during naturally acquired gonococcal infection. Panel A and panel B show large and small membrane protrusions associated with gonococci (designated by arrows) that are similar to those seen in FIG. 6.

FIG. 8. Differential interference contrast (DIC) and LSCM analysis demonstrate co-localization of *N. gonorrhoeae* 1291-green with a concentrated accumulation of the actin-associated protein, vinculin. In panel A, vinculin was immunolabeled with a TRITC-conjugated antibody and in a colored version of this figure was visible as a red fluorescence (A); in panel B, bacteria were transformed with green fluorescent protein (GFP) and in a colored version of this figure were visible as a green fluorescence. (C) In a merged image of panels A and B, arrows denote co-localization of bacteria with vinculin, which was visualized in a colored version of this figure as a yellow-orange because of the combined signal of the individual fluorophores. (D) Merged LSCM and DIC image (of the ectocervical cells). Similar results were seen with endocervical cells and for the actin-associated proteins ezrin and myosin, but the focal accumulation of a-actinin and talin was less pronounced. No accumulation of actin-associated proteins was observed in uninfected (control) cervical epithelial cells. Magnification, ×20.

FIG. 9. *Neisseria gonorrhoeae* co-localizes with CR3 in vivo. Cryosections of a clinical biopsy derived from a women with documented gonococcal cervicitis were immunolabeled with anti-CD18 (visible as a green fluorescence) and 2C3 (specific for gonococcal H.8 outer membrane protein, visible as a red fluorescence) antibodies. Co-localization of CR3 with gonococci occurs as a yellow fluorescence because of the combined signal of the two fluorophores. A) 63× oil B) 5× zoom image of the area designated by the white box in A. Co-localization is confirmed as a profile plot of the area designated by the red line where the individual fluorescence of each fluorophore is recorded and plotted, individually, by the viewing system. C) Areas of confirmed co-localization are observed where the peaks of the lines of the graph overlap.

FIG. 10. Bacterial products that are released with gonococcal infection.

FIG. 11. Proteomic analysis of gonococcal products released upon infection of primary cervical epithelia.

Figure 14:
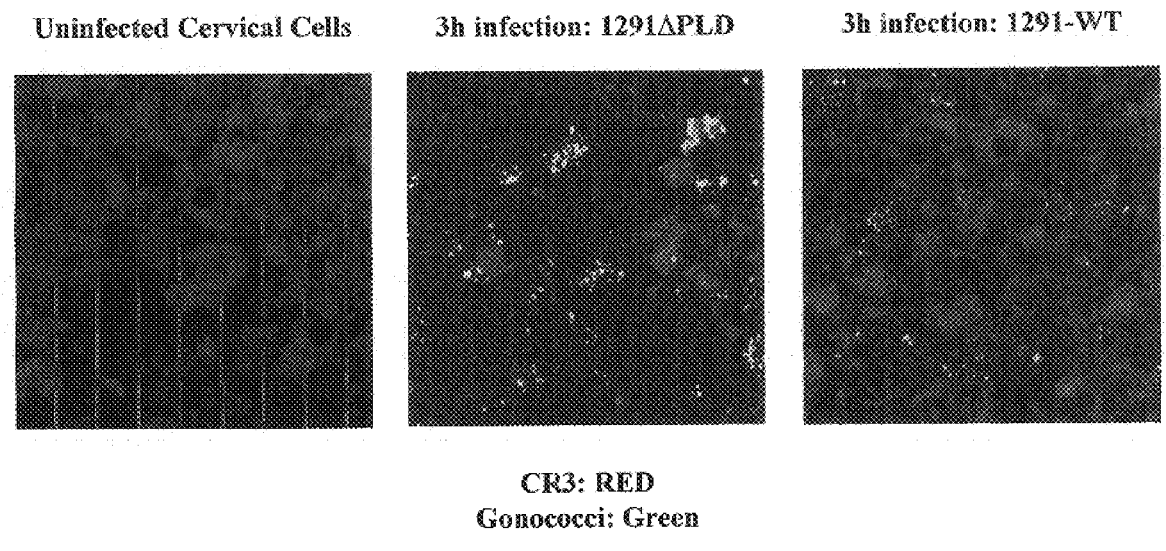

FIG. 14 depicts photographs from confocal microscopy showing that PLD-deficient gonococci are impaired in their ability to elicit increased levels of CR3 surface expression on primary cervical cells. CR3 (CD18, CR3 β-subunit) was immunolabeled with a TRITC-conjugated antibody and is visible as a red fluorescence; gonococci were immunolabeled with an antibody to the highly conserved outer membrane protein, H.8. Application of a FITC-conjugated secondary antibody allowed visualization of gonococci as a green fluorescence. Co-localization of CR3 with gonococci occurs as a yellow fluorescence because of the combined signal of the two fluorophores. Magnification 60×.

Figure 15:
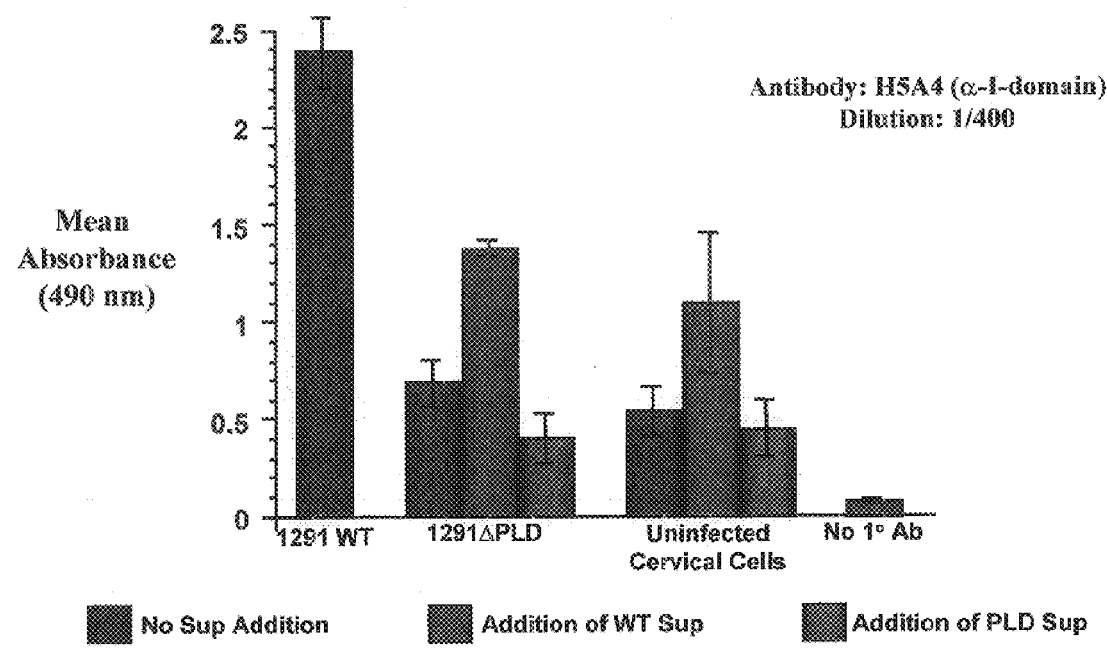

FIG. 15 depicts histograms showing surface level expression of CR3 on primary cervical cells. Wild-type gonococci cells (1291-WT), but not PLD-deficient gonococci (1291ΔPLD) elicit increased levels of CR3 surface expression. The antibody used was H5A4 (α-I-domain) diluted 1/400.

Figure 16:
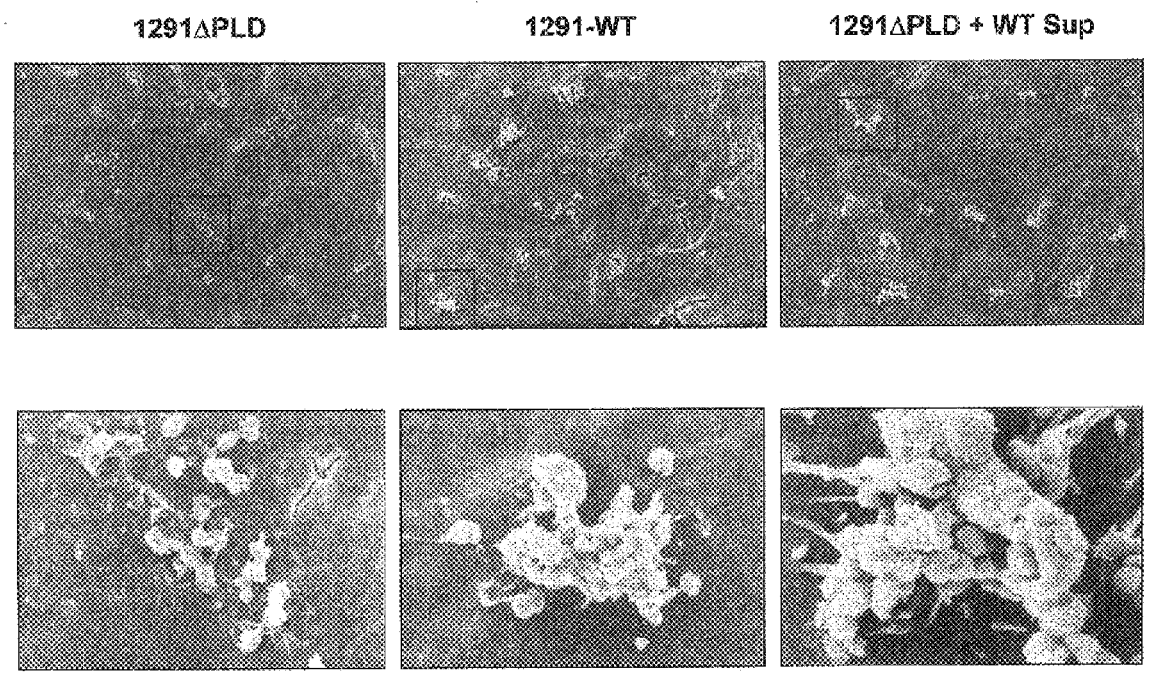

FIG. 16. To determine if gonococcal PLD plays a role in the cytoskeletal rearrangements leading to membrane ruffling of the cervical epithelium, scanning electron microscopy (SEM) was performed. SEM analysis demonstrated that aberrant cytoskeletal rearrangements occur upon infection of cervical epithelia with PLD-mutant gonococci when compared to infection with wild-type gonococci. Endocytosis mediated by CR3 requires receptor clustering. The absence of bacterial clusters in electrographs taken of mutant gonococci at 3 hours post-infection (upper panel) may be reflective of the inability of these bacteria to elicit up-regulation of CR3 or of their inability to initiate signaling cascades required for CR3 clustering. Similarly, the absence of membrane ruffles (lower panel) in PLD infected cells suggests gonococcal PLD may be required to potentiate the cytoskeletal rearrangements required to form membrane ruffles. These processes are restored when assays are performed with PLD-mutant gonococci in the presence of primed wild-type supernatants. No observable differences between mutant or wild-type gonococci were noted in the ability of gonococci to interact with each other or with cervical cells at earlier points of infection. Electrographs shown in the lower panel correspond to the respective boxed areas shown in the upper panel. Magnification: A)×1 k, B)×1.1 k C)800 k D)×9 k, E)×10 k, and F)×15 k.

Figure 17:
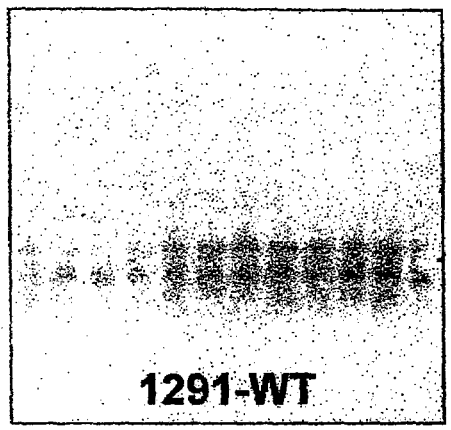
Figure 17:
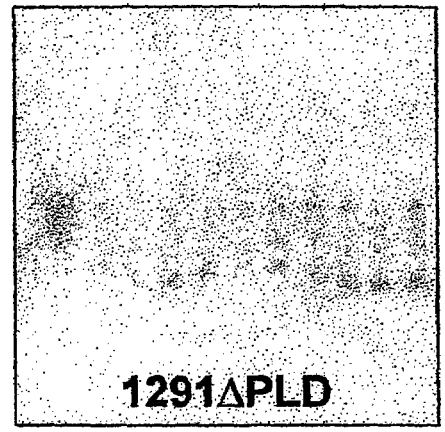
Figure 17:
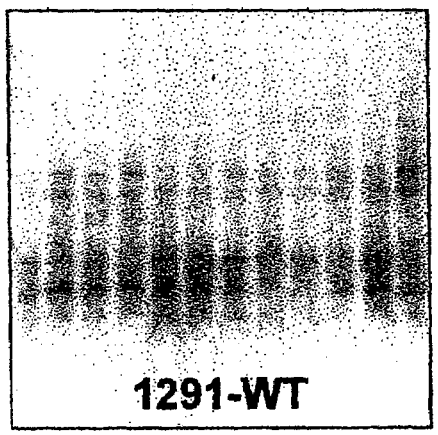
Figure 17:
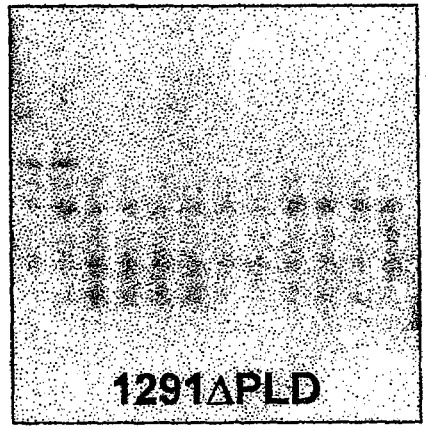

FIG. 17 depicts Western blots of primary cervical cells infected with wild-type gonococci (1291-WT) (A, C) and PLD-deficient gonococci (1291ΔPLD) (B, D). Cervical cell lysates were harvested at variable times post-infection (A and C: lane 1 (0 minutes), lane 2 (five minutes), lane 3 (10 minutes), lane 4 (15 minutes), lane 5 (30 minutes), lane 6 (45 minutes), lane 7 (60 minutes), lane 8 (90 minutes), lane 9 (2 hours), lane 10 (2.5 hours), lane 11 (3 hours), lane 12 (4 hours); B and D: lane 1 (4 hours), lane 2 (3 hours), lane 3 (2.5 hours), lane 4 (2 hours), lane 5 (90 minutes), lane 6 (60 minutes), lane 7 (45 minutes), lane 8 (30 minutes), lane 9 (15 minutes), lane 10 (10 minutes), lane 11 (five minutes), lane 12 (0 minutes)). Blots were probed with antibodies specific for phosphorylated tyrosine (A, B) or threonine target residues (C, D).

Figure 18:
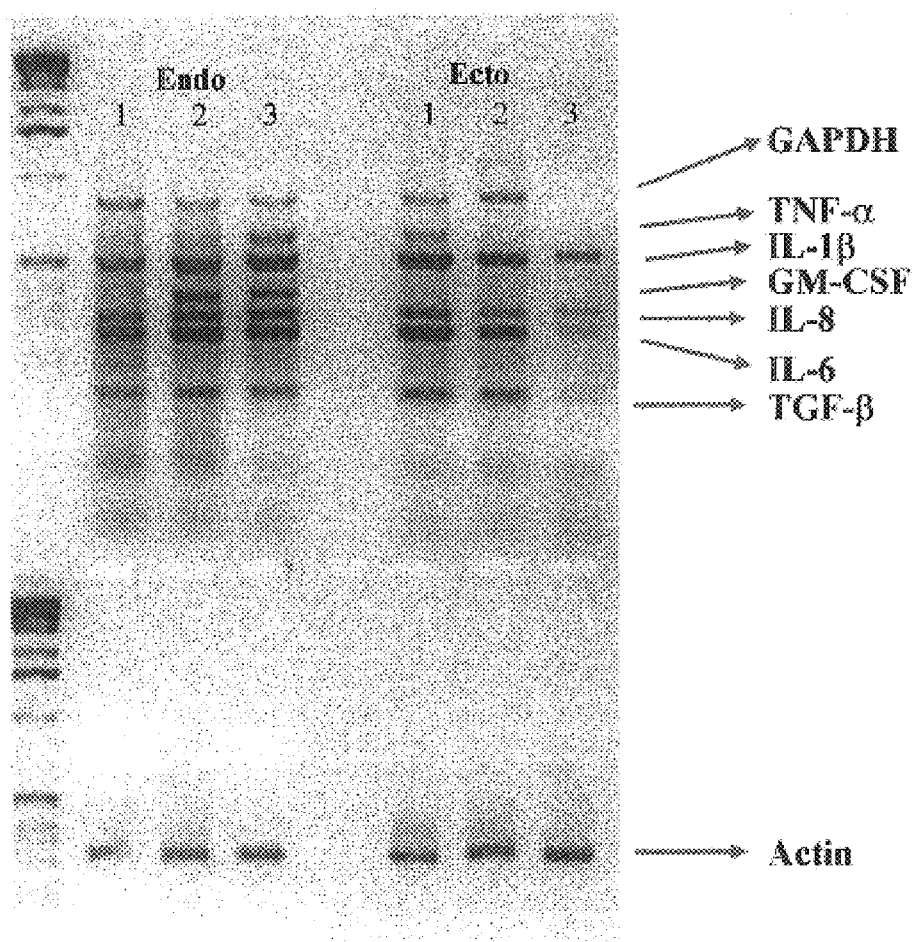

FIG. 18 depicts multiplex RT-PCR for analysis of cytokine cDNA in primary human cervical cells. Lane 1 is DNA from uninfected primary cells (endo- or ectocervical (as noted)); lane 2 is primary cells infected with wild-type gonoccocal cells (1291) and lane 3 is primary cells (endo- or ectocervical (as noted)) infected with PLD-deficient gonoccocal cells (1291 PLD mutant).

Figure 19:
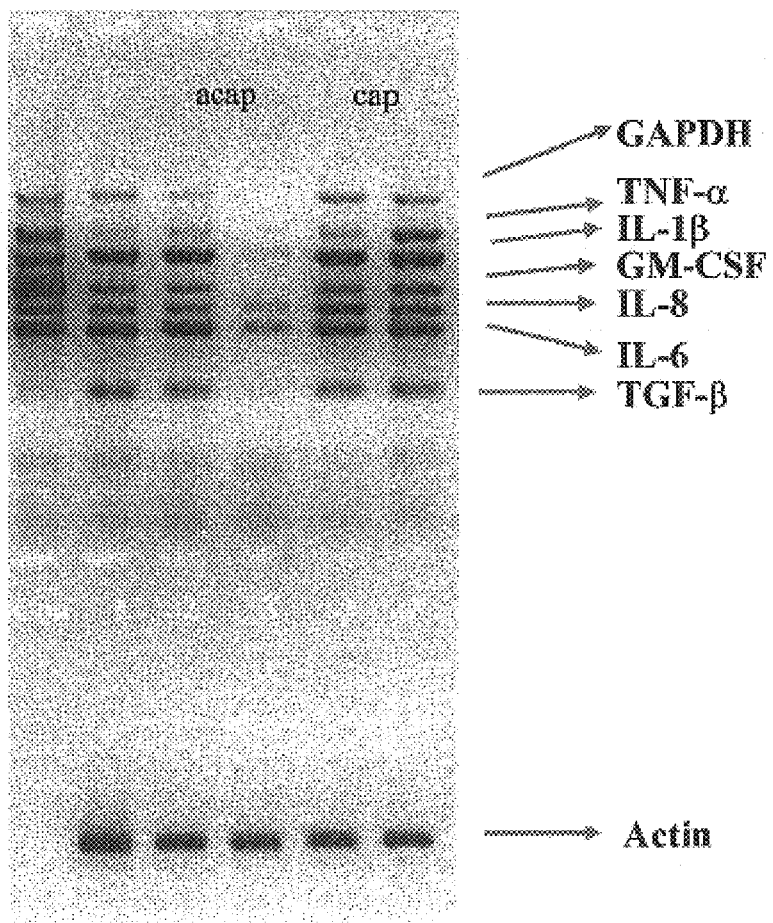

FIG. 19 depicts multiplex RT-PCR for cytokine cDNA analysis in secondary bronchial epithelial cells. Lane 1 is DNA from uninfected bronchial epithelial cells; lane 2 is bronchial epithelial cells infected with wild-type *Neisseria meningitidis* type B (NMB WT) and lane 3 is bronchial epithelial cells infected with PLD-deficient *Neisseria meningitidis* type B (NMB PLD mutant).

Figure 20:
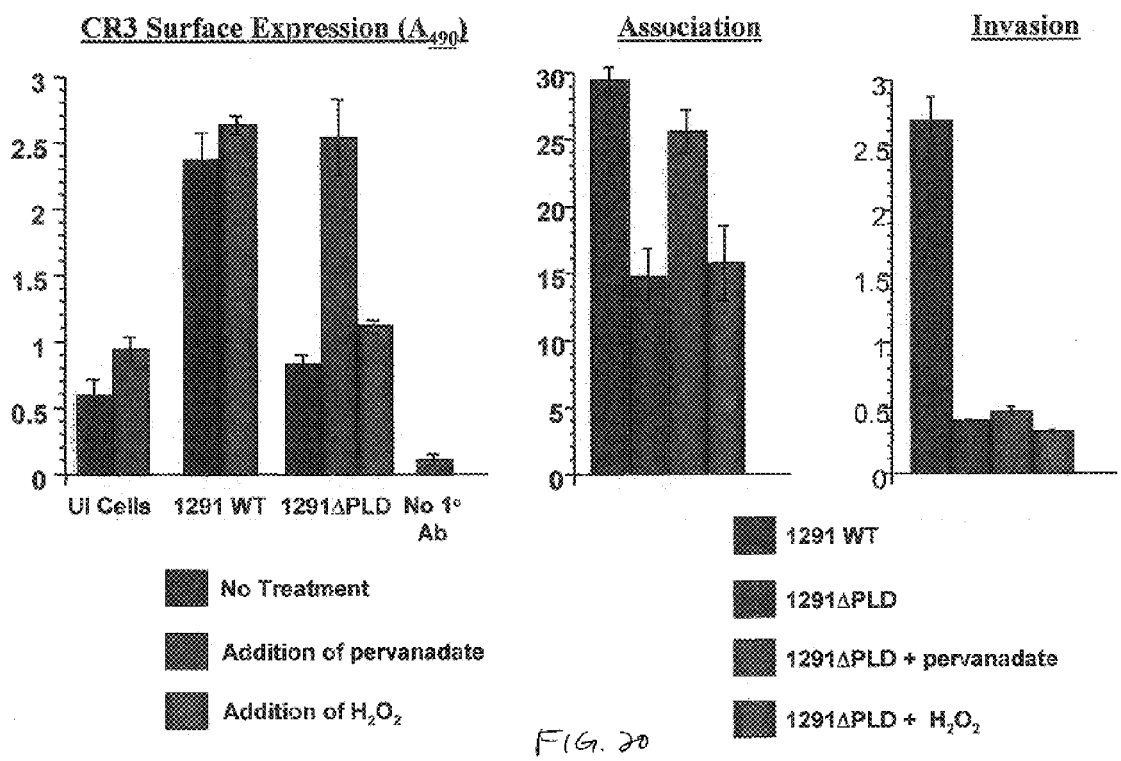

FIG. 20 depicts histograms showing that tyrosine kinase activation partially rescues phenotypic PLD-deficiency observed with *N. gonorrhoeae* infection of primary cervical cells.

Figure 21:
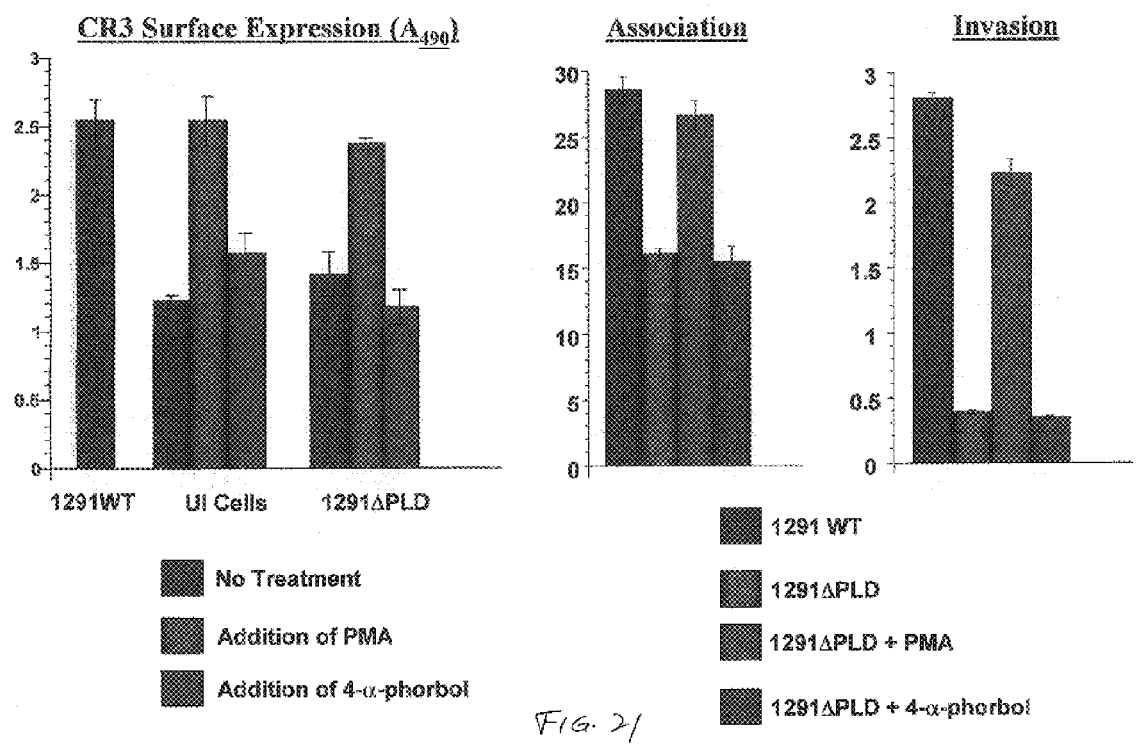

FIG. 21 depicts histograms showing that protein kinase C activation rescues phenotypic PLD-deficiency observed with *N. gonorrhoeae* infection of primary cervical cells.

Figure 22:
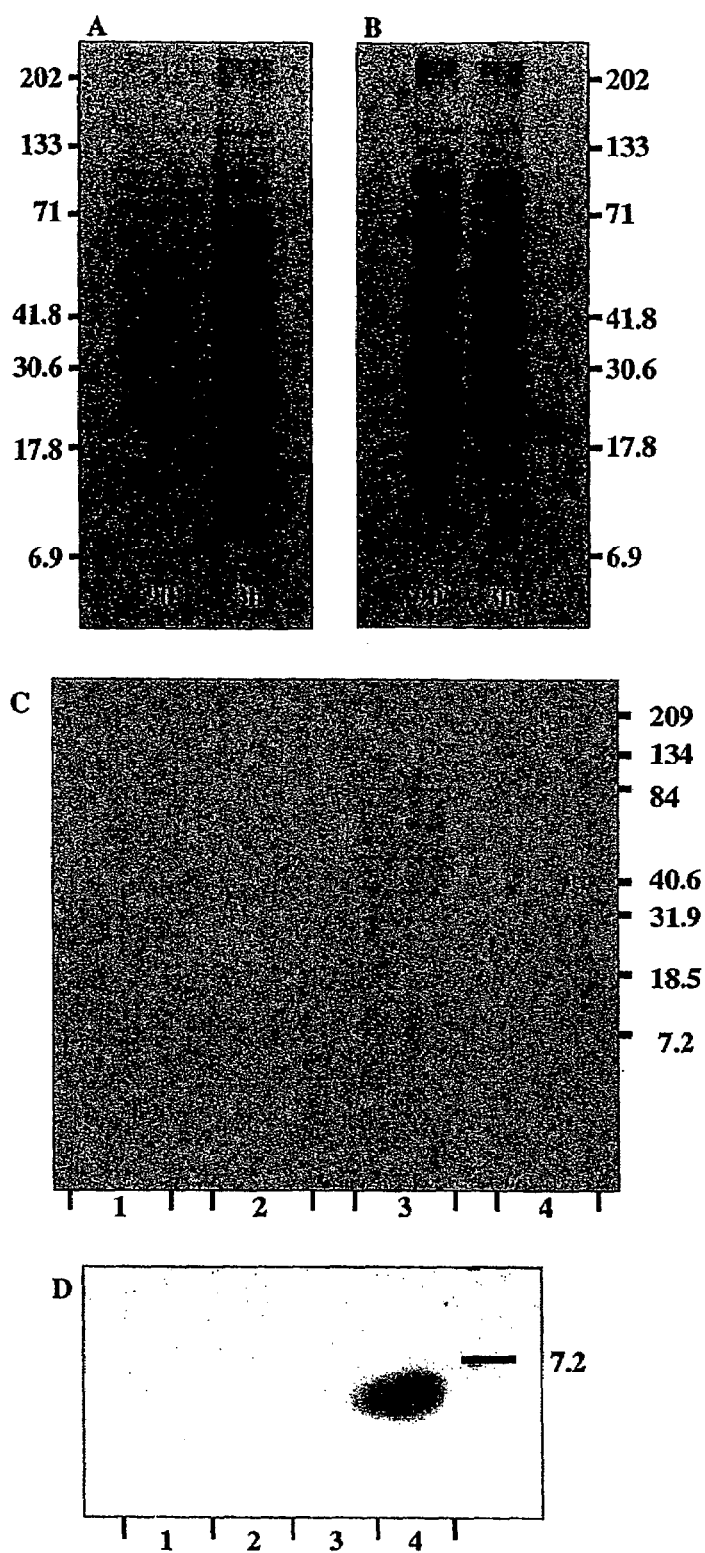

FIG. 22 shows that gonococcal products released with cervical cell infection are not released with infection of male urethral cells. Analysis of infection supernatants demonstrated that gonococcal products are released upon infection of cervical epithelia. Similar results are observed upon analysis of supernatants obtained from 90 minute and 3 hour infections, from pex (A) and pen (B) cells, and from these same cells obtained from different tissue donors. An identical protein pattern is observed with *N. gonorrhoeae* strains 1291 (shown), FA1090, or MS11 indicating protein release is not strain-dependent. To determine if gonococcal proteins released upon cervical infection were specific to cervical cell invasion, these studies were repeated using male urethral epithelial cells. Autoradiography revealed that, while a minimal amount of protein products is released by 90 minutes post-infection, these proteins are not present by 3 hours of infection of uec (C). Collectively, these data suggest that a small basal level of gonococcal products are released constitutively, but, also that the continued release of gonococcal products was specific to gonococcal cervicitis. Western Blot analysis failed to reveal the presence of gonococcal LOS in culture supernatants, indicating the protein products identified were not present as the result of bacterial lysis (D). These data demonstrate the exquisite ability of the gonococcus to sense its extracellular environment and modify its pathogenicity accordingly. Lanes: C1) gonococci incubated in tissue culture dishes devoid of cervical cells, C2) uninfected cervical cells, C3) 90 minutes infection of uec, C4) 3 hours infection of uec, D1) 3 hours infection of pen cells, D2) 90 minutes infection of pen, D3) uninfected pen cells, and D4) *N. gonorrhoeae* LOS.

Figure 23:
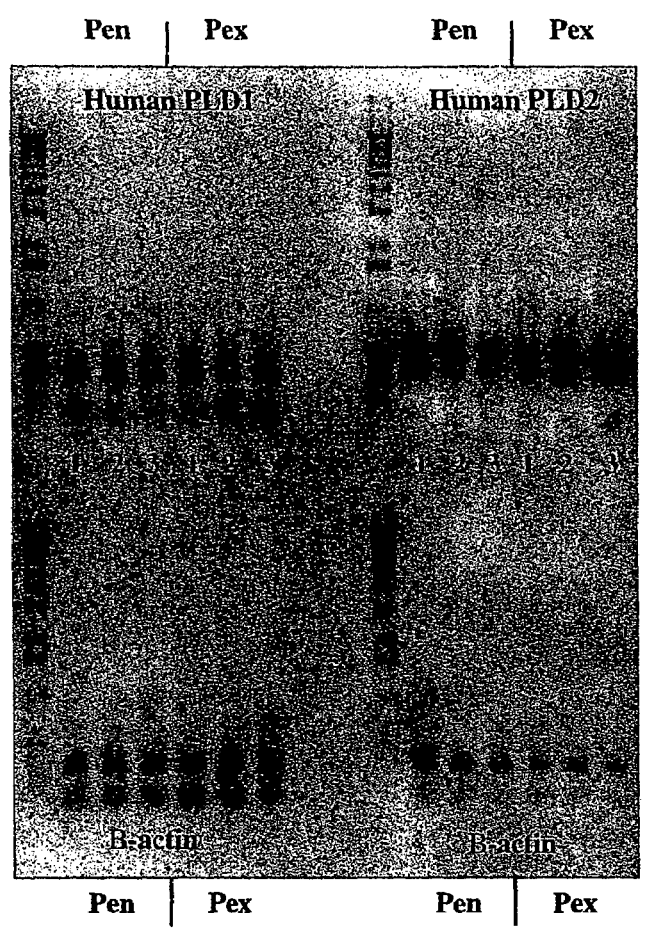

FIG. 23. RT-PCR analysis demonstrates that endogenous cervical cell PLD activity does not account for the observed increased in total PLD activity in gonococci infected cervical cell. Lanes: 1) uninfected pex or pen cells, 2) 3 hours infection of pex or pen cells with wild-type *N. gonorrhoeae* strain 1291, and 3) 3 hours infection of pex or pen cells with *N. gonorrhoeae* strain 1291ΔPLD.

DETAILED DESCRIPTION OF THE INVENTION

Definitions

As used herein, "disrupted pld gene" or "disrupted gene" refers to an insertion, substitution, or deletion either in the gene encoding phospholipase D or in the vicinity of the gene, i.e., upstream (5') or downstream (3') of the gene, which results in the reduction of the biological activity or the loss of substantially all of the biological activity associated with the gene's product. For example, a disrupted pld gene would be unable to express a protein having substantial phospholipase D activity. By disrupting a neisserial pld gene, neisserial phospholipase D synthesis and/or function, e.g., enzymatic activity related to PLD such as the catalysis of phospholipase D-related hydrolysis and/or phosphatidyltransferase reactions, is reduced, e.g., inhibited, as compared to wild-type biological activity. Methods for measuring PLD activity are known in the art. The synthesis and/or function of a pld gene can be inhibited by any one of a number of methods known to the art, for example, by administration of chemical inhibitors of protein synthesis, by site-directed mutagenesis, by antisense methodology or using siRNA techniques. For example, PLD synthesis and/or function can be inhibited by the "disruption" of a gene encoding a neisserial PLD, e.g., by insertion, substitution and/or deletion, in the pld gene or in a gene in the vicinity, i.e., either upstream (5') or downstream (3') of the pld gene, which results in the reduction of the biological activity or the loss of substantially all of the biological activity associated with the gene's product.

As used herein, the term "neisserial PLD" includes homologs, variants or biologically active or inactive fragments of PLD from any *Neisserial* spp., e.g., *N. gonorrhoeae* or PLD from *N. meningitidis*. A "variant" of the polypeptide is a neisserial protein that is not completely identical to a native neisserial protein. A variant neisserial protein can be obtained by altering the amino acid sequence by insertion, deletion or substitution of one or more amino acid. The amino acid sequence of the protein is modified, for example by substitution, to create a polypeptide having substantially the same or improved qualities as compared to the native (i.e., wild type) polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains. Stryer, L. *Biochemistry* (2d edition) W. H. Freeman and Co. San Francisco (1981), p. 14–15; Lehninger, A. *Biochemistry* (2d ed., 1975), p. 73–75.

It is known that variant polypeptides can be obtained based on substituting certain amino acids for other amino acids in the polypeptide structure in order to modify or improve biological activity. For example, through substitution of alternative amino acids, small conformational changes may be conferred upon a polypeptide that result in increased bioactivity. Alternatively, amino acid substitutions in certain polypeptides may be used to provide residues that may then be linked to other molecules to provide peptide-molecule conjugates that retain sufficient properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated in intended for use in immunological embodiments. The greatest local average hydrophilicity of a protein, as governed by the hydrophilicity of its adjacent amino acids, correlates with its immunogenicity. U.S. Pat. No. 4,554,101. Accordingly, it is noted that substitutions can be made based on the hydrophilicity assigned to each amino acid. In using either the hydrophilicity index or hydropathic index, which assigns values to each amino acid, substitutions may be conducted, for example, where these values are ±2, ±1 or ±0.5.

The variant neisserial protein comprises at least seven amino acid residues, preferably about 20 to about 2000 residues, and more preferably about 50 to about 1000 residues, and even more preferably about 80 to about 200 residues, wherein the variant neisserial protein has at least 50%, preferably at least about 80%, and more preferably at least about 90% but less than 100%, contiguous amino acid sequence homology or identity to the amino acid sequence of a corresponding native neisserial protein.

The amino acid sequence of the variant neisserial protein corresponds essentially to the native neisserial protein amino acid sequence. As used herein "correspond essentially to" refers to a polypeptide sequence that will elicit a protective immunological response substantially the same as the response generated by native neisserial protein. Such a response may be at least 60% of the level generated by native neisserial protein, and may even be at least 80% of the level generated by native neisserial protein. An immunological response to a composition or vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest.

A variant of the invention may include amino acid residues not present in the corresponding native neisserial protein, or may include deletions relative to the corresponding native neisserial protein. A variant may also be a truncated "fragment" as compared to the corresponding native neisserial protein, i.e., only a portion of a full-length protein. Neisserial protein variants also include peptides having at least one D-amino acid.

The neisserial protein of the present invention may be expressed from an isolated nucleic acid (DNA or RNA) sequence encoding the neisserial protein. Amino acid changes from the native to the variant neisserial protein may be achieved by changing the codons of the corresponding nucleic acid sequence. "Recombinant" is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence. The terms "protein," "peptide" and "polypeptide" are used interchangeably herein.

The neisserial protein as described above may be operably linked to an amino acid sequence for a therapeutic agent. An amino acid or nucleic acid is "operably linked" when it is placed into a functional relationship with another amino acid or nucleic acid sequence. For example, DNA a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the amino acid or nucleic acid sequences being linked are contiguous, and, in the case of a secretory leader in DNA, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucl. Acids Res.*, 19:508 (1991); Ohtsuka et al., *JBC*, 260:2605 (1985); Rossolini et al., *Mol. Cell. Probes*, 8:91 (1994)). A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid", "nucleic acid molecule", "nucleic acid fragment", "nucleic acid sequence or segment", or "polynucleotide" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

The term "chimeric" refers to any gene or DNA that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, DNA that is either heterologous or homologous to the DNA of a particular cell to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

The terms "protein," "peptide" and "polypeptide" are used interchangeably herein.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis which encode the native protein, as well as those that encode a polypeptide having amino acid substitutions.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell (2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Wild-type" refers to the native gene or organism as found in nature.

"Genome" refers to the complete genetic material of an organism.

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., *Mol. Biotech.*, 3:225 (1995).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene or a transgene in cells. For example, in the case of antisense constructs, expression may refer to the transcription of the antisense DNA only. In addition, expression refers to the transcription and stable accumulation of sense (mRNA) or functional RNA. Expression may also refer to the production of protein.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller, *CABIOS*, 4:11 (1988); the local homology algorithm of Smith et al., *Adv. Appl. Math.*, 2:482 (1981); the homology alignment algorithm of Needleman and Wunsch, *JMB*, 48:443 (1970); the search-for-similarity-method of Pearson and Lipman, *Proc. Natl. Acad. Sci. USA*, 85:2444 (1988); the algorithm of Karlin and Altschul, *Proc. Natl. Acad. Sci. USA*, 87:2264 (1990), modified as in Karlin and Altschul, *Proc. Natl. Acad. Sci. USA*, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., *Gene*, 73:237 (1988); Higgins et al., *CABIOS*, 5:151 (1989); Corpet et al., *Nucl. Acids Res.*, 16:10881 (1988); Huang et al., *CABIOS*, 8:155 (1992); and Pearson et al., *Meth. Mol. Biol.*, 24:307 (1994). The ALIGN program is based on the algorithm of Myers and Miller, supra. The BLAST programs of Altschul et al., *JMB*, 215: 403 (1990); *Nucl. Acids Res.*, 25:3389 (1990), are based on the algorithm of Karlin and Altschul supra.

Software for performing BLAST analyses is publicly available through the National Center for Biotechnology Information on the World Wide Web cnbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., *Nucleic Acids Res.* 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the World Wide Web (cnbi.nlm.nih.gov) http://www.ncbi.nlm.nih.gov. Alignment may also be performed manually by inspection.

For purposes of the present invention, comparison of nucleotide sequences for determination of percent sequence identity to the promoter sequences disclosed herein can be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the BlastN program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared.

When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration can be increased so that a higher temperature can be used. An extensive guide to the hybridization of nucleic acids is found in Tijssen, Laboratory Techniques in Biochemistry and Molecular Biology Hybridization with Nucleic Acid Probes, part I chapter 2 "Overview of principles of hybridization and the strategy of nucleic acid probe assays" Elsevier, New York (1993). Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.5 M, for example, about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 MNaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, Proc. Natl. Acad. Sci. USA, 82:488 (1985); Kunkel et al., Meth. Enzymol., 154:367 (1987); U.S. Pat. No. 4,873,192; Walker and Gaastra, Techniques in Mol. Biol. (MacMillan Publishing Co. (1983), and the references cited therein. Guidance as to appropriate amino acid substitutions that do not affect biological activity of the protein of interest may be found in the model of Dayhoff et al., Atlas of Protein Sequence and Structure (Natl. Biomed. Res.

Found. 1978). In one embodiment of the invention, conservative substitutions, such as exchanging one amino acid with another having similar properties, are made.

Thus, the genes and nucleotide sequences of the invention include both the naturally occurring sequences as well as mutant forms. Likewise, the polypeptides of the invention encompass both naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome generally known in the art and are disclosed in Sambrook et al., *Molecular Cloning: A Laboratory Manual* (2d ed., Cold Spring Harbor Laboratory Press, Plainview, N.Y.) (1989). See also Innis et al., *PCR Protocols*, Academic Press (1995); and Gelfand, *PCR Strategies*, Academic Press (1995); and Innis and Gelfand, *PCR Methods Manual*, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

A "transgenic" organism is an organism having one or more cells that contain an expression vector.

By "portion" or "fragment", as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

As used herein, the term "therapeutic agent" refers to any agent or material that has a beneficial effect on the mammalian recipient. Thus, "therapeutic agent" embraces both therapeutic and prophylactic molecules having nucleic acid or protein components.

The term "antibody" includes intact molecules of polyclonal or monoclonal antibodies, as well as fragments thereof, such as Fab and F(ab')$_2$. For example, monoclonal antibodies are made from antigen containing fragments of a protein by methods well known to those skilled in the art (Kohler et al., *Nature*, 256, 495 (1975)).

By "immunize" is meant to stimulate an immune response (humoral and/or cellular), e.g., such that may render immune a vaccine recipient. "Immunization" refers to the production of antibodies directed against an infecting agent and/or its toxic product. It may also initiate a cellular response. For example, a vaccine of the invention may be used to immunize a mammal, such as a human, against current or subsequent infection caused by one or more *Neisseria* spp. A vaccine of the invention is effective for eliciting antibodies that are immunoreactive with a *Neisseria* spp. that expresses one or more phospholipase D protein(s).

Direct Association of CR3 with Pathogenic *Neisseria*

Phagocytosis that is mediated by complement receptor type 3 (CR3) occurs independently of a proinflammatory response in immune cells (Caron et al. 1998). CR3 exists as an integrin heterodimer composed of an alpha ($\alpha_M$ or CD11b) and a beta ($\beta_2$ or CD18) subunit. The distribution of CR3 is thought to be limited to professional phagocytes; however, Hussain et al. (1995) demonstrated the expression of CR3 in rectal epithelia. Additionally, Hussain et al. (1995) were able to detect the presence of CD11b in a small subpopulation of cervicovaginal epithelia, although they were unable to detect the presence of CD18.

Up-regulation of CD11b in neutrophils has been documented in response to *Neisseria meningiditis* infection (Kragsbjerg et al. 2000). The direct association of CR3 with pathogenic *Neisseria*, however, has not been demonstrated. The present inventors herein describe the occurrence of CR3 expression in primary human cervical epithelial cells and its co-localization with *N. gonorrhoeae* upon infection of these primary epithelial cells. They also describe the distribution of CR3 in immortalized tissue culture cell lines and within tissue biopsies derived from the male and female urogenital tracts. Monoclonal antibodies directed against CR3 inhibit gonococcal invasion of primary cervical cells and of CR3-transfected CHO cells suggesting that CR3 serves as a receptor for *N. gonorrhoeae* during infection. In addition, these studies help to explain why the inflammatory response initiated by gonococcal infection of the lower female genital tract differs from that observed with gonococcal infection of the male urogenital tract.

The distribution of CR3 in tissue biopsies derived from defined sites within the human male and female genital tracts and in primary, immortalized, and malignant epithelial cells derived from these sites is described in Example 2 below. Laser scanning confocal microscopy (LSCM) demonstrated CR3 was not present in tissues and cells derived from the male urogenital tract and from tissue derived from the female urethra; however, CR3 was present on tissues and cells derived from the female genital tract. CR3 expression was greatest within the ectocervix tissue. Surface levels of CR3 appeared to decrease progressively from the ectocervix to the upper female genital tract in these tissues. A low level of CR3-associated immunofluorescence was observed in fallopian tube tissue. Consistent with results obtained with LSCM analysis of tissue biopsies, primary endo- and ectocervical cells possessed both CR3 subunits, and CR3 expression appeared to be greater on primary ectocervical cells in comparison to primary endocervical cells.

Figure 1:
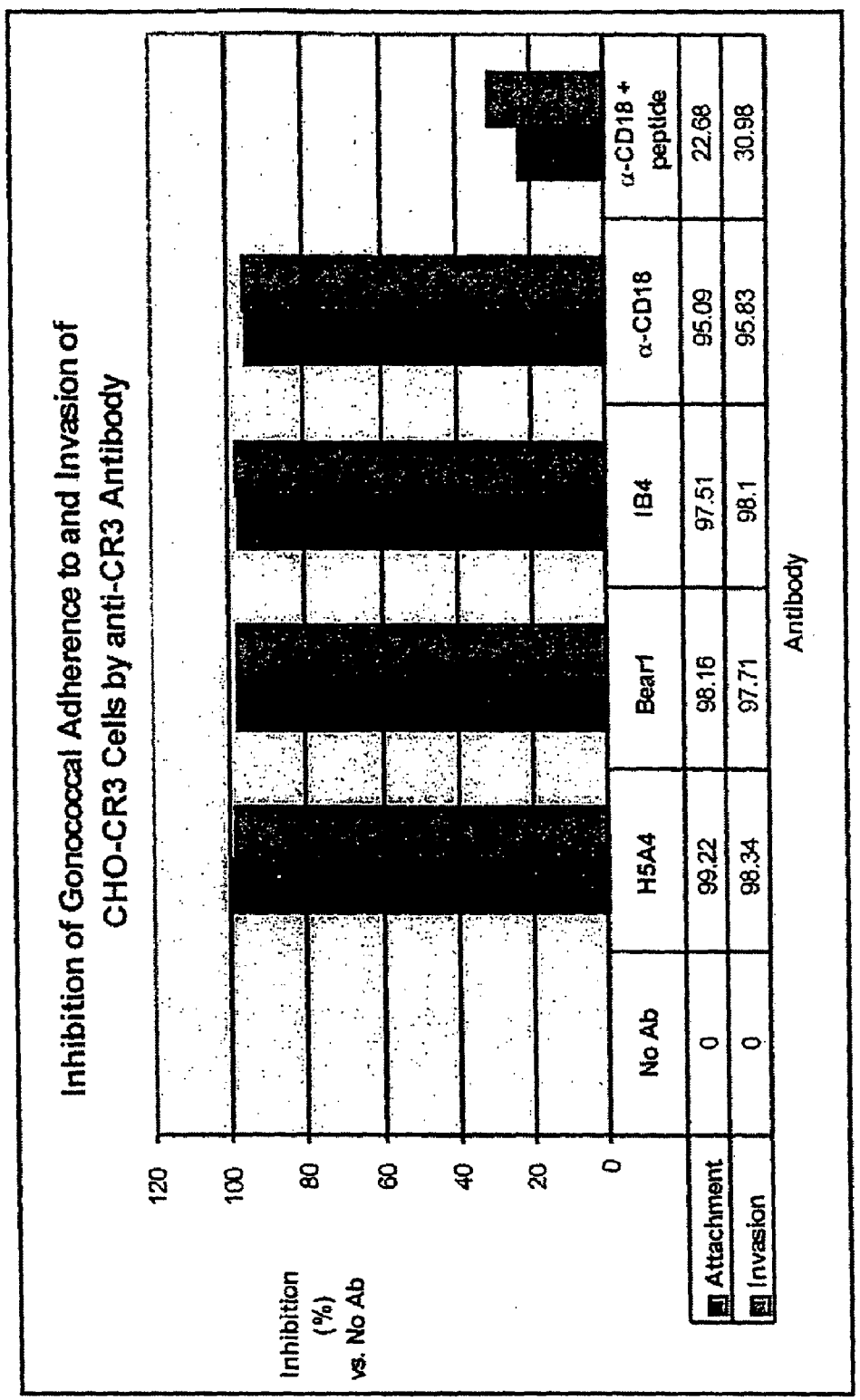
Figure 2:
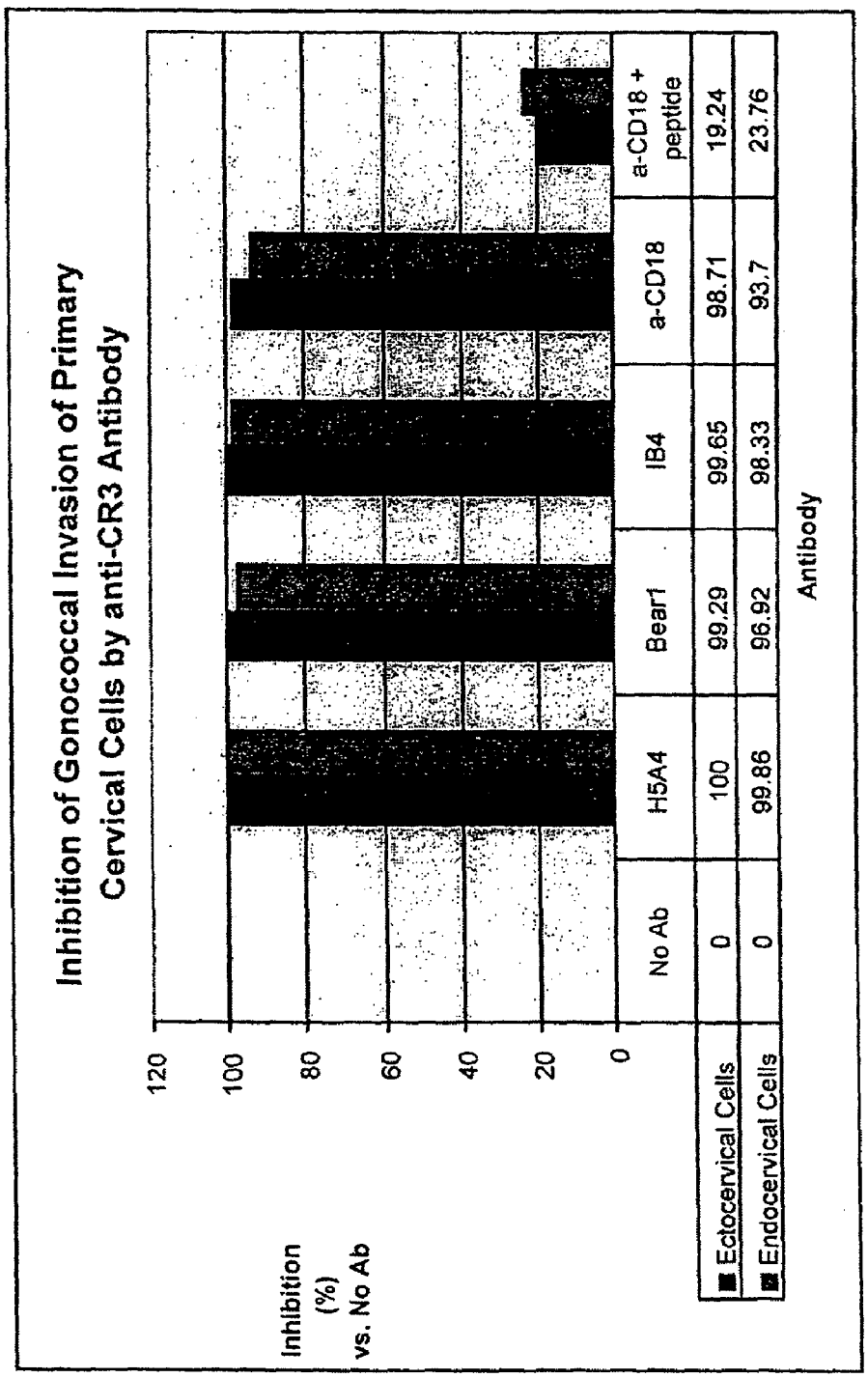

In contrast to results obtained with analysis of tissue biopsies and primary cervical cells, CR3 expression was negligible on immortalized and malignant cell lines (i.e., HCK, End1, ME180, Hec1B). Infection studies using *N. gonorrhoeae* strains 1291, 1291-green, MS11-green, or FA1090-green did not significantly influence the level of CR3 surface expression on these immortalized or malignant cell lines. However, *N. gonorrhoeae* did appear in induce up-regulation of CR3 surface expression on primary endo- and ectocervical cells. Gonococci were observed to co-localize with CR3 on primary cervical cells, and co-localization became increasingly prominent with extended infection. Immunoprecipitation studies confirmed the presence of CD11b and CD18 in primary cervical cells and CR3 co-localization with the gonococcus. Gonococci bound CR3-transfected K562 and CHO cells, and binding could be inhibited by the presence of anti-CD11b or -CD18 antibodies (FIG. 1). Similarly, invasion of primary cervical cells and CHO-CR3 cells could be inhibited by the addition of anti-CR3 antibodies to gentamicin-survival assays (FIGS. 1 and 2). Gonococcal invasion of primary endo- and ectocervical cells was also inhibited by the addition of *Clostridium* C3 neurotoxin to invasion assays (FIG. 3), which is consistent with CR3-mediated phagocytosis (Caron et al. 1998).

Extensive membrane ruffling could be induced to occur in the absence of gonococci in primary endo- and ectocervical cells and in CHO-CR3 cells by the addition of anti-CD11b or —CD18 antibodies to infection assays. This suggests that engagement of CR3 elicits membrane ruffling, which occurs in response to *N. gonorrhoeae* infection of the cervical epithelium.

The role of complement (C') in innate immunity is multifactorial; however, C' predominately serves to eliminate foreign antigens and to regulate the inflammatory response directed towards these exogenous particles. C' protein C3 of the C' alternative pathway (AP) plays a paramount role in AP C' regulation in that it serves to amplify the complement-mediated response by a positive feedback regulatory loop, which converts a relatively inefficient response to a highly efficient defense mechanism. Activation of the AP occurs constitutively at a low rate, which is tightly regulated by C' regulatory proteins, e.g., factors H (fH) and I (fI). Deposition of C3 on an exogenous surface (e.g. a bacterium) results in spontaneous C3 hydrolysis to produce C3b. C3b can bind factor B (fB) to generate C3 convertase activity leading to the formation of the membrane attack complex. Alternatively, C3b can bind fH leading to C' inactivation via cleavage of C3b by fI to produce iC3b, a ligand for CR3.

CR3 distribution has generally been considered to be limited to immune cells (e.g., monocytes, neutrophils, and macrophages); however, CR3 has also been found on renal glomerular (Sandilands et al. 1985) and rectal (Hussain et al. 1995) epithelial cells. By in situ hybridization Hussain et al. (1995) detected CD11b in a sub-population of endocervical tissue specimens, but they were unable to detect CD18. The inability to detect CD18 was attributed to a level of CR3 expression that was below the sensitivity of the antibody and detection method used (Hussain et al. 1995). LSCM of surgical biopsies and of primary endo- and ectocervical cell monolayers (using two, well defined, antibodies to each CR3 subunit) demonstrated CR3 within the ectocervical, endocervical, endometrial, and fallopian tube epithelia; however, CR3 expression appeared to progressively decrease from the ectocervix to the fallopian tubes. Although CR3 is structurally and functionally related to the very late antigen (VLA) sub-family of integrins, which are present within the female genital tract (Sülz et al. 1998), these two distinct groups of proteins are not immunologically cross-reactive (Hynes, R. O. 1987). Additionally, isotype control antibodies failed to label primary cell monolayers or tissue cryosections.

The present inventors' immunohistochemical data provide evidence for the presence of CR3 within the female genital tract. Furthermore, immunoprecipitation of primary cervical cell lysates confirmed the presence of CR3 within the endo- and ectocervix by the presence of the appropriate 95 kDa (CD18) and 170 kDa (CD11b) bands with subsequent western blotting. These data suggest that the distribution of CR3 should now be extended to include the endo- and ectocervix and, possibly, the epithelia of the endometrium and fallopian tubes. The female reproductive tract and seminal fluid have been hypothesized to exhibit anomalous C' regulatory characteristics that exist to ensure successful reproduction by hindering an amplified immune response to seminal plasma (Vanderpuye et al. 1992). Seminal plasma has been demonstrated to contain unidentified C1 and C3 C' component inhibitors, trace amounts of fH and fI, and a soluble form of the C3 regulatory protein, CD46 (Hussain et al. 1995), but fB has not been detected (Vanderpuye et al. 1992).

Full AP complement activity has been reported in cervical mucous (Price et al. 1979; Vanderpuye et al. 1992); however, C4 of the complement classical pathway (CP) was only detected in a small sub-population of luteal-phase cervical secretions (Vanderpuye et al. 1992). Additionally, AP, but not CP, components are produced by the vaginal epithelium (Price et al. 1979), and there are some data to suggest that C' components are synthesized by the endometrium (Vanderpuye et al. 1992). Collectively these data suggest that CR3 present within the female genital tract would function to eliminate exogenous antigens (with the absence of neutrophil influx), following C' inactivation of these antigens in seminal fluid or cervical mucous.

In contrast to the results obtained with female genital tissue and primary endo- and ectocervical cells, the presence of CR3 was not detected in vas deferens or male and female urethral tissue. The absence of CR3 in these tissues may be the result of divergent embryonic development that occurs after differentiation of the nephrogenic mesoderm. CR3 belongs to a large family of cell adhesion molecules that exhibit broad ligand specificity, and, in this respect, differential expression of integrin receptors has been implicated to play a role in morphogenesis and differentiation.

*Drosophila* spp. differentially express surface antigens, which structurally resemble human integrins, during the course of imaginal disc formation (Hynes, R. O. 1987). These cell surface molecules are hypothesized to influence embryonic development through differential cell adhesion (Hynes, R. O. 1987). In terms of evolutionary development, it is generally accepted that the female urogenital systems of apes and humans are more evolved than their male counterparts. In humans, the nephrogenic mesoderm differentiates to form the mesonephros and the metanephros. The metanephros gives rise to the renal glomerulus while the mesonephros regresses. Remnants of the mesonephric tubules exist in males as the vas deferens and in females as blind tubules in the ovarian dorsal mesentery. Muellerian ducts differentiate in females to form that portion of the female genital tract ranging from the fallopian tubes to the cephalic vagina. A complete division of the cloaca gives rise to the rectum and a urogenital sinus in both males and females. In males the muellerian ducts regress, and the urogenital sinus receives the mesonephric ducts, after which the rectum elongates and differentiation occurs. In females an additional portioning event of the urogenital sinus occurs to form the terminal vagina, the rectum, and the urethra. Since CR3 has been demonstrated on renal glomerular epithelium, rectal epithelium, and (considering the data of Hussain et al. (1995) and herein) the cervical epithelium, it is possible, although speculative, that the presence of CR3 in these tissues may correlate with a higher degree of embryonic development or cellular differentiation.

The absence of CR3 on the immortalized (End1, HCK) and the malignant (ME180, Hec1B) cell lines used in these studies may be reflective of the functional properties of integrins in general or CR3 specifically. Tumor cells are frequently altered in their integrin expression patterns (Jones et al. 1999) as well as the expression of other cellular receptors, e.g., complement receptor type 1 (CR1) (Seya et al. 1990) and the insulin-like growth factor-II/mannose-6-phosphate receptor (O'Gorman et al. 1999). Generally, adhesion and/or stimulation of integrins initiate signaling events that allow cytoskeletal rearrangements, cellular migration, and immunological activation. Adhesive and cytoskeletal defects are associated with fibronectin loss on transformed cells; these defects are reasoned to be due to altered integrin function (Hynes, R. O. 1987). CR3 initiates a signaling cascade in which PI 3-kinase functions as one effector (Elemer et al. 1994).

One function of PI-3 kinase is activation of the Rho family of small GTPases that, in turn, activate Jun-N-terminal kinase (JNK) (Hauck et al. 1998; Obermeier et al. 1998). Effector functions of JNK include regulation of gene expression and induction of apoptosis (Hauck et al. 1998). Some tumor cells express proteases most of which have been described to cleave C3 (Jurianz et al. 1999). Binding of C3 cleavage products (e.g., iC3b) to their respective receptors (e.g., CR3) could trigger multiple cellular responses, including apoptosis. Additionally, CR3 can also play a role in antibody-dependent cell-mediated cytotoxicity (ADCC) and complement-dependent cell-mediated cytotoxicity (CDCC) (Perlmann et al. 1983; Ramos et al. 1988; Ramos et al. 1985; Wåhlin et al. 1983), which facilitate tumor killing (Becherer et al. 1989; Erdei et al. 1991). Therefore, it could be reasoned that the absence of CR3 in immortal or malignant cells might confer a survival advantage to these cells.

A number of microorganisms have adapted mechanisms not only to evade complement-mediated killing but also to pilfer C' components for their own advantage. Microorganisms that initiate infection via C' receptors frequently activate C', which subsequently results in C3 deposition on their cell surface (Hondalus et al. 1993). The effect of C' deposition is two-fold: 1) it allows for evasion of immune surveillance, and 2) it allows targeting to the appropriate host cell (Cooper, N. R. 1991). Microbial entry of host cells in a CR3 opsonic-dependent manner is thought to lead to a milder respiratory burst thereby promoting increased intracellular survival (Mosser et al. 1987; Würzner, R. 1999). Additionally, complement-mediated endocytosis occurs independently of a proinflammatory response (Caron et al. 1998).

Asymptomatic gonococcal urethritis develops in a small proportion of men. In contrast, fifty to sixty percent of women with gonorrhea exhibit asymptomatic infections, and seventy percent of women with disseminated gonococcal infection (DGI) lack symptoms of genital track infection (Densen et al. 1982). The ability of pathogenic *Neisseria* to cause the range of disease states associated with infection requires highly efficient methods of immune avoidance. Although strain specific properties have been associated with resistance to complement-mediated killing (i.e., serum resistance) in vitro, most clinically isolated gonococci initially exhibit serum resistance, a property that is lost with sub-culturing (Densen, P. 1989; de la Paz et al. 1995; Ram et al. 1999; Ram et al. 1998; Vogel et al. 1999).

Ram et al. (1998) suggest that an increased conversion of C3b to iC3b on the gonococcal surface might contribute to serum resistance in vivo. This idea is supported by in vitro studies of gonococcal infection of neutrophils where a predominance of iC3b is found on the surface of gonococci in comparison to C3b deposition (Jarvis et al. 1999; McQuillen et al. 1999; Vogel et al. 1999). Conversion of C3b to iC3b on the gonococcal surface would permit efficient internalization of infecting gonococci into the cervical epithelium. Standard gentamicin-resistance assays measuring gonococcal invasion of primary endo- and ectocervical cells in the presence of anti-CR3 antibodies demonstrated greater than ninety-three percent invasion inhibition with the antibody inhibitors used.

Similar studies performed previously in the inventors' laboratory, using antibody inhibitors specific for other putative gonococcal ligands such as an antibody specific for (i) CEACAM (commercially available from Santa Cruz Biotechnology Inc.); (ii) receptors for Opa proteins; (iii) E4.3 (a monoclonal antibody specific for CD46; commercially available from Santa Cruz Biotechnology Inc.); and (iv) a receptor for pilus, failed to inhibit invasion of or association with primary endo- and ectocervical cells. Additional support for a CR3-mediated mode of gonococcal invasion of the cervical epithelium is obtained from LSCM analysis of clinical biopsies derived from women with naturally acquired gonorrhea. Confirmed co-localization of gonococci with CR3 in these tissue sections provide evidence that CR3-mediated gonococcal invasion probably occurs in vivo. Collectively these data suggest that CR3-mediated phagocytosis may serve as the primary mode of gonococcal invasion of the cervical epithelium.

Only a small proportion of total cellular CR3 is found on the surface of resting cells (Frank et al. 1991; Ram et al. 1998). This CR3 population is relatively immobile in the plane of the cell membrane (van Kooyk et al. 1999) and is thought to facilitate phagocytosis triggered by other cell surface receptors, e.g., CR1 and Fcγ receptors (Frank et al. 1991). A mobile, intracellular CR3 store is associated with iC3b-dependent adherence (Frank et al. 1991). Upon activation this latent CR3 population, which resides in peroxidase-negative granules, is rapidly released, resulting in up to a ten-fold increase in CR3 surface expression (Elemer et al. 1994; Frank et al. 1991; Kishimoto et al. 1989). Early in the stages of phagocytosis CR3 aggregation also occurs (Caron et al. 1998; Elemer et al. 1994; Frank et al. 1991; Kishimoto et al. 1989; van Kooyk et al. 1999). LSCM analysis of *N. gonorrhoeae* infected primary endo- and ectocervical cells were reflective of these events. Co-localization of infecting gonococci was readily visible by thirty minutes post-infection of endo- and ectocervical cells, and this association became more pronounced by ninety minutes and three hours post-infection suggesting an increase in surface level expression of CR3. Additionally, co-localization of gonococci with CR3 was evident as clusters on the endo- and ectocervical cell surfaces.

Several studies have demonstrated that efficient signal transduction mediated through CR3 that subsequently allows phagocytosis may require co-operation among receptors that share adherence to a particular organism (Elemer et al. 1994; Frank et al. 1991; Hayashi et al. 1997; Ingalls et al. 1998; Kishimoto et al. 1989; Mesri et al. 1998; Stocks et al. 1995; Stocks et al. 1996; Wright et al. 1983). Cross-linking of this/these co-receptors to CR3 is thought to induce a conformational change in CR3 that leads to its increased ligand avidity and/or affinity followed by an increase in cell surface expression, a process called inside-out signaling. Studies focusing on the interaction of putative neisserial virulence factors with host cells have clearly demonstrated that the establishment of productive infection is multifactorial and several bacterial products may play a synergistic role in successful invasion.

The present inventors have demonstrated a role for CR3-mediated invasion of primary endo- and ectocervical cells by the gonococcus. The mechanism used by this bacterium to achieve CR3 adherence is reported in Edwards and Apicella, 2002 and Edwards et al., 2002. Anti-CR3 immunoprecipitation studies of infected, primary endo- and ectocervical cell lysates demonstrated that gonococcal porin, pili, and opa proteins associate with CR3. These data maybe indicative of opsonic (i.e., iC3b-mediated) adherence, alternatively, unopsonic binding of porin, pili, and opa proteins each to either CR3 or their respective co-receptor may facilitate CR3-mediated entry. CR3 up-regulation can be blocked by neutrophil treatment with an anion-specific channel blocker, but binding of neutrophils to endothelial cells remained unaffected (Kishimoto et al. 1989). *N. gonorrhoeae* porin proteins are anion selective water-filled channels that are capable of transmigration to and insertion into eukaryotic cell membranes (Bjerknes et al. 1995; Lynch et al. 1984); therefore, it is possible that these proteins play a role in up-regulation of CR3 upon gonococcal attachment.

Recent data has suggested that an association with selective members of the carcinoembryonic antigen family of cell adhesion molecules (CEACAM) (Stocks et al. 1995; Stocks et al. 1996) may augment CR3 activity. CEACAM are suggested to initiate a priming signal in neutrophils that results in activation of adhesion receptors without the release of inflammatory mediators or the induction of a respiratory burst (Stocks et al 1995). CEACAM1 and CEACAM5 are also present on epithelial cells and have been shown to bind gonococcal Opa. It is tempting to speculate a role for an Opa-CEACAM interaction in CR3-mediated invasion. However, previous data and unpublished work in the inventors' laboratory has demonstrated that invasion of a *N. gonorrhoeae* strain FA1090 Opa deletion mutant and strain 1291 Opa⁻ phase variant (isolated on the basis of colony morphology) is comparable to their respective wild type counterparts. Additionally, membrane ruffling was observed upon SEM analysis of these Opa⁻ strains. Therefore the significance of Opa proteins to these studies is unclear.

One possibility is that binding of heparin to Opa facilitates fH (which possesses three heparin-binding domains (Zipfel et al. 1999)) adherence to surface bound C3. Support of this idea is that Chen et al. (1995) demonstrated that heparin treatment of gonococci resulted in a fifty-five to eighty-five percent increase in survival in normal human serum. fH has also been demonstrated to bind gonococcal porin. fH possesses a sialic acid binding site that has been shown to bind sialylated gonococcal LOS; consequently, the redundancy of the ability of fH to bind the gonococcus would preclude the absolute requirement for Opa proteins for successful infection by the gonococcus.

Membrane co-factor protein (CD46) serves as a C' regulatory protein on the surface of all nucleated cells thereby protecting them from C' mediated lysis. Similar to fH, CD46 functions on the cell surface as a co-factor for fI-mediated C' inactivation (Seya et al. 1990). CD46 has been shown to function as a receptor for gonococcus pili on unpolarized ME180 cells (Källström et al. 1997); however, in polarized epithelial cells CD46 exists on the basolateral surface (Maisner et al. 1997). Additionally, CD46 is not efficiently endocytosed and those surface molecules that are internalized are rapidly degraded (Maisner et al. 1997). These findings preclude the possibility of receptor recycling to the apical cell surface. The inventors' unpublished data and the work of others strongly suggests that gonococcal pili play a crucial role in gonococcal pathogenesis. A soluble form of CD46 (sCD46) also exists (Jurianz et al. 1999) and is present in seminal fluid (Vanderpuye et al. 1992); however, the significance of this molecule is unclear. In view of this work, its intriguing to speculate that the interaction of gonococcal pili with sCD46 may augment the function of CR3 possibly by binding to or near the divalent cation binding domain of CR3.

The presence of $Mn^{2+}$ and $Ca^{2+}$ are speculated to directly induce integrin changes required for efficient ligand binding by circumventing physiological triggering events (Altieri, D. C. 1991; Stewart et al. 1996; Violette et al. 1995). Kallstrom et al. (2000) recently demonstrated that adherence of non-piliated *N. gonorrhoeae* strain MS11 could be induced to occur on ME180 cells in the presence of $Ca^{2+}$. Although the inventors were unable to detect CR3 in any of the immortalized or malignant cell lines examined in this work (including ME180 cells), the $Ca^{2+}$-mediated invasion of non-piliated gonococci observed by Kallstom et al. might have occurred through an alternative integrin receptor. The cation-dependent induction of receptor function is a property attributed to integrins in general (Altieri, D. C. 1991).

SEM analysis demonstrated that the addition of anti-CR3 antibodies to CHO-CR3 and primary endo- and ectocervical cell monolayers resulted in membrane ruffles, suggesting that this phenomenon is elicited by CR3 activation. Upon gonococcal infection of primary human endo- and ectocervical cells membrane ruffling is induced to occur (Edwards et al. 2000). TEM analysis of clinical cervical biopsies, which were derived from women with documented gonococcal cervicitis, suggested that membrane ruffling also occurred in vivo (Edwards et al. 2000). Additionally, membrane ruffling was predominately accompanied by a concentrated accumulation of the actin-associated proteins ezrin and vinculin (Edwards et al. 2000).

Jones et al. (1998) recently described two CR3 signaling pathways: 1) FcγR-induced, PI-3 kinase dependent and 2) formylmethionylleucylphenylalanine (fMLP)-induced, PI-3 kinase independent pathways. Both modes of CR3 signaling lead to the activation of p21 activating kinase 1 (PAK1) (Jones et al. 1998). PAK1 is a serine/threonine kinase demonstrated to exhibit multiple effector functions. PAK1 can regulate membrane ruffling both independently and dependently of the action of Rac (Obermeier et al. 1998; *Sells* 1997). Additionally, PAK1 regulates the formation of vinculin-containing focal complexes (Obermeier et al. 1998;

Sells 1997). The ability of PAK1 to regulate membrane ruffling and vinculin accumulation through a CR3-dependent signaling cascade corresponds well with previously described data, and data presented herein. Additionally, this supports evidence for the induction of membrane ruffling of primary, human endo- and ectocervical cells by the binding of the gonococcus to CR3.

It is interesting to note that *Shigella* are capable of membrane ruffle induction and that these organisms parasitize the rectal epithelium (Tran Van Mhieu et al. 1999), which also exhibits CR3 expression (Hussain et al. 1995). Also of interest is that the sexually transmitted organisms, *Candida* and HIV, are both capable of CR3-mediated internalization of host cells (Cooper, N. R. 1991; Hussain et al. 1995; Würzner, R. 1999). The pathogenic *Neisseria* have evolved multiple efficient mechanisms by which to evade host defense mechanisms. Among these immune avoidance mechanisms are the strain-specific attributes that confer serum-resistance e.g., sialylation of some LOS glycoforms and a P.1A porin serotype (Densen, P. 1989; Ram et al. 1999; Vogel et al. 1999; et al. 1992). In vitro gonococcal infection studies and examination of clinically isolated gonococci have revealed C' components (predominately iC3b) on the surface of gonococci (Densen, P. 1989; Jarvis et al. 1999; McQuillen et al. 1999; Ross et al. 1985). Additionally, gonococci have been demonstrated to activate both the classical and alternative C' pathways; however, gonococcal killing primarily occurs via the CP (Densen et al. 1982). This would suggest a role for AP inactivation (and possibly subsequent CR3-mediated internalization) as one mechanism by which the gonococcus persists within its primary niche, the human reproductive tract. The inventors' data suggests that CR3-mediated invasion serves as a primary mechanism by which *N. gonorrhoeae* invades the cervical epithelium. This process involves ruffling of the cervical epithelium, which appears to be triggered by CR3 engagement.

Vaccine Preparations

The present invention thus provides a vaccine for use to protect mammals against *Neisseria* colonization or infection, e.g., *N. gonorrhoeae* and/or *N. meningitidis*. For example, the vaccine may contain an immunogenic amount of polypeptide PLD, also known as p55, from *N. gonorrhoeae*, or an immunogenic amount of polypeptide PLD from *N. meningitidis* in combination with a physiologically-acceptable, non-toxic vehicle. Vaccines of the present invention can also include effective amounts of immunological adjuvants known to enhance an immune response.

The immunogenic neisserial protein can be conjugated or linked to another peptide or to a polysaccharide. For example, immunogenic proteins well-known in the art, also known as "carriers," may be employed. Useful immunogenic proteins include keyhole limpet hemocyanin (KLH), bovine serum albumin (BSA), ovalbumin, human serum albumin, human gamma globulin, chicken immunoglobulin G and bovine gamma globulin.

Further provided are isolated and purified nucleic acid molecules, e.g., DNA molecules, comprising a nucleic acid segment that encodes at least a portion of a neisserial protein. For example, the invention provides an expression cassette comprising a DNA segment that codes for an RNA molecule that is substantially identical (sense) to all or a portion of a messenger RNA ("target" mRNA), i.e., an endogenous or "native" neisserial protein mRNA. The DNA segment in the expression cassette is operably linked to a promoter. As used herein, "substantially identical" in sequence means that two nucleic acid sequences have, for example, at least about 65%, about 70%, about 90%, or about 98% contiguous nucleotide sequence identity to each other. As an example, the preselected DNA segment hybridizes under hybridization conditions, such as stringent hybridization conditions, to a nucleic acid molecule encoding the corresponding native neisserial protein.

As used herein, "substantially pure" means an object species is the predominant species present (i.e., on a molar basis it is more abundant than any other individual species in the composition). For example, a substantially purified fraction is a composition wherein the object species comprises at least about 50 percent (on a molar basis) of all macromolecular species present. Generally, a substantially pure composition will comprise more than about 80 percent of all macromolecular species present in the composition, for example, more than about 85%, about 90%, about 95%, and about 99%. The object species can be purified to essential homogeneity (contaminant species cannot be detected in the composition by conventional detection methods) wherein the composition consists essentially of a single macromolecular species.

As used herein, the term "recombinant nucleic acid" or "nucleic acid," e.g., "recombinant DNA sequence or segment" refers to a nucleic acid, e.g., to DNA, that has been derived or isolated from any appropriate source, that may be subsequently chemically altered in vitro, so that its sequence is not naturally occurring, or corresponds to naturally occurring sequences that are not positioned as they would be positioned in a genome that has not been transformed with exogenous DNA. An example of DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). Therefore, "DNA" includes completely synthetic DNA sequences, semi-synthetic DNA sequences, DNA sequences isolated from biological sources, and DNA sequences derived from RNA, as well as mixtures thereof. As used herein, the term "derived" with respect to a RNA molecule means that the RNA molecule has complementary sequence identity to a particular DNA molecule.

Nucleic acid molecules encoding amino acid sequence variants of a neisserial protein are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the neisserial protein.

To immunize a subject, the neisserial protein is administered parenterally, usually by intramuscular or subcutaneous injection in an appropriate vehicle. Other modes of administration, however, are also acceptable. For example, the vaccine may be administered orally, or via a mucosal route, such as a nasal, gastrointestinal or genital site. Vaccine formulations will contain an effective amount of the active ingredient in a vehicle. The effective amount is sufficient to prevent, ameliorate or reduce the incidence of *N. gonorrhoeae* colonization in the target mammal. The effective amount is readily determined by one skilled in the art. The active ingredient may typically range from about 1% to about 95% (w/w) of the composition, or even higher or lower if appropriate. The quantity to be administered depends upon factors such as the age, weight and physical condition of the human subject considered for vaccination. The quantity also depends upon the capacity of the person's immune system to synthesize antibodies, and the degree of protection desired. Effective dosages can be readily established by one of ordinary skill in the art through routine trials establishing dose response curves. The subject is immunized by administration of the neisserial protein in one or more doses. Multiple doses may be administered as is required to maintain a state of immunity to streptococci.

To prepare a vaccine, the purified neisserial protein can be isolated, lyophilized and stabilized. The neisserial protein may then be adjusted to an appropriate concentration, optionally combined with a suitable vaccine adjuvant, and packaged for use. Suitable adjuvants include but are not limited to surfactants, e.g., hexadecylamine, octadecylamine, lysolecithin, dimethyldioctadecylammonium bromide, N,N-dioctadecyl-N'-N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, MPL, aimethylglycine, tuftsin, oil emulsions, alum, and mixtures thereof. Other potential adjuvants include the B peptide subunits of *E. coli* heat labile toxin or of the *cholera* toxin. McGhee, J. R., et al., "On vaccine development," *Sem. Hematol.*, 30:3–15 (1993). Finally, the immunogenic product may be incorporated into liposomes for use in a vaccine formulation, or may be conjugated to proteins such as keyhole limpet hemocyanin (KLH) or human serum albumin (HSA) or other polymers.

Antibodies

The antibodies of the invention are prepared by using standard techniques. To prepare polyclonal antibodies or "antisera," an animal is inoculated with an antigen, i.e., a purified immunogenic PLD peptide or polypeptide, and immunoglobulins are recovered from a fluid, such as blood serum, that contains the immunoglobulins, after the animal has had an immune response. For inoculation, the antigen is preferably bound to a carrier peptide and emulsified using a biologically suitable emulsifying agent, such as Freund's incomplete adjuvant. A variety of mammalian or avian host organisms may be used to prepare polyclonal antibodies against gonococcol or meningococcal PLD.

Following immunization, Ig is purified from the immunized bird or mammal, e.g., goat, rabbit, mouse, rat, or donkey and the like. For certain applications, particularly certain pharmaceutical applications, it is preferable to obtain a composition in which the antibodies are essentially free of antibodies that do not react with the immunogen. This composition is composed virtually entirely of the high titer, monospecific, purified polyclonal antibodies to PLD, or peptides thereof. Antibodies can be purified by affinity chromatography, using purified PLD, or peptides thereof. Purification of antibodies by affinity chromatography is generally known to those skilled in the art (see, for example, U.S. Pat. No. 4,533,630). Briefly, the purified antibody is contacted with the purified PLD, or peptide thereof, bound to a solid support for a sufficient time and under appropriate conditions for the antibody to bind to the polypeptide or peptide. Such time and conditions are readily determinable by those skilled in the art. The unbound, unreacted antibody is then removed, such as by washing. The bound antibody is then recovered from the column by eluting the antibodies, so as to yield purified, monospecific polyclonal antibodies.

Monoclonal antibodies can be also prepared, using known hybridoma cell culture techniques. In general, this method involves preparing an antibody-producing fused cell line, e.g., of primary spleen cells fused with a compatible continuous line of myeloma cells, and growing the fused cells either in mass culture or in an animal species, such as a murine species, from which the myeloma cell line used was derived or is compatible. Such antibodies offer many advantages in comparison to those produced by inoculation of animals, as they are highly specific and sensitive and relatively "pure" immunochemically. Immunologically active fragments of the present antibodies are also within the scope of the present invention, e.g., the $F_{(ab)}$ fragment scFv antibodies, as are partially humanized monoclonal antibodies.

Thus, it will be understood by those skilled in the art that the hybridomas herein referred to may be subject to genetic mutation or other changes while still retaining the ability to produce monoclonal antibody of the same desired specificity. The present invention encompasses mutants, other derivatives and descendants of the hybridomas.

It will be further understood by those skilled in the art that a monoclonal antibody may be subjected to the techniques of recombinant DNA technology to produce other derivative antibodies, humanized or chimeric molecules or antibody fragments that retain the specificity of the original monoclonal antibody. Such techniques may involve combining DNA encoding the immunoglobulin variable region, or the complementarity determining regions (CDRs), of the monoclonal antibody with DNA coding the constant regions, or constant regions plus framework regions, of a different immunoglobulin, for example, to convert a mouse-derived monoclonal antibody into one having largely human immunoglobulin characteristics (see EP 184187A, 2188638A, herein incorporated by reference).

Inhibitory Compounds

The present invention provides a method of preventing entry of *Neisseria gonorrhoeae* and/or *N. meningitidis* into a cell (or treating an existing infection) by administering a compound that inhibits, e.g., reduces the activity of, neisserial PLD. In particular, it has been discovered that it is possible to prevent the infection of cervical cells (endocervical or ectocervical cells) by blocking the activity of *N. gonorrhoeae* PLD. Any inhibitor could be used. For example, the inhibitor could be an antibody (e.g., a monoclonal or polyclonal antibody, or a fragment of an antibody) that specifically binds to *N. gonorrhoeae* PLD, i.e., *N. gonorrhoeae* PLD, or a compound such as a divalent cation chelator that inhibits gonococcal association and/or invasion or primary ectocervical cells and/or endocervical cells.

Formulations of Compounds and Methods of Administration

In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts are obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids also are made.

The compounds may be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The following examples are intended to illustrate but not limit the invention.

EXAMPLE 1

Membrane Ruffling and Cytoskeletal Rearrangements in *Neisseria gonorrhoeae*

The sexually transmitted pathogen *Neisseria gonorrhoeae*, the causative agent in gonorrhea, can infect the male and female genital tract. Studies have shown that the organism can discriminate between the sexes and uses different mechanisms for infection of men than for infection of women. During the course of female infection, it appears that the organism releases a group of proteins that initiate a process called membrane ruffling on endocervical and exocervical epithelial cells. Organisms adherent to or proximal to the ruffled area invade the epithelial cell. The gonococcus can proliferate within the intracellular environment, cause the death of the infected cell and are released. They re-enter new cells and the cycle continues until an inflammatory response ensues or the organisms spreads to the endometrium and fallopian tubes.

Bacteria: *N. gonorrhoeae* strains 1291, 1291-green (1291 expressing green fluorescent protein and to be described elsewhere, the plasmid pLES98 was a gift from V. Clark), FA1090, MS11-A, and MS11mkC were used in these infection studies. These strains are $P^+$ and $Opa^+$. Strains 1291, 1291-green, MS11-A, and MS11$_{mk}$C contain the pathogenicity island recently described by Dillard (Dillard, J. 1999).

Development of Primary Cervical Cell Culture Systems: Surgical biopsies were obtained from 30 pre-menopausal women undergoing hysterectomy at the University of Iowa Hospitals and Clinics (Iowa City, Iowa). Endocervical (proximal to the cervical os) and ectocervical (distal to the cervical os) tissue biopsies were obtained in 4–6 mm$^2$ sections and further subdivided into 2–3 mm$^2$ sections. Sectioned tissues were rinsed twice for 10 min in Hanks Balanced Salt Solution (HBSS) supplemented with 1% fungizone (Irvine Scientific, Santa Ana, Calif.) and 1% penicillin (100 U/ml)-streptomycin (1 mg/ml). The tissue was placed with the epithelium downward on polystyrene, 35 mm tissue culture dishes (Falcon, Becton Dickinson; Franklin Lake, N.J.). Tissue explants were incubated in filtered airway medium (1 part Dulbecco Modified Eagle Medium, 1 part Ham's F12, 5% fetal calf serum (FCS), 1% nonessential amino acids (Sigma-Aldrich, St. Louis, Mo.), 1% penicillin-streptomycin, and insulin (10 µg/ml)). After 48 h, airway medium was replaced with keratinocyte growth medium (KGM)-2 Bullet Kit (Clonetics, San Diego, Calif.). KGM-2 was replaced every 2–3 days until near-confluence was obtained (1–2 weeks) at which time the cells were passaged as outlined below. Although variability exists among tissue samples, this process allows for an average of three passages of cell growth to fresh tissue culture dishes from a single tissue explant prior to fibroblast development, at which time tissue explants were discarded.

Cell Passage: At near-confluent growth cells were passaged by a 5 min, 37° C. incubation in HBSS-0.25% Trypsin-0.1% EDTA. Cell suspensions were collected and centrifuged at 5000 rpm for 5 min. The resulting cell pellet was rinsed in HBSS, resuspended in KGM-2, and used to seed transwell membrane systems (Biocoat Cell Environments, Becton Dickinson, Bedford, Mass.) (to allow for polarized cell growth); glass, 8-well chamber slides (Nalge Nunc International, Naperville, Ill.); or human, placental collagen-coated, 12 mm glass coverslips previously placed in 24-well tissue culture dishes (Falcon). Primary cervical cells were maintained in KGM-2 until near-confluence was again obtained at which time they were infected with *N. gonorrhoeae* as outlined below. Where applicable, cellular polarity was determined as an electrical resistance greater than 2KΩ/cm$^2$ as measured across the cell monolayer. Infected and uninfected (i.e., control) cervical cell-harboring membranes (from transwell systems) were subsequently subdivided into equal sections. Sections to be used for scanning electron microscopy (SEM) were processed while attached to the well apparatus so that the cellular orientation would be maintained. Remaining sections were removed from the well structure and subsequently processed independently for either confocal, transmission electron, or bright-field light microscopy.

Infection of the Primary Cells: *N. gonorrhoeae* cells allowed to grow overnight (37° C., 5% $CO_2$) on GC- IsoVitaleX agar plates were harvested using a sterile swab and resuspended in sterile saline. Culture density was determined spectrophotometrically where an optical density (OD) of 1 at 600 nm was equivalent to $10^9$ bacteria $ml^{-1}$ of cell culture. Bacterial cells were then diluted to a concentration of $10^7$ bacteria $ml^{-1}$ in KGM-2 lacking gentamycin and used to infect $10^5$ primary cervical cells (maintained as outlined above). Gonococcal infection was allowed to progress for variable time periods after which the infection was stopped by the removal of the infection medium, rinsing infected cervical cells with phosphate buffered saline (PBS), and cell fixation. Samples to be used in laser scanning confocal microscopy (LSCM) or differential interference contrast (DIC) analysis were immunolabeled directly following fixation. SEM, transmission electron microscopy (TEM), and bright field light microscopy (BFLM) samples were further processed by graded ethanol dehydration and resin (TEM) or paraffin (BFLM) embedment. Embedded samples were sectioned and immunolabeled as noted. Where indicated, the infection medium was harvested from the cervical cell monolayer and reused to infect fresh, uninfected cell cultures, which were subsequently processed for SEM analysis.

Invasion Assays in the Presence of Inhibitors of Cytoskeletal Motility and Protein Synthesis: Cervical cells were passed to 12 mm collagen-coated coverslips as outlined above. Prior to infection with *N. gonorrhoeae* 1291 wild-type cells, primary cell cultures were left untreated, or they were pre-incubated with 300 nM wortmannin (Sigma), 1 µM cytochalasin D (Sigma), or 400 mM ethylene glycol bis-(2-aminoethyl ether)-N,N, N', N' tetraacetic acid ((EGTA) Amresco, Solon, Ohio) for 2 h, 30 min, and 30 min, respectively, or they were pretreated with 100 g/ml nocodazole (Calbiochem-Novabiochem Corp., La Jolla, Calif.) for 1 h at 4° C. followed by a 30 min incubation at 37° C. The requirement for de novo protein synthesis, either by the bacteria or by the primary cervical cells, was tested by pretreatment (30 min, 37° C.) of the bacterial cultures or cervical cell monolayers with 4 µg/ml chloramphenicol (Sigma) or 25 µM cycloheximide (Calbiochem-Novabiochem Corp.), respectively. All chemical reagents used were maintained in the infection medium throughout the course of the infection. Trypan blue exclusion revealed no significant toxicity to the primary cervical cells at the indicated concentrations for each of the chemical reagents used. Infection was allowed to progress at 37° C., 5% $CO_2$, for 1.5 h after which the medium was removed, the cells were rinsed with PBS, and then incubated with KGM-2 containing 100 µg/ml gentamycin to kill extracellular bacteria. Post incubation the cervical cells were lysed with 0.5% saponin to release invasive bacteria. Percent invasion was determined as a function of the original inoculum and the number of colonies formed with subsequent plating of the cellular lysate. A Kruskal-Wallace ANOVA was used to determine the statistical significance of the calculated percent invasion for each of the cytoskeletal motility inhibitors used with respect to the untreated, infected cell cultures.

Microscopy: Samples were processed for LSCM, SEM, or TEM as previously described (Ketterer et al. 1999). Samples to be analyzed by BFLM were paraffin embedded using an automated tissue processor (RMC 1530 Paraffin Tissue Processor, Tucson, Ariz.), cut into thick (1 µm) sections, and mounted onto glass microscope slides. Immunolabeling of infected and uninfected cervical cells for TEM analysis was performed using the monoclonal antibody 2C3, which specifically recognizes the H.8 gonococcal surface protein, or the anti-gonococcal porin monoclonal antibody, 3H1 (a gift from Mylan Blake); in conjunction with a polyclonal antibody to filamentous (F) actin. Secondary labeling proceeded with the use of 30 nm and 10 nm colloidal gold-beaded antibody conjugates (Amersham Pharmacia Biotech, Piscataway, N.J.) to the bacterial- and actin-specific antibodies, respectively. B. A. Evans generously provided clinical biopsies used in TEM analysis. The samples were viewed with an H-7000 Hitachi Transmission Electron Microscope (Hitachi Corporation, Mountain View, Calif.).

Primary antibodies used for LSCM or DIC microscopy were as follows: anti-cytokeratin 8.12 (Sigma), -cytokeratin 4 (Sigma), -talin (Sigma), -vinculin (Sigma), -α-actinin (Sigma), -myosin (Sigma), -ezrin (Santa Cruz Biotechnology, Santa Cruz, Calif.), -CD66 (DAKO, Carpinteria, Calif.), -CD46 (Santa Cruz Biotechnology), and 2C3. Immunolabeling of cervical cell monolayers with anti-cytokeratin, -talin, -vinculin, -myosin, -ezrin, and -α-actinin occurred subsequent to a 15 min incubation in 0.2% Triton X-100 to allow cervical cells to become permeable. Where indicated, counter staining occurred at room temperature (RT) for 6 min. Counter stains used were specific for nucleic acids and consisted of YOYO-1 (Molecular Probes, Eugene, Oreg.) or ethidium bromide. Samples were viewed using the BioRad MRC-1024 or the Zeiss 510 Laser Scanning Confocal viewing systems.

Cervical tissue biopsies (obtained as outlined above) to be used for LSCM cytokeratin analysis were processed (within 1–2 h of obtaining the tissue specimen) for cyrosectioning by a 30 min incubation in 1% paraformaldehyde followed by infiltration with 30% sucrose prior to embedment in Tissue-Tek O. C. T. compound (Sakura Finetek USA, Inc., Torrance, Calif.) and sectioning (6–8 nm). Frozen sections were allowed to stand at RT for 1 h prior to immunolabeling with the indicated anti-cytokeratin antibody. A fluoroscein isothiocyanate (FITC)-conjugated secondary antibody was applied and tissues were subsequently counter-stained with ethidium bromide (0.5 ng/ml, 6 min).

Cervical cells passaged to 12 mm coverslips were used to assay for gonococcal-induced macropinocytosis. Cervical cell monolayers were infected with 1291-green for variable time periods in the presence of 1 mg/ml tetramethylrhodamine B isothiocyanate (TRITC)-dextran (MW 150, 000). Infection was stopped by the removal of the infection medium. Infected monolayers were extensively washed prior to fixation with 2% paraformaldehyde. Coverslips were mounted onto glass microscope slides and viewed using the BioRad MRC-1024 Laser Scanning Confocal viewing system.

Slides prepared for BFLM were hematoxylin-eosin stained using a standard protocol and viewed with a Leitz Diaplan microscope with an Optronics Engineering viewing system. SEM analysis was performed using an H-4000 Hitachi Scanning Electron Microscope (Hitachi).

Results

Characterization of Primary Human Endocervical Epithelial Cells: Primary cervical epithelial cells were allowed to grow as described above. Epithelial cells could be seen extending from the cervical explants within two to three days from the start of the cultures. Growth radiated from the tissue foci in a contiguous monolayer, and confluence was observed within ten to fourteen days. Transfer of endocervical-derived cells to transwell membrane systems resulted in polarized cell growth.

Figure 4:
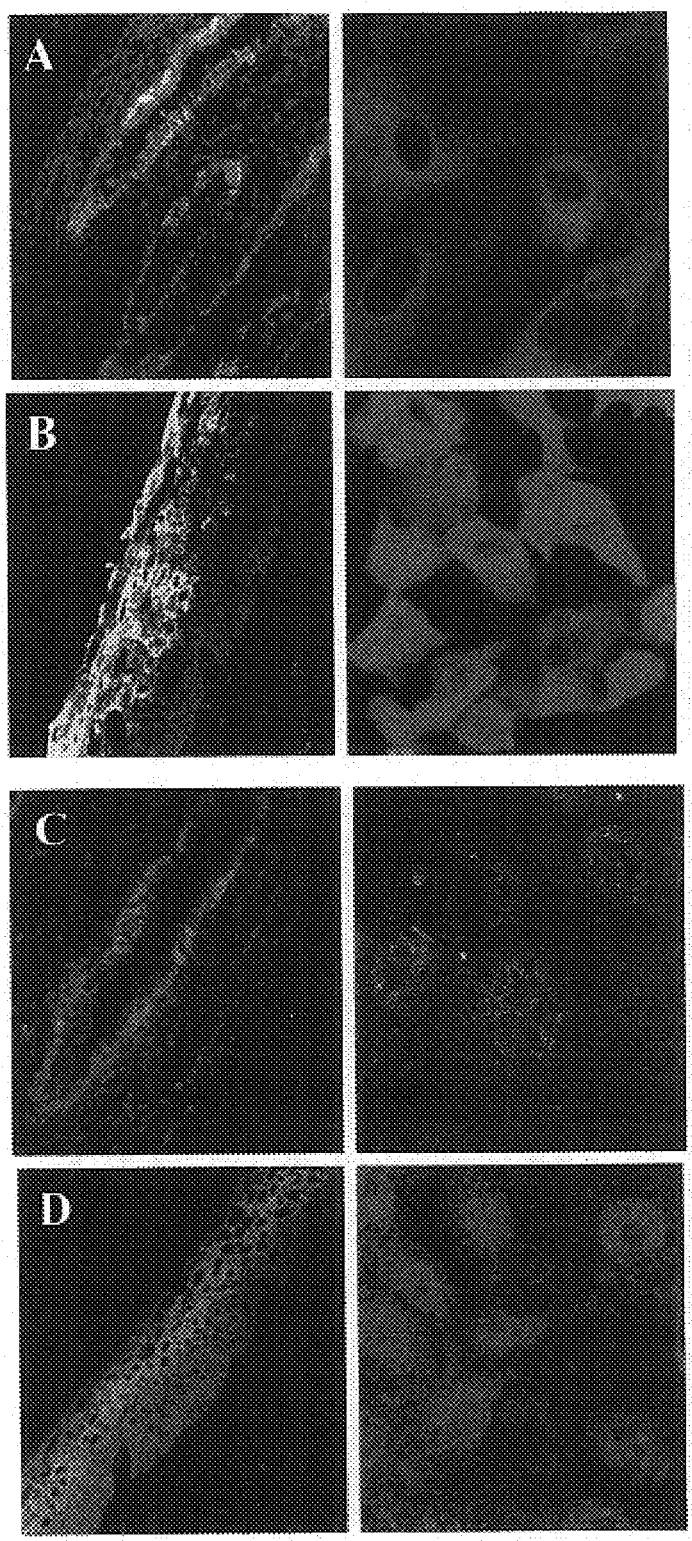

The cytokeratin expression pattern of the normal human uterine cervix has been well characterized. LSCM was used to determine the cytokeratin expression pattern of the primary cervical cell monolayers with respect to the tissue from which they were derived. Sectioned tissue biopsies (obtained from the endo- and ectocervix) and the cervical-derived cell monolayers were immunohistochemically examined with antibodies to cytokeratins 4, 13, 15, and 16. The results of these studies can be seen in FIG. 4. The specific cytokeratin staining character of the endo- and ectocervical tissue was retained in the primary cell monolayers (FIG. 4).

LSCM analysis of sectioned tissue biopsies and cervical-derived cell monolayers demonstrated the expression of CD66 and CD46 in both the endo- and ectocervix.

Figure 5:
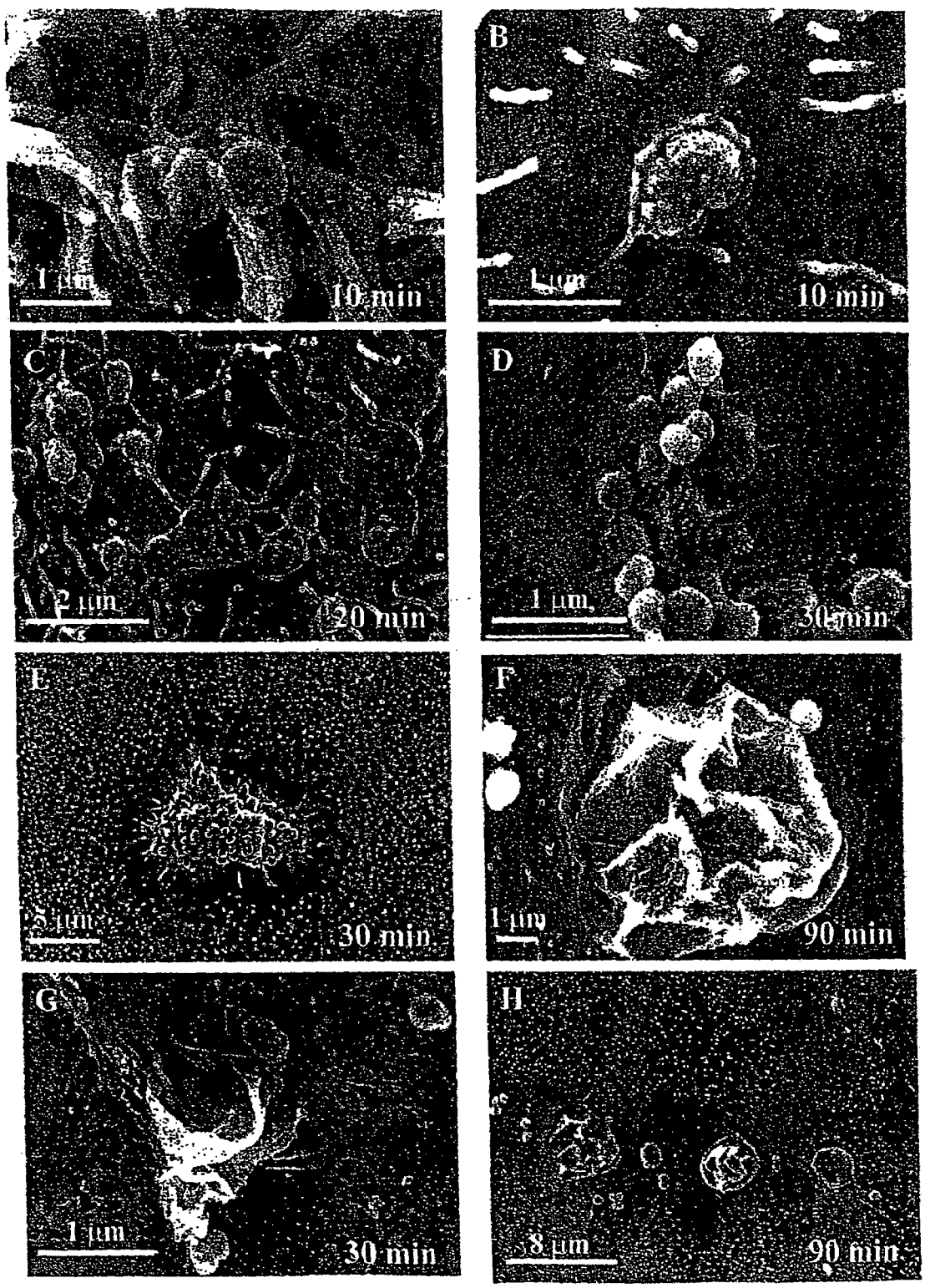

N. gonorrhoeae Infection of Primary Cervical Epithelial Cells: SEM analysis of N. gonorrhoeae 1291 infected polarized and non-polarized cells showed bacteria could adhere to both types of primary cervical cells. Bacteria were found distributed across the monolayer surface. The interaction of the bacteria with the cervical cell surface appeared to occur by multiple mechanisms. At approximately ten minutes post infection gonococci could be found associated with the cervical cell membrane both dependent (FIG. 5A) and independent of microvilli (FIG. 5B). Small tufts of microvilli were associated with bacteria on some cervical cells. Gonococci associated with the cervical cells independent of microvilli appeared to be entering the cervical cell by an endocytic process. At approximately 20 and 30 minutes post-infection, filopodia and lamellipodia formation was readily observed (FIG. 5C) and bacteria appeared to be undergoing internalization (FIG. 5D). Additionally, a visible smoothing of the cervical cell membrane was evident around the periphery of some sites of bacterial infection (FIG. 5E). By 60 minutes post-infection, the filopodia and lamellipodia became less prominent. Large membrane ruffles (FIGS. 5F and 5G) became prominent at about 90 minutes post infection of cervical cells. Membrane ruffles were abutting and contiguous with gonococci. Generally, ruffles could be readily identified by a smoothing of the cervical cell membrane that encircled the ruffle (FIG. 5H). At 3 h post-gonococcal infection, membrane ruffles and bacteria associated with microvilli were still evident. Perturbations of the cell membrane that were reminiscent of ruffles were also evident. Ruffling could be induced to occur at approximately thirty minutes post-gonococcal infection in both primary cell systems when uninfected cervical cells were infected with a primed infection inoculum (i.e., infection medium transferred from an immediately prior N. gonorrhoeae cervical cell infection) derived from one hour (ectocervical) (FIG. 5G) and ninety minute (endocervical) infections.

Figure 6:
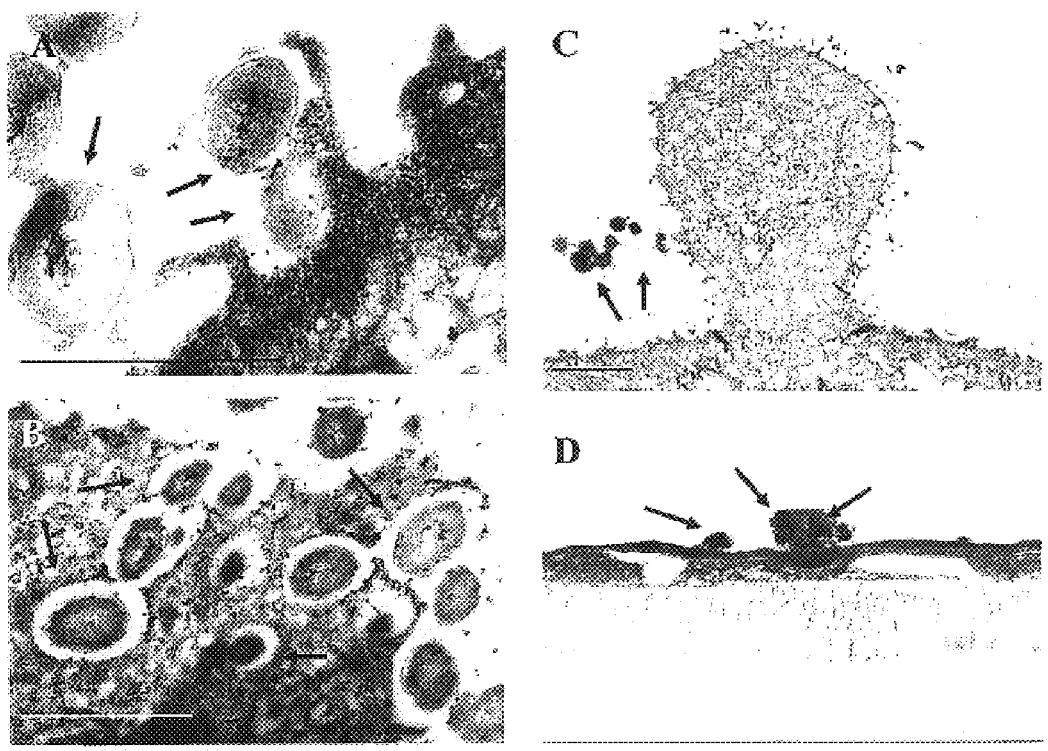
Figure 7:
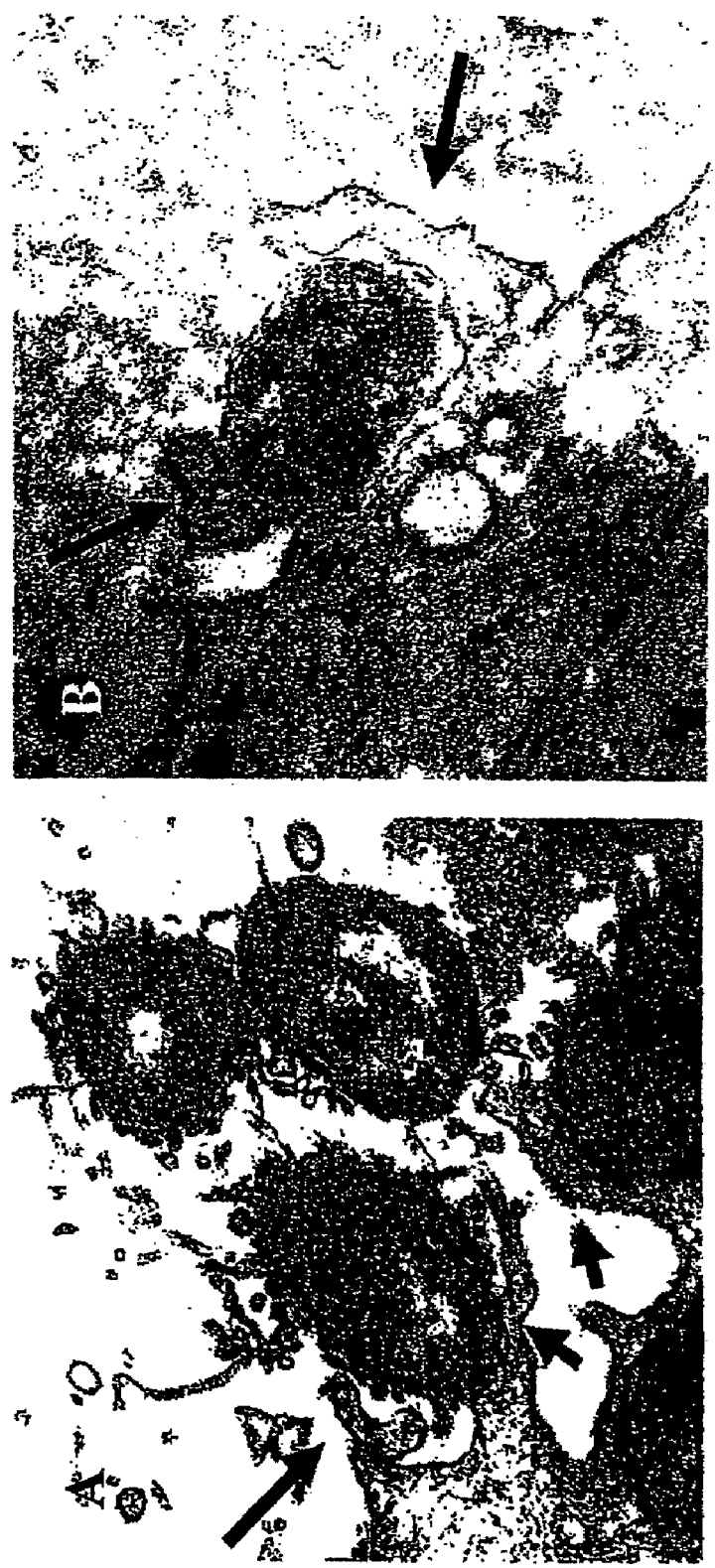

Bright-field light microscopy and TEM analysis of polarized endocervical cells infected with N. gonorrhoeae 1291 confirmed the observation made with SEM analysis (FIG. 6). Actin-filled membrane protrusions were readily observed encompassing gonococci at ninety minutes and three hours post infection. Clusters of bacteria were found breaching the superficial cervical epithelial layer; however, bacteria entered the cervical cells as single entities with each bacterium being surrounded by its own actin-lined vacuole (FIG. 6B). Consistent with SEM analysis, gonococcus-associated membrane ruffles were readily observed at 3 h post-infection by both high-powered (TEM, FIG. 6C) and low-powered (BFLM, FIG. 6D) magnification with microscopy. TEM analysis revealed that, within the host cell cytoplasm, bacteria-containing vacuoles appeared to coalesce prior to bacterial exocytosis to the subepithelial space. TEM analysis of epon-embedded, clinically-derived cervical biopsies from women naturally infected with gonococci revealed similar processes (FIG. 7). Large membrane protrusions (indicative of ruffles) (FIG. 7B) and smaller, less organized membrane structures (FIG. 7A), were readily observed. Gonococci were, again, observed to enter the cervical cells as single entities in spacious vacuoles.

Primary cell monolayers infected with gonococci in the presence of a TRITC-conjugated dextran, which would be excluded by non-macropinocytic cellular events, demonstrated that, upon invasion, gonococci reside within macropinosomes.

LSCM analysis of infection studies performed using polarized endocervical cells and ectocervical cell monolayers suggested co-localization of CD66 and CD46 with gonococci. With extended infection (i.e., six hours) clustering of CD46 molecules, which was not observed to occur at earlier time points in the infection, became prevalent in response to gonococci.

Figure 8:
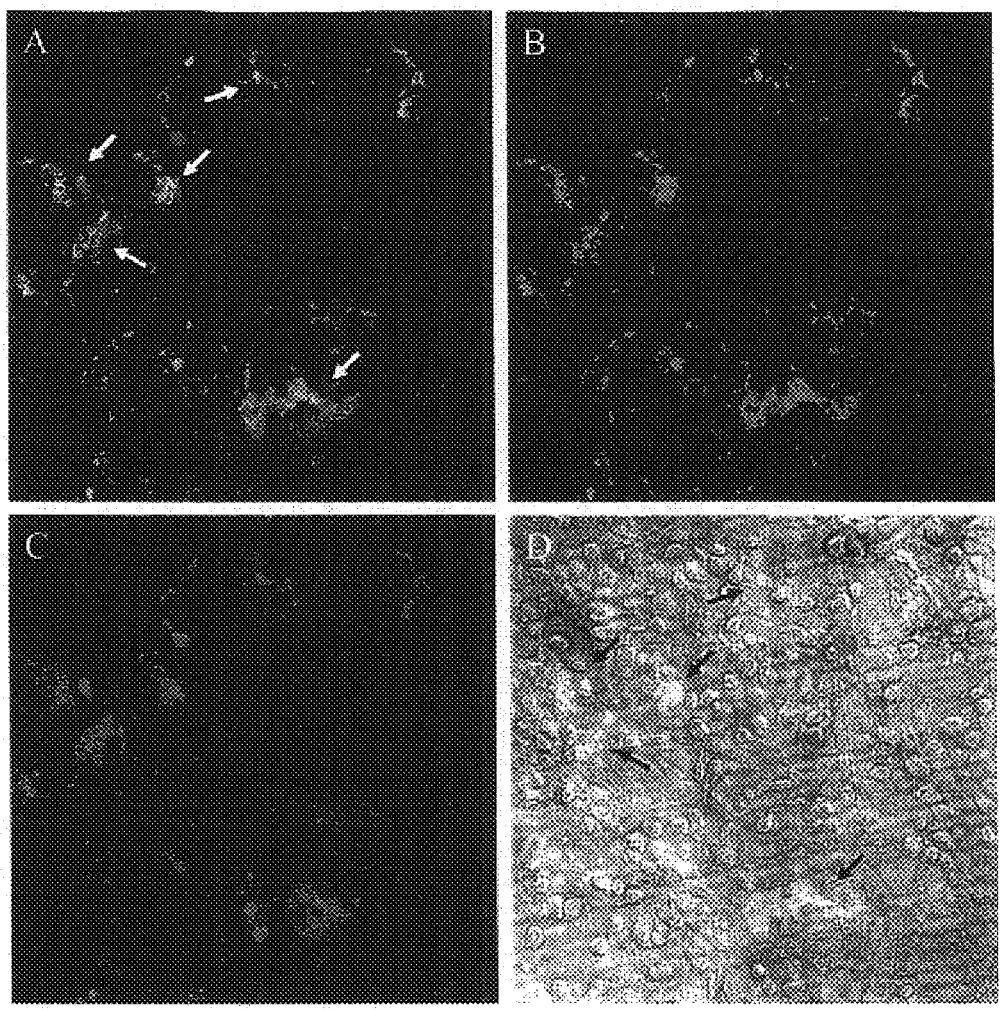

Cytoskeletal Changes Occur in Cervical Cells with Gonococcal Infection: Immunolabeling of N. gonorrhoeae infected primary cells with antibody-conjugates to actin-associated proteins confirmed that changes of the cervical cell cytoskeletal network were occurring (FIG. 8). Antibodies to talin, vinculin, ezrin, myosin, and α-actinin demonstrated a focused accumulation of these proteins, in membrane projections, at ten minutes post infection with gonococci. Membrane projections were also observed to co-localize with gonococci. This effect was most pronounced with the use of vinculin and ezrin; however, a modest accumulation of talin and α-actinin was also observed to occur. Immunolabeled projections were not observed upon analysis of uninfected cervical cells.

Gonococcal Invasion of Cervical Cells Occurs Primarily in an Actin-Dependent Manner and Does Not Require de novo Protein Synthesis: Standard gentamycin-resistance assays performed with endo- and ectocervical-derived cells confirmed results obtained by BFLM and TEM analysis and the invasive nature of gonococci with respect to both the endo- and ectocervix. Gonococci were found to invade endocervical-derived cells at a proportion of 1.57% (Table 1). A slightly higher percentage (2.70%) was observed to occur with gonococcal invasion of the ectocervical-derived cells (Table 1). The inclusion of wortmannin, cytochalasin D, and EGTA in the invasion assay prohibited bacterial entry into both cell types (Table 1). Pretreatment of primary cervical cell monolayers with the microtubule-specific depolymerizing agent, nocodazole, resulted in an approximate 67% decrease in gonococcal invasion (Table 1). Chloramphenicol and cycloheximide, which inhibit gonococcal and eukaryotic cell protein synthesis (respectively), did not inhibit gonococcal invasion of the primary cervical cell monolayers (table 1).

TABLE 1

Percent invasion of *N. gonorrhoeae* 1291 in primary cervical cells

| | Endocervical cells | | | Ectocervical cells | | |
|---|---|---|---|---|---|---|
| Cell treatment | Mean % invasion[a] | Variance of the mean | p[b] | Mean % invasion[a] | Variance of the mean | p[b] |
| None | 1.5517 | 0.3030 | NA[c] | 2.6953 | 1.3569 | NA |
| Cytochalasin D | 0.0358 | 0.0186 | 0.05 | 0.0233 | 0.0046 | 0.025 |
| Wortmannin | 0.0177 | 0.0180 | 0.05 | 0.0260 | 0.0158 | 0.025 |
| EGTA | 0.0431 | 0.0087 | 0.05 | 0.0303 | 0.0052 | 0.025 |
| Nocodazole | ND[d] | ND | ND | 0.9000 | 0.7906 | 0.25 |
| Cycloheximide | ND | ND | ND | 2.5601 | 1.8816 | 0.75 |
| Chloramphenicol | ND | ND | ND | 2.6688 | 1.9590 | 0.50 |

[a]The mean is the average percentage of at least three trials in which the percent invasion was determined as a function of the original inoculum and the subsequent CFU.
[b]P values given were determined using a Kruskal-Wallis κ-sample test of the percent gonococcal invasion determined for each cellular treatment applied to primary cervical cells in comparison to the percent gonococcal invasion of untreated, primary cervical cells.
[c]NA, not applicable.
[d]ND, not determined.

Discussion

Primary human ecto- and endocervical epithelial cell models have been described whose cytokeratin, CD66, and CD46 profiles are identical to the tissue from which they were derived. Confocal and electron microscopic analysis of primary, human, cervical cells infected with *N. gonorrhoeae* 1291, FA1090, and MS11 have demonstrated the ability of gonococci to adhere to and to induce cytoskeletal changes within both of these cell systems. Bacteria were found to associate with the primary cervical cells by more than one mechanism as evidenced by microvillus-dependent and -independent modes of bacterial attachment. Membrane perturbations resulted in the formation of membrane ruffles, which became prominent by ninety minutes post infection and after which ruffles remained readily observable. Ruffling could be induced to occur at thirty minutes post gonococcal infection in both primary cell systems when uninfected cervical cells were infected with a primed infection inoculum; however, de novo protein synthesis was not required to prime the infection process for invasion. Actin-associated proteins were also observed to accumulate in response to gonococcal infection. Gonococci were found to be internalized within the cervical cells in actin-lined spacious vacuoles.

The ability of gonococci to attach to the endocervical epithelium is well accepted. In contrast, attachment to the stratified squamous epithelium of the ectocervix and to transitional cells of the cervical squamocolumnar junction (Draper et al. 1980; Evans, B. A. 1977) remains controversial. Studies, in vitro, with the inventors' primary cell culture systems demonstrated gonococcal adherence to both the endo- and ectocervix. Considerable anatomical variation exists in the length of the squamocolumnar transition zone of the cervix (Fluhmann, C. F. 1959). Additionally, to a variable measure, columnar epithelium may overlap the stratified squamous epithelium (of the ectocervix) at the transition zone. This may, in part, account for the controversy associated with gonococcal attachment to the cervical epithelium. Cervical biopsies, used in the studies described herein, were obtained from sites distinct from the transformation zone i.e., greater than 0.5 cm from the squamocolumnar junction. Of the thirty cervical specimens used to generate primary cell cultures for use in these studies, all have supported gonococcal adherence with minimal variability. Gonococcal adherence, to date, has primarily been associated with microvilli formation; however, gonococci associated with the cervical epithelium were found both dependent and independent of microvilli.

Attachment is not synonymous with tissue damage or with the initiation of a diseased state; it is a discrete event from phagocytic internalization i.e., invasion. Four general mechanisms of bacterial invasion of host cells have been proposed to occur: receptor mediated endocytosis (Robinson, M. S. 1994), microtubule-dependent endocytosis (Mukherjee et al. 1997; Oelschlager et al. 1993; Silverstein et al. 1977), zippering (Griffin, Jr., et al. 1976; Griffin, Jr., et al. 1975), and triggering (Dramsi et al. 1998; Finlay et al. 1997; Moulder, J. W. 1985; Rabinovitch, M. 1995; Watarai et al. 1996). Several eukaryotic cell surface molecules have been proposed to serve as receptors for gonococcal invasion (for review Dehio et al. 1998; Dramsi et al. 1998; Jerse et al. 1997; McGee et al. 1983; Meyer, T. F. 1999; Nassif et al. 1999; Nassif et al. 1995; Naumann et al. 1999). In fallopian tube organ culture (FTOC) gonococcal invasion has been proposed to occur in a manner reminiscent of "zipper" type phagocytosis. (Dramsi et al. 1998; McGee et al. 1983; Stephens, D. S. 1989).

The observation that gonococci appear to induce membrane ruffling is a novel finding. Ruffling is the result of a complex interaction that occurs between a bacterium and a host cell and is associated with a triggering mechanism (Silverstein et al. 1977) that leads to macropinocytosis (Alpuche-Aranda et al., 1994; Francis et al. 1993; Garcia-del Portiilo et al. 1994; Swanson et al. 1995). Infection of the inventors' primary cell culture systems resulted in ruffling of both the endo- and ectocervical-derived cells. Ruffling was evident in the endocervical cells as convoluted spheres whereas ruffling of the ectocervical cells was observed to occur as long, ribbon-like folds. The characteristic structural morphology of endo- and ectocervical-associated ruffles appeared to be specific for each of their respective cell types; hence, the ruffles found on the ectocervical cells were termed "ribbons."

*Salmonella* and *Shigella* have been shown to induce membrane ruffling in a contact-dependent manner in which a (highly conserved) type III secretion system (TTSS) allows for the secretion of numerous effector proteins that initiate the cellular response required for the observed cytoskeletal rearrangements (Finlay et al. 1991; Rosqvist et al. 1995; Tran Van Mhieu et al. 1999). A TTSS has not been described for *N. gonorrhoeae*. A search of the *N. gonorrhoeae* strain FA 1090 genome data base (University of Oklahoma Advanced Center for Genome Technology) for the possible existence of *Salmonella* and *Shigella* TTSS and effector protein homologs yielded no significant matches to ruffling-associated proteins. Dillard et al. (1999) recently described the existence of a pathogenicity island in *N. gonorrhoeae* strain MS11, which encodes a secretion system. This pathogenicity island is also present in *N. gonorrhoeae* strain 1291, but it is absent in *N. gonorrhoeae* strain FA 1090. This pathogenicity island (and its encoded secretion system) may, therefore, share homology to *Salmonella* and *Shigella* TTSS and effector proteins; however, this data is currently unavailable.

Ruffling and subsequent invasion by *Salmonella* and *Shigella* shows an actin-dependence but occurs independent of microtubules. It has previously been demonstrated that gonococcal invasion of tissue culture cell lines is dependent upon microtubules and a functional actin cytoskeleton (Bessen et al. 1986; Grassmé et al. 1996; Richardson et al. 1998). Using standard gentamycin-resistance assays endo- and ectocervical cells were examined to determine if these primary cells displayed a microtubule- or actin-dependence for gonococcal invasion. Cytochalasin D, wortmannin, and EGTA brought invasion levels down to (essentially) zero in both cell systems suggesting that gonococcal entry is dependent upon actin rearrangements. TEM analysis of *N. gonorrhoeae* infected polarized cervical cells supported a role for actin in the gonococcal invasion process in that actin-filled ruffles and large, spacious, actin-lined vacuoles encompassed invading gonococci. The latter finding is in contrast to Grassmé et al. (1996) who demonstrated that gonococcal association with actin was transient. In multiple experiments, using cervical cell monolayers derived from different patients, invasion was not significantly inhibited when primary cervical cells were pretreated with nocadazole to disrupt microtubules.

A concentrated accumulation of actin-associated proteins has been demonstrated to occur in response to membrane ruffling (Clerc et al. 1987; Finlay et al. 1991; Skoudy et al. 1999). To the knowledge of the present inventors, the role of actin-associated proteins in gonococcal infection has not been examined. It was found that in response to gonococcal invasion a concentrated accumulation of predominately ezrin and vinculin occurs in a manner analogous to *Shigella*. A modest accumulation of talin and α-actinin also was observed during gonococcal infection of cervical cells. Additionally, although myosin was observed to accumulate in response to, and co-localize with, gonococci at five and ten minutes post infection, myosin was also observed to be fairly diffuse throughout some of the infected cervical cells. This may reflect the relative abundance of this protein in comparison to the other actin-associated proteins that were examined. Alternatively, the observed myosin distribution may be indicative of the initiation of a concurrent change occurring in the actin cytoskeleton, or it is possible that gonococci elicit only a minimal recruitment of myosin upon ruffle induction.

The host cell surface molecule exploited by *Salmonella* to initiate ruffling has, to date, not been elucidated. The *Shigella* protein complex of IpaB/C/D has been shown to bind the fibronectin receptor, integrin $\alpha_5\beta_1$ (Watarai et al. 1996). The predominant accumulation of ezrin and vinculin in *N. gonorrhoeae* infected primary cervical cells and the ability of these actin-associated proteins to directly interact with integrin molecules to initiate cellular responses (Clarke et al. 1977; Schmidt et al 1998) make integrin molecules attractive candidates as potential gonococcal receptors that serve to initiate gonococcal-induced ruffling. Studies using the larynx carcinoma cell line, HEp-2, have demonstrated that gonococcal binding of fibronectin results in co-ligation of heparin sulphate proteoglycan (HSPG) to gonococcal Opa proteins and subsequent binding to the $\alpha_5\beta_1$, integrin (Naumann et al. 1999). Ruffling was not observed to occur in these cells suggesting that gonococcal induction of ruffles may be unique to the cervical epithelium. Investigation of male primary urethral cells has shown that some gonococci can enter these cells by focal macropinocytosis, but no evidence of ruffling was seen. This would suggest that perhaps a cell surface molecule unique to the cervical epithelium may be involved in ruffle induction and that gonococci invoke membrane ruffles by a mechanism distinct from that observed for *Shigella*. *Salmonella* and *Shigella* share many common characteristics with respect to their ability to induce membrane ruffles; however, they each also display ruffling characteristics that are unique to their genus.

Through co-evolution with their exclusive human hosts the pathogenic *Neisseria* have developed several mechanisms by which they successfully persist in the general population. Previous studies of *N. gonorrhoeae* have demonstrated the ability of these organisms to invade eukaryotic cells by receptor-mediated endocytosis, microtubule-dependent endocytosis, and zippering. Here yet another mechanism by which gonococci are able to exploit their human host is described. Ruffling, via a triggering mechanism, has not been observed to occur in male primary urethral cells, tissue culture cell lines, or FTOC nor has ruffling been described to occur with *Neisseria meningiditis* infections. Ruffling of primary cervical cells, which is induced with gonococcal infection, therefore, is a novel finding.

EXAMPLE 2

Complement Receptor 3 (CR3) Is the Factor Responsible for Ruffling

Tissues and Cell Culture. Surgical biopsies derived from the endo- and the ectocervix that were used to seed primary cervical epithelial cell systems were procured and maintained as described (Example 1 above) in Defined Keratinocyte Serum Free Medium (dk-SFM) (Life Technologies, Rockville, Md.). Urethra epithelia was obtained from adult males undergoing urologic surgery at the University of Iowa Hospitals and Clinics and used to seed primary urethral cell culture systems as described by Harvey et al. (1997). Primary male urethral cells were immortalized with the E6 and E7 genes from the Human Papilloma Virus prior to use. E6E7 immortalized human ectocervical keratinocytes (HCK) and endocervical (End1) cells (generously provided by A. Klinglehutz (University of Iowa, Iowa City, Iowa) and D. Anderson (Fearing Research Laboratory, Boston, Mass.), respectively) were cultured in dk-SFM. ME180 cervical carcinoma cells (ATCC # HTB-33) were cultured in McCoy's 5A medium (Life Technologies) according to ATCC recommendations. Hec1B endometrial carcinoma cells, Chinese hamster ovary cells (CHO-K1), and K562 myeloid cells were maintained in RPMI tissue culture medium (Life Technologies). CR3-expressing CHO(CHO-CR3) and K562 (K562-CR3) cells were maintained in RPMI-G418 (100 μg/ml). CHO cells were generously provided by L. A. Allen and L. Schlsinger (University of Iowa) with permission from D. Golenbock (Boston Medical Center, Boston, Mass.). E. Brown (University of Calif., San Francisco, Calif.) generously provided K562 and K562-CR3 cells. McCoy's 5A and RPMI media were replaced with dk-SFM 48 h prior to infection studies. Surgical biopsies derived from the fallopian tube, endometrium, endocervix, ectocervix, vas deferens, and the male and the female urethra that were to be used for immunohistochemical tissue analysis were processed for cryosectioning as previously described in Example 1 above. Clinical biopsies derived from the cervix of women with documented gonorrhea were provided by D. Fortenberry (Indiana University School of Medicine, Indianapolis, Ind.) and were processed for immunohistochemical analysis as previously described in Example 1 above.

Bacteria and Infection Studies. *N. gonorrhoeae* strains 1291, 1291-green, FA1090-green, and MS11-green were used in the infection studies described below. *N. gonorrhoeae* strains 1291-green, FA1090-green, and MS11-green express green fluorescent protein and will be described elsewhere; the plasmid pLES98 was a gift from V. Clark (University of Rochester, Rochester, N.Y.). *N. gonorrhoeae* 1291 and FA1090- and MS11-green parental strains (*N. gonorrhoeae* FA1090 and MS11-A, respectively) are clinically isolated gonococci. *N. gonorrhoeae* FA1090 is a serum-resistant, genital isolate from a patient with disseminated gonococcal infection. *N. gonorrhoeae* 1291 is a serum-sensitive, urethral isolate obtained from a male patient with gonococcal urethritis. *N. gonorrhoeae* 1291, 1291-green, and MS11-green contain the pathogenicity island described by Dillard et al. (1999). For infection studies bacteria were allowed to grow overnight (37° C., 5% $CO_2$) on GC-IsoVitaleX agar plates prior to harvesting with a sterile swab and resuspending in sterile saline. Culture density was determined spectrophotometrically where an optical density of 1 at 600 nm was equivalent to $10^9$ bacteria/ml. Bacterial cultures were further diluted in dk-SFM to a density of $10^7$ bacteria/ml and used to infect cell monolayers at a multiplicity of infection of 100. Infection was allowed to progress for variable time periods after which the infection medium was removed and the cell monolayers were extensively washed with phosphate-buffered saline (PBS) prior to fixation with 2% paraformaldehyde. Uninfected, control cell monolayers were simultaneously processed with challenged cell monolayers. Infected and uninfected (control) cell monolayers were subsequently processed for Laser Scanning Confocal Microscopy (LSCM), Scanning Electron Microscopy (SEM), or Transmission Electron Microscopy (TEM) as described previously in Example 1 above; or the cells were harvested for immunoprecipitation assays.

Immunolabeling and Microscopy. Immunolabeling of frozen tissue sections and cell monolayers was performed as described in Example 1 above. Primary antibodies used for immunolabeling were specific for CD11b (H5A4 (Developmental Studies Hybridoma Bank (DSHB), the University of Iowa, Iowa City, Iowa) and Bear1 (Immunotech, Marseille, France)) or CD18 (anti-CD18 (Santa Cruz Biotechnology, Santa Cruz, Calif.) and IB4, generously provided by E. Brown (University of Calif.)). Tetramethyl rhodamine isothiocyanate (TRITC)- or fluorescein isothiocyanate (FITC)-conjugated secondary antibodies were applied to cell monolayers and bacteria, as noted. Uninfected, tissue cryosections were labeled with FITC-conjugated secondary antibodies and counter stained with ethidium bromide (0.5 ng/ml, 6 min). Clinical biopsy cryosections were incubated with 2C3 and anti-CD18 primary antibodies followed by immunolabeling with TRITC- and FITC-conjugated secondary antibodies, respectively. The 2C3 monoclonal antibody recognizes the H.8 gonococcal surface protein. Infected and uninfected (control) K562 and K562-CR3 cells to be used for TEM analysis were labeled with colloidal-gold secondary antibodies as indicated. Immunolabeled cryosections, cell monolayers, and K562 cells were viewed using the Bio-Rad MRC-1024, the Zeiss 510 Laser Scanning Confocal, or the H-7000 (Hitachi Corp., CA) transmission electron viewing systems. Primary cervical cell and CHO cell monolayers processed for SEM analyses were viewed using the Hitachi S-4000 scanning electron microscope.

Immunoprecipitation and Western Blot Analysis. Immunoprecipitation was performed as described by Wen et al. (2000). Anti-CD18 or H5A4 were used as capture antibodies. Western blotting was subsequently performed using monoclonal antibodies to gonococcal porin (3H1), pili ($IE_8G_8$), or to the opacity associated outer membrane proteins, Opa, (4B12), all of which were generously provided by M. Blake (North American Vaccine, Beltsville, Md.). Antibody 6B4, which recognizes the Galβ1-4GlcNAc conserved epitope of gonococcal lipooligosaccharide (LOS), was used to probe for the association of LOS with CR3.

Inhibition of *N. gonorrhoeae* Attachment and Invasion. Primary cervical cell monolayers, CHO-CR3 and -K1 cells, and K562-CR3 and K562 cells were pretreated (30 min, 4° C.) with 20 µg/ml H5A4, Bear1, 1134, or anti-CD18 antibody competitors prior to infection with gonococci as outlined above. Where indicated anti-CD18 blocking peptide (Santa Cruz Biotechnology) was included in the inhibition assay. Infected, control cell assays (devoid of antibody competitors) and uninfected, control cell assays (with anti-CR3 antibodies) were treated in parallel with inhibition assays. The ability of gonococci to bind primary cervical, K562-CR3, or CHO-CR3 cells in the presence or absence of antibody competitors was assessed by LSCM, TEM, or SEM qualitative analysis. Quantitative analysis of the ability of gonococci to invade primary endo- and ectocervical cells and CHO-CR3 and -K1 cells was determined by standard gentamicin-resistance assays as described previously in Example 1 above and in which antibody competitors were included or excluded from the invasion assay as described above. Where indicated primary endo- and ectocervical cell monolayers were pretreated (2 h, 37° C.) with 10 ng/ml *Clostridium* C3 neurotoxin prior to infection. The ability of anti-CR3 antibodies to inhibit gonococcal invasion was determined as a normalized function of the ability of gonococci to invade primary endo- and ectocervical cells and CHO cells in the absence of antibody inhibitors. A Kruskal-Wallis non-parametric analysis of variance was used to determine the statistical significance of invasion assays performed in the presence of the C3 neurotoxin.

Results

Analysis of CR3 Expression in Tissue Biopsies. LSCM of surgical biopsies derived from the ectocervix, endocervix, endometrium, and fallopian tube revealed the presence of both the alpha and beta subunits of CR3. Immunolabeling of tissue sections with anti-CD18 and anti-CD11b (H5A4) antibodies revealed comparable levels of immunofluorescence for each antibody in each of the tissues examined. CR3 expression appeared to be greatest in the ectocervix. Expression levels decreased progressively from the ectocervix to the upper female genital tract with a low level of CR3 expression being observed in the fallopian tube tissue. Immunohistological examination of male urethra and vas deferens tissues failed to reveal the presence of either CR3 subunit. Similarly, tissue derived from the female urethra failed to label positively for CR3. An isotype control antibody yielded no immunofluorescence.

Analysis of CR3 expression in Primary Human Cervical Epithelial Cells. Consistent with results obtained by immunohistochemical examination of endocervical and ectocervical tissue biopsies, primary endo- and ectocervical epithelial cells labeled positive for both CD11b and CD18, and no immunofluorescence was observed with an isotype control. Equivalent fluorescence was observed with either anti-CD18 or H5A4 antibodies. Immunofluorescence paralleled results obtained with immunohistological examination of tissue biopsies in that a lower level of expression was qualitatively observed in endocervical-derived cells in comparison to ectocervical-derived cells. LSCM analysis of infection studies using N. gonorrhoeae strains 1291, 1291-green, MS11-green, and FA1090-green suggested that a higher level of CR3 surface expression occurred in the presence of the gonococcus. However, the level of CR3 expression in infected endocervical cells did not obtain that level observed for infected ectocervical cells. Infected ectocervical cells exhibited very high levels of CR3 expression. Co-localization of gonococci with CR3 was observed to occur by thirty minutes post-infection; however, the gonococcus-CR3 association became more prominent by ninety minutes and three hours post-infection.

Analysis of CR3 Expression in Immortalized Epithelial Cells. In contrast to results obtained with primary cervical epithelial cells, cervical and endometrial carcinoma cell lines (ME180 and Hec1B, respectively) failed to demonstrate CR3 expression as determined by LSCM. CR3 could not be identified on E6E7 transfected endo- and ectocervical or male urethral cells by immunofluorescence using anti-CD18 antibody or monoclonal antibody H5A4. Infection of these cell lines with gonococci revealed the presence of minimal amounts of CD18 after ninety minutes and three hours; however, in comparison to results obtained with the primary cervical cells, the level of CR3 expression in the immortalized and carcinoma-derived cells was negligible. CD11b expression was not observed in ME 180, Hec1B, HCK, or End1 cells subsequent to gonococcal infection.

Western Blot Analysis Confirmed the Presence of CR3 in Primary Cervical Cells. To confirm the presence of CR3 in primary cervical epithelial cells immunoprecipitation was performed in which an antibody to CD11b or CD18 was used to capture CR3. Confirmation of CR3 expression was subsequently demonstrated by Western Blot analysis using antibodies to CD18 or CD11b and chemiluminescence. Immunoprecipitation using the monoclonal antibody, H5A4, specific for CD11b and subsequent western blotting with anti-CD18 antibody revealed the presence of an approximately 90 kDa band consistent with CD18. The reverse experiment, in which immunoprecipitation was performed with an anti-CD 18 antibody and which the respective western blot was probed with H5A4, demonstrated the presence of an approximately 150 kDa band indicative of CD11b. Parallel immunoprecipitation and Western Blot experiments using male urethral epithelial cells did not reveal the presence of either CR3 subunit. Control immunoprecipitation experiments in which the H5A4 or anti-CD18 capture antibody was omitted, or in which an isotype control was used as the capture antibody, failed to show the 90 or 150 kDa bands with subsequent western blotting.

CR3 Associates with N. gonorrhoeae Porin, Pilus, and Opa Proteins. To confirm LSCM analysis of gonococcal co-localization with CR3, immunoprecipitation was performed in which antibodies to CD11b or CD18 were used to capture CR3 on infected and uninfected primary endo- and ectocervical cells. The association of gonococci with CR3 was subsequently examined by Western Blot analysis using antibodies to gonococcal porin, opa, or pili proteins or to LOS. Membranes probed with antibodies to LOS failed to reveal a CR3 association. Western blots probed with the monoclonal antibodies; 3H11, specific for gonococcal porin, $IE_8G_8$, specific for gonococcal pili, or 4B12, which recognizes a conserved epitope of gonococcal Opa proteins, revealed that these proteins associated with CR3 present on primary endo- and ectocervical epithelial cells. Antibody probes to porin, Opa, pili, and LOS did not reveal the presence of these N. gonorhoeae-associated molecules in uninfected endo- and ectocervical cells. Immunoprecipitation (control) experiments in which the antibody to CR3 was omitted also failed to demonstrate the presence of the gonococcal-associated molecules examined.

Anti-CR3 Antibodies Inhibit N. gonorrhoeae Binding to Cell Surfaces.

To more closely examine the association of the gonococcus with CR3 TEM and SEM analysis was performed of the ability of N. gonorrhoeae to bind CR3-transformed K562 myeloid cells and CHO cells in the presence of antibodies to both the alpha and beta subunits of CR3. TEM analysis demonstrated N. gonorrhoeae binding to K562-CR3 cells and inhibition of N. gonorrhoeae binding in the presence of the anti-CR3 antibodies H5A4, Bear1, IB4, and anti-CD18. Similar results were obtained with SEM analysis of infected endo- and ectocervical cells and CHO-CR3 cells. Binding of gonococci could be inhibited by the addition of the same anti-CR3 antibodies. Binding inhibition that occurred in the presence of anti-CD18 could be reversed by the addition of the anti-CD18 blocking peptide to the infection assay. Binding of gonococci to CHO-K1 (control) cells, which do not express CR3, was not observed.

Figure 9:
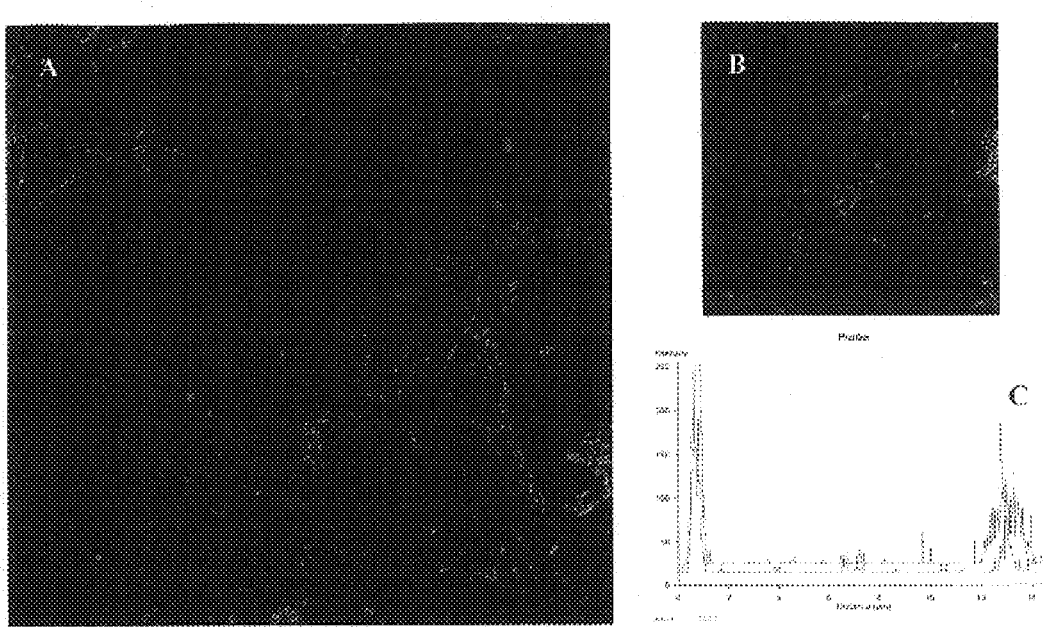

N. gonorrhoeae Co-localizes with CD18 in vivo. The studies outlined above demonstrate that CR3 serves as a receptor for gonococcal attachment and invasion of the cervical epithelium in vitro. To determine if CR3 is bound by the gonococcus in vivo, LSCM analysis was performed of cervical biopsies derived from women with documented gonorrhea. Immunolabeling of these tissue cryosections demonstrated the presence of CD18 as a green fluorescence and gonococci as a red fluorescence. Gonococci were found to co-localize with CD18, which was visible as a yellow fluorescence. Co-localization was confirmed as a profile plot where the individual fluorescence of each fluorophore (within a designated area of presumed co-localization) was recorded and plotted, individually, by the Zeiss 510 Laser Scanning Confocal viewing system (FIGS. 9A, B). These studies confirm in vitro studies using primary endo- and ectocervical cells and provide evidence that CR3 can serve as a receptor for N. gonorrhoeae infection in vivo.

Binding of CR3 Stimulates Membrane Ruffling. Extensive membrane ruffling of N. gonorrhoeae-infected K562-CR3, CHO-CR3, and primary cervical cells was observed by TEM, SEM, and LSCM analysis. Ruffles were observed in the presence of gonococci or gonococci in the presence of anti-CR3 antibody, but membrane ruffles were not observed in uninfected cells to which antibody had not been added. Uninfected endocervical, ectocervical, and CHO-CR3 cell monolayers treated with the anti-CR3 antibodies H5A4, Bear1, IB4, and anti-CD18 also revealed extensive membrane ruffling by SEM analysis. Membrane ruffling was most pronounced with the use of the anti-CD18 antibody, IB4. Control assays using CHO-K1 cells failed to reveal the presence of membrane ruffles. These studies suggest that engagement of these cells by anti-CR3 antibodies can initiate membrane ruffling.

*N. gonorrhoeae* Invasion of Primary Endocervical and Ectocervical Cells is Dependent on CR3. Standard gentamicin-resistance assays of infected endo- and ectocervical cells performed in the presence of antibodies to both the alpha and beta subunits of CR3 confirmed results obtained by TEM and SEM analysis of CR3-transfected myeloid and CHO cells. The addition of anti-CD11b and anti-CD18 antibodies to the invasion assays resulted in greater than 93% invasion inhibition of both endo- and ectocervical cells (FIG. 2) with greatest inhibition (99.86% for endocervical cells, 100% for ectocervical cells) being observed with the addition of the anti-CD11b monoclonal antibody, H5A4. Invasion inhibition that occurred in the presence of the anti-CD18 antibody could be reversed by the addition (to the invasion assay) of a blocking peptide to the anti-CD18 antibody. Pretreatment of endo- and ectocervical cells with *Clostridium* C3 neurotoxin, which inactivates the effector domain of the Rho subfamily of GTPases, also significantly inhibited gonococcal invasion supporting a role for CR3-mediated phagocytosis (FIG. 3).

EXAMPLE 3

Identification of Inhibitory Peptides

The present inventors have a phage display library that contains 100 million different copies of 15-mer amino acids. This library is used to screen for phage particles that bind to the CR3 receptor. Briefly, the library is amplified and approximately $10^{12}$ phage are applied to a petri dish contain CHO cells expressing CR3. The phage are allowed to interact with the cells for 1 hour and the dish is washed to remove unbound phage. The bound phage are released with a high pH (9.6–10) buffer, reamplified and the process repeated six more times to enrich for phages particles specific for the CHO-CR3 cells. After the final enrichment, the resulting phage are placed over CHO cells lacking CR3. In this case, the unbound phage (containing CR3 binding peptides) are collected after one hour and amplified, and this process repeated six times.

At that point, enriched CR3 binding phage are plaque purified and tested for the ability to inhibit gonococcal interaction with CHO-CR3 cells. It is estimated that 100 plaque purified phages will be examined to find a phage that inhibits this interaction. When this phage is identified, the 15 mer peptide is sequenced and the peptide synthesized. Gonococcal-CHO-CR3 inhibition studies are then performed with the purified peptide.

EXAMPLE 4

Radiolabeling and Collection of Gonococcal Products Released with Infection of Primary Cervical Cells.

Gonococci allowed to grow overnight on GC agar were harvested with a sterile swab and used to inoculate 5 ml cultures of Morse's Defined Medium (MDM). MDM was prepared such that half the recommended methionine and cysteine was replaced with 125 µCi Redivue Pro-mix L-[$^{35}$S] in vitro cell labeling mix (Amersham Pharmacia Biotech Inc, Piscataway, N.J.). After approximately 4 h gonococci were collected by centrifugation (4000 rpm, 5 min), rinsed with sterile physiological saline to remove excess label, and resuspended in cold MDM such that a culture density of $10^7$ bacteria ml$^{-1}$ was obtained. MDM containing the $^{35}$S-labeled gonococci was then used to infect approximately $10^5$ primary, human, ecto- and endocervical cells or 35 mm tissue culture dishes devoid of cervical cells. Prior to infection ecto- and endocervical cells were pretreated (30 min, 37° C.) with 250 mM cycloheximide to inhibit cervical cell protein synthesis. Cycloheximide was maintained in the culture medium through out the course of the infection. Cervical cells and tissue culture plates lacking cervical cells were challenged with gonococci for 90 min and 3 h time periods after which the culture supernatants were collected. Gonococci were removed from the culture supernatants by filtration through low-protein binding 0.22 µm syringe filter units. Supernatant filtrates were concentrated using Centricon YM-3 centrifugal filter units (Millipore Corporation, Bedford, Mass.) prior to suspension in 1M Tris-1% SDS. Concentrated supernatants were separated on a SDS 12% to 4% polyacrylamide gradient gel prior to gel-extraction for mass spectrometry at the Mass Spectrometry Facility located at the University of California (San Francisco, Calif.). Analysis of mass data was performed using Protein Prospector (University of California San Francisco, Calif.) (Clauser et al., 1999) and ProFound (Rockefeller University, New York, N.Y.) (Zhang et al., 2000) database systems for protein identification.

Figure 10:
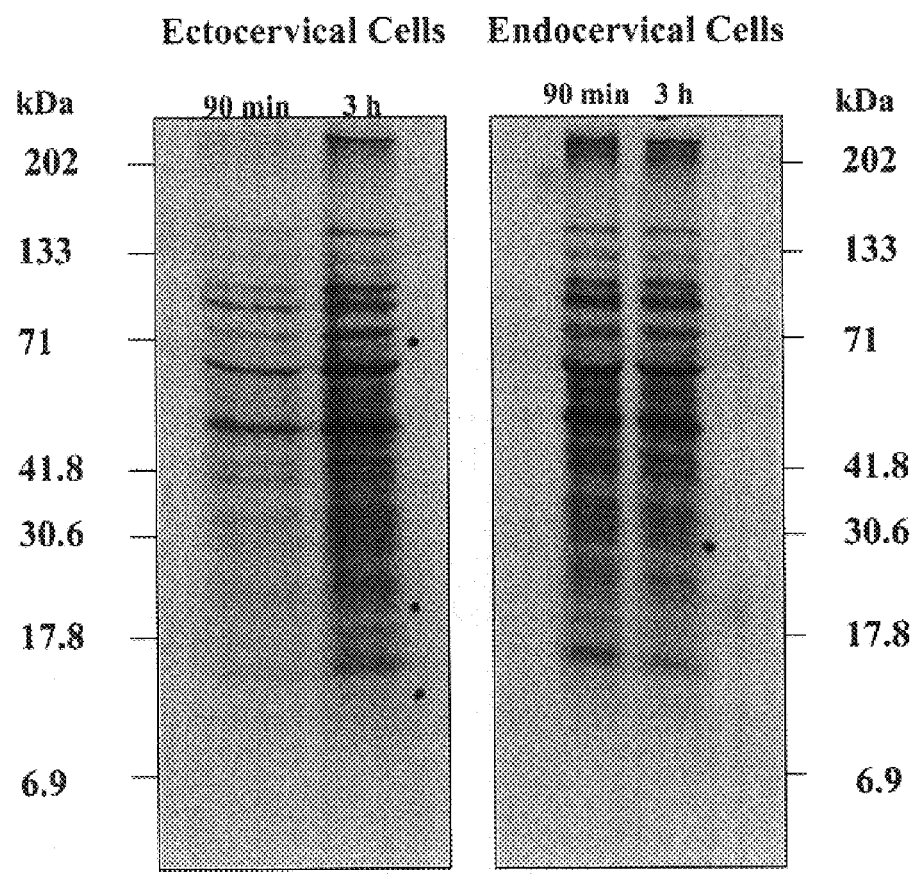

During in vitro infection of primary endocervical and exocervical cells, the inventors have found that there is a 60 to 90 minute delay in the onset of ruffle formation after infection begins. This suggested as one possibility that the gonococcus must be releasing a factor that needed to be at a critical concentration to be effective to induce ruffling. Using bacteria labeled with $^{35}$S cysteine/methionine, the inventors studied the tissue culture supernatant being released by the bacteria (FIG. 10). Using mass spectroscopy and proteomic analysis of a SDS-Gel, the inventors identified a number of the proteins being released by the bacteria. These proteins include the following (see, FIG. 11): gonococcal protein p177, gonococcal protein p88, gonococcal protein p64, gonococcal protein p55, gonococcal protein p46, gonococcal porin, gonococcal pilE, and gonococcal pilC.

Five of these proteins have not been previously described as important in gonococcal pathogenesis (p1177, p88, p64, p55, and p46). Homologues of three of the five genes are present in the *Neisseria meningitidis* genomic database. The inventors have confirmed that the genes for two of the proteins (p177 and p55) were present in gonococcal DNA. Protein p177 encodes a 100 amino acid region that has high homology to the filamentous hemagglutinin of *Bordetella pertussis*. This protein is a bridging molecules (can span two structures) that has been shown capable of engaging and activating CR3. Protein p55 has enzymatic activity that involves modification of phospholipid membranes and could be involved in modification of the cell membrane enhancing bacterial entry.

EXAMPLE 5

Inhibition of Cellular Invasion by *Neisseria gonorrhoeae*

Experiments have been performed showing that recombinant murine I-domain from the Alpha-subunit of the complement type 3 receptor inhibits *Neisseria gonorrhoeae* from invading primary human cervical cells.

The recombinant murine I-domain (rI domain) is a 23 kilodalton peptide that contains Myc and His domains. It is recognized by monoclonal antibodies specific for human CR3 I-domain. The amino acid identity to the human I domain is over 90%. The amino acid sequence of the peptide is given below (SEQ ID NO: 11).

FPQQESDIVFLIDGSGSINNIDFQKMKEFVSTVMEQFKKSKTLFSLMQYS

DEFRIHFTFNDFKRNPSPRSHVSPIKQLNGRTKTASGIRKVVRELFHKTN

GARENAAKILVVITDGEKFGDPLDYKDVIPEADRAGVIRYVIGVGNAFNK

PQSRRELDTIASKPAGEHVFQVDNFEALNTIQNQLQEKIFAIPAAASFL

The peptide is encoded by the nucleotide sequence given below (SEQ ID NO: 12).

TTCCCTCAGCAGGAGAGTGACATTCTCTTCTTGATTGATGGCTCCGGTAG

CATCAACAACATTGACTTTCAGAAGATGAAGGAGTTTGTCTCAACTGTGA

TGGAGCAGTTCAAAAAGTCTAAAACCTTGTTCTCTTTGATGCAGTACTCG

GACGAGTTCCGGATTCACTTCACCTTCAATGACTTCAAGAGAAACCCTAG

CCCAAGATCACATGTGAGCCCCATAAAGCAGCTGAATGGAGGACAAAAA

CTGCCTCAGGGATCCGGAAAGTAGTGAGAGAACTGTTTCACAAAACCAAT

GGGGCCCGGGAGAATGCTGCCAAGATCCTAGTTGTCATCACAGATGGAGA

AAAATTCGGTGATCCCTTGGATTATAAGGATGTCATCCCCGAGGCAFACA

GAGCAGGGGTCATTCGCTACGTAATTGGGGTGGGAAATGCCTTCAACAAA

CCACAGTCCCGCAGAGAGCTCGACACCATCGCATCTAAGCCAGCTGGTGA

ACACGTGTTCCAAGTGGACAACTTTGAAGCCCTGAATACCATTCAGAACC

AGCTTCAGGAAAAGATCTTTGCAATTCCCGCGGCCGCCAGCTTTCTA

Studies were performed evaluating the ability of the rI-domain to inhibit adherence and invasion of primary human ectocervical cells by *Neisseria gonorrhoeae*. The cervical cells were infected with 107 *N. gonorrhoeae* strain 1291. The results of these studies are shown in table 2 below. Recombinant I-domain is a potent inhibitor of ectocervical cell association by *Neisseria gonorrhoeae*. As little as 1 ng of rI-domain gives over 90% inhibition of invasion. With decreasing amounts of rI-domain the inhibition decreases in a dose dependent fashion.

TABLE 2

| rI domain concentration | % inhibition of invasion of primary exocervical cells |
|---|---|
| 1 µg/ml | 98.56 |
| 100 ng/ml | 96.8 |
| 10 ng/ml | 94.6 |
| 1 ng/ml | 92.1 |
| 100 pg/ml | 77.5 |
| 10 pg/ml | 56.3 |
| 1 pg/ml | 17.4 |

Individual, smaller peptides based on the sequence of rI-domain duplicate the inhibitory activity of the rI-domain.

EXAMPLE 6

Phospholipase D (PLD) of *Neisseria gonorrhoeae* and *Neisseria meningitidis*

Phospholipase D (PLD) is an important molecule involved in cell signaling. It hydrolyzes phosphatidylcholine (PC) to phosphatidic acid (PA) and choline in response to various extracellular stimuli. Phosphatidic acid has been implicated as a lipid second messenger to a variety of extracellular stimuli. Phosphatidic acid has been implicated as a lipid second messenger in the regulation of protein kinases, GTPase-activating proteins, PI kinases, adenyl cyclase and other signaling molecules. Phospholipase D has been implicated in membrane trafficking and vesicular transport, in which processes, acidic phospholipids may facilitate membrane budding and/or fusion.

Two biochemically distinct phospholipase D activities have been characterized. One is dependent upon the small GTPase Arf and upon phosphatidylinositol 4,5-bisphosphate (PIP2) and another is stimulated by oleate. Phospholipase D activation by v-Src depends upon a GTPase cascade containing Ras and Ral. Ral constitutively associates with phospholipase D through Ral's novel amino terminus. Evidence also implicates Rho in phospholipase D activation suggesting a complex interplay of multiple small GTPases.

Figure 11:
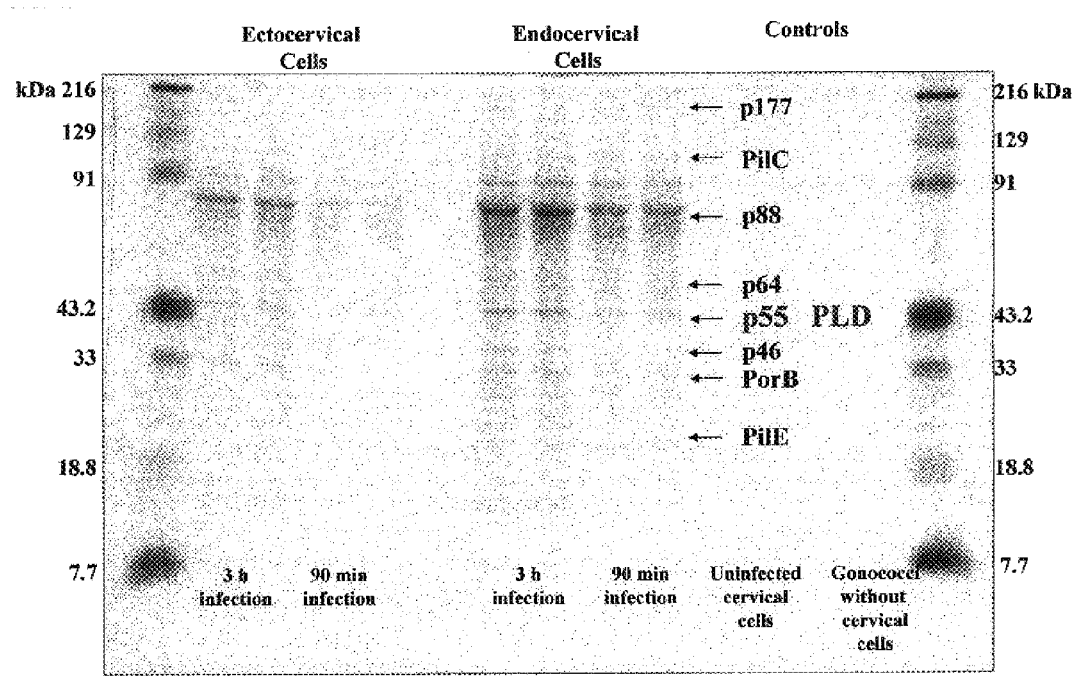
Figure 12:
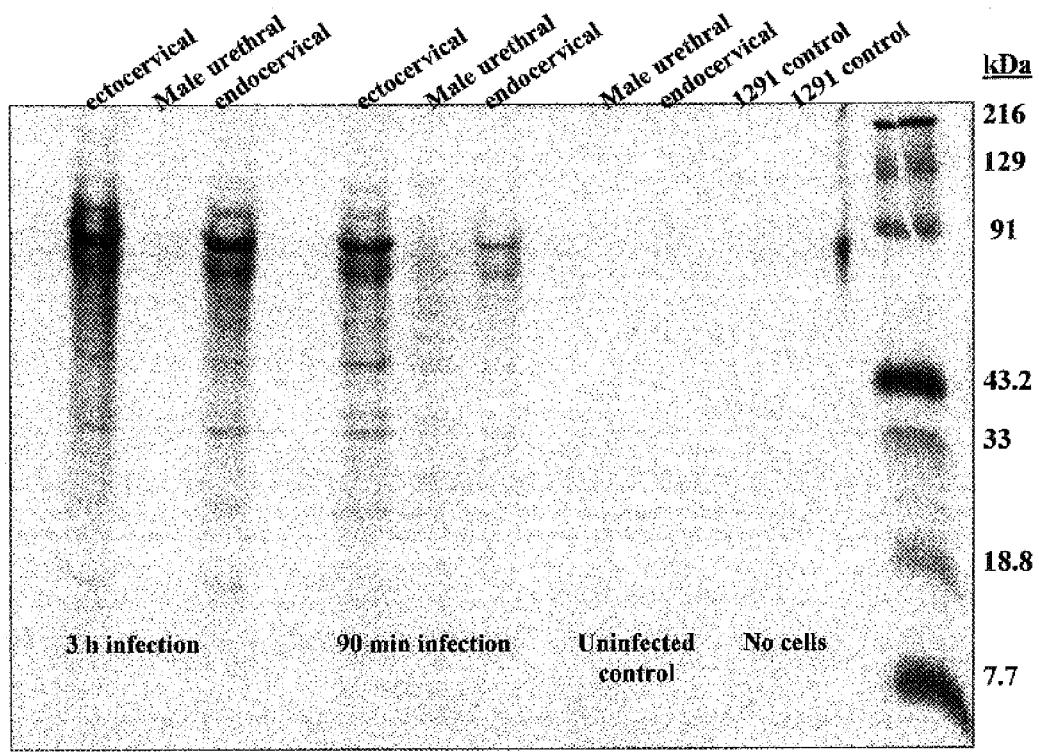
FIG. 12 depicts a coomassie-stained polyacrylamide gel showing that the gonococcal products released from a cervical cell infection are not released with an infection of male urethral cells. Supernatants were obtained from 90 minute and 3 hour infections of ecto- and endocervical cells.

The present inventors have found that polypeptide p55 is neisserial phospholipase D (PLD) (FIG. 11). PLD is released from gonococci when exposed to primary human cervical epithelial cells (FIG. 12). Identification of the gene encoding *N. gonorrhoeae* PLD, e.g., SEQ ID NO:9, SEQ ID NO:13, SEQ ID NO:15 and SEQ ID NO:17, which encode the polypeptides SEQ ID NO:4, SEQ ID NO:14, SEQ ID NO:16 and SEQ ID NO:18, respectively, is disclosed herein. Also disclosed herein is identification of the pld gene from *N. meningitidis* SEQ ID NO:19 encoding the PLD polypeptide SEQ ID NO:20.

The Neisserial pld DNA sequences disclosed herein were compared to other Neisserial genome sequences. Analysis revealed a more than 99% identity between a *N. gonorrhoeae* 1090 pld nucleic acid sequence (SEQ ID NO:25) and a more than 99% identity between a *N. gonorrhoeae* 1291 pld nucleic acid sequence (SEQ ID NO:27) to the Neisserial genomic sequence at the University of Oklahoma's database (SEQ ID NO:26); and a 96% identity between SEQ ID NO:25 and a 97% identity between SEQ ID NO:27 to the Neisserial genomic sequence at the Sanger database (SEQ ID NO:24).

In addition, disclosed herein is the construction of a mutant in this gene in both *Neisseria gonorrhoeae* and *N. meningitidis*, which mutants do not produce the PLD enzyme (Tables 3 and 4). The mutants have been designated 1291ΔPLD and NMBΔPLD, respectively.

TABLE 3

|  | Ectocervical Cells | Endocervical Cells | No cervical cells |
|---|---|---|---|
| WT 1291 | 0.785 | 0.767 | 0.563 |
| 1291ΔPLD | 0.409 | 0.401 | 0.208 |
| Uninfected | 0.616 | 0.560 | NA |
| Positive Control ($H_2O_2$) | NA | NA | 0.961 |
| Negative Control (Buffer) | NA | NA | 0.187 |

TABLE 4

A. Cervical Cell Lysates

|  | Ectocervical Cells | Endocervical Cells | No cervical cells |
| --- | --- | --- | --- |
| WT 1291 | 0.597 | 0.636 | 0.527 |
| 1291ΔPLD | 0.461 | 0.348 | 0.203 |
| Uninfected | 0.435 | 0.380 | NA |

B. Infection Supernatants

|  | Ectocervical Sups | Endocervical Sups | No cervical cells |
| --- | --- | --- | --- |
| WT 1291 | 0.408 | 0.435 | 0.563 |
| 1291ΔPLD | 0.309 | 0.393 | 0.208 |
| Uninfected | 0.207 | 0.368 | NA |

C. Assay Controls

| | |
| --- | --- |
| Positive Control ($H_2O_2$) | 0.781 |
| Negative Control (Buffer) | 0.217 |

The present inventors cloned the gene encoding PLD, i.e., pld, from *Neisseria gonorrhoeae* and *N. meningitidis*, and have expressed the neisserial PLD in *Escherichia coli* using the pBAD Directional TOPO Expression Kit (Invitrogen, Carlsbad, Calif.) according to the manufacturer's protocol.

A. Gonococcal PLD

Primary ecto- and endocervical cell monolayers were pretreated and maintained with cycloheximide as described in Example 1, above, to inhibit the protein synthesis of the monolayer cells. At variable times post-infection (90 minutes and 3 hours), infection supernatants were collected from gonococci-infected and uninfected cervical cell monolayers. Supernatant filtrates were concentrated using Centricon YM-3 centrifugal filter units (Millipore) before suspension in 0.1M Tris-0.1% SDS. Concentrated supernatants were separated (18 mA) on a SDS 12% to 4% polyacrylamide gel. Secreted products were originally identified by autoradiography. Subsequent gels were stained with Coomassie Blue for mass spectroscopy analysis, which was performed at the Mass Spectrometry Facility located at the University of California (San Francisco, Calif.).

While gonococcal porin and pilus have been implicated in *N. gonorrhoeae* pathogenesis, PLD has not been described in the gonococcus. Gonococcal phospholipase D (FIG. 11) is of interest because it is required for complement mediated endocytosis in professional phagocytic cells.

Analysis of infection supernatants demonstrated that gonococcal products are released upon infection of cervical epithelia. Similar results are observed upon analysis of supernatants obtained from 90 minute and 3 hour infections, from ecto- and endocervical cells, and from these same cells obtained from different tissue donors (FIG. 11).

To determine if gonococcal proteins released upon cervical infection were specific to cervical cell invasion, these studies were repeated using male urethral epithelial cells (FIG. 12). Briefly, autoradiography of pulse-labeled gonococci and Coomassie-stained gels were analyzed to determine if gonococcal products are secreted in response to infection of urethral epithelial cells. Coomassie staining was performed according to standard protocols, gels were then fixed in a methanol-acetic acid solution before staining overnight at room temperature. Destaining was performed with 40% methanol with frequent exchange of the destaining solution with fresh 40% methanol, as needed. Analysis revealed that while protein products are released at 90 minutes post-infection, these proteins are not present by 3 hours of infection. Collectively, these data suggest that a small basal level of gonococcal products are released constitutively and that the continued release of gonococcal products was specific to gonococcal cervicitis.

Thus, FIG. 11 and FIG. 12 show that gonococcal PLD is released preferentially in the presence of cervical epithelial cells.

B. Gonoccal PLD Recruits CR3

PLD deficient gonococci were prepared as described hereinbelow.

Figure 13:
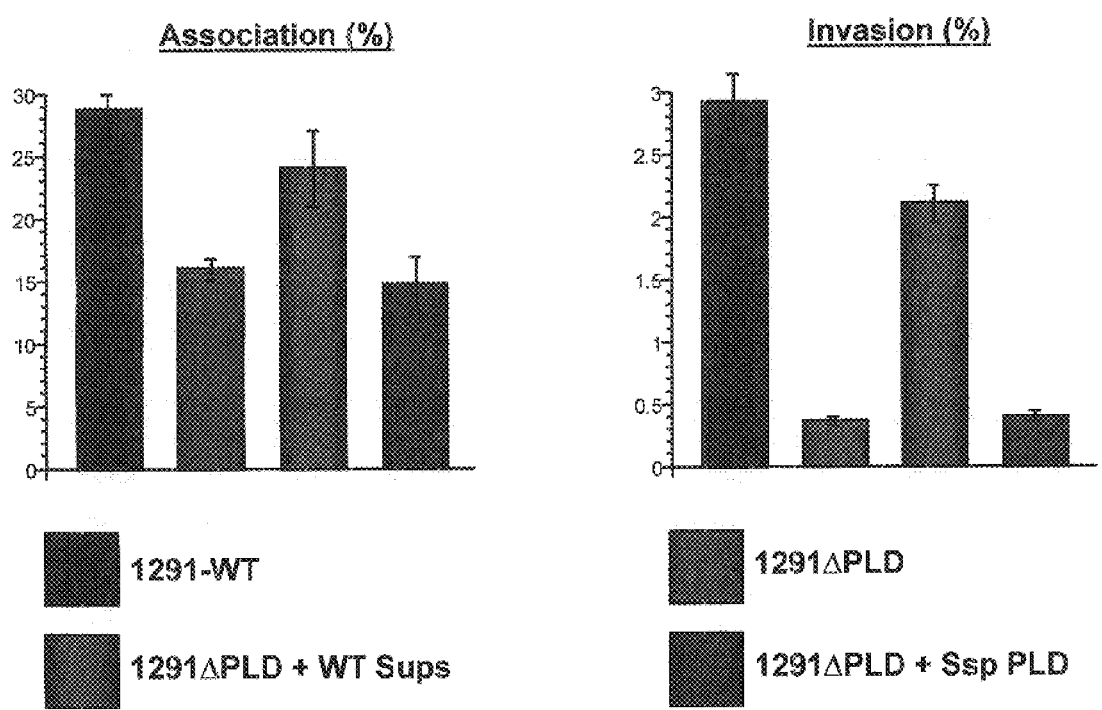
FIG. 13 depicts histograms from quantitative association and invasion assays that show that PLD-deficient gonococci are impaired in their adhere to and to invade primary cervical cells.

Both quantitative association and invasion assays, performed as described herein, demonstrate a role for gonococcal PLD in cervical cell infection (FIG. 13). PLD-deficient (when compared to wild-type) gonococci have impaired ability to adhere to and to invade primary cervical cells. The decrease in adherence observed for mutant gonococci may be indicative of the inability of these bacteria to elicit up-regulation of CR3 surface level expression. The striking decrease in the ability of these bacteria to invade cervical epithelia may suggest a role for gonococcal PLD in CR3-mediated endocytosis or engagement of an aberrant trafficking pathway once internalized, which does not permit gonococcal intracellular survival. These processes are restored when association and/or invasion assays are performed with PLD-mutant gonococci in the presence of primed wild-type supernatants (i.e., supernatants collected from a previous infection using wild-type gonococci and which have been filtered to remove bacteria), which would contain secreted gonococcal PLD. The exogenous addition of PLD from *Streptomyces* spp. to association and invasion assays of *N. gonorrhoeae* ΔPLD infected cervical cells does not compensate for the absence of gonococcal PLD. This suggests that gonococcal PLD exhibits unique effector functions in addition to sharing structural and functional properties with *Streptomyces* spp. PLD.

Methods for CR3 detection by confocal microscopy are described hereinbelow and in Edwards et al. (2001). Confocal microscopy suggests that PLD-deficient gonococci do not elicit up-regulation of CR3 surface level expression (FIG. 14). CR3 (CD18, CR3β-subunit) was immunolabeled with a TRITC-conjugated antibody (commercially available from Sigma and Jackson ImmunoResearch, West Grove, Pa.) and was visible as a red fluorescence. Gonococci were immunolabeled with an antibody to the highly conserved outer membrane protein, H.8 (antibody 2C3). Application of a FITC-conjugated secondary antibody (commercially available from Sigma and Jackson ImmunoResearch, West Grove, Pa.) allowed visualization of gonococci as a green fluorescence. Co-localization of CR3 with gonococci appeared as a yellow fluorescence because of the combined signal of the two fluorophores (FIG. 15). After 3 hours of infection of primary cervical cells with wild-type gonococci, CR3 was readily visible on the cervical epithelial surface, and the vast majority of gonococci were co-localized with this receptor. In contrast, infection with PLD-mutant gonococci revealed that only a small, sub-population of cervical cells still express CR3 on their surface. Additionally, a significant proportion of mutant gonococci are not co-localized with CR3.

As described hereinbelow, primary cervical cells were seeded in 96-well microtiter plates to comparatively quantitate surface level expression of CR3. In the procedure, cells were (i) uninfected; (ii) challenged with wild-type gonococci; (iii) challenged with PLD-mutant gonococci; and/or (iv) challenged with filtered, primed (see infra) wild-type or PLD-mutant gonococcal supernatants. After removal of the infection supernatant, cell monolayers were rinsed, fixed and subsequently labeled with an antibody (anti-CD11b antibody H5A4; Hildreth and August, 1985) specific for the CR3 I-domain subunit followed by an HRP antibody-conjugate (commercially available from Kirkegaard & Perry Laboratories, Gaithersburg, Md.) using standard ELISA protocols. Absorbance of the o-phenylenediamine dihydrochloride peroxidase substrate was determined spectrophotometrically at 490 nm (FIG. 15). These data indicate that gonococcal PLD facilitates the up-regulation of CR3 surface level expression and confirm the observations made by confocal microscopy.

FIG. 13, FIG. 14 and FIG. 15 show that gonococcal PLD enhances the invasiveness of gonococci through the recruitment of CR3.

C. Gonoccal PLD Plays a Role in Membrane Ruffling, Leading to Gonococcal Invasion Through Phosphotyrosine and Phosphothreonine Signal Transduction Events Phospholipase D activation in mammalian cells is thought to occur early in the phagocytic process, before the onset of actin reorganization. To determine if gonococcal PLD plays a role in the cytoskeletal rearrangements leading to membrane ruffling of the cervical epithelium, scanning electron microscopy (SEM) was performed as described hereinbelow and as in Ketterer et al., 1999.

SEM analysis demonstrated that aberrant cytoskeletal rearrangements occur upon infection of cervical epithelia with PLD-mutant gonococci, when compared to infection with wild-type gonococci (FIG. 16). Endocytosis mediated by CR3 requires receptor clustering. The absence of bacterial clusters in electrographs taken of mutant gonococci at 3 hours post-infection may be reflective of the inability of these bacteria to elicit up-regulation of CR3 or of their inability to initiate signaling cascades required for CR3 clustering (FIG. 16). Similarly, the absence of membrane ruffles in PLD infected cells suggests gonococcal PLD may be required to potentiate the cytoskeletal rearrangements required to form membrane ruffles. These processes are restored when assays are performed with PLD-mutant gonococci in the presence of primed supernatants as described above. No observable differences between mutant or wild-type gonococci were noted in the ability of gonococci to interact with each other or with cervical cells at earlier points of infection (i.e., less than 90 minutes).

D. Signal Transduction

Protein kinases (e.g., tyrosine kinases and protein kinase C (PKC)) play an integral role in CR3-mediated signal transduction in professional phagocytic cells. Additionally, in eukaryotic cell systems phospholipase D activation triggers a complex signal transduction cascade. This signal transduction cascade involves PKC and protein tyrosine stimulation, as well as the activation of small G-protein binding-proteins. To determine if signal transduction initiated upon gonococcal infection of the cervical epithelium is altered in the absence of gonococcal PLD, Western blot analysis of cervical cell lysates was performed.

Western blotting was performed using standard protocols. Cervical cell lysates were harvested at variable times post-infection (0 minutes, 5 minutes, 10 minutes, 15 minutes, 30 minutes, 45 minutes, 60 minutes, 90 minutes, two hours, 2.5 hours, 3 hours and 4 hours) and lysed in a Tris-0.1% SDS solution. Cell lysates were separated (18 mA) on a 4% to 12% gradient polyacrylamide gel and then transferred to Immobilon-P membranes (Millipore) over-night at 150 mA. Membranes were blocked 30 minutes in 0.25% bovine serum albumin (BSA)-tris buffered saline 0.5% tween-20 (TBST) at room temperature with rotation for two hours. Membranes were then incubated with an appropriate dilution of the primary antibody. The antibody solution was removed, and membranes were rinsed 5 times for ten minutes each in wash buffer (TBST). Membranes were then incubated (1 hour, room temperature with rotation) in BSA-TBST containing a 1:10,000 dilution of the appropriate HRP secondary antibody conjugate. Membranes were rinsed five times for 5–10 minutes per rinse in wash buffer. Following the final rinse, membranes were incubated in SuperSignal (Pierce) chemiluminescent substrate and allowed to stand approximately 5 minutes in the dark before exposure to BioMax MR film (Kodak).

Western blot analyses of membranes probed with antibodies specific for phosphorylated tyrosine (anti-phosphotyrosine antibody obtained from Santa Cruz) or threonine (anti-phosphothreonine antibody obtained from Kirkegaard & Perry Laboratories) target residues revealed that alternative proteins serve as kinase and phosphatase targets in the absence of gonococcal PLD. (FIG. 17). The mass of each tyrosine kinase target (Table 5) and Ser-Thr kinase target (Table 6) was determined. Masses corresponding to targets unique to their specific experimental condition are shown in regular type, bold type corresponds to peptides too close in mass to be defined as different, and italicized type corresponds to a shared target.

TABLE 5

Masses of Tyrosine Kinase Targets

| 1291-Wild-Type | 1291ΔPLD |
|---|---|
| p16.7 | p21.5 |
| p22.1 | p27.2 |
| p27.8 | p40.9 |
| p30.1 | |
| p39.3 | |
| p47.3 | |
| p57.2 | |

TABLE 6

Masses of Ser-Thr Kinase Targets

| 1291-Wild-Type | 1291ΔPLD |
|---|---|
| p9.9 | p22.9 |
| p21.7 | p28.2 |
| p25.9 | p39.2 |
| p28.2 | p48.6 |
| p40.1 | |
| p48.4 | |
| p58.3 | |

Following RNA isolation and cDNA synthesis as described hereinbelow, multiplex RT-PCR was performed using the CytoXpress MPCR Kit for Human Inflammatory Genes Set-I according to manufacturer's protocol. The analysis of cytokine message levels provided further evidence that alternative signal transduction events are triggered in the absence of gonococcal PLD (FIG. 18).

The most striking differences were observed in ectocervical cells in which the absence of gonococcal PLD resulted in decreased message levels of GAPDH, TNF-α, IL-6, IL-8, and TGF-β when compared to wild-type infected cells.

As shown in FIG. 18, gonococcol PLD is able to modify human cell signaling.

E. NMB PLD Mutants

The *Neisseria meningitidis* B PLD mutants were prepared as described hereinbelow.

F. NMB PLD Augments Cytokine Cellular Transcription

Human PMNLs have been shown to react differentially when stimulated with pathogenic and nonpathogenic *N. meningitidis* (Kragsbjerg et al., 2000).

Using multiplex RT-PCR, the present inventors detected a number of cytokine transcripts in *N. meningitidis* infected secondary bronchial epithelial cells. Multiplex RT-PCR was performed using the CytoXpress MPCR Kit for Human Inflammatory Genes Set-I (Biosource). Briefly, total RNA was isolated from secondary bronchial epithelial cells infected with pathogenic *N. meningitidis* NMB and NMB-cap- and the corresponding PLD mutants. PCR was set up using DNA from uninfected primary (bronchial) cells (lane 1, FIG. 19), NMB wild-type infected cells (lane 2, FIG. 19) and NMB PLD mutant infected cells (lane 3, FIG. 19), and primers for GAPDH, TNF-α, IL-1β, GM-CSF, IL-8, IL-6 and TGF-β. Actin was used as an internal control.

Multiplex RT-PCR was performed according to the manufacturer's protocol (BioSource) following RNA isolation and cDNA synthesis as described hereinbelow. Multiplex RT-PCR analysis of cytokine message levels provided evidence that, similar to gonococcal PLD, alternative signal transduction events are triggered in the absence of meningococcal PLD in primary human bronchial cells (FIG. 19). Differences in levels of cytokine message were restricted to un-encapsulated organisms, which is consistent with these organisms' ability to associate with and invade airway epithelia. As compared to uninfected cells or cells infected with wild-type meningococci, decreased cytokine message levels were observed in bronchial cells that were infected with PLD mutant meningococci.

EXAMPLE 7

By disrupting a neisserial pld gene, neisserial phospholipase D synthesis and/or function, e.g., enzymatic activity related to PLD such as the catalysis of phospholipase D-related hydrolysis and/or phosphatidyl-transferase reactions, is reduced, e.g., inhibited.

TABLE 7

Mean PLD activity in A) uninfected and 1291 wild-type and 1291ΔPLD infected cervical cell lysates and in B) 1291 wild-type and 1291ΔPLD gonococci. C) Assay controls

| A. | Ectocervical Cells | | Endocervical Cells | |
|---|---|---|---|---|
| | Mean | Variance | Mean | Variance |
| WT 1291 | 0.777 | 0.06 | 0.772 | 0.03 |
| 1291ΔPLD | 0.398 | 0.02 | 0.381 | 0.03 |
| Uninfected | 0.515 | 0.08 | 0.526 | 0.06 |

TABLE 7-continued

Mean PLD activity in A) uninfected and 1291 wild-type and 1291ΔPLD infected cervical cell lysates and in B) 1291 wild-type and 1291ΔPLD gonococci. C) Assay controls

| | No Cells | |
|---|---|---|
| | Mean | Variance |
| B. | | |
| WT 1291 | 0.600 | 0.04 |
| 1291ΔPLD | 0.179 | 0.03 |
| C. | | |
| Positive Control (H$_2$O$_2$) | 0.885 | 0.11 |
| Negative Control (Buffer) | 0.182 | 0.03 |

EXAMPLE 8

Anti-PLD sera was generated by BioSource International (Camarillo, Calif.) by injecting rabbits with a peptide designed to the first HKD region of PLD (RRMHNKS-FTADNRAC comprising amino acids 181–195' (SEQ ID NO:21)). The anti-PLD antibody was screened for specificity to PLD using assays well-known to the art. This anti-PLD sera was found to inhibit PLD activity and the association and invasion of cervical cells by gonococci (Table 8).

TABLE 8

PLD Activity in presence or absence of 1307 anti-PLD Ab or 1307 pre-bleed serum

A. PLD activity

| | 1291 WT | | 1291ΔPLD | | *Steptomyces* spp. PLD | |
|---|---|---|---|---|---|---|
| | mean | variance | mean | variance | mean | variance |
| w/1307 α-PLD Ab | 0.274 | 0.01 | 0.312 | 0.01 | 0.212 | 0.01 |
| w/o 1307 α-PLD Ab | 1.255 | 0.01 | 0.154 | 0.02 | 1.364 | 0.01 |
| W/1307 pre-bleed | 1.579 | 0.01 | 0.238 | 0.03 | 1.423 | 0.05 |

| Assay Controls | mean | variance |
|---|---|---|
| Positive Control (H$_2$0$_2$) | 1.557 | 0.01 |
| Negative Control (Buffer) | 0.125 | 0.01 |

| | 1291 WT | | 1291ΔPLD | |
|---|---|---|---|---|
| | mean | variance | mean | variance |
| B. Association of primary cervical cells | | | | |
| w/1307 α-PLD Ab | 28.13 | 0.42 | 14.84 | 0.94 |
| w/o 1307 α-PLD-AB | 7.92 | 0.78 | 14.37 | 1.08 |
| C. Invasion of primary cervical cells | | | | |
| w/1307 α-PLD Ab | 2.7272 | 0.12 | 0.349 | 0.02 |
| w/o 1307 α-PLD-AB | 0.7969 | 0.03 | 0.3581 | 0.03 |

EXAMPLE 9

2,3-diphosphoglycerate (DPG) is a specific inhibitor of PLD activity and inhibits gonococcal association and invasion of primary ecto-(pex) and endocervical (pen) cells (Table 9).

TABLE 9

|  | Ectocervical Cells | | Endocervical cells | |
| --- | --- | --- | --- | --- |
|  | Mean | Variance | Mean | Variance |
| Association | | | | |
| WT 1291 | 27.72 | 1.44 | 18.12 | 0.66 |
| 1291 + 100 nM DPG | 15.31 | 1.68 | 6.97 | 1.05 |
| Invasion | | | | |
| WT 1291 | 2.66 | 0.16 | 1.78 | 0.07 |
| 1291 + 100 nM DPG | 0.36 | 0.01 | 0.21 | 0.01 |

EXAMPLE 10

Experimental Procedures

1. Cell Culture. Surgical biopsies derived from the ecto- and the endocervix that were used to seed primary cervical epithelial cell systems were procured and maintained as described previously (Edwards et al., 2000) in Defined Keratinocyte Serum Free Medium (dk-SFM) (Life Technologies, Rockville, Md.). The primary (uec) and immortal (tuec), male urethral epithelial cells used in these studies have been described (Harvey et al. 1997; Harvey et al. 2003) and were maintained according to the methods of Harvey et al. (1997, 2003).

2. Bacteria and Infection Studies. *N. gonorrhoeae* strains 1291 (Apicella, 1974; Dudas and Apicella, 1988), FA1090 (Cohen et al., 1994), and MS11 (Schoolnik et al., 1984; Segal et al., 1985) were used in the infection studies outlined below, which were performed as previously described (Edwards et al., 2000). Briefly, overnight cultures of gonococci were harvested from GC-IsoVitaleX agar plates with a sterile swab and resuspended in sterile physiological saline. Optical density of the bacterial suspension was determined spectrophotometrically where an optical density of 1 at 600 nm was equivalent to $10^9$ bacteria $ml^{-1}$. $10^7$ gonococci were used to infect cervical cell monolayers at a multiplicity of infection of 100. Primary cervical cells were challenged with gonococci for variable time-periods (as noted) after which the infection medium was removed, and the cell monolayers were extensively washed with phosphate-buffered saline (PBS). Uninfected control cell monolayers were simultaneously processed with challenged cell monolayers. Infected and uninfected (control) cell monolayers were subsequently harvested for cellular fractionation, quantitative association (i.e., adherence and invasion) or invasion assays, or they were processed for microscopic analyses. Alternatively (as noted), infection supernatants were harvested, immediately transferred to ice, and gonococci were then removed by filtration through a 0.22 μm filter. For PLD activity assays, supernatants depleted of gonococci were filtered using Centricon YM-30 centrifugal filter units (Millipore Corporation, Bedford, Mass.). Protein products were then collected with an equal volume of PLD assay buffer.

*N. gonorrhoeae* strain 1291ΔPLD was constructed by the insertion of a kanamycin-resistance cassette using the EZ:: TN <KAN-2> Insertion Kit (EPICENTRE, Madison, Wis.). Polymerase chain reaction (PCR) of full-length NgPLD, using the primer pair of 5'-GGT GGT CAT ATG ATG CAT ACA GAC CCC AAA AT-3' (SEQ ID NO:22) and 5'-GGT GGT TGCTCT TCC GCA TAA TAA ACC TTC TTC GAT GGG CAG-3' (SEQ ID NO. 23), suggested the insertion of the kanamycin-resistance cassette within the pld gene, which was then confirmed by sequence analysis performed at the University of Iowa DNA Sequencing Facility (Iowa City, Iowa).

3. Radiolabeling and Collection of Gonococcal Products Released with Infection of Primary Cervical Cells. Gonococci allowed to grow overnight on GC agar were harvested with a sterile swab and used to inoculate 5 ml cultures of Morse's Defined Medium (MDM) (Morse and Barenstein, 1980). MDM was prepared such that half the recommended methionine and cysteine was replaced with 125 μCi Redivue Pro-mix L-[$^{35}$S] in vitro cell labeling mix (Amersham Pharmacia Biotech Inc, Piscataway, N.J.). After approximately 4 hours, gonococci were collected by centrifugation (4000 rpm, 5 minutes), rinsed with sterile physiological saline to remove excess label, and resuspended in cold MDM such that a culture density of $10^7$ bacteria $ml^{-1}$ was obtained. MDM containing the $^{35}$S-labeled gonococci was then used to infect approximately $10^5$ primary, human, ecto-(pex) and endocervical (pen) cells or 35 mm tissue culture dishes devoid of cervical cells. Alternatively, gonococci were labeled during the course of infection by a 30-minute pulse with $^{35}$S-MDM at 1 hour and 2.5 hours post-infection. Before infection pex and pen cells were treated (30 minutes, 37° C.) with 250 μM cycloheximide to inhibit cervical cell protein synthesis. Cycloheximide was maintained in the culture medium through out the course of the infection. Cervical cells and tissue culture plates lacking cervical cells were challenged with gonococci for 90 minutes and 3 hours after which the culture supernatants were collected. Gonococci were removed from the culture supernatants by filtration through low-protein binding 0.22 μm syringe filter units. Supernatant filtrates were concentrated using Centricon YM-3 centrifugal filter units (Millipore) before suspension in 0.1M Tris-0.1% SDS. Concentrated supernatants were separated (18 mA) on a SDS 12% to 4% polyacrylamide gel before autoradiography or gel-extraction for mass spectrometry at the Mass Spectrometry Facility located at the University of California (San Francisco, Calif.). Analysis of mass data was performed using the Protein Prospector (University of California San Francisco, Calif.) and the ProFound (Rockefeller) mass analysis databases.

4. Determination of PLD Activity. PLD activity was accessed using the Amplex™ Red Phospholipase D Assay Kit (Molecular Probes, Eugene Oreg.). Wild-type and PLD mutant gonococci were suspended in PLD assay buffer to a final concentration of $10^7$ bacteria $ml^{-1}$, and activity was determined according to the manufacturer's protocol. Assessment of PLD activity at acidic pH was determined in a two-step assay according to the manufacturer's protocol. For the first step, $10^8$ gonococci were suspended in PBS with the pH adjusted to 3.0, 4.5, or 6.0. Gonococcal suspensions were diluted 10-fold in PLD assay buffer for the second step of the reaction. Cervical cell fractions were prepared as outlined below and PLD activity was assessed at neutral pH according to the manufacturer's protocol.

5. Fractionation of Primary Cervical Cells. Uninfected (control) and infected cervical cell monolayers were lysed in buffer A (50 mM tris, pH 7.5; 10 mM NaCl, 1 mM KCl; 2 mM $MgCl_2$, 1 mM PMSF) by scraping cervical cells from tissue culture dishes placed on ice. The cell lysate was sonicated (two bursts of 20 seconds each). Cell debris and the nuclear fraction was removed by centrifugation (750×g, 10 minutes), and the supernatant from this spin was then subjected to filtration through a low-protein binding 0.22 μm syringe filter to ensure removal of gonococci. Alternatively, gonococci were removed by immunoprecipitation (as described by Wen et al., 2000) using the monoclonal antibody, 2C3, which recognizes the H.8 outer membrane protein of the pathogenic *Neisseria*. Sucrose was added to the resulting gonococcus-depleted supernatant (S1) to a final concentration of 300 mM. Ultracentrifugation (150,000×g, 90 minutes) was then performed to produce the plasma membrane-(pellet) and cytosol (supernatant 2, S2)-enriched fractions. The membrane-enriched fraction was resuspended in PLD assay buffer (50 mM Tris, 5 mM $CaCl_2$, pH 8.0). S2 was concentrated by filtration through Centricon YM-30 centrifugal filter units (Millipore) after which cytosolic constituents were recovered in PLD assay buffer. Where indicated, prior to infection studies primary pex and pen cell monolayers were treated with 300 nM wortmannin (Sigma) (2 hours, 37° C.) or 1 µM cytochalasin D (Sigma) (30 minutes, 37° C.) to inhibit macropinocytosis of gonococci. Wortmannin and cytochalasin D were maintained in cervical cell cultures during the course of infection.

6. RNA Isolation and RT-PCR of Primary, Human, Cervical Epithelial Cells. Primary, pex and pen cell monolayers were challenged with *N. gonorrhoeae* 1291 or 1291ΔPLD, or they were left uninfected. After 3 hours, infection supernatants were removed and cell monolayers were extensively rinsed with PBS. Total RNA (intracellular gonococcal and cervical cell RNA) was isolated using the RNAqueous-4PCR kit (Ambion, Inc., Austin, Tex.) according to the manufacturer's protocol. Ribosomal RNA was removed from the total RNA using the MICROBExpress kit (Ambion) according to the manufacturer's protocol, yielding message-enriched bacterial and cervical cell RNA. Cervical cell RNA was then separated from intracellular bacterial RNA using the Poly(A)Purist kit (Ambion) according to the manufacturer's protocol with slight modification. Supernatants from the capture and wash steps, which contained gonococcal RNA, were saved and pooled. Gonococcal RNA was recovered by ethanol precipitation. cDNA was synthesized using RETROscript™ First Strand Synthesis Kit for RT-PCR (Ambion); reactions lacking the reverse transcriptase (RT) (negative control) were run simultaneously with reactions containing RT. PCR analysis of reverse-transcribed and of mock reactions using primers to α-actin and to gonococcal reduction modifiable protein (Rmp) demonstrated the absence of contaminating DNA and of gonococcal DNA and RNA in the isolated cervical cell RNA. PCR of reverse-transcribed cervical cell RNA was performed using the primer pairs 5'-TCC ATG CAA GAA TCT GGT TTC-3' (SEQ ID NO:28) and 5'-CGA CAA TGA GCA CAG ACT CAC A-3' (SEQ ID NO:29) for human PLD1 to yield a 462 bp product and 5'-CCT TCA GGA TTC TGT CCA CAA-3' (SEQ ID NO:30) and 5'-CCT CTC TCA CAA CCA ATT CTT C-3' (SEQ ID NO:31) for human PLD2 to yield a 508 bp product.

7. Determination of CR3 Surface Expression on Primary Cervical Cells. Pex and pen cells were passed to 96-well microtiter plates and allowed to grow to confluence. Cervical cells were then challenged with wild-type or PLD mutant gonococci after which the infection medium was removed and cells were rinsed thrice with PBS. Cells were fixed with 2% paraformaldehyde. Prior to immuno-analysis of CR3 surface level expression, cells were again rinsed with PBS. Immunoassays were then performed according to standard ELISA protocols using the H5A4 anti-CD11b (i.e., CR3) primary and peroxidase-conjugated secondary antibodies. Absorbance of the o-phenylenediamine dihydrochloride peroxidase substrate was determined spectrophotometrically at 490 nm. Primary antibody was omitted from one well, and the secondary antibody was omitted from a second well, which served as a control for endogenous peroxidase activity. Where indicated 200 nM phorbol myristate (PMA), 200 nM 4-α phorbol, 100 µM pervanadate, 3 mM hydrogen peroxide, or gonococci-depleted supernatants collected from wild-type or PLD mutant infection studies were included in the infection studies as outlined below.

Gonococcal PLD Augments Cytokine Cellular Transcription

Alternative functional responses occur within cervical cells in the absence of gonococcal PLD. The data herein indicate that tyrosine and serine-threonine kinases play an integral role in CR3-mediated gonococcal cervical invasion. Pervanadate, a tyrosine kinase activator/phosphatase inhibitor, or PMA, an activator of the serine-threonine kinase, PKC, were included in infection studies to determine if protein kinase activation could rescue the observed decrease in CR3 recruitment and cervical cell association and invasion, which occurs in the absence of gonococcal PLD (FIG. 21A and FIG. 21B). These data indicate that tyrosine kinase activation rescues CR3 recruitment, but it is not sufficient to allow gonococcal intracellular survival in the absence of gonococcal PLD. Similarly, PKC activation rescues CR3 recruitment and partially restores intracellular survival of gonococci.

The role for PLD in gonococcal cervicitis is multifactorial. PLD modulates signaling events upstream of PKC, which are required for gonococcal survival. PLD plays an early role in modulating signal transduction events leading to CR3 recruitment at the cervical cell surface.

8. *N. gonorrhoeae* Attachment to and Invasion of Primary, Human, Cervical Cells. Primary cervical cell monolayers were infected with wild-type or PLD mutant gonococci as outlined above. Variable concentrations of *Streptomyces* spp. PLD (SsPLD) (Sigma), PMA, or 4-α phorbol were included in association (adherence and invasion) or invasion assays, as noted. Cervical cells were preincubated (30 minutes, 37° C.) with 200 nM PMA or 4-α phorbol before the addition of gonococci. 10 units $ml^{-1}$ SsPLD was added simultaneously with gonococci. Alternatively, where noted, cervical cell monolayers were pre-incubated (30 minutes, 37° C.) with pervanadate, which was made by mixing 100 µM ortho-sodium vanadate in 3 mM hydrogen peroxide. In separate assays, infection supernatants were collected from wild-type or PLD mutant-infected cervical cell monolayers, gonococci were removed by filtration through a 0.22 µm syringe filter (i.e., wild-type or mutant primed supernatants) and were added to association and/or invasion assays, as noted. The ability of gonococci to adhere to and/or invade pex and pen cells was quantitatively determined using standard gentimicin-resistance assays, performed as described previously (Edwards et al., 2000), and in which chemical or protein additives were included or excluded from the invasion assay as described above. The total association (i.e., adherence and invasion) of gonococci with pex and pen cells was quantitated by the omission of gentimicin from the above described invasion assay. Percent invasion of *N. gonorrhoeae* 1291 or 1291ΔPLDin the presence or absence of experimental additives was determined as a function of the original inoculum and the number of colonies formed with subsequent plating of the cellular lysate. A Kruskal-Wallis non-parametric analysis of variance was used to determine the statistical significance of the association and invasion assays described above.

9. Immunolabeling and Microscopy. Immunolabeling of *N. gonorrhoeae* 1291 or 1291ΔPLD infected pex cell monolayers was performed as described previously (Edwards et al., 2000). Primary antibodies used for immunolabeling were specific for the CR3 beta-subunit, CD18 (anti-CD18) (Santa Cruz Biotechnology, Santa Cruz, Calif.) or for the gonococcal H.8 outer membrane protein (antibody 2C3). FITC- and TRITC-conjugated secondary antibodies were applied to cell monolayers, as noted. Infected and uninfected (control) cell monolayers were viewed using the Bio-Rad MRC-1024 or the Zeiss 510 Laser Scanning Confocal viewing systems. Primary cervical cell monolayers were processed for SEM analyses (as described by Edwards et al., 2000) and viewed using the Hitachi S-4000 scanning electron microscope. All the microscopes used in these studies are located at the Central Microscopy Research Facility at the University of Iowa (Iowa City, Iowa).

Results

Gonococcal PLD Acts at Multiple Levels in Cervical Cell Infection. Alternative functional responses occur within cervical cells in the absence of gonococcal PLD. Protein kinases (e.g., tyrosine kinases and protein kinase C (PKC)) play an integral role in CR3-mediated signal transduction in professional phagocytic cells. Additionally, extensive PLD activity occurs upon CR3 ligation with iC3b-opsonized particles. PLD activation also triggers a complex signal transduction cascade involving PKC and protein tyrosine stimulation as well as the activation of small G-proteins. Pervanadate, a potent phosphatase inhibitor/tyrosine kinase activator, or PMA, an activator of the serine-threonine kinase, PKC, were included in infection studies to determine if protein kinase activation could rescue the observed decrease in CR3 cell surface recruitment and cervical cell association and invasion by PLD mutant gonococci. The addition of pervanadate to infection studies demonstrated that tyrosine kinase activation rescues CR3 recruitment in the absence of NgPLD, but it is not sufficient to allow the intracellular survival of PLD mutant gonococci. No effect was observed in the association or invasion of wild-type or mutant gonococci with cervical cells or with CR3 cell surface recruitment with the addition of 3 mM hydrogen peroxide (negative control) to infection assays. Similarly, PKC activation by the addition of PMA to infection studies rescued CR3 recruitment to the cervical cell surface and partially restored intracellular survival of PLD mutant gonococci. The addition of PMA to uninfected cervical cell monolayers increased CR3 surface level expression to levels comparable to those observed with wild-type infected cells, suggesting PKC plays a critical role in CR3 recruitment to the cervical cell surface. The addition of 4-α-phorbol, a non-activating analog of PMA, had no affect on gonococcal association with or invasion of cervical epithelia or on CR3 cell surface recruitment. Collectively, these data indicate that NgPLD exerts multiple effects on cervical epithelia during gonococcal infection.

Discussion

Phospholipases play critical roles in many important cellular functions. All members of the PLD superfamily contain (usually) two HKD motifs, which are thought to associate to form a catalytic center. Within this superfamily, unique to PLD is the ability to catalyze a transphosphatidylation reaction in which a primary alcohol preferentially serves as a nucleophilic acceptor instead of water, resulting in the near-exclusive production of a phosphatidylalcohol (PtOH) at the expense of PA. The resulting PtOH is metabolically stable and, thus, serves as a specific indicator of PLD activity. Few bacterial PLDs have been described, although a role for these enzymes in bacterial pathogenesis is suggested. Herein is described PLD activity in *N. gonorrhoeae*. A role for this secreted protein in gonococcal pathogenesis of cervical epithelia is demonstrated. Characteristic PLD activity (i.e., removal of Cho by cleavage of the terminal phosphodiester bond of PtC) was observed in gonococcal whole cell lysates but was absent in gonococci in which pld was mutated by the insertion of a kan$^R$ cassette. PLD activity was observed over a pH range of 3.0 to 7.4, consistent with its ability to function as an effector protein within the lower female genital tract under normal (uninfected) or diseased states. The addition of SsPLD to association and invasion assays of *N. gonorrhoeae* PLD infected cervical cells did not compensate for the absence of NGPLD, suggesting NgPLD exhibits unique effector functions in addition to sharing structural and functional properties with SsPLD. An observed increase in PLD activity in infected pex and pen cells was attributed to NgPLD and not endogenous PLD activity. The ability of NgPLD activity to promote gonococcal invasion of primary cervical cells was inhibited in the presence of PtC and ethanol (a primary alcohol) but not 2-butanol (a secondary alcohol). These data definitively demonstrate that this gonococcal protein does indeed exhibit characteristic PLD function and argue against a role for endogenous pex or pen cell phospholipase C (PLC) activity in CR3-mediated invasion of cervical epithelia by gonococci. (A BLAST search of the *N. gonorrhoeae* and *N. meningitidis* genomic databases using sequences to several bacterial PLCs failed to reveal the presence of this enzyme in the pathogenic *Neisseria*.) Furthermore, these data indicate that the generation of PA or its catabolic products are required for CR3-mediated macropinocytosis of gonococci.

NgPLD appears to modulate cervical cell function, either directly or indirectly in a cooperative manner with host cell effector molecules, to promote the appropriate targeting of gonococci to permissive host cells (i.e., CR3-expressing ecto- and endocervical cells) and to ensure their intracellular survival. The association with and invasion of primary cervical epithelia is impaired in the absence of NgPLD. CR3, the primary receptor by which gonococci invade the cervical epithelia, is not recruited to the cervical cell surface in the absence of NgPLD. Membrane ruffling is not evident in the absence of NgPLD with extended infection. Cervical cell tyrosine kinase and PKC activation (at least partially) rescue signal transduction events occurring in the absence of NgPLD.

Integrin receptors are thought to not possess intrinsic enzymatic function, although they do interact with other cellular factors to transduce the signals required for effector functions. The cytoplasmic region of CR3 contains a constitutively phosphorylated serine residue (in resting professional phagocytic cells) on the CD11bα-subunit (Ahearn and Rosengard, 1998). The CD18 (β-subunit) cytoplasmic tail is not constitutively phosphorylated but does contain one tyrosine, three threonine, and four serine residues (Ahearn and Rosengard, 1998). Upon CR3 activation with phorbol esters (e.g., PMA), phosphorylation of primarily serine residues occurs, but small amounts of phosphotryrosine and phosphothreonine are also observed (Ahearn and Rosengard, 1998; Gahmberg et al., 1998). Recent data suggest that a phosphorylation/dephosphorylation cycle occurs on the three contiguous threonine residues whereas serine phosphorylation remains stable (Gahmberg et al., 1998). Mutation of the three threonine residues results in diminished adhesive function, suggesting threonine phosphorylation plays a role in CR3 ligand binding (Gahmberg et al., 1998). It is currently not known if a similar phosphorylation cycle occurs on the CD18 cytoplasmic tyrosine residue. However, the protein tyrosine kinases Fyn, Lyk, Hck, and Frg are proposed to function in CR3-mediated signal transduction (Morley and Walport, 2000), suggesting that phosphorylation of the cytoplasmic tyrosine residue may also modulate CR3 function.

The absence of CR3 recruitment to the cervical cell surface and the ability of pervanadate to restore this phenotype in *N. gonorrhoeae* PLD infected primary cervical cells indicates that tyrosine phosphorylation is critical for CR3 recruitment to the infected cervical cell surface. Pervanadate does not stimulate CR3 surface recruitment in uninfected cells, suggesting that the pathway triggered by gonococci that results in CR3 surface recruitment may be unique from that pathway promoting CR3 trafficking in resting cells. These data strongly suggest an early role for NgPLD in, directly or indirectly, modulating CR3 effector function possibly by initiating phosphorylation of the cytoplasmic tyrosine residue of the CR3β-subunit, CD18. Studies using *Streptomyces chromofuscus* PLD (ScPLD) indicate that exogenous ScPLD can cause rapid choline release from vascular smooth muscle cells and can mimic endogenous PLD activity within these cells by triggering cytoskeletal rearrangements, DNA synthesis, and cell proliferation. Lysophosphatidylcholine (LPtC), within the outer leaflet of the plasma membrane, serves as the substrate for ScPLD cleavage resulting in the formation of lysophosphatidic acid (LPA), which, in turn, activates a PLC- and Rho-dependent signal transduction cascade upon LPA binding to its cognate G-protein coupled receptor. NgPLD, a secreted bacterial protein, modulates CR3 effector function in primary cervical epithelial cells.

In contrast to tyrosine kinase activation, PMA-stimulated PKC activation was capable of rescuing CR3 recruitment to the cervical cell surface and of partially rescuing the ability of gonococci to survive the mortal insult of gentamicin treatment. These data are consistent with the ability of PLD activity to regulate or to be regulated by kinase activity (Houle and Bourgoin, 1999; Choi et al., 2002). These data also suggest that NgPLD acts at several levels during gonococcal invasion of cervical epithelia in that signal transduction events leading to CR3 recruitment to the cervical cell surface (tyrosine- and/or serine-threonine kinase dependent) are distinct from intracellular trafficking and/or signaling events promoting gonococcal survival (tyrosine kinase independent, PKC dependent). Several studies have linked PLD to the generation of anti-microbial reactive oxygen species (ROS) in mammalian cells. Recent evidence indicates that Ymt promotes the survival of *Y. pestis* within the flea midgut from a cytotoxic digestion product present in blood plasma and, consequently, promotes disease transmission. Data herein indicate that the presence of a functional NgPLD is essential for the tyrosine kinase independent, PKC-dependent survival of these bacteria within primary cervical cells and that it plays a role in gonococcal survival within urethral epithelial cells.

Reorganization of the actin cytoskeleton is the result of the activation of a complex network of signal transduction pathways involving many effector molecules. Bacterial, plant, and human PLDs directly bind polymeric F-actin, which in turn increases PLD activity. In contrast, monomeric G-actin inhibits PLD activity in a species-specific manner in that, in vitro, G-actin-induced PLD inhibition is twenty-fold greater for human PLD1 than it is for SsPLD. The greatest degree of inhibition occurs upon the initiation of PLD activity in the presence of G-actin; less inhibition is observed when G-actin is added to previously activated PLD. Phosphatidylinositol 4,5-bisphosphate ($PIP_2$) is a required co-factor in human PLD activity. In contrast, bacterial PLD activity does not exhibit a cofactor requirement. Previous data have indicated that vinculin, ezrin, and α-actinin co-localize with gonococci and accumulate in focal contacts in infected primary cervical cells before the onset of membrane ruffling. Previous data also show that consistent with CR3-mediated endocytosis in professional phagocytic cells, gonococcal invasion of the cervical epithelium requires the activation of Rho proteins. Activation of Rho can cause the activation of phosphatidylinositol-4-phosphate kinase, resulting in $PIP_2$ formation. In resting cells, mammalian PLD resides in an inactive state because $PIP_2$, which remains bound to actin-associated proteins (e.g. vinculin, α-actinin, fodrin), is unavailable as a required co-factor. Fukami et al. (1994) have demonstrated that activation of Balb/c 3T3 cells with platelet-derived growth factor resulted in a rapid decrease in the amount of $PIP_2$ that was bound by vinculin and α-actinin, but which was gradually reversed over a one hour incubation.

In the absence of gonococcal PLD microvilli/filopodia were formed because of the negative effects of vinculin and α-actinin on the availability of PIP2 and because of the presence of a (relatively) large pool of monomeric G-actin. The inhibitory effect of G-actin on bacterial PLD was significantly less than human PLD, and bacterial PLDs did not require co-factor activity for function; consequently, induction of actin polymerization may be kinetically favored and, thus, be more extensive and sustained. F-actin produced would be anticipated to stimulate directly and indirectly (by depleting intracellular levels of G-actin) both gonococcal and cervical cell PLD activity, ultimately leading to membrane ruffles. Kusner et al. (2002) have demonstrated that actin binding to PLD occurs through the conserved region of this protein, which is found in all PLDs (including NgPLD), but have also suggested that heterogeneic regions may modulate this interaction. In this regard, it is of interest that PLD homologs exhibiting the highest similarity to NgPLD are found in other bacterial species (i.e., *Salmonella, Shigella, Escherichia*) capable of eliciting extensive cytoskeletal rearrangements in their respective target cells.

EXAMPLE 11

Gonococcal Phospholipase D Modulates the Expression and Function of Complement Receptor 3 in Primary Cervical Epithelial Cells Complement receptor 3 (CR3)-mediated endocytosis is a primary mechanism by which *N. gonorrhoeae* elicits membrane ruffling and cellular invasion of the cervical epithelia. Data disclosed herein indicate that, upon infection of cervical epithelia, *N. gonorrhoeae* specifically release proteins, including a phospholipase D (PLD) homolog, which facilitate membrane ruffling. To elucidate the function of gonococcal PLD in infection of the cervical epithelia, a *N. gonorrhoeae* PLD mutant was constructed. By comparative association and/or invasion assays, the PLD mutant gonococci were found to be impaired in their ability to adhere to and to invade primary cervical cells. This defect was rescued by the addition of supernatants obtained from wildtype-infected cell monolayers, but not by exogenously added *Streptomyces* PLD. The decreased level of total cell association (i.e., adherence and invasion) observed for mutant gonococci is, in part, attributed to the inability of these bacteria to recruit CR3 to the cervical cell surface with extended infection. Using electron microscopy, it was demonstrated that gonococcal PLD may be necessary to potentiate membrane ruffling and clustering of gonococci on the cervical cell surface. Data herein indicate that PLD augments CR3-mediated gonococcus invasion of, and survival within, cervical epithelia.

Introduction

*Neisseria gonorrhoeae* is a strict human pathogen causing the sexually transmitted disease gonorrhea. *N. gonorrhoeae* possesses multiple mechanisms by which it is able to colonize its human host and which are dependent upon the particular microenvironment of the infection site. In this respect, the gonococcus is unique in that it senses its particular microenvironment and adjusts its mode of pathogenicity accordingly. Several gonococcal constituents have been implicated in its pathogenicity including lipooligosaccharide (LOS), porin, pilus, and the opacity-associated (Opa) outer membrane proteins. Invasion of male urethral epithelial cells is mediated by LOS, the terminal galactose of which serves as a ligand for the asialoglycoprotein receptor (ASGP-R) (Harvey et al., 2001). An intimate association between the gonococcal and host cell membranes precedes clathrin-dependent endocytosis (Harvey et al., 2001). In contrast, complement (C') receptor type 3 (CR3)-mediated endocytosis is a primary mechanism by which *N. gonorrhoeae* invade primary human cervical epithelial cells (Edwards et al., 2001). This process is dependent upon the cooperative binding of (gonococcal-bound, host-derived) iC3b, gonococcal porin, and gonococcal pilus to the I-domain of CR3 (Edwards and Apicella, 2002; Edwards et al., 2002). Engagement of CR3 results in membrane ruffling (Edwards et al., 2001) and internalization of gonococci in macropinosomes (Edwards et al., 2000).

Ruffling induced by gonococci during cervical cell infection is delayed from the onset of infection by 60 to 90 minutes (Edwards et al., 2000). The onset of ruffling can be accelerated to 30 minutes by the addition of filtered, preconditioned (i.e., derived from a previous infection) media. Factors responsible for expediting the cytoskeletal changes induced by gonococcal infection were sought. Herein is disclosed the identification of gonococcal phospholipase D (PLD), which is specifically released upon infection of cervical epithelial. Gonococcal PLD (NgPLD) was found to play a role in membrane ruffling, CR3 recruitment to the cervical cell surface, and, consequently, in gonococcal invasion of the cervical epithelia. This secreted protein is a novel, neisserial virulence factor, capable of modulating effector functions within host cells.

Experimental Procedures

Cell Culture. Surgical biopsies derived from the ecto- and the endocervix that were used to seed primary cervical epithelial cell systems were procured and maintained as described previously (Edwards et al., 2000) in Defined Keratinocyte Serum Free Medium (dk-SFM) (Life Technologies, Rockville, Md.). The primary (uec) (Harvey et al., 1997) and immortal (tuec) (Harvey et al., 2002), male urethral epithelial cells used in these studies have been described and were maintained according to the methods of Harvey et al. (Harvey et al., 2001; Harvey et al., 1997). Pharmacological agents used, as described in the studies outlined below, were not cytotoxic at the indicated concentrations as determined by trypan blue exclusion.

Bacteria and Infection Studies. *N. gonorrhoeae* strains 1291 (Apicella, 1974; Dudas and Apicella, 1988), FA1090 (Cohen et al., 1994), and MS11 (Schoolnik et al., 1984; Segal et al., 1985) were used in the infection studies outlined below, which were performed as previously described (Edwards et al., 2000). Briefly, overnight cultures of gonococci were harvested from GC-IsoVitaleX agar plates and suspended in sterile physiological saline. Optical density of the bacterial suspension was determined spectrophotometrically where an optical density of 1 at 600 nm was equivalent to $10^9$ bacteria $ml^{-1}$. $10^7$ gonococci were used to infect cervical cell monolayers at a multiplicity of infection of 100. Primary cervical cells were challenged with gonococci for variable time-periods (as noted) after which the infection medium was removed, and the cell monolayers were extensively washed with phosphate-buffered saline (PBS). Uninfected control cell monolayers were simultaneously processed with challenged cell monolayers. Infected and uninfected (control) cell monolayers were subsequently harvested for cellular fractionation, quantitative association (i.e., adherence and invasion) or invasion assays, or they were processed for microscopic analyses. Alternatively (as noted), infection supernatants were harvested, immediately transferred to ice, and gonococci were removed by filtration through a 0.22 μm low protein-binding syringe filter. For PLD activity assays, supernatants depleted of gonococci were filtered using Centricon YM-30 centrifugal filter units (Millipore Corporation, Bedford, Mass.). Protein products were then collected with an equal volume of PLD assay buffer.

*N. gonorrhoeae* strain 1291ΔPLD was constructed by the insertion of a kanamycin-resistance cassette using the EZ:: TN <KAN-2> Insertion Kit (EPICENTRE, Madison, Wis.). Polymerase chain reaction (PCR) of full-length NgPLD, using the primer pair of 5'-GGT GGT CAT ATG ATG CAT ACA GAC CCC AAA AT-3' (SEQ ID NO:22) and 5'-GGT GGT TGCTCT TCC GCA TAA TAA ACC TTC TTC GAT GGG CAG-3' (SEQ ID NO:23), suggested the insertion of the kanamycin-resistance cassette within the pld gene, which was then confirmed by sequence analysis performed at the University of Iowa DNA Sequencing Facility (Iowa City, Iowa).

Radiolabeling and Collection of Gonococcal Products Released with Infection of Primary Cervical Cells. Gonococci allowed to grow overnight on GC agar were harvested with a sterile swab and used to inoculate 5 ml cultures of Morse's Defined Medium (MDM) (Morse and Barenstein, 1980). MDM was prepared such that half the recommended methionine and cysteine was replaced with 125 μCi Redivue Pro-mix L-[$^{35}$S] in vitro cell labeling mix (Amersham Pharmacia Biotech Inc, Piscataway, N.J.). After approximately 4 hours, gonococci were collected by centrifugation (4000 rpm, 5 minutes), rinsed with sterile physiological saline to remove excess label, and resuspended in cold MDM such that a culture density of $10^7$ bacteria $ml^{-1}$ was obtained. MDM containing the $^{35}$S-labeled gonococci was then used to infect approximately $10^5$ primary, human, ecto-(pex) and endocervical (pen) cells or 35 mm tissue culture dishes devoid of cervical cells. Alternatively, gonococci were labeled during the course of infection by a 30-minute pulse with $^{35}$S-MDM at 1 hour and 2.5 hours post-infection. Before infection pex and pen cells were treated (30 minutes, 37° C.) with 250 μM cycloheximide to inhibit cervical cell protein synthesis. Cycloheximide was maintained in the culture medium through out the course of the infection. Cervical cells and tissue culture plates lacking cervical cells were challenged with gonococci for 90 minutes and 3 hours after which the culture supernatants were collected. Gonococci were removed from the culture supernatants by filtration through low-protein binding 0.22 μm syringe filter units. Supernatant filtrates were concentrated using Centricon YM-3 centrifugal filter units (Millipore) before suspension in 0.1M Tris-0.1% SDS. Concentrated supernatants were separated on a SDS 4% to 12% polyacrylamide gel before autoradiography or gel-extraction for mass spectrometry at the Mass Spectrometry Facility located at the University of California (San Francisco, Calif.). Analysis of mass data was performed using the Protein Prospector (University of California San Francisco, Calif.) and the ProFound (Rockefeller University, NY) mass analysis databases.

Western Blot Analysis. Infection supernatants depleted of gonococci (as described above) were separated on 4% to 12% denaturing polyacrylamide gradient gels and transferred to Immobilon-P membranes (Millipore). Membranes were incubated (2 hours, 37° C.) with 50 µU/ml neuraminmidase (Roche Diagnostics, Indianapolis, Ind.) prior to immunodetection. Western blotting was subsequently performed according to standard protocols using the anti-lipooligosaccharide (LOS) monoclonal antibody, 6B4. This antibody recognizes the conserved Gal($\beta$1–4)GlcNac epitope of gonococcal LOS. Chemiluminescent detection was used to visualize labeled LOS.

Determination of PLD Activity. PLD activity was accessed using the Amplex™ Red Phospholipase D Assay Kit (Molecular Probes, Eugene Oreg.). Wild-type and PLD mutant gonococci were suspended in PLD assay buffer to a final concentration of $10^7$ bacteria $ml^{-1}$, and activity was determined according to the manufacturer's protocol. Assessment of gonococcal PLD activity at acidic pH was determined in a two-step assay according to the manufacturer's protocol. For the first step, $10^8$ gonococci were suspended in PBS with the pH adjusted to 3.0, 4.5, or 6.0. Gonococcal suspensions were diluted 10-fold in PLD assay buffer for the second step of the reaction. Cervical cell fractions were prepared as outlined below and PLD activity was assessed at neutral pH according to the manufacturer's protocol.

Fractionation of Primary Cervical Cells. Uninfected (control) and infected cervical cell monolayers were lysed in buffer A (50 mM tris, pH 7.5; 10 mM NaCl, 1 mM KCl; 2 mM $MgCl_2$, 1 mM PMSF) by scraping cervical cells from tissue culture dishes placed on ice. The cell lysate was sonicated (two bursts of 20 seconds each). Cells that did not lyse and the nuclear fraction were removed by centrifugation (750×g, 10 minutes), and the supernatant from this spin was then subjected to filtration through a low-protein binding 0.22 µm syringe filter to ensure removal of gonococci. Sucrose was added to the resulting gonococcus-depleted supernatant (S1) to a final concentration of 300 mM. Ultracentrifugation (150,000×g, 90 minutes) was then performed to produce the plasma membrane-(pellet) and cytosol (supernatant 2, S2)-enriched fractions. The membrane-enriched fraction was resuspended in PLD assay buffer (50 mM Tris, 5 mM $CaCl_2$, pH 8.0). S2 was concentrated by filtration through Centricon YM-30 centrifugal filter units (Millipore) after which cytosolic constituents were recovered in PLD assay buffer. Where indicated, prior to infection studies, primary pex and pen cell monolayers were treated with 300 nM wortmannin (Sigma) (2 hours, 37° C.) or 1 µM cytochalasin D (Sigma) (30 minutes, 37° C.) to inhibit macropinocytosis of gonococci. Wortmannin and cytochalasin D were maintained in cervical cell cultures during the course of infection.

RNA Isolation and RT-PCR of Primary, Human, Cervical Epithelial Cells. Primary, pex and pen cell monolayers were challenged with *N. gonorrhoeae* 1291 or 1291$\Delta$PLD, or they were left uninfected. After 3 hours, infection supernatants were removed and cell monolayers were extensively rinsed with PBS. Total RNA (intracellular gonococcal and cervical cell RNA) was isolated using the RNAqueous-4PCR kit (Ambion, Inc., Austin, Tex.) according to the manufacturer's protocol. Ribosomal RNA was removed from the total RNA using the MICROBExpress kit (Ambion) according to the manufacturer's protocol, yielding message-enriched bacterial and cervical cell RNA. Cervical cell RNA was then separated from intracellular bacterial RNA using the Poly (A)Purist kit (Ambion) according to the manufacturer's protocol with slight modification. Supernatants from the capture and wash steps, which contained gonococcal RNA, were saved and pooled. Gonococcal RNA was recovered by ethanol precipitation. cDNA was synthesized using RET-ROscript™ First Strand Synthesis Kit for RT-PCR (Ambion); reactions lacking the reverse transcriptase (RT) (negative control) were run simultaneously with reactions containing RT. PCR analysis of reverse-transcribed and of mock reactions using primers to $\beta$-actin and to gonococcal reduction modifiable protein (Rmp) demonstrated the absence of contaminating DNA and of gonococcal DNA and RNA in the isolated cervical cell RNA. PCR of reverse-transcribed cervical cell RNA was performed using the primer pairs 5'-TCC ATG CAA GAA TCT GGT TTC-3' (SEQ ID NO:28) and 5'-CGA CAA TGA GCA CAG ACT CAC A-3' (SEQ ID NO:29) for human PLD1 to yield a 462 bp product and 5'-CCT TCA GGA TTC TGT CCA CAA-3' (SEQ ID NO:30) and 5'-CCT CTC TCA CAA CCA ATT CTT C-3' (SEQ ID NO:31) for human PLD2 to yield a 508 bp product.

Determination of CR3 Surface Expression on Primary Cervical Cells. Pex and pen cells were passed to 96-well microtiter plates and allowed to grow to confluence. Cervical cells were then challenged with wild-type or PLD mutant gonococci after which the infection medium was removed and cells were rinsed thrice with PBS. Cells were fixed with 2% paraformaldehyde. Prior to immuno-analysis of CR3 surface level expression, cells were again rinsed with PBS. Immunoassays were then performed according to standard ELISA protocols using the H5A4 anti-CD11b (i.e., CR3) primary and peroxidase-conjugated secondary antibodies. Absorbance of the o-phenylenediamine dihydrochloride peroxidase substrate was determined spectrophotometrically at 495 nm. Primary antibody was omitted from one well, and the secondary antibody was omitted from a second well, which served as controls for non-specific binding and endogenous peroxidase activity, respectively. Where indicated gonococci-depleted supernatants collected from wild-type or PLD mutant infection studies were included in the infection studies, performed as outlined below.

*N. gonorrhoeae* Attachment to and Invasion of Primary, Human, Cervical Cells. Primary cervical cell monolayers were infected with wild-type or PLD mutant gonococci as outlined above. Variable concentrations of PtC (Sigma), ethanol, 2-butanol, or *Streptomyces* spp. PLD (SsPLD) (Sigma) were included in association (adherence and invasion) or invasion assays, as noted. PtC, ethanol, 2-butanol, or 10 units $ml^{-1}$ SsPLD were added simultaneously with gonococci. In separate assays, infection supernatants were collected from wild-type or PLD mutant-infected cervical cell monolayers, gonococci were removed by filtration through a 0.22 µm syringe filter (to yield primed wild-type or mutant supernatants), which were then added to association and/or invasion assays, as noted. The ability of gonococci to adhere to and/or invade pex and pen cells was quantitatively determined using standard gentimicin-resistance assays, performed as described previously (Edwards et al., 2000) and in which chemical or protein additives were included or excluded from the invasion assay as described above. The total association (i.e., adherence and invasion) of gonococci with pex and pen cells was quantitated by the omission of gentimicin from the above described invasion assay. Percent invasion of *N. gonorrhoeae* 1291 or 1291ΔPLD in the presence or absence of experimental additives was determined as a function of the original inoculum and the number of colonies formed with subsequent plating of the cellular lysate. Inhibition of gonococcal attachment and/or invasion by exogenous PtC, ethanol, or 2-butanol was determined as a normalized function of the ability of gonococci to attach to and/or invade primary cervical cells in the absence of the competimer inhibitor. A Kruskal-Wallis non-parametric analysis of variance was used to determine the statistical significance of the association and invasion assays described above.

Immunolabeling and Microscopy. Immunolabeling of *N. gonorrhoeae* 1291 or 1291ΔPLD infected pex cell monolayers was performed as described previously (Edwards et al., 2000). Primary antibodies used for immunolabeling were specific for the CR3 β-subunit, CD18 (anti-CD18 CTB104 (Santa Cruz Biotechnology, Santa Cruz, Calif.)) or for the gonococcal H.8 outer membrane protein (antibody 2C3). FITC- and TRITC-conjugated secondary antibodies were applied to cell monolayers, as noted. Infected and uninfected (control) cell monolayers were viewed using the Bio-Rad MRC-1024 Laser Scanning Confocal viewing system. Primary cervical cell monolayers were processed for SEM analyses (Edwards et al., 2000) and viewed using the Hitachi S-4000 scanning electron microscope. All the microscopes used in these studies are located at the Central Microscopy Research Facility at the University of Iowa (Iowa City, Iowa).

Results

*N. gonorrhoeae* Specifically Release Protein Products upon Infection of Cervical Epithelia. Previous studies show that membrane ruffling of *N. gonorrhoeae*-infected primary human cervical cells occurs by approximately 90 minutes post-infection (Edwards et al., 2000). These same studies also demonstrate that the onset of membrane ruffling in response to gonococcal infection can be expedited by the use of a primed infection inoculum, that is, an inoculum derived from a previous infection. Based on these studies, it was reasoned that gonococcal products were being released upon infection that facilitated membrane ruffling. Autoradiography of infection supernatants demonstrated that gonococcal products were, in fact, being released with infection of primary, human, ecto- and endocervical epithelium. Release of these gonococcal products was not strain specific in that an identical protein pattern was observed with autoradiography of infection supernatants obtained from *N. gonorrhoeae* strains 1291-(FIG. 22), FA1090—(data not shown), or MS11-infected primary cervical cells (data not shown). In contrast, analysis of supernatants derived from an identical time course of infection of uec revealed that only a small amount of gonococcal products are released by 90 minute post-infection, and by 3 hours of infection no products could be detected (FIG. 22). Collectively, these data suggested that a small basal level of gonococcal products are released constitutively, but, also that the continued release of gonococcal products was specific to gonococcal cervicitis. Western Blot analysis of infection supernatants using the anti-LOS 6B4 antibody probe did not reveal the presence of gonococcal LOS. This indicated the release of gonococcal products with cervical cell infection was the result of bacterial secretion and not of bacterial lysis (FIG. 22).

Characterization of a *N. gonorrhoeae* PLD Homolog. Using mass spectroscopy a subset of gonococcal products that are secreted upon cervical cell infection were identified. One secreted product, p55, was identified by mass analysis using Protein Prospector and Profound data bases as sharing significant homology to a *Neisseria meningitidis* hypothetical PLD homolog. Primers for PCR were designed based on the *N. meningitidis* serogroup B sequence and used to amplify pld from *N. gonorrhoeae* strains 1291, FA1090, and MS11. Sequences obtained from cloning of the PCR amplicons were then used in a BLAST search of the *N. gonorrhoeae* genome database to identify p55 as a *N. gonorrhoeae* PLD homolog (GenBank accession number AY307929). The p55 sequence was used to perform a BLAST search of the National Center for Biotechnology Information (NCBI) database, which revealed significant sequence homology of p55 to *Neisseria meningitidis* serogroups A and B hypothetical PLD homologs, hypothetical and/or putative synthases of *Escherichia coli* and *Shigella flexneri*, and a putative phospholipase of *Salmonella*. Further sequence analysis of p55 revealed that this protein contains two HKD (amino acids 184–201 and 422–439) motifs, which are required for PLD activity, and two regions of hydrophobicity (amino acids 24–34 and 217–231) that might serve as lipid association domains. Comparative assessment of PLD activity in *N. gonorrhoeae* strains 1291 and 1291ΔPLD (performed at pH 7.4) demonstrated PLD activity in wild-type but not mutant gonococci (Table 10), indicating p55 functions as a phospholipase D. In separate assays, NgPLD exhibited characteristic PLD activity at pH 3.0, 4.5, and 6.0 (Table 10), consistent with the capability of this enzyme to function within the lower female genital tract under normal conditions or during bacterial vaginosis and/or cervicitis.

TABLE 10

PLD activity in *N. gonorrhoeae* cell lysates.
PLD Activity in Gonococci
Fluorescence Units [Mean (variance)]

| | pH 7.4 | pH 6.0 | pH 4.5 | pH 3.0 |
|---|---|---|---|---|
| WT 1291 | 0.999 (0.12) | 1.489 (0.01) | 1.516 (0.06) | 1.537 (0.04) |
| 1291ΔPLD | 0.172 (0.03) | 0.097 (0.01) | 0.101 (0.01) | 0.110 (0.01) |
| Positive control | 0.930 (0.12) | 1.525 (0.03) | 1.468 (0.02) | 1.470 (0.01) |
| Negative control | 0.195 (0.01) | 0.096 (0.01) | 0.089 (0.01) | 0.110 (0.01) |

PLD activity was determined as described in the text. Values given are the mean values of three trials.

*N. gonorrhoeae* PLD Augments Gonococcal Infection of Cervical Epithelial Cells. To determine if NgPLD plays a role in infection of cervical epithelia, quantitative association and/or invasion assays were performed using *N. gonorrhoeae* strains 1291 and 1291ΔPLD. Association and invasion assays demonstrated a role for NgPLD in gonococcal cervicitis as indicated by the decreased levels of association and of invasion observed with infection of primary cervical cells with the PLD mutant upon comparison to the wild-type bacteria (Table 11). The addition of SsPLD to association and/or invasion assays performed using mutant gonococci could not rescue the decreased levels of association and of invasion observed in the absence of NgPLD. Although efforts to isolate NgPLD have, to date, been unsuccessful, the addition of primed wild-type supernatants to infection assays performed using mutant gonococci restored association and invasion to near-wildtype levels. However, the addition of primed mutant supernatants had no effect on the ability of PLD mutant gonococci to adhere to or to invade primary cervical cells (Table 11).

TABLE 11

Percent adherence to and/or invasion of primary cervical cells by gonococci in the presence or absence of primed media or exogenous PLD.

| | Ectocervical Cells | | Endocervical Cells | |
|---|---|---|---|---|
| | Association (%) | Invasion (%) | Association (%) | Invasion (%) |
| A. | | | | |
| 1291 wt | 28.6625 +/− 1.35 | 2.9086 +/− 0.22 | 16.7904 +/− 0.54 | 1.5907 +/− 0.02 |
| 1291ΔPLD | 15.9325 +/− 0.80 (<0.05) | 0.3496 +/− 0.04 (<0.05) | 6.9787 +/− 0.83 (<0.05) | 0.2378 +/− 0.02 (<0.05) |
| 1291ΔPLD + wt sup | 23.9946 +/− 3.06 (<0.05) | 2.0890 +/− 0.15 (<0.05) | 11.9021 +/− 1.28 (<0.05) | 1.3444 +/− 0.21 (<0.05) |
| B. | | | | |
| 1291 wt | 27.7631 +/− 0.14 | 2.6521 +/− 0.04 | 15.5504 +/− 0.80 | 1.6408 +/− 0.12 |
| 1291ΔPLD | 15.3918 +/− 0.99 (<0.05) | 0.3200 +/− 0.02 (<0.05) | 6.8529 +/− 0.67 (<0.05) | 0.2421 +/− 0.01 (<0.05) |
| 1291ΔPLD + pld sup | 15.6207 +/− 0.87 (<0.05) | 0.3087 +/− 0.03 (<0.05) | 6.3615 +/− 0.57 (<0.05) | 0.2379 +/− 0.02 (<0.05) |
| C. | | | | |
| 1291 wt | 30.6436 +/− 1.69 | 2.9106 +/− 0.39 | 17.0786 +/− 1.43 | 1.6367 +/− 0.11 |
| 1291ΔPLD | 13.6266 +/− 0.63 (<0.05) | 0.3671 +/− 0.03 (<0.05) | 7.2765 +/− 0.19 (<0.05) | 0.2009 +/− 0.03 (<0.05) |
| 1291ΔPLD + SsPLD | 14.6986 +/− 2.16 (<0.05) | 0.3862 +/− 0.05 (<0.05) | 6.8087 +/− 0.41 (<0.05) | 0.1748 +/− 0.01 (<0.05) |

Values given are the mean values in which the percent total association (adherence and/or invasion) and the percent invasion were determined as a function of the original inoculum and the subsequent number of colony forming units formed with subsequent plating of the ecto- or endocervical cell lysates. Data given are the mean values obtained from at least three trials performed in triplicate. p-values (notedparenthetically) were determined using a Kruskal-Wallis k-sample analysis of variance calculated for association and/or invasion of wild-type or mutant gonococci in the presence of wild-type (A) or PLD mutant (B) primed medium or 10 U/ml SsPLD (C) in comparison to the absence of primed medium or exogenous SsPLD, as outlines in the text.

Similar studies in which tuec were challenged with *N. gonorrhoeae* strains 1291 or 1291ΔPLD revealed NgPLD does not play a role in the association of gonococci with the urethral epithelium but may promote the intracellular survival of these organisms. The association of 1291ΔPLD with tuec was comparable to that of wild-type gonococci; whereas, invasion levels were decreased in the absence of NgPLD (Table 12).

TABLE 12

Percent adherence to and/or invasion of urethral epithelial cells by wild-type and PLD mutant gonococci

| | Association (%) | Invasion (%) |
|---|---|---|
| 1291 wt | 25.1601 +/− 1.69 | 2.4285 +/− 0.05 |
| 1291ΔPLD | 25.1132 +/− 1.01 (>0.75) | 1.1616 +/− 0.11 (<0.05) |

Values given are the mean values in which the percent total association (adherence and/or invasion) and the percent invasion were determined as a function of the original inoculum and the subsequent number of colony forming units formed with subsequent plating of TUEC lysates. Data given are the mean values obtained from at least three trials performed in triplicate. p-values (noted parenthetically) weredetermined using a Kruskal-Wallis k-sample analysis of variance calculated for association and/or invasion of mutant gonococci in comparison to wild-type gonococci.

*N. gonorrhoeae* PLD Plays a Role in CR3 recruitment to the Cervical Cell Surface. CR3 serves as the primary receptor for gonococcal adherence to and invasion of the cervical epithelium (Edwards et al., 2001). Previous studies have also indicated that surface levels of CR3 increase with gonococcal infection (Edwards et al., 2001). Laser scanning confocal microscopy (LSCM) was performed to examine the gonococcus-CR3 association in mutant gonococci to determine if the decrease in gonococcal cervical cell association observed with use of the PLD mutant was because of the inability of mutant gonococci to recruit CR3 to the cervical cell surface. LSCM revealed that in comparison to wild-type infected pex cells, which exhibited abundant CR3 on the monolayer surface, pex cells infected with PLD mutant gonococci exhibited decreased fluorescence, indicative of a decreased level of CR3 on their cell surface (data not shown). To quantitate these findings an ELISA assay was developed to measure cervical cell surface expression of CR3 in uninfected pex and pen cells and cells challenged with *N. gonorrhoeae* strains 1291 and 1291ΔPLD (Table 13). Immuno-analysis of the presence of CR3 on the surface of pex and pen cells confirmed our LSCM data. The amount of CR3 present on the surface of wild-type infected cervical cells was significantly greater than levels of CR3 measured on either the PLD mutant infected or uninfected cervical cells. The addition of primed wild-type supernatants to PLD mutant infected and uninfected cells increased CR3 recruitment to the cervical cell surface. However, the addition of primed supernatants from the PLD mutant had no affect on CR3 recruitment to the cervical cell surface of PLD mutant infected or uninfected cells.

TABLE 13

Semi-quantitative immuno-analysis of CR3 expression on the surface of primary cervical cells

| | Absorbance (490 nm) | |
|---|---|---|
| | Ectocervical Cells | Endocervical Cells |
| Uninfected control | 0.531 +/− 0.13 | 0.303 +/− 0.03 |
| WT 1291 | 2.367 +/− 0.18 | 1.648 +/− 0.17 |
| 1291ΔPLD | 0.677 +/− 0.12 | 0.340 +/− 0.11 |
| Uninfected control w/primed wt sup | 1.083 +/− 0.36 | 0.731 +/− 0.06 |
| Uninfected control w/primed pld sup | 0.441 +/− 0.14 | 0.378 +/− 0.05 |
| 1291ΔPLD w/primed wt sup | 1.364 +/− 0.43 | 1.131 +/− 0.28 |
| 1291ΔPLD w/primed pld sup | 0.387 +/− 0.13 | 0.305 +/− 0.08 |
| No primary Ab | 0.063 +/− 0.01 | 0.083 +/− 0.01 |

Values given are the mean values in which the presence of CR3 on the cervical cell surface was measured by an immuno-assay using the monoclonal antibody H5A4 as outlined in the text.

*N. gonorrhoeae* PLD Plays a Role in Membrane Ruffling of the Cervical Epithelium. PLD activation in mammalian cells is thought to occur early in the phagocytic process, before the onset of actin reorganization. To determine if gonococcal PLD plays a role in the cytoskeletal rearrangements leading to membrane ruffling of the cervical epithelium, scanning electron microscopy (SEM) was performed. SEM analysis demonstrated that aberrant cytoskeletal rearrangements occur upon infection of cervical epithelia with PLD-mutant gonococci, when compared to infection with wild-type gonococci. At 15 minutes post-infection, no significant difference was observed between PLD mutant and wild-type infected pex cells (data not shown). Small bacterial clusters were evident as were microvilli/filopodia. However, by 3 hours post-infection, bacterial clusters and membrane ruffles were not readily evident on cell monolayers infected with mutant gonococci, but were characteristically prevalent on wild-type infected cell monolayers (FIG. 16). The addition of primed wild-type supernatants, but not primed PLD mutant supernatants, to *N. gonorrhoeae* 1291ΔPLD infection studies restored bacterial clustering and membrane ruffling (FIG. 16), suggesting NgPLD plays a role in signal transduction events leading to CR3 clustering and membrane ruffling.

Activity and Subcellular Localization of *N. gonorrhoeae* PLD in Cervical Epithelia. To determine if PLD activity is increased in infected cervical cells, PLD activity was measured in infected and uninfected cervical cell lysates. Comparison of wild-type infected cervical cells to that of the PLD mutant infected or uninfected cells demonstrated that overall PLD activity is increased in wild-type infected pex and pen cells. There was no significant difference between uninfected cells and mutant infected cervical cells, suggesting that the observed increase in PLD activity is primarily due to gonococcal PLD. RT-PCR analysis of human PLD1 and PLD2 in pex and pen cells demonstrated that endogenous cervical cell PLD message levels are not up-regulated in cells infected with *N. gonorrhoeae* strains 1291 and 1291ΔPLD when compared to uninfected cells (FIG. 23). These data support a role for NgPLD, rather than endogenous cervical cell PLD, in the observed increase in PLD activity described above.

Analysis of PLD activity in infected and uninfected cervical cell fractions revealed a significant portion of gonococcal and cervical cell PLD activity lies within the membrane-enriched portion of cervical cell lysates. However, PLD activity was also observed in the cytosolic-enriched cell fraction. No significant difference was observed between PLD activity in uninfected cervical cells and the PLD mutant infected cells.

Membrane ruffling followed by macropinocytosis of gonococci serves as a primary mechanism by which these bacteria invade the cervical epithelium. To determine if NgPLD non-specifically gains access to the cervical cell cytosol during macropinocytosis of gonococci, cell fractionation studies were performed of infected and uninfected pex cells treated or untreated with wortmannin or cytochalasin D (Table 14). PLD activity was significantly reduced in membrane- and cytosol-enriched cell fractions when wortmannin and cytochalasin D were included in wild-type infection studies. No significant difference was observed in PLD activity in uninfected or 1291ΔPLD infected pex cells when these same cytoskeletal inhibitors were included or excluded from the assay. Collectively, these data indicate that macropinocytosis of invasive gonococci allows NgPLD to enter primary cervical cells.

TABLE 14

PLD activity in cervical cells treated with cytoskeletal inhibitors.

| | PLD Activity in Ectocervical Cell Fractions Fluorescence Units [Mean (variance)] | | | |
|---|---|---|---|---|
| | +/−Wortmannin Treatment | | +/−Cytochalasin D Treatment | |
| Cell Fraction | Membrane | Cytosolic | Membrane | Cytosolic |
| Uninfected w/o | 0.578 (0.04) | 0.388 (0.02) | 0.368 (0.04) | 0.479 (0.05) |
| Uninfected w/ | 0.474 (0.05) | 0.403 (0.01) | 0.389 (0.01) | 0.395 (0.03) |
| WT 1291 w/o | 0.992 (0.10) | 0.863 (0.08) | 1.035 (0.06) | 0.846 (0.09) |
| WT 1291 w/ | 0.784 (0.06) | 0.413 (0.03) | 0.436 (0.03) | 0.462 ((0.03) |
| 1291ΔPLD w/o | 0.410 (0.01) | 0.406 (0.02) | 0.343 (0.01) | 0.392 (0.01) |
| 1291ΔPLD w/ | 0.418 (0.02) | 0.408 (0.01) | 0.393 (0.01) | 0.330 (0.07) |

| Assay Controls | | | |
|---|---|---|---|
| Positive Control | 1.133 (0.29) | Negative control | 0.180 (0.04) |

Cellular fractionation and PLD activity were assayed as described in the text. Data given are the mean values obtained from three trials in which gonococci were removed by filtration through a 0.22 μm syringe filter (see materials and methods).

Gonococcal PLD Acts at Multiple Levels in Cervical Cell Infection. Studies using *Streptomyces* PLD have indicated that the exogenous addition of PLD to vascular smooth muscle cells mimics endogenous PLD activity within these cells (Kondo et al., 1992). Consequently, it was determined if exogenously added PLD substrates could compete with cervical cell constituents for NgPLD activity and in doing so interfere with the role of NgPLD in gonococcal invasion. The addition of 10, 1, 0.1, or 0.01 μg/ml of phosphatidylcholine (PtC) or 1.0, 0.1, or 0.01 percent ethanol to infection studies impaired the ability of gonococci to invade pex cells in a dose-dependent manner (Table 15). In contrast, no effect was observed in gonococcal association with and/or their invasion of primary cervical cells in the presence of 1.0, 0.1, or 0.01 percent 2-butanol (Table 15), which can not serve as a substrate in PLD-catalyzed transphosphatidylation. There was no significant difference in survival observed between gonococci incubated in the presence or absence of 1.0, 0.1, or 0.01 percent ethanol or 2-butanol in the absence of cervical cells (data not shown). These data suggest a role for gonococcal PLD in modulating cervical cell signaling events (e.g., through phosphatidic acid (PA) generation) and suggest that NgPLD may function at several different levels in gonococcal invasion of cervical epithelia.

TABLE 15

Percent adherence to and/or invasion of primary cervical cells by gonococci in the presence or absence of PLD substrate competimers

A.

| Competimer | 1291 WT | | 1291ΔPLD |
|---|---|---|---|
| | Inhibition[1] (%) | Invasion[1] (%) | Invasion[2] (%) |
| None | NA | 2.7833 (0.16) | 0.3371 (0.02) |
| Ethanol (%) | | | |
| 1.0 | 90.7346 (0.92) $p < 0.05$ | 0.2564 (0.01) $p < 0.05$ | 0.3288 (0.03) $p > 0.75$ |
| 0.1 | 80.9243 (1.41) $p < 0.05$ | 0.5288 (0.01) $p < 0.05$ | 0.3419 (0.04) $p > 0.90$ |
| 0.01 | 74.9582 (0.87) $p < 0.05$ | 0.6957 (0.02) $p < 0.05$ | 0.3360 (0.04) $p > 0.90$ |
| 2-Butanol (%) | | | |
| 1.0 | ND | 2.6869 (0.47) $p > 0.90$ | 0.2960 (0.05) $p > 0.25$ |
| 0.1 | ND | 2.7087 (0.47) $p > 0.75$ | 0.3172 (0.03) $p > 0.25$ |
| 0.01 | ND | 2.8661 (0.53) $p > 0.75$ | 0.2819 (0.02) $p > 0.25$ |

B.

| PtC (g/ml) | Inhibition[1] (%) | Invasion[1] (%) |
|---|---|---|
| 10.0 | 98.7786 (0.08) $p < 0.05$ | 0.0331 (0.01) $p < 0.05$ |
| 1.0 | 92.4681 (0.38) $p < 0.05$ | 0.2038 (0.01) $p < 0.05$ |
| 0.1 | 87.3571 (0.28) $p < 0.05$ | 0.3418 (0.01) $p < 0.05$ |
| 0.01 | 68.8105 (2.15) $p < 0.05$ | 0.8379 (0.03) $p < 0.05$ |
| 0.0 | NA | 2.7052 (0.11) $p < 0.05$ |

Values given are the mean values in which the percent invasion was determined as a function of the original inoculum and the subsequent number of colony forming units formed with subsequent plating of the ecto- or endocervical cell lysates. Inhibition values given were determined as a normalized function of the ability of the gonococcus to invade primary ectocervical cells in the presence of, incomparison to the absence of, an alcohol and phosphatidylcholine competimers as outlined in the text. Data given are the mean values obtained from at least three trials performed in triplicate. Variances are noted parenthetically. P-values were determined using a Kruskal-Wallis k-sample analysis of variance.
NA—Not applicable
ND—Not determined
[1]p-values were calculated for wild-type gonococci in the presence of competimer compared to the absence of the competimer
[2]p-values were calculated for PLD mutant gonococci in the presence of competimer as compared to the absence of the competimer Discussion Phopholipases are a diverse group of hydrolytic enzymes, which are classified by the specificity they exert for the site of phospholipid cleavage. In eukaryotic systems, homologs of PLD can be activated by a variety of stimuli (e.g., hormones and growth factors) after which they catalyze the hydrolysis of PtC to choline (Cho) and PA (Exton, 1997; Jones et al., 1999; Waite, 1999). PLDs belong to a large superfamily of proteins, which can be divided into eight classes (Ponting and Kerr, 1996). Included in the PLD superfamily are prokaryotic and eukaryotic PLDs, cardiolipin and phosphatidylserine synthases, Vaccinia and Fowlpox viral proteins of unknown function, an Escherichia coli nuclease and an E. coli helicase (Ponting and Kerr, 1996). All members of the PLD superfamily contain (usually) two HKD motifs, which are thought to associate to form a catalytic center. However, unique to PLD is the ability to catalyze a transphosphatidylation reaction in which a primary alcohol preferentially serves as a nucleophilic acceptor instead of water, resulting in the near-exclusive production of a phosphatidylalcohol (PtOH) at the expense of PA. The resulting PtOH is metabolically stable and, thus, serves as a specific indicator of PLD activity. Although eukaryotic PLDs have been well studied, much less is known about bacterial PLDs, and, in fact, only a handful have been identified. Some bacterial PLDs are associated with virulence, e.g., the Yersinia murine toxin (Ymt) (Hinnebusch et al., 2002) and PLDs of Corynebacterium spp. (McNamara et al., 1995), pathogens of humans and domestic animals. It is demonstrated in Corynebacterium pseudotuberculosis that PLD mutation results in the attenuation of this microbe (Hodgson et al., 1992; Simmons et al., 1998).

PLD activity in N. gonorrhoeae is disclosed herein, as well as a role for this secreted protein in gonococcal pathogenesis of cervical epithelia. Characteristic PLD activity (i.e., removal of Cho by cleavage of the terminal phosphodiester bond of PtC) was observed in gonococcal whole cell lysates but was absent in gonococci in which pld was mutated by the insertion of a kan$^R$ cassette. PLD activity was observed over a pH range of 3.0 to 7.4, which is consistent with its ability to function as an effector protein within the lower female genital tract under normal (uninfected) or diseased states. The ability of NgPLD activity to promote gonococcal invasion of primary cervical cells was inhibited in the presence of PtC and ethanol (a primary alcohol) but not 2-butanol (a secondary alcohol). These data definitively demonstrate that this gonococcal protein does indeed exhibit characteristic PLD function and argue against a role for endogenous pex or pen cell phospholipase C (PLC) activity in CR3-mediated invasion of cervical epithelia by gonococci. A BLAST search of the N. gonorrhoeae and N. meningitidis genomic databases using sequences to several bacterial PLCs failed to reveal the presence of this enzyme in the pathogenic Neisseria. Furthermore, these data indicate that the generation of PA or its catabolic products are required for CR3-mediated macropinocytosis of gonococci.

Recent evidence indicates that Ymt promotes the survival of Y. pestis within the flea midgut from a cytotoxic digestion product present in blood plasma and, consequently, promotes disease transmission (Hinnebusch et al., 2002). Data herein indicate that the presence of a functional NgPLD is essential for the survival of gonococci within primary cervical cells. Although an interaction with the ASGP-R does not appear to sustain NgPLD secretion in culture supernatants, NgPLD does play a role in gonococcal survival within urethral epithelial cells. The addition of SsPLD to association and invasion assays of N. gonorrhoeae ΔPLD infected cervical cells did not compensate for the absence of NgPLD, suggesting NgPLD exhibits unique effector functions in addition to sharing structural and functional properties with SsPLD. This is supported by the finding that, although all PLDs contain (usually) two HKD motifs, sequences outside these regions are not necessarily highly conserved and may confer specific effector functions to their respective proteins (Waite, 1999).

Total PLD activity was greater in infected pex and pen cells upon comparison to uninfected or PLD mutant infected cells, which was attributed to NgPLD and not endogenous PLD activity. NgPLD appears to modulate cervical cell function, either directly or indirectly in a cooperative manner with host cell effector molecules, to promote the appropriate targeting of gonococci to permissive host cells (i.e., CR3-expressing ecto- and endocervical cells) and to ensure their intracellular survival.

The association with and invasion of primary cervical epithelia is impaired in the absence of NgPLD. CR3, the primary receptor by which gonococci invade the cervical epithelia, is not recruited to the cervical cell surface in the absence of NgPLD. Membrane ruffling is not evident in the absence of NgPLD with extended infection. Thus, NgPLD is unique among prokaryotic proteins identified to date.

The ability of PLD to cause the release of secondary granules in neutrophils suggests that this molecule may play a role in the recruitment of CR3 to the surface of these cells. Additionally, products of PLD-catalyzed phospholipid hydrolysis serve as second messengers, eliciting a variety of cellular responses and are thought to function in complement (C')-mediated endocytosis (Fällman et al., 1992) and in cytoskeletal rearrangements (Colley et al., 1997; Ha and Exton, 1993; Jones et al., 1999). The absence of CR3 recruitment to the cell surface in N. gonorrhoeae ΔPLD infected primary cervical cells strongly suggests an early role for NgPLD in, directly or indirectly, modulating CR3 effector function. Studies using *Streptomyces chromofuscus* PLD (ScPLD) indicate that exogenous ScPLD can mimic endogenous PLD activity by triggering cytoskeletal rearrangements, DNA synthesis, and cell proliferation (van Dijk et al., 1998; Kondo et al., 1992). These data provide a precedent for the observations herein demonstrating the ability of exogenous NgPLD, a secreted bacterial protein, to modulate CR3 effector function in primary cervical epithelial cells.

Reorganization of the actin cytoskeleton is the result of the activation of a complex network of signal transduction pathways involving many effector molecules. Bacterial, plant, and human PLDs directly bind polymeric F-actin, which in turn increases PLD activity (Kusner et al., 2003). In contrast, monomeric G-actin inhibits PLD activity in a species-specific manner in that (Kusner et al., 2002), in vitro, G-actin-induced PLD inhibition is twenty-fold greater for human PLD1 than it is for SsPLD (Kusner et al., 2003). The greatest degree of inhibition occurs upon the initiation of PLD activity in the presence of G-actin; less inhibition is observed when G-actin is added to previously activated PLD (Kusner et al., 2003). Phosphatidylinositol 4,5-bisphosphate ($PIP_2$) is a required co-factor in human PLD activity; in contrast, bacterial PLD activity does not exhibit a cofactor requirement. In resting cells, mammalian PLD resides in an inactive state because $PIP_2$, which remains bound to actin-associated proteins (e.g., vinculin, -actinin, fodrin), is unavailable as a required co-factor (Lukowski et al., 1996).

Cervical cells infected with the N. gonorrhoeae ΔPLD mutant failed to elicit membrane ruffling but did promote microvilli/filopodia formation, suggesting NgPLD might be required to potentiate the extensive cytoskeletal rearrangements necessary for ruffle formation. NgPLD may act in a synergistic or an additive manner with endogenous cervical cell PLD to potentiate membrane ruffling by stabilizing actin filaments in a manner similar to what is observed with phalloidin.

Disclosed herein are studies that elucidate the signaling pathways that participate in the response of cervical epithelia to N. gonorrhoeae infection. In this respect, a novel gonococcal virulence factor, NgPLD, which modulates CR3 effector function in conjunction with cervical cell effector molecules to trigger alternative signal transduction pathways is identified. This secreted gonococcal product serves a critical role in ensuring appropriate targeting of the gonococcus to the ecto-and endocervical epithelium by recruiting CR3 to the cervical cell surface and promotes intracellular survival of gonococci following CR3-mediated macropinocytosis.

All publications, patents and patent documents are incorporated by reference herein, as though individually incorporated by reference. The invention has been described with reference to various specific and preferred embodiments and techniques. However, it should be understood that many variations and modifications may be made while remaining within the scope of the invention.

REFERENCES

Alpuche-Aranda et al., *J. Exp. Med.*, 179, 601–608 (1994).
Altieri, *J. Immunol.*, 147, 1891–1898 (1991).
Apicella, *J. Infect. Dis.*, 130, 619–625 (1974).
Becherer et al., *Complement Inflamm.*, 6, 142–165 (1989).
Bessen and Gotschlich, *Infect. Immun.*, 54 (11), 154–160 (1986).
Bjerknes et al., *Infect. Immun.*, 63, 160–167 (1995).
Caron and Hall, *Science*, 282, 1717–1720 (1998).
Carrea et al., *Biochim. Biophys. Acta.*, 1255, 273–279 (1995).
Chen et al., *Infect. Immun.*, 63, 1790–1795 (1995).
Christodoulides et al., *Mol. Microbiol.*, 35, 32–43 (2000).
Clarke and Spudich, *Ann. Rev. Biochem.*, 46, 797–822 (1977).
Clauser et al., *Anal. Chem.*, 71, 2871 (1999).
Clerc, P. and P. J. Sansonetti, Infect. Immun., 55, 2681–2688 (1987).
Cohen et al., *J. Infect. Dis.*, 169, 532–537 (1994).
Colley et al., *Curr. Biol.*, 7, 191–201 (1997).
Cooper, *Immunol. Today*, 12, 327–331 (1991).
Dehio et al., *Trends Microbiol.*, 6, 489–495 (1998).
Densen, *Clin. Microbiol. Rev.*, 2, S11–S17 (1989).
Densen et al., *Infect. Immun.*, 38, 563–572 (1982).
van Dijk et al., *Curr. Biol.*, 8, 386–392 (1998).
Dillard, "A variable pathogenicity island associated with disseminated gonooccocal infection," Midwest Microbial Pathogenesis Group, Sixth Annual Midwest Microbial Pathogenesis Meeting, Milwaukee, Wis. (1999).
DiPaolo et al., *Crit. Rev. Oncogen.*, 4, 337–360 (1993).
Dramsi and Cossart, *Ann. Rev. Cell Dev. Biol.*, 14, 137–166 (1998).
Draper et al., *Am. J. Obstet. Gynecol.*, 138, 818–826 (1980).
Dudas and Apicella, *Infect. Immun.*, 56, 499–504 (1988).
Edwards et al., *Infect. Immun.*, 68, 5354–5363 (2000).
Edwards et al., *Cell. Microbiol.*, 3, 611–622 (2001).
Edwards and Apicella, *Cell. Microbiol.*, 4, 584–598 (2002).
Edwards et al., *Cell. Microbiol.*, 4, 571–584 (2002).
Edwards et al., "Gonococcal Phospholipase D Modulates the Expression and Function of Complement Receptor 3 in Primary Cervical Epithelial Cells," (manuscript submitted).
Elemer and Edgington, *J. Biol. Chem.*, 269, 3159–3166 (1994).
Erdei et al., *Immun. Today*, 12, 332–337 (1991).
Evans, *J. Infect. Dis.*, 136 (2), 248–255 (1977).
Exton, *J. Biol. Chem.*, 272, 15579–15582 (1997).
Fällman et al., *J. Biol. Chem.*, 267, 2656–2663 (1992).

Finlay and Falkow, *Microbiol. Mol. Biol. Rev.*, 61, 136–169 (1997).
Finlay and Ruschkowski, *J. Cell Sci.*, 99, 283–296 (1991).
Fluhmann, *Obstet. Gynecol.*, 14, 133–148 (1959).
Francis et al., *Nature*, 364, 639–642 (1993).
Frank and Fries, *Immunol. Today*, 12, 322–326 (1991).
Fukami et al., *J. Biol. Chem.*, 269, 1518–1522 (1994).
Gadzar et al., *Int. J. Cancer*, 78, 766–774 (1998).
Garcia-del Portiilo and Finlay, *Infect. Immun.*, 62, 4641–4645 (1994).
Goeddel et al., *Nucleic Acids Res.*, 8, 4057 (1980).
Grassméet al., *Infect. Immun.*, 64 (5), 1621–1630 (1996).
Griffin et al., *J. Exp. Med.*, 144, 788–809 (1976).
Griffin et al., *J. Exp. Med.*, 142, 1263–1282 (1975).
Ha and Exton, *J. Cell Biol.*, 123, 1789–1796 (1993).
Handsfield, *Neisseria gonorrhoeae* in *Principles and Practice of Infectious Disease* 3$^{rd}$ Ed. Mandell, G. L., R. G. Douglas, Jr., and J. E. Bennett (eds) Churchill Livingstone, New York (1990).
Harkness, *Br. J. Vener. Dis.*, 24, 137–147 (1948).
Harvey et al., *Infect. Immun.*, 65, 2420–2427 (1997).
Harvey et al., *Mol. Microbiol.*, 42, 659–672 (2001).
Harvey et al., *Infect. Immun.*, 70, 5808–5815 (2002)
Hauck et al., *EMBO J.*, 17, 443–454 (1998).
Hayashi et al., *Infect. Immun.*, 65, 1211–1216 (1997).
Hildreth and August, *J. Immunol.*, 134, 3272–3280 (1985).
Hinnebusch et al., *Science*, 296, 733–735 (2002).
Hodgson et al., *Infect. Immun.*, 60, 2900–2905 (1992).
Hondalus et al., *Infect. Immun.*, 61, 2919–2929 (1993).
Hook and Handsfield, 1999. Gonococcal infections in the adult in *Sexually Transmitted Diseases* 3$^{rd}$ Ed. Holmes, K. K., P-A Mårdh, P. F. Sparling, S. M. Lemon, W. E. Stamm, P. Piot, and J. N. Wasserheit (eds). McGraw-Hill, New York (1999).
Hussain et al., *Clin. Exp. Imunnol.*, 102, 384–388 (1995).
Hynes, *Cell*, 48, 549–554 (1987).
Iglesias et al., *Am. J. Pathol.*, 146, 944–952 (1995).
Ingalls et al., *Prog. Clin. Biol. Res.*, 397, 107–117 (1998).
Jarvis et al., *Infect. Immun.*, 67, 1149–1156 (1999).
Jerse and Jerse, *Trends Microbiol.*, 5, 217–221 (1997).
Jones and Walker, *J. Clin. Pathol: Mol. Pathol.*, 52, 208–213 (1999).
Jones et al., *J. Biol. Chem.*, 273, 10556–10566 (1998).
Jones et al., *Biochim. Biophys. Acta.*, 1439, 229–224 (1999).
Jurianz et al., *Mol. Immunol.*, 36, 929–939 (1999).
Källström et al., *Mol. Micobiol.*, 25, 639–647 (1997).
Källström et al., *Cell Microbiol.*, 2, 341–351 (2000).
Kaur and McDougall, *J. Virol.*, 62, 1917–1924 (1988).
Ketterer et al., *Infect. Immun.*, 67 (8), 4161–4170 (1999).
Kishimoto et al., *Adv. Immunol.*, 46, 149–182 (1989).
Kondo et al., *J. Biol. Chem.*, 267, 23609–23616 (1992).
Kondo et al., *Electrophoresis*, 17, 1638–1642 (1996).
van Kooyk et al., *J. Biol. Chem.*, 274, 26869–26877 (1999).
Kragsbjerg et al., *APMIS*, 108, 276–282 (2000).
Kusner et al., *J. Biol. Chem.*, 277, 50683–50692 (2002).
Kusner et al., *Arch. Biochem. Biophys.*, 412, 231–241 (2003).
Lawn et al., *Nucleic Acids Res.*, 9, 6103 (1981).
Lin et al., *J. Clin. Endocrinol. Metab.*, 79, 1483–1491 (1994).
Lukowski et al., *J. Biol. Chem.*, 271, 24164–24171 (1996).
Lynch et al., *Biophys. J.*, 45, 104–107 (1984).
Maisner et al., *J. Biol. Chem.*, 272, 20793–20799 (1997).
Maitra et al., *Nature Med.*, 5, 459–463 (1999).
McGee et al. et al., *Rev. Infect. Dis.*, 5, S708–S714 (1983).
McGhee et al., *Sem. Hematol.*, 30, 3–15 (1993).
McNamara et al., *Gene*, 156, 113–118 (1995).
McNeely, *Sex. Trans. Dis.*, 16, 467–478 (1989).
McQuillen et al., *J. Infect. Dis.*, 179, 124–135 (1999).
Mesri et al., *J. Biol. Chem.*, 273, 744–748 (1998).
Meyer, *Clin. Infect. Dis.*, 28, 433–441 (1999).
Moll et al., *Cell*, 31, 11–24 (1982).
Morse and Barenstein, *Canadian J. Microbiol.*, 26, 13–20 (1980)
Mosser and Edelson, *Nature*, 327, 329–331 (1987).
Moulder, *Microbiol. Rev.*, 49, 298–337 (1985).
Mukherjee et al., *Physiol. Rev.*, 77, 759–803 (1997).
Nassif et al., *Mol. Microbiol.*, 32, 1124–1132 (1999).
Nassif and So, *Clin. Microbiol. Rev.*, 8, 376–388 (1995).
Naumann et al., *Curr. Opin. Microbiol.*, 2, 62–70 (1999).
Obermeier et al., *EMBO J.*, 17, 4328–4339 (1998).
Oelschlager et al., *Proc. Natl. Acad. Sci.*, 90, 6884–6888 (1993).
O'Gorman et al., *Cancer Res.*, 59, 5692–5694 (1999).
de la Paz et al., *Microbiol.*, 141, 913–920 (1995).
Perlmann et al., *J. Immunol.*, 130, 2831–2836 (1983).
Ponting and Kerr, *Prot. Science*, 5, 914–922 (1996).
Price and Boettcher, *Fertil. Steril.*, 32, 61–66 (1979).
Rabinovitch, *Trends Cell Biol.*, 5, 85–88 (1995).
Ram et al., *Mol. Immunol.*, 36, 915–928 (1999).
Ram et al., *J. Exp. Med.*, 187, 743–752 (1998).
Ramos et al., *J. Immunol.*, 140, 1239–1243 (1988).
Ramos et al., *Proc. Natl. Acad. Sci. USA*, 82, 5470–5474 (1985).
Relman et al., *Cell*, 61, 1375–1382 (1990).
Richardson and Sadoff, *Infect. Immun.*, 56, 2512–2514 (1998).
Robinson, *Curr. Opin. Cell Biol.*, 6, 538–544 (1994).
Rosqvist et al., *EMBO J.*, 14,4187–4195 (1995).
Ross and Densen, *J. Infect. Dis.*, 151,33–41 (1985).
Sandilands and Whaley, *Methods in Complement for Clinical Immunologists*, (1985).
Sambrook and Russell, *Molecular Cloning: A Laboratory Manual*, Cold Spring Harbor Laboratory Press, Cold Spring Harbor, N.Y. (3$^{rd}$ edition, 2001).
Schmidt and Hall. *Annu. Rev. Cell Dev. Biol.* 14,305–338 (1998).
Schoolnik et al., *J. Exp. Med.*, 159, 1351–1370 (1984).
Segal et al., *Cell*, 40, 293–300 (1985).
Sells et al., *Curr. Biol.*, 7, 202–210 (1997).
Seya et al., *J. Immunol.*, 145, 238–245 (1990).
Silverstein et al., *Ann. Rev. Biochem.*, 46, 669–722 (1997).
Simmons et al., *Infect. Immun.*, 66, 474–479 (1998).
Sizemore and Rorke, *Cancer Res.*, 53, 4511–4517 (1993).
Skoudy et al., *J. Cell Sci.* 112, 2059–2068 (1999).
Smedts et al., 1990. *Am. J. Pathol.*, 136, 657–668 (1990).
Smedts et al., *Am. J. Pathol.*, 141, 497–511 (1992).
Stephens, *Clin. Microbiol. Rev.*, 2, S104–S111 (1989).
Stewart et al., *J. Immunol.*, 156, 1810–1817 (1996).
Stocks et al, *J. Leuk. Biol.*, 58, 40–48 (1995).
Stocks et al., *Eur. J. Immunol.* 2924–2932 (1996).
Stryer, *Biochemistry* (2d edition) 14–15 (1981); Lehninger, *Biochemistry* (2d ed.), 73–75 (1975).
Sülz et al., *Hum. Reprod.*, 13, 2916–2920 (1998).
Sun et al., *Int. J. Cancer*, 54, 656–662 (1993).
Swanson and Baer, *Trends Cell Biol.*, 5, 89–93 (1995).
Swanson and Watts, *Trends Cell Biol.*, 5, 424–428 (1995).
Tran Van Mhieu and Sansonetti, *Curr. Opin. Microbiol.*, 2, 51–55 (1999).

Vanderpuye et al., *Fertil. Immunol.*, 27, 145–155 (1992).
Violette et al., *J. Immunol.*, 155, 3092–3101 (1995).
Vogel and Frosch, *Mol. Microbiol.*, 32, 1133–1139 (1999).
Wåhlin et al., *J. Immunol.*, 130, 2831–2836 (1983).
Waite, *Biochim. Biophys. Acta.*, 1439, 187–197 (1999).
Watarai et al., *J. Exp. Med.*, 183, 991–999 (1996).
Wen et al., *Biochem.*, 39, 8638–8647 (2000).
Wetzler et al., *Infect. Immun.*, 60, 39–43 (1992).
Wright et al., *Proc. Natl. Acad. Sci. USA*, 80, 5699–5703 (1983).
Würzner, *Mol. Immunol.*, 36, 249–260 (1999).
Zhang and Chait, *Anal. Chem.*, 72, 2482–2489 (2000).
Zipfel et al., *Mol. Immunol.*, 36, 241–248 (1999).
U.S. Pat. No. 4,533,630.
U.S. Pat. No. 4,554,101.
EP 184187A, 2188638A.

What is claimed is:

1. An isolated and purified polypeptide comprising amino acid sequence set forth as SEQ ID NO: 14 for *Neisseria gonorrhoeae* encoded by nucleic acid sequence set forth as SEQ ID NO: 13.

2. An isolated and purified phospholipase D polypeptide from *Neisseria gonorrhoeae*, comprising amino acid sequence set forth as SEQ ID NO: 14.

3. The polypeptide of claim 2 that is conjugated or linked to a second peptide.

4. The polypeptide of claim 2 that is conjugated or linked to a polysaccharide.

5. A composition comprising the polypeptide of claim 2 and a pharmaceutically-acceptable vehicle.

6. The composition of claim 5, wherein the polypeptide is encoded by a polynucleotide comprising SEQ ID NO: 13.

7. The composition of claim 5, which further comprises an effective amount of an immunological adjuvant.

8. The composition of claim 5, wherein the polypeptide is conjugated or linked to a second peptide.

9. The composition of claim 5, wherein the polypeptide is conjugated or linked to a polysaccharide.

* * * * *